(12) United States Patent
Clube et al.

(10) Patent No.: US 12,226,430 B2
(45) Date of Patent: *Feb. 18, 2025

(54) ALTERING MICROBIAL POPULATIONS AND MODIFYING MICROBIOTA

(71) Applicant: SNIPR Technologies Limited, Peterborough (GB)

(72) Inventors: Jasper Clube, London (GB); Morten Sommer, London (GB); Christian Grøndahl, London (GB); Eric Van Der Helm, London (GB); Ruben Vazquez-Uribe, London (GB)

(73) Assignee: SNIPR TECHNOLOGIES LIMITED, Peterborough (GB)

(*) Notice: Subject to any disclaimer, the term of this patent is extended or adjusted under 35 U.S.C. 154(b) by 0 days.

This patent is subject to a terminal disclaimer.

(21) Appl. No.: 18/501,825

(22) Filed: Nov. 3, 2023

(65) Prior Publication Data

US 2024/0082289 A1 Mar. 14, 2024

Related U.S. Application Data

(60) Continuation of application No. 16/813,615, filed on Mar. 9, 2020, now Pat. No. 11,844,760, which is a
(Continued)

(30) Foreign Application Priority Data

| May 6, 2015 | (GB) | 1507773.8 |
|---|---|---|
| May 6, 2015 | (GB) | 1507774.6 |
| May 6, 2015 | (GB) | 1507775.3 |
| May 6, 2015 | (GB) | 1507776.1 |
| May 17, 2015 | (GB) | 1508461.9 |
| May 31, 2015 | (GB) | 1509366.9 |
| Jun. 20, 2015 | (GB) | 1510891.3 |
| Oct. 17, 2015 | (GB) | 1518402.1 |
| Jan. 10, 2016 | (GB) | 1600417.8 |
| Jan. 10, 2016 | (GB) | 1600418.6 |

(51) Int. Cl.

| A61K 31/711 | (2006.01) |
|---|---|
| A01N 63/00 | (2020.01) |
| A01N 63/50 | (2020.01) |
| A01N 63/60 | (2020.01) |
| A61K 31/7105 | (2006.01) |
| A61K 35/74 | (2015.01) |
| A61K 45/06 | (2006.01) |
| A61K 48/00 | (2006.01) |
| C12N 1/20 | (2006.01) |
| C12N 7/00 | (2006.01) |
| C12N 9/16 | (2006.01) |
| C12N 15/10 | (2006.01) |
| C12N 15/113 | (2010.01) |
| C12N 15/70 | (2006.01) |
| C12N 15/74 | (2006.01) |
| C12N 15/90 | (2006.01) |
| A61K 35/00 | (2006.01) |

(52) U.S. Cl.
CPC .......... *A61K 31/7105* (2013.01); *A01N 63/00* (2013.01); *A01N 63/50* (2020.01); *A01N 63/60* (2020.01); *A61K 31/711* (2013.01); *A61K 35/74* (2013.01); *A61K 45/06* (2013.01); *A61K 48/005* (2013.01); *C12N 1/20* (2013.01); *C12N 7/00* (2013.01); *C12N 9/16* (2013.01); *C12N 15/102* (2013.01); *C12N 15/113* (2013.01); *C12N 15/70* (2013.01); *C12N 15/746* (2013.01); *C12N 15/902* (2013.01); *A61K 2035/11* (2013.01); *A61K 2300/00* (2013.01); *C12N 2310/20* (2017.05); *C12N 2320/31* (2013.01); *C12N 2795/00032* (2013.01); *C12N 2795/10132* (2013.01); *Y02A 50/30* (2018.01)

(58) Field of Classification Search
None
See application file for complete search history.

(56) References Cited

U.S. PATENT DOCUMENTS

| 4,626,504 A | 12/1986 | Puhler |
|---|---|---|
| 4,870,287 A | 9/1989 | Cole |

(Continued)

FOREIGN PATENT DOCUMENTS

| CA | 3010891 A1 | 7/2017 |
|---|---|---|
| EP | 2320940 B1 | 5/2011 |

(Continued)

OTHER PUBLICATIONS

Abedon, S.T. et al. (Dec. 2003). "Experimental Examination of Bacteriophage Latent-Period Evolution as a Response to Bacterial Availability," Applied and Environmental Microbiology 69(12):7499-7506.
Abernethy, J. K. et al. (Mar. 2015, e-pub. Jan. 14, 2015). "Thirty Day All-Cause Mortality In Patients With *Escherichia coli* Bacteraemia In England," Clin. Microbial. Infect. 21:251.e1-251.e8.
Advisory Action, mailed Dec. 9, 2021 for U.S. Appl. No. 90/014,705, filed Mar. 23, 2021, 9 pages.
Aguiliar, C. et al. (2010, e-pub. Dec. 16, 2009). "Chapter 2: Cell-Cell Communication in Biofilms of Gram-Negative Bacteria," Bacterial Signaling pp. 23-40.

(Continued)

*Primary Examiner* — Jennifer E Graser
(74) *Attorney, Agent, or Firm* — MORRISON & FOERSTER LLP

(57) ABSTRACT

The invention relates to methods, uses, systems, arrays, engineered nucleotide sequences and vectors for inhibiting bacterial population growth or for altering the relative ratio of sub-populations of first and second bacteria in a mixed population of bacteria. The invention is particularly useful, for example, for treatment of microbes such as for environmental, medical, food and beverage use. The invention relates inter alia to methods of controlling microbiologically influenced corrosion (MIC) or biofouling of a substrate or fluid in an industrial or domestic system.

16 Claims, 12 Drawing Sheets

Specification includes a Sequence Listing.

Related U.S. Application Data division of application No. 15/460,962, filed on Mar. 16, 2017, now Pat. No. 10,582,712, which is a continuation of application No. 15/160,405, filed on May 20, 2016, now Pat. No. 9,701,964, which is a continuation of application No. PCT/EP2016/059803, filed on May 3, 2016.

(56) References Cited

U.S. PATENT DOCUMENTS

| | | |
|---|---|---|
| 5,633,154 A | 5/1997 | Schaefer |
| 5,760,395 A | 6/1998 | Johnstone |
| 5,844,905 A | 12/1998 | Mckay |
| 5,885,796 A | 3/1999 | Linsley |
| 6,207,156 B1 | 3/2001 | Kuchroo |
| 7,459,272 B2 | 12/2008 | Morris |
| 8,003,323 B2 | 8/2011 | Morris |
| 8,008,449 B2 | 8/2011 | Korman |
| 8,017,114 B2 | 9/2011 | Korman |
| 8,119,129 B2 | 2/2012 | Jure-Kunkel |
| 8,241,498 B2 | 8/2012 | Summer |
| 8,252,576 B2 | 8/2012 | Campbell |
| 8,329,867 B2 | 12/2012 | Lazar |
| 8,354,509 B2 | 1/2013 | Carven |
| 8,735,553 B1 | 5/2014 | Li |
| 8,906,682 B2 | 12/2014 | June |
| 8,911,993 B2 | 12/2014 | June |
| 8,916,381 B1 | 12/2014 | June |
| 8,975,071 B1 | 3/2015 | June |
| 9,101,584 B2 | 8/2015 | June |
| 9,102,760 B2 | 8/2015 | June |
| 9,102,761 B2 | 8/2015 | June |
| 9,113,616 B2 | 8/2015 | MacDonald et al. |
| 9,328,156 B2 | 5/2016 | June |
| 9,464,140 B2 | 10/2016 | June |
| 9,481,728 B2 | 11/2016 | June |
| 9,499,629 B2 | 11/2016 | June |
| 9,518,123 B2 | 12/2016 | June |
| 9,540,445 B2 | 1/2017 | June |
| 9,593,339 B1 | 3/2017 | Bermudes |
| 9,701,964 B2 | 7/2017 | Clube |
| 9,758,583 B2 | 9/2017 | Wang |
| 9,822,372 B2 | 11/2017 | Zhang |
| 9,879,269 B2 | 1/2018 | Barrangou |
| 9,889,164 B2 | 2/2018 | Falb et al. |
| 10,066,233 B2 | 9/2018 | Barrangou |
| 10,136,639 B2 | 11/2018 | Wuest |
| 10,136,649 B2 | 11/2018 | Barrangou |
| 10,195,273 B2 | 2/2019 | Clube |
| 10,300,138 B2 | 5/2019 | Clube |
| 10,300,139 B2 | 5/2019 | Clube |
| 10,303,379 B2 | 5/2019 | Bab-Dinitz et al. |
| 10,363,308 B2 | 7/2019 | Clube |
| 10,463,049 B2 | 11/2019 | Clube |
| 10,506,812 B2 | 12/2019 | Clube |
| 10,524,477 B2 | 1/2020 | Clube |
| 10,561,148 B2 | 2/2020 | Clube |
| 10,582,712 B2 | 3/2020 | Clube |
| 10,596,255 B2 | 3/2020 | Clube |
| 10,603,379 B2 | 3/2020 | Clube |
| 10,624,349 B2 | 4/2020 | Clube |
| 10,660,943 B2 | 5/2020 | Bikard et al. |
| 10,760,065 B2 | 9/2020 | Lu et al. |
| 10,760,075 B2 | 9/2020 | Sommer et al. |
| 10,765,740 B2 | 9/2020 | Clube et al. |
| 10,920,222 B2 | 2/2021 | Sommer et al. |
| 10,953,090 B2 | 3/2021 | Clube et al. |
| 11,141,481 B2 | 10/2021 | Clube |
| 11,147,830 B2 | 10/2021 | Clube |
| 11,166,994 B2 | 11/2021 | Lichtenstein et al. |
| 11,274,317 B2 | 3/2022 | Fricke et al. |
| 11,291,693 B2 | 4/2022 | Falb et al. |
| 11,291,723 B2 | 4/2022 | Clube |
| 11,351,252 B2 | 6/2022 | Clube |
| 11,400,110 B2 | 8/2022 | Clube |
| 11,471,530 B2 | 10/2022 | Clube |
| 11,517,582 B2 | 12/2022 | Clube et al. |
| 11,547,716 B2 | 1/2023 | Clube |
| 11,578,333 B2 | 2/2023 | Martinez et al. |
| 11,612,617 B2 | 3/2023 | Clube |
| 11,629,350 B2 | 4/2023 | Martinez et al. |
| 11,642,363 B2 | 5/2023 | Clube |
| 11,844,760 B2 | 12/2023 | Clube |
| 2003/0049841 A1 | 3/2003 | Short |
| 2004/0096974 A1 | 5/2004 | Herron |
| 2005/0118719 A1 | 6/2005 | Schmidt |
| 2009/0155768 A1 | 6/2009 | Scholl |
| 2010/0076057 A1 | 3/2010 | Sontheimer |
| 2010/0093617 A1 | 4/2010 | Barrangou |
| 2010/0172874 A1 | 7/2010 | Turnbaugh |
| 2011/0002889 A1 | 1/2011 | Barrangou |
| 2011/0008369 A1 | 1/2011 | Finnefrock |
| 2011/0136688 A1 | 6/2011 | Scholl |
| 2011/0143997 A1 | 6/2011 | Henry et al. |
| 2012/0177645 A1 | 7/2012 | Langermann |
| 2012/0269859 A1 | 10/2012 | Minato |
| 2012/0294796 A1 | 11/2012 | Johnson |
| 2013/0011828 A1 | 1/2013 | Barrangou |
| 2013/0109053 A1 | 5/2013 | Macdonald |
| 2013/0121968 A1 | 5/2013 | Quay |
| 2013/0287748 A1 | 10/2013 | June |
| 2013/0288368 A1 | 10/2013 | June |
| 2013/0309258 A1 | 11/2013 | June |
| 2014/0022021 A1 | 1/2014 | Kusachi |
| 2014/0068797 A1 | 3/2014 | Doudna |
| 2014/0105912 A1 | 4/2014 | Noelle |
| 2014/0106449 A1 | 4/2014 | June |
| 2014/0107092 A1 | 4/2014 | Meyerson |
| 2014/0179726 A1 | 6/2014 | Bajaj |
| 2014/0199767 A1 | 7/2014 | Barrangou |
| 2014/0234972 A1 | 8/2014 | Zhang |
| 2014/0294898 A1 | 10/2014 | Miller |
| 2014/0341920 A1 | 11/2014 | Noelle |
| 2014/0349400 A1 | 11/2014 | Jakimo et al. |
| 2014/0370017 A1 | 12/2014 | June |
| 2015/0004705 A1 | 1/2015 | Lu et al. |
| 2015/0031134 A1 | 1/2015 | Zhang |
| 2015/0032263 A1 | 1/2015 | Keyl et al. |
| 2015/0044772 A1 | 2/2015 | Zhao |
| 2015/0050699 A1 | 2/2015 | Siksnys |
| 2015/0050729 A1 | 2/2015 | June |
| 2015/0064138 A1 | 3/2015 | Lu |
| 2015/0093822 A1 | 4/2015 | June |
| 2015/0099299 A1 | 4/2015 | June |
| 2015/0118202 A1 | 4/2015 | June |
| 2015/0125463 A1 | 5/2015 | Cogswell |
| 2015/0132263 A1 | 5/2015 | Liu et al. |
| 2015/0132419 A1 | 5/2015 | Arvik |
| 2015/0139943 A1 | 5/2015 | Campana |
| 2015/0140001 A1 | 5/2015 | Lee |
| 2015/0184139 A1 | 7/2015 | Zhang |
| 2015/0225730 A1 | 8/2015 | Minshull et al. |
| 2015/0232881 A1 | 8/2015 | Glucksmann |
| 2015/0290244 A1 | 10/2015 | June |
| 2015/0353905 A1 | 12/2015 | Weiss |
| 2016/0009805 A1 | 1/2016 | Kowanetz |
| 2016/0009813 A1 | 1/2016 | Themeli |
| 2016/0024510 A1 | 1/2016 | Bikard |
| 2016/0040215 A1 | 2/2016 | Henn et al. |
| 2016/0081314 A1 | 3/2016 | Thurston |
| 2016/0115488 A1 | 4/2016 | Zhang |
| 2016/0115489 A1 | 4/2016 | Zhang |
| 2016/0130355 A1 | 5/2016 | June |
| 2016/0159905 A1 | 6/2016 | Abdiche |
| 2016/0159907 A1 | 6/2016 | June |
| 2016/0160186 A1 | 6/2016 | Parsley |
| 2016/0194404 A1 | 7/2016 | June |
| 2016/0208012 A1 | 7/2016 | June |
| 2016/0237455 A1 | 8/2016 | Glucksmann |
| 2016/0244784 A1 | 8/2016 | Jacobson et al. |
| 2016/0281053 A1 | 9/2016 | Sorek |
| 2016/0324938 A1 | 11/2016 | Bikard |
| 2016/0333348 A1 | 11/2016 | Clube |
| 2016/0345578 A1 | 12/2016 | Barrangou |

(56) References Cited

U.S. PATENT DOCUMENTS

| | | |
|---|---|---|
| 2016/0347836 A1 | 12/2016 | Grosso |
| 2016/0354416 A1 | 12/2016 | Gajewski |
| 2017/0022499 A1 | 1/2017 | Lu |
| 2017/0037416 A1 | 2/2017 | Barrangou |
| 2017/0106026 A1 | 4/2017 | Kovarik |
| 2017/0114351 A1 | 4/2017 | Mahfouz |
| 2017/0143772 A1 | 5/2017 | Mulder |
| 2017/0173085 A1 | 6/2017 | Kovarik |
| 2017/0173086 A1 | 6/2017 | Boyle et al. |
| 2017/0174713 A1 | 6/2017 | Du |
| 2017/0175142 A1 | 6/2017 | Zhang |
| 2017/0196225 A1 | 7/2017 | Clube |
| 2017/0216370 A1 | 8/2017 | Falb et al. |
| 2017/0246221 A1 | 8/2017 | Clube |
| 2017/0247690 A1 | 8/2017 | Quake |
| 2017/0304443 A1 | 10/2017 | Lebwohl |
| 2017/0314015 A1 | 11/2017 | Friedland et al. |
| 2017/0327582 A1 | 11/2017 | Bissonnette |
| 2017/0340733 A1 | 11/2017 | Cao |
| 2018/0015131 A1 | 1/2018 | Gajewski |
| 2018/0055852 A1 | 3/2018 | Kutok |
| 2018/0064114 A1 | 3/2018 | Clube |
| 2018/0064115 A1 | 3/2018 | Clube |
| 2018/0070594 A1 | 3/2018 | Clube |
| 2018/0084785 A1 | 3/2018 | Clube |
| 2018/0084786 A1 | 3/2018 | Clube |
| 2018/0140698 A1 | 5/2018 | Clube |
| 2018/0146681 A1 | 5/2018 | Clube |
| 2018/0147221 A1 | 5/2018 | Von Maltzahn et al. |
| 2018/0155721 A1 | 6/2018 | Lu |
| 2018/0155729 A1 | 6/2018 | Beisel |
| 2018/0161368 A1 | 6/2018 | Odegard |
| 2018/0179547 A1 | 6/2018 | Zhang |
| 2018/0200342 A1 | 7/2018 | Bikard |
| 2018/0273937 A1 | 9/2018 | Beisel et al. |
| 2018/0273940 A1 | 9/2018 | Sommer |
| 2018/0303934 A1 | 10/2018 | Clube |
| 2018/0326057 A1 | 11/2018 | Clube |
| 2018/0355378 A1 | 12/2018 | Krom et al. |
| 2018/0371405 A1 | 12/2018 | Barrangou |
| 2019/0010506 A1 | 1/2019 | Falb et al. |
| 2019/0015441 A1 | 1/2019 | Shachar |
| 2019/0021343 A1 | 1/2019 | Barrangou |
| 2019/0070233 A1 | 3/2019 | Yeung |
| 2019/0117709 A1 | 4/2019 | Kovarik |
| 2019/0133135 A1 | 5/2019 | Clube |
| 2019/0134194 A1 | 5/2019 | Clube |
| 2019/0136230 A1 | 5/2019 | Sather |
| 2019/0142881 A1 | 5/2019 | Turner et al. |
| 2019/0160120 A1 | 5/2019 | Haaber |
| 2019/0230936 A1 | 8/2019 | Clube |
| 2019/0240325 A1 | 8/2019 | Clube |
| 2019/0240326 A1 | 8/2019 | Clube |
| 2019/0255084 A1 | 8/2019 | Schentag |
| 2019/0256900 A1 | 8/2019 | Zhang |
| 2019/0282628 A1 | 9/2019 | Falb et al. |
| 2019/0298779 A1 | 10/2019 | Falb |
| 2019/0321468 A1 | 10/2019 | Clube |
| 2019/0321469 A1 | 10/2019 | Clube |
| 2019/0321470 A1 | 10/2019 | Clube |
| 2019/0359933 A1 | 11/2019 | Swee |
| 2020/0030444 A1 | 1/2020 | Clube |
| 2020/0046773 A1 | 2/2020 | Borody |
| 2020/0068901 A1 | 3/2020 | Clube |
| 2020/0077663 A1 | 3/2020 | Clube |
| 2020/0085066 A1 | 3/2020 | Clube |
| 2020/0087660 A1 | 3/2020 | Sommer |
| 2020/0102551 A1 | 4/2020 | Barrangou |
| 2020/0115716 A1 | 4/2020 | Martinez |
| 2020/0121787 A1 | 4/2020 | Clube |
| 2020/0128832 A1 | 4/2020 | Clube |
| 2020/0157237 A1 | 5/2020 | Regev |
| 2020/0164070 A1 | 5/2020 | Clube |
| 2020/0179460 A1 | 6/2020 | Kovarik |
| 2020/0199570 A1 | 6/2020 | Novick |
| 2020/0205416 A1 | 7/2020 | Clube |
| 2020/0267992 A1 | 8/2020 | Clube |
| 2020/0282027 A1 | 9/2020 | Bikard et al. |
| 2020/0337313 A1 | 10/2020 | Clube |
| 2020/0354690 A1 | 11/2020 | Garofolo |
| 2020/0390886 A1 | 12/2020 | Clube |
| 2021/0009996 A1 | 1/2021 | Sommer |
| 2021/0113689 A1 | 4/2021 | Clube |
| 2021/0145006 A1 | 5/2021 | Clube |
| 2021/0147827 A1 | 5/2021 | Clube |
| 2021/0147857 A1 | 5/2021 | Clube |
| 2021/0163960 A1 | 6/2021 | Martinez et al. |
| 2021/0169942 A1 | 6/2021 | Falb et al. |
| 2021/0189406 A1 | 6/2021 | Martinez et al. |
| 2021/0198665 A1 | 7/2021 | Sommer et al. |
| 2021/0230559 A1 | 7/2021 | Clube |
| 2021/0238167 A1 | 8/2021 | Glimcher et al. |
| 2021/0283167 A1 | 9/2021 | Clube |
| 2021/0290654 A1 | 9/2021 | Clube |
| 2021/0386773 A1 | 12/2021 | Clube |
| 2022/0056457 A1 | 2/2022 | Edgell et al. |
| 2022/0233575 A1 | 7/2022 | Clube et al. |
| 2022/0241318 A1 | 8/2022 | Clube et al. |
| 2022/0273696 A1 | 9/2022 | Clube |
| 2022/0362280 A1 | 11/2022 | Clube |

FOREIGN PATENT DOCUMENTS

| | | |
|---|---|---|
| EP | 2325332 A1 | 5/2011 |
| EP | 2840140 A1 | 2/2015 |
| EP | 3461337 A1 | 4/2019 |
| EP | 3132035 B8 | 4/2020 |
| EP | 3132036 B8 | 4/2020 |
| EP | 3630975 A1 | 4/2020 |
| EP | 3633032 A2 | 4/2020 |
| EP | 3634442 A1 | 4/2020 |
| EP | 3634473 A1 | 4/2020 |
| JP | 2010285425 A | 12/2010 |
| RU | 2531343 C2 | 10/2014 |
| WO | 198702702 A1 | 5/1987 |
| WO | 1995001994 A1 | 1/1995 |
| WO | 1998042752 A1 | 10/1998 |
| WO | 2000037504 A2 | 6/2000 |
| WO | 2000037504 A3 | 9/2000 |
| WO | 2001014424 A2 | 3/2001 |
| WO | 2001014424 A3 | 9/2001 |
| WO | 2005003168 A2 | 1/2005 |
| WO | 2005009465 A1 | 2/2005 |
| WO | 2005003168 A3 | 5/2005 |
| WO | 2005046579 A2 | 5/2005 |
| WO | 2005046579 A3 | 8/2005 |
| WO | 2006003179 A2 | 1/2006 |
| WO | 2006003179 A3 | 5/2006 |
| WO | 2006072625 A2 | 7/2006 |
| WO | 2006072626 A1 | 7/2006 |
| WO | 2006121168 A1 | 11/2006 |
| WO | 2006072625 A3 | 12/2006 |
| WO | 2007025097 A2 | 3/2007 |
| WO | 2007042573 A2 | 4/2007 |
| WO | 2007025097 A3 | 7/2007 |
| WO | 2007042573 A3 | 7/2007 |
| WO | 2008084106 A1 | 7/2008 |
| WO | 2008108989 A2 | 9/2008 |
| WO | 2008132601 A1 | 11/2008 |
| WO | 2008108989 A3 | 3/2009 |
| WO | 2009044273 A2 | 4/2009 |
| WO | 2009101611 A1 | 8/2009 |
| WO | 2008084106 A9 | 9/2009 |
| WO | 2009044273 A3 | 9/2009 |
| WO | 2009114335 A2 | 9/2009 |
| WO | 2010011961 A1 | 1/2010 |
| WO | 2010027827 A2 | 3/2010 |
| WO | 2010027827 A3 | 5/2010 |
| WO | 2009114335 A3 | 6/2010 |
| WO | 2010065939 A1 | 6/2010 |
| WO | 2010075424 A2 | 7/2010 |
| WO | 2010075424 A3 | 9/2010 |
| WO | 2011014438 A1 | 2/2011 |
| WO | 2011066342 A2 | 6/2011 |

(56) References Cited

FOREIGN PATENT DOCUMENTS

| | | |
|---|---|---|
| WO | 2011066342 A3 | 7/2011 |
| WO | 2012054726 A1 | 4/2012 |
| WO | 2012071411 A2 | 5/2012 |
| WO | 2012079000 A1 | 6/2012 |
| WO | 2012071411 A3 | 8/2012 |
| WO | 2012079000 A4 | 8/2012 |
| WO | 2012160448 A2 | 11/2012 |
| WO | 2012164565 A1 | 12/2012 |
| WO | 2013006490 A2 | 1/2013 |
| WO | 2013025779 A1 | 2/2013 |
| WO | 2012160448 A3 | 5/2013 |
| WO | 2013063361 A1 | 5/2013 |
| WO | 2013067492 A1 | 5/2013 |
| WO | 2013176772 A1 | 11/2013 |
| WO | 2014012001 A2 | 1/2014 |
| WO | 2014018423 A2 | 1/2014 |
| WO | 2014018423 A3 | 1/2014 |
| WO | 2014040962 A1 | 3/2014 |
| WO | 2014043432 A1 | 3/2014 |
| WO | 2013006490 A3 | 5/2014 |
| WO | 2014093595 A1 | 6/2014 |
| WO | 2014093661 A2 | 6/2014 |
| WO | 2014093661 A3 | 8/2014 |
| WO | 2014124226 A1 | 8/2014 |
| WO | 2014150624 A1 | 9/2014 |
| WO | 2014093661 A9 | 10/2014 |
| WO | 2014204725 A1 | 12/2014 |
| WO | 2015016718 A1 | 2/2015 |
| WO | 2015034872 A2 | 3/2015 |
| WO | 2014012001 A3 | 4/2015 |
| WO | 2015034872 A3 | 4/2015 |
| WO | 2015058018 A1 | 4/2015 |
| WO | 2015069682 A2 | 5/2015 |
| WO | 2015070083 A1 | 5/2015 |
| WO | 2015070193 A1 | 5/2015 |
| WO | 2015071474 A2 | 5/2015 |
| WO | 2015075688 A1 | 5/2015 |
| WO | 2015088643 A1 | 6/2015 |
| WO | 2015089351 A1 | 6/2015 |
| WO | 2015089419 A2 | 6/2015 |
| WO | 2015069682 A3 | 7/2015 |
| WO | 2015071474 A3 | 8/2015 |
| WO | 2015089419 A3 | 9/2015 |
| WO | 2015136541 A2 | 9/2015 |
| WO | 2015148680 A1 | 10/2015 |
| WO | 2015153940 A1 | 10/2015 |
| WO | 2015155686 A2 | 10/2015 |
| WO | 2015159068 A1 | 10/2015 |
| WO | 2015159086 A1 | 10/2015 |
| WO | 2015159087 A1 | 10/2015 |
| WO | 2015136541 A3 | 11/2015 |
| WO | 2016044745 A1 | 3/2016 |
| WO | 2016063263 A2 | 4/2016 |
| WO | 2016063263 A3 | 6/2016 |
| WO | 2016084088 A1 | 6/2016 |
| WO | 2016141108 A1 | 9/2016 |
| WO | 2016177682 A1 | 11/2016 |
| WO | 2016183532 A1 | 11/2016 |
| WO | 2016196361 A1 | 12/2016 |
| WO | 2016196605 A1 | 12/2016 |
| WO | 2016205276 A1 | 12/2016 |
| WO | 2017009399 A1 | 1/2017 |
| WO | 2017042347 A1 | 3/2017 |
| WO | 2017058751 A1 | 4/2017 |
| WO | 2017074566 A1 | 5/2017 |
| WO | 2017112620 A1 | 6/2017 |
| WO | 2017118598 A1 | 7/2017 |
| WO | 2017123418 A1 | 7/2017 |
| WO | 2017136795 A1 | 8/2017 |
| WO | 2017211753 A1 | 12/2017 |
| WO | 2018064165 A2 | 4/2018 |
| WO | 2018081502 A1 | 5/2018 |
| WO | 2018112194 A1 | 6/2018 |
| WO | 2018115519 A1 | 6/2018 |
| WO | 2018217351 A1 | 11/2018 |
| WO | 2018217981 A1 | 11/2018 |
| WO | 2018222969 A1 | 12/2018 |
| WO | 2018226853 A1 | 12/2018 |
| WO | 2019243307 A1 | 12/2019 |
| WO | 2020072248 A1 | 4/2020 |
| WO | 2020072250 A1 | 4/2020 |
| WO | 2020072253 A1 | 4/2020 |
| WO | 2020072254 A1 | 4/2020 |
| WO | 2020118435 A1 | 6/2020 |
| WO | 2020152369 A1 | 7/2020 |
| WO | 2021097118 A1 | 5/2021 |
| WO | 2022003209 A1 | 1/2022 |
| WO | 2022063986 A2 | 3/2022 |
| WO | 2022063986 A3 | 6/2022 |

OTHER PUBLICATIONS

Aklujkar, M. et al. (2010) "Interference With Histidyl-tRNA Synthetase By a CRISPR Spacer Sequence As a Factor In The Evolution Of Pelobacter Carbinolicus," BMC Evolutionary Biology 10:203, 15 pages.
Allonsius, C.N. et al. (2019). "The Microbiome of the Invertebrate Model Host Galleria mellonella is Dominated by Enterococcus," Animal Microbiome 1:7, 7 pages.
Almeida, A. et al. (Jan. 2021, e-pub. Jul. 20, 2020). "A Unified Catalog of 204,938 Reference Genomes from the Human Gut Microbilome," Nat. Biotechnol. 39(1):105-114, 25 pages.
American Lung Association (2019). "Preventing COPD," retrieved from https://www.lung.org/lung-health-and-diseases/lung-disease-lookup/copd/symptoms-causes-risk-factors/preventing-copd.html, last visited Aug. 5, 2019, 1 page.
Anatoliotaki, M. et al. (2004). "Bloodstream Infections in Patients with Solid Tumors: Associated Factors, Microbial Spectrum and Outcome," Infection 32(2):65-71.
Andrea, A. et al. (Mar. 19, 2019). "Methods and Challenges of Using the Greater Wax Moth (Galleria mellonella) as a Model Organism in Antimicrobial Compound Discovery," Microorganisms 7:85, 9 pages.
Ang, Y.L.E et al. (2015). "Best Practice In The Treatment Of Advanced Squamous Cell Lung Cancer," Ther. Adv. Respir. Dis. 9(5):224-235.
Anonymous (Apr. 2016). "Checkpoint Inhibition: A Promising Immunotherapeutic Approach for Colorectal Cancer," Oncology, 5(3):1-5, retrieved from http//www.personalizedmedonc.com/publications/prno/april-2016-vol-5-no-3/checkpoint-inhibition-a-prornising-irmunotherapeutic-approach-for-colorectal-cancer-2/, last visited Aug. 27, 2019, 5 pages.
Arnold, I.C. et al. (Apr. 8, 2015, e-pub. Mar. 4, 2015). "Helicobacter Hepaticus Infection In BALB/c Mice Abolishes Subunit-Vaccine-Induced Protection Against M. Tuberculosis," Vaccine 33(15):1808-1814.
Arslan, Z. et al. (May 7, 2013). "RcsB-BglJ-Mediated Activation of Cascade Operon Does Not Induce The Maturation of CRISPR RNAs in E. coli K12," RNA Biology 10(5):708-715.
Arumugam, M. et al. (May 12, 2011). "Enterotypes of the Human Gut Microbiome," Nature 473(7346): 174-180, 16 pages.
Bae, T. et al. (2006). "Prophages of Staphylococcus aureus Newman and Their Contribution to Virulence," Molecular Microbiology pp. 1-13.
Barrangou, R. et al. (Mar. 23, 2007). "CRISPR Provides Acquired Resistance Against Viruses in Prokaryotes," Science, 315:1709-1712.
Beisel, C.L. et al. (2014). "A CRISPR Design For Next-Generation Antimicrobials," Genome Biology 15:516, 4 pages.
Belizario, J.E. et al. (Oct. 6, 2015). "Human Microbiomes and Their Roles In Dysbiosis, Common Diseases, and Novel Therapeutic Approaches," Frontiers in Microbiology 6(1050):1-16.
Bellanger, X. et al. (Jul. 1, 2014, e-pub. Jan. 27, 2014). "Conjugative and Mobilizable Genomic Islands in Bacteria: Evolution and Diversity," FEMS Microbiology Reviews 38(20144):720-760.
Bikard, D. et al. (2013, e-pub. Jun. 12, 2013). "Programmable Repression and Activation Of Bacterial Gene Expression Using an Engineered CRISPR-Cas System," Nucleic Acids Research 41(15):7429-7437.

(56) References Cited

OTHER PUBLICATIONS

Bikard, D. et al. (2017, e-pub. Sep. 6, 2017). "Using CRISPR-Cas Systems as Antimicrobials," Current Opinion in Microbiology 37:155-160.
Bikard, D. et al. (Aug. 16, 2012). "CRISPR Interference Can Prevent Natural Transformation and Virulence Acquisition during In Vivo Bacterial Infection," Cell Host & Microbe 12(2):177-186.
Bikard, D. et al. (Nov. 2014, e-pub. May 1, 2015). "Development of Sequence-Specific Antimicrobials Based On Programmable CRISPR-Cas Nucleases," Nature Biotechnology 32(11):1146-1150, 16 pages.
Broaders, E. et al. (Jul./Aug. 2013). "Mobile Genetic Elements Of The Human Gastrointestinal Tract," Gut Microbes 4(4):271-280.
Brouns, S.J.J. et al. (Aug. 15, 2008). Supplemental Material for "Small CRISPR RNAs Guide Antiviral Defense in Prokaryotes," Science 321:960-964.
Brouns, S.J.J. et al. (Aug. 15, 2008). "Small CRISPR RNAs Guide Antiviral Defense in Prokaryotes," Science 321:960-964.
Bryksin, A. V. et al. (Oct. 8, 2010). "Rational Design Of a Plasmid Origin That Replicates Efficiently In Both Gram-Positive and Gram-Negative Bacteria," PloS One 5(10):e13244, 9 pages.
Bugrysheva, J.V. et al. (Jul. 2011, E-Pub. Apr. 29, 2011). "The Histone-Like Protein Hlp Is Essential For Growth Of *Streptococcus pyogenes*: Comparison Of Genetic Approaches To Study Essential Genes," Appl. Environ. Microbiol. 77(13):4422-4428.
Bullman, S. et al. (Nov. 23, 2017). "Analysis of Fusobacterium Persistence and Antibiotic Response In Colorectal Cancer," Science pp. 1443-1448,10 pages total.
Burns, M.B. et al. (2015). "Virulence Genes Are a Signature of the Microbiome in the Colorectal Tumor Microenvironment," Genome Medicine 7:55, 12 pages.
Cash, H.L. et al. (Aug. 25, 2006, e-pub. Jul. 28, 2009). "Symbiotic Bacteria Direct Expression of an Intestinal Bactericidal Lectin," Science 313(5790):1126-1130, 13 pages.
Catalao, M.J. et al. (Jul. 2013, e-pub. Nov. 8, 2012). "Diversity in Bacterial Lysis Systems: Bacteriophages Show the Way," FEMS Microbiology Reviews 37(4):554-571.
Chan, B.K. et al. (2013). "Phage Cocktails and the Future of Phage Therapy," Future Microbiol. 8(6):769-783.
Chan, C.T.Y. et al. (Dec. 2015). "'Deadman' and 'Passcode' Microbial Kill Switches For Bacterial Containment," Nat. Chem. Biol. 12(2):82-86, 19 pages.
Chasteen, L. et al. (2006, e-pub. Nov. 6, 2006). "Eliminating Helper Phage from Phage Display," Nucleic Acids Research 34(21):e145, 11 pages.
Cheadle, E.J. et al. (2012). "Chimeric Antigen Receptors For T-Cell Based Therapy," Methods Mol. Biol. 907:645-666, 36 pages.
Chen, Z. et al. (Aug. 7, 2020). "Akkermansia muciniphila Enhances the Antitumor Effect of Cisplatin in Lewis Lung Cancer Mice," Journal of Immunology Research 2020(2969287):1-13.
Citorik, R.J. et al. (Nov. 2014, e-pub Sep. 21, 2014). "Sequence-Specific Antimicrobials Using Efficiently Delivered RNA-Guided Nucleases," Nat. Biotechnol. 32(11):1141-1145, 18 pages.
Cobb, R.E. et al. (Dec. 2, 2015). "High-Efficiency Multiplex Genome Editing of *Streptomyces* Species Using an Engineered CRISPR/Cas System," ACS Synth. Biol. 4:723-728.
Cochrane, K. et al. (2016, e-pub. Nov. 3, 2015). "Complete Genome Sequences and Analysis Of The *Fusobacterium nucleatum* Subspecies Animalis 7-1 Bacteripophage Φfunu1 and Φfunu2," Anaerobe 38:125-129. Abstract Only.
Communication of Notice of Opposition, dated Aug. 24, 2022, for 16719873.8, 6 pages.
Cong, L. et al. (Feb. 15, 2013, e-pub. Oct. 11, 2013). "Multiplex Genome Engineering Using CRISPR/Cas Systems," Science 339(6121):819-823, 9 pages.
Consolidated List—16719873.8, (Sep. 14, 2022), 6 pages.
Consumer Updates (2019). "Combating Antibiotic Resistance," retrieved from https://www.fda.gov/ForConsumers/ConsumerUpdates/ucm092810.htm, last visited Jan. 28, 2019, 4 pages.
Coyne, M.J. et al. (2014). "Evidence of Extensive DNA Transfer between *Bacteroidales* Species Within The Human Gut," mBio 5(3):e01305-14, 12 pages.
Cronan, J.E. (Jan. 2013). "Improved Plasmid-Based System for Fully Regulated Off-To-On Gene Expression in *Escherichia coli*: Application to Production of Toxic Proteins," Plasmid 69(1):81-89, 17 pages.
CUI, L. et al. (2016, e-pub. Apr. 8, 2016). "Consequences of Cas9 Cleavage in the Chromosome of *Escherichia coli*," Nucleic Acids Research 44(9):4243-4251.
D10—Declaration of Gautam Dantas, (Feb. 3, 2021), 14 pages.
D11—Declaration of David Ousterout Jr, (Sep. 12, 2022), 18 pages.
D11—Declaration of Gautam Dantas, (Feb. 3, 2021), 14 pages.
D11—Declaration of Prof. Dr. Chase Beisel, (Sep. 13, 2022), 9 pages.
D11—Exhibit 14—Hausner, M. et al. (Aug. 1999). "High Rates of Conjugation in Bacterial Biofilms as Determined by Quantitative in Situ Analysis," Applied and Environmental Microbiology 65(8):3710-3713.
D11—Exhibit 15—Wang,P. et al. (2015). "Development of an Efficient Conjugation-Based Genetic Manipulation System for Pseudoalteromonas," Microbial Cell Factories 14:11, 12 pages.
D11—Exhibit 16—Model Calculation as to the Impact of Horizontal Gene Transfer on the Ratio of Targeted and Non-Targeted Species in a Mixed Population Like that of Example 8 of EP3291679B1, 2 pages. No Date.
D11—Exhibit 16—Fontaine, L. et al. (Dec. 2010). "Development of a Versatile Procedure Based on Natural Transformation for Marker-Free Targeted Genetic Modification in *Streptococcus thermophilus*," Applied and Environmental Microbiology 76(23):7870-7877.
D11—Exhibit 17—Kenzaka, T. et al. (May 2007). "High-Frequency Phage-Mediated Gene Transfer Among *Escherichia coli* Cells, Determined at the Single-Cell Level," Applied and Environmental Microbiology 73(10):3291-3299.
D11—Exhibit 19—Fineran,P.C. et al. (2009). "Transduction: Hose DNA Transfer by Bacteriophages," Genetics, Genomics, pp. 666-679, 14 pages.
D11—Exhibit 21—Mondhe, M. et al. (Feb. 18, 2014). "Species-Selective Killing of Bacteria by Antimicrobial Peptide-PNAs," PLoS One 9(2):e89082, 8 pages.
D11—Exhibit 3-Convoluted Submission for 16719873.8, (Feb. 8, 2021), 27 pages.
D11—Exhibit 7—Koonin, E.V. et al. (May 2013). "CRISPR-CAS: Evolution of an RNA-Based Adaptive Immunity System in Prokaryotes," RNA Biology 10(5):679-686.
D11—Exhibit 8—Hsu, P.D. et al. (Jun. 5, 2014). "Development and Application of CRISPR-Cas9 for Genome Engineering," Cell 157:1262-1278, 17 pages.
D11—Exhibit 9—Scheper, T. et al. (2013). Yellow Biotechnology I: Insect Biotechnologie in Drug Discovery and Preclinical Research, 27 pages.
D11a—Curriculum Vitae of Dr. Chase L. Beisel, 7 pages. No Date.
D12—Wikipedia, Methicillin-Resistant *Staphylococcus aureus*, (Mar. 9, 2022), 30 pages.
D13—Wikipedia, *Escherichia coli*, (Apr. 9, 2022), 19 pages.
D15—GB1508461.9, (Jun. 29, 2015), 107 pages.
D15—Makarova, K.S. et al. (Feb. 2020, e-pub. Mar. 9, 2022). "Evolutionary Classification of CRIPSR-Cas Systems: A Burst of Class 2 and Derived Variants," Nat. Rev. Microbiol. 18(2):67-83, 36 pages.
D16—GB1509366.9, (May 9, 2016), 114 pages.
D17—GB1510891.3, (Aug. 3, 2015), 147 pages.
D18—GB1518402.1, (Nov. 30, 2015), 200 pages.
D19—Belkaid, Y. et al. (Nov. 21, 2014). "Dialogue Between Skin Microbiota and Immunity," Science 346 (6212):954-959, 7 pages.
D20—Abe, Y. et al. (1993). "Furuncle-Like Lesion in Mouse Experimental Skin Infections with *Staphylococcus aureus*," The Journal of Dermatology 20:198-202.
D21—Naik, S. et al. (Jul. 26, 2012). "Compartmentalized Control of Skin Immunity by Resident Commensals," Scienceexpress, 6 pages.
D22—Declaration of Gautam Dantas, (Feb. 3, 2021), 14 pages.

(56) References Cited

OTHER PUBLICATIONS

D23—Gomaa, E.Z. (2020, e-pub. Nov. 2, 2020). "Human Gut Microbiota/Microbiome in Health and Diseases: A Review," Antonie van Leewenhoek, 22 pages.
D24—Sorek, R. et al. (Mar. 2008). "CRISPR—A Widespread System That Provides Acquired Resistance Against Phages in Bacteria and Archaea," Nature Reviews Microbiology 6:181-186.
D25—Burstein, D. et al. (Feb. 3, 2016). "Major Bacterial Lineages Are Essentially Devoid of CRISPR-Cas Viral Defence Systems," Nature Communications 7:10613, 8 pages.
D26—Reichel, M. et al. (Nov. 2009). "Alcohols for Skin Antisepsis at Clinically Relevant Skin Sites," Antimicrobial Agents and Chemotherapy 53(11):4778-4782.
D27—Zeeuwen, P.L.J.M. et al. (2012). "Microbiome Dynamics of Human Epidermis Following Skin Barrier Disruption," Genome Biology 13:R101, 18 pages.
D28—Letter of Patentee for 16719873.8, (Jul. 15, 2001), 2 pages.
D4—Declaration of Van Der Oost, (Sep. 14, 2022), 21 pages.
D4—WO-2015/070193-A1, (May 14, 2015), 44 pages.
D5—Abil, Z. et al. (2015, e-pub. Aug. 6, 2014). "Synthetic Biology for Therapeutic Applications," Molecular Pharmaceutics 12:322-331.
D5—Reproduction of Mouse Skin Surface Treatment as Described in Examples 6 & 8 of WO-2014/124226 Application, (Aug. 14, 2014), 2 pages.
D7—Letter of Patentee for 16719873.8, dated Feb. 8, 2021, 12 pages.
D8—Annex 1—Example 1—Specific CRISPR Killing in an in vivo Mouse Model of Gut Decolonization, 2 pages. No Date.
Daillere, R. et al. (Oct. 18, 2016). "Enterococcus hirae and Barnesiella intestinihominis Facilitate Cyclophosphamide-Induced Therapeutic Immunomodulatory Effects," Immunity 95:931-943.
Dantas, G. et al. (Oct. 2012, e-pub. Sep. 3, 2012). "Context Matters—The Complex Interplay Between Resitome Genotypes and Resistance Phenotypes," Curr. Opin. Microbiol 15(5):577-582.
Datsenko, K.A. et al. (Jul. 10, 2012). "Molecular Memory of Prior Infections Activates the CRISPR/Cas Adaptive Bacterial Immunity System," Nature Communication 3:945, 7 pages.
De Filippo, C. et al. (Aug. 33 2010). "Impact Of Diet In Shaping Gut Microbiota Revealed By a Comparative Study In Children From Europe and Rural Africa," Proc. Natl. Acad. Sci. USA 107(33):14691-14696, 6 pages.
De Paepe, M. et al. (Mar. 28, 2014). "Bacteriophages: An Underestimated Role In Human and Animal Health?" Frontiers in Cellular and Infection Microbiology 4(39):1-11.
Deeks, E.D. (2014, e-pub. Jul. 15, 2014). "Nivolumab: A Review Of Its Use In Patients With Malignant Melanoma," Drugs 74:1233-1239.
Deghorain, M. et al. (Nov. 23, 2012). "The Staphylococci Phages Family: An Overview," Viruses 4:3316-3335.
Del Castillo, M. et al. (Dec. 1, 2016). "The Spectrum of Serious Infections Among Patients Receiving Immune Checkpoint Blockade for the Treatment of Melanoma," Clin. Infect. Dis. 63:1490-1493.
Denham, J.D. et al. (2018). "Case Report: Treatment of Enteropathogenic Escherichia coli Diarrhea in Cancer Patients: A Series of Three Cases," Case Reports in Infectious Diseases Article ID 8438701:1-3.
Derosa, L. et al. (2018, e-pub. Mar. 30, 2018). "Negative Association Of Antibiotics On Clinical Activity Of Immune Checkpoint Inhibitors In Patients With Advanced Renal Cell and Non-Small-Cell Lung Cancer," Annals of Oncology. 2 pages.
Desbois, A.P. et al. (2012). "Chapter 2—Utility of Greater Wax Moth Larva (*Galleria mellonella*) for Evaluating the Toxicity and Efficacy of New Antimicrobial Agents," in Advances in Applied Microbiology vol. 78, 29 pages.
Dhar, A.D. (Jul. 20, 2018). "Overview Of Bacterial Skin Infections," Merck Manual retrieved from https://www.merckmanuals.com/home/skin-disorders/bacterial-skin-infections/overview-of-bacterial-skin-infections, last visited Jul. 20, 2018, 3 pages.
Dickson, R.P. et al. (Jan./Feb. 2017). "Bacterial Topography of the Healthy Human Lower Respiratory Tract," American Society for Microbiology 8(1):e02287-6, 12 pages.
Diez-Villasenor, C. et al. (May 2013). "CRISPR-Spacer Integration Reporter Plasmids Reveal Distinct Genuine Acquisition Specificities Among CROSPR-Cas 1-E Variants of *Escherichia coli*," RNA Biology 10(5):792-802.
Dillion, S.C. et al. (2010, e-pub. Apr. 29, 2010). "Genome-Wide Analysis of the H-NS and Sfh Regulatory Networks in *Salmonella typhimurium* Identifies a Plasmid-Encoded Transcription Silencing Mechanism," Molecular Microbiology 76(5):1250-1265.
Dorman, C.J. (2009). "Chapter 2 Nucleoid-Associated Proteins and Bacterial Physiology," Advances in Applied Microbiology 67:47-64.
Doyle, M. et al. (Jan. 12, 2007). "An H-NS-Like Stealth Protein Aids Horizontal DNA Transmission In Bacteria," Science 315: 251-252.
Dutilh, B.E. et al. (Jul. 24, 2014). "A Highly Abundant Bacteriophage Discovered In The Unknown Sequences Of Human Faecal Metagenomes," Nature Communications 5(4498):1-11.
Ebrahimizadeh, W. et al. (Mar. 18, 2014). "Bacteriophage Vehicles for Phage Display: Biology, Mechanism, and Application," Current Microbiology 69(2):109-120.
Edgar et al. (Dec. 2010). "The *Escherichia coli* CRISPR System Protects From λ Lysogenization, Lysogens, and Prophage Induction," Journal of Bacteriology 192(23):6291-6294, Supplemental Material, 2 pages.
Edgar, R. et al. (Dec. 2010). "The *Escherichia coli* CRISPR System Protects From λ Lysogenization, Lysogens, and Prophage Induction," Journal of Bacteriology 192(23):6291-6294.
Elias, S. et al. (Sep. 2012, e-pub. Feb. 2, 2012). "Multi-Species Biofilms: Living with Friendly Neighbors," FEMS Microbiol. Rev. 36(5):990-1004.
Elmore, J.R. et al. (May 2013, e-pub. Mar. 27, 2013). "Programmable Plasmid Interference by the CRISPR-Cas System in Thermococcus kodakarensis," RNA Biology 10(5):828-840.
EP Opposition Letter, dated Dec. 15, 2021, for 16719873.8, 8 pages.
EP Opposition Letter, dated Sep. 14, 2022, for 16719873.8, 54 pages.
EP Opposition Letter, dated Sep. 15, 2022, for 16719873.8, 56 pages.
EP Opposition Letter, dated Sep. 19, 2022, for 16719873.8, 1 page.
EP Opposition Letter, dated Sep. 23, 2022, for 16719873.8, 71 pages.
Esvelt, K.M. et al. (Nov. 2013). "Orthogonal Cas9 Proteins for RNA-Guided Gene Regulation and Editing," Nature Methods 10(11):1116-1123.
European Office Action, dated Jun. 29, 2021, for European Patent Application No. 16719873.8, 24 pages.
European Opposition, dated Jul. 5, 2023, for European Patent Application No. 3291679, 17 pages.
European Search Report, dated Oct. 4, 2021, for European Patent Application No. 21170379.8, 6 pages.
European Search Report, dated Oct. 8, 2021, for European Patent Application No. 21170380.6, 7 pages.
European Third Party Observation, dated Aug. 3, 2023, for European Patent Application No. 20720177.3, 35 pages.
Evans, D.R. et al. (Apr. 14, 2020). "Systematic Detection of Horizontal Gene Transfer Across Genera Among Multidrug-Resistant Bacteria in a Single Hospital," eLife 9:e53886, 20 pages.
Ex Parte Re-Exam Communication Transmittal Form, dated Jun. 30, 2021, for U.S. Appl. No. 90/014,705, for Reexamination U.S. Pat. No. 10,953,090, 26 pages.
Ex Parte Re-Exam, mailed Apr. 21, 2021, for U.S. Appl. No. 90/014,705, filed Mar. 26, 2021, for Reexamination U.S. Pat. No. 10,953,090, 15 pages.
Ex Parte Re-Exam, mailed Apr. 30, 2021, for U.S. Appl. No. 90/014,681, filed Feb. 16, 2021, for U.S. Pat. No. 10,920,222, 25 pages.
Ex Parte Re-Exam, mailed Dec. 10, 2018, for U.S. Appl. No. 90/014,184, filed Aug. 10, 2018, for U.S. Pat. No. 9,701,964 102 pages.

(56) References Cited

OTHER PUBLICATIONS

Ex Parte Re-Exam, mailed Dec. 16, 2021, for U.S. Appl. No. 90/014,877, filed Oct. 6, 2021, for U.S. Pat. No. 10,953,090, 12 pages.
Ex Parte Re-Exam, mailed Feb. 22, 2021, for U.S. Appl. No. 16/700,856, filed Dec. 2, 2019, for U.S. Pat. No. 10,920,222, 459 pages.
Ex Parte Re-Exam, mailed Mar. 23, 2021, for U.S. Appl. No. 16/453,604, filed Jun. 26, 2019, for U.S. Pat. No. 10,953,090, 235 pages.
Ex Parte Re-Exam, mailed Mar. 24, 2021, for U.S. Appl. No. 90/014,681, filed Mar. 24, 2021, for U.S. Pat. No. 10,920,222, 18 pages.
Ex Parte Re-Exam, mailed Nov. 15, 2021, for U.S. Appl. No. 90/014,877, 12 pages.
Ex Parte Re-Exam, mailed Sep. 27, 2021, for U.S. Appl. No. 90/014,705, filed Mar. 23, 2021, for U.S. Pat. No. 10,953,090, 16 pages.
Extended European Search Report, dated Jul. 27, 2020, for European Patent Application No. 20155001.9, 9 pages.
Extended European Search Report, dated Sep. 24, 2020, for European Patent Application No. 20154858.3, 12 pages.
Fact Sheet (Oct. 2010). "Antimicrobial Resistance," National Institutes of Health, pp. 1-2.
Federle, M.J. et al. (Nov. 2003). "Interspecies Communication in Bacteria," J. Clin. Invest. 112(9):1291-1299.
Fineran, P.C. et al. (2009). "Transduction: Host DNA Transfer by Bacteriophages," Genetics, Genomics pp. 666-679.
Fitzgerald, S. et al. (2020, e-pub. Sep. 7, 2020). "Redefining the H-NS Protein Family: A Diversity of Specialized Core and Accessory Forms Exhibit Hierarchical Transcriptional Network Integration," Nucl. Acids Res. 48(18):10184-10198.
Foca, A. et al. (2015, e-pub. Apr. 7, 2015). Gut Inflammation and Immunity: What Is The Role Of The Human Gut Virome? Mediators of Inflammation 2015(326032):1-7.
Fox, G.E. et al. (Jan. 1992). "How Close is Close: 16S rRNA Sequence Identity May Not Be Sufficient To Guarantee Species Identify," International Journal of Systematic Bacteriology 42(1):166-170.
Fujita, K. et al. (2017). "Emerging Concern Of Infectious Diseases In Lung Cancer Patients Receiving Immune Checkpoint Inhibitor Therapy," Eur. Resp. J. 50, OA1478. (Abstract Only), 4 pages.
Galperin, M.Y. (Dec. 2013). "Genome Diversity of Spore-Forming Firmicutes," Microbiology Spectrum 1(2): TBS-0015-2012, 27 pages.
Gao, R. et al. (Dec. 2015, e-pub. Sep. 11, 2015). "Genome-Wide RNA Sequencing Analysis of Quorum Sensing-Controlled Regulons in the Plant-Associated Burkholderia glumae PG1 Strain," Applied and Environmental Microbiology 81(23):7993-8007.
Garneau, J. E. et al. (Nov. 4, 2010). "The CRISPR/Cas Bacterial Immune System Cleaves Phage and Plasmid DNA," Nature 468(7320):67-71, 28 pages.
Garon, E.B. (Oct. 2015). "Current Perspectives In Immunotherapy For Non-Small Cell Lung Cancer," Seminars In Oncology 42(5 Supp. 2):S11-S18.
Garrett W.S. et al. (Oct. 5, 2007). "Communicable Ulcerative Colitis Induced By T-Bet Deficiency In The Innate Immune System," Cell 131(1):33-45, 23 pages.
Gauer, R.L. et al. (Jul. 1, 2013). "Early Recognition and Management of Sepsis in Adults: The First Six Hours," American Family Physician 88(1):44-53.
Gohil, N. et al. (Apr. 4, 2018). "Book Review: Quorum Sensing vs. Quorum Quenching: A Battle With No End in Sight," Frontiers in Cellular and Infection Microbiology 8(106):1-3.
Goldwater, P.N. et al. (2012). "Treatment Of Enterohemorrhagic *Escherichia coli* (EHEC) Infection and Hemolytic Uremic Syndrome (HUS)," BMC Medicine 10:12, 8 pages.
Golubovskaya, V. et al. (Mar. 15, 2016). "Different Subsets of T Cells, Memory, Effector Functions, and CAR-T Immunotherapy," Cancers 8(36), 12 pages.

Gomaa et al. (Jan. 28, 2014). "Programmable Removal Of Bacterial Strains By Use Of Genome-Targeting CRISPR-Cas Systems," mBio, 5(1):e000928-13, pp. 1-9.
Gomaa, A.A et al. (Jan./Feb. 2014). Supplemental Material to "Programmable Removal of Bacterial Strains by Use of Genome Targeting CRISPR-Cas Systems," American Society for Microbiology 5(1):1-9, 20 pages.
Gomaa, A.A.M. (2016). "Sequence Specific CRISPR-Based Antimicrobials From Treating Multidrug-Resistant Infections," Dissertation to the Graduate Faculty of North Carolina State University, 188 pages.
González Barrios, A.F. et al. (Jan. 2006). "Autoinducer 2 Controls Biofilm Formation in *Escherichia coli* Through a novel Motility Quorum-Sensing Regulator (MqsR, B3022)," J. Bacteriol 188(1):305-316.
Goodall, E.C.A. et al. (Feb. 20, 2018). "The Essential Genome of *Escherichia coli* K-12," Am. Society for Microbiology—mBio 9(1):e02096-17, 18 pages.
Gopalakrishnan, V. et al. (Jan. 5, 2018). "Gut Microbiome Modulates Response To Anti-PD-1 Immunotherapy In Melanoma Patients," Science 359:97-103, 20 pages.
Green, J. (Jul. 20, 2018). "Eight Common Oral Infections," Colgate retrieved from the Internet: <https://www.colgate.com/en-us/oral-health/conditions/mouth-sores-and-infections/eight-common-oral-infections-0615>, last visited Jul. 20, 2018, 4 pages.
Grice, E.A. et al. (2008). "A Diversity Profile of the Human Skin Microbiota," Genome Research 18:1043-1050.
Grøndahl, C. (Apr. 20, 2022). "SNIPR Biome Initiates First-In-Human Clinical Trial with SNIPR001," Snipr Biome ApS, 4 pages.
Gudbergsdottir, S. et al. (2011, e-pub. Nov. 18, 2010). "Dynamic Properties of The Sulfolobus CRISPR/Cas and CRISPR/Cmr Systems When Challenged With Vector-Borne Viral and Plasmid Genes and Protospacers," Molecular Microbiology 79(1):35-49.
Gudiol, C. et al. (2016). "Bloodstream Infections In Patients With Solid Tumors," Virulence 7(3):298-308.
Guedan, S. et al. (Aug. 14, 2014). "ICOS-Based Chimeric Antigen Receptors Program Bipolar TH17/TH1 Cells," Blood 124(7):1070-1080.
Guglielmi, G. (2020). "How Gut Bacteria Boost Cancer Immunotherapy," retrieved from the Internet https://microbiomepost.com/how--gut-bacteria-boost-cancer-immunotherapy/, last visited Jul. 25, 2021, 2 pages.
Gupta, R. et al. (2011). "P-27/HP Endolysin as Antibacterial Agent for Antibiotic Resistant *Staphylococcus aureus* of Human Infections," Curr. Microbiol. 63:39-45.
Ha, Y.E. et al. (2013). "Epidemiology and Clinical Outcomes Of Bloodstream Infections Caused By Extended-Spectrum β-Lactamase-Producing *Escherichia coli* In Patients With Cancer," Int. J. Antimicr. Agen. 42(5):403-409.
Hagen, S.J. (2015). "Chapter 1—Introduction The Physical Basis of Bacterial Quorum Communication," Biological and Medical Physics, Biomedical Engineering, 5 pages.
Hamanishi, J. et al. (2016, e-pub. Feb. 22, 2016). "PD-1/PD-L1 Blockade In Cancer Treatment: Perspectives and Issues," International Journal of Clinical Oncology 21:462-473.
Hargreaves, K.R. et al. (Aug. 26, 2014). "Abundant and Diverse Clustered Regularly Interspaced Short Palindromic Repeat Spacers in Clostridium difficile Strains and Prophages Target Multiple Phage Types within This Pathogen," mBio 5(5):e01045-13, 10 pages.
Harrington, L.E. (Nov. 2005, e-pub. Oct. 2, 2005). "Interleukin 17-producing CD4+ Effector T Cells Develop Via a Lineage Distinct From The T Helper Type 1 and 2 Lineages," Nat. Immunol. 6(11):1123-1132.
Hartland, E.L. et al. (Apr. 30, 2013). "Enteropathogenic and Enterohemorrhagic *E. coli*: Ecology, Pathogenesis, and Evolution," Frontiers in Cellular and Infection Microbiology 3(15):1-3.
Hatoum-Aslan, A. (Jun. 19, 2018). "Phage Genetic Engineering Using CRISPR-Cas Systems," Viruses 10:335, 11 pages.
Healthline (2019). "Cystic Fibrosis," retrieved from https://www.healthline.conn/health/cystic-fibrosis#prevention, last visited Aug. 5, 2019, 14 pages.

(56) References Cited

OTHER PUBLICATIONS

Hooper, L.V. et al. (Jun. 8, 2012). "Interactions Between The Microbiota and The Immune System," Science 336 (6086):1268-1273, 16 pages.
Horvath, P. et al. (2008, e-pub. Dec. 7, 2007). "Diversity, Activity, and Evolution Of CRISPR Loci In *Streptococcus thermophiles*," Journal of Bacteriology 190(4):1401-1412.
Hotta, K. et al. (2011, e-pub. Sep. 20, 2011). "Prognostic Significance of CD45RO+ Memory T Cells in Renal Cell Carcinoma," British Journal of Cancer 105:1191-1196.
Huddleston, J.R. (Jun. 20, 2014). "Horizontal Gene Transfer In The Human Gastrointestinal Tract: Potential Spread Of Antibiotic Resistance Genes," Infection and Drug Resistance 7:167-176.
Huo, Y. et al. (Sep. 2014). "Structures of CRISPR Cas3 Offer Mechanistic Insights Into Cascade-Activated DNA Unwinding and Degradations," Nat. Struct. Mol. Biol. 21(9):771-777, 21 pages.
Hurwitz, A.A. et al. (Aug. 1998). "CTLA-4 Blockade Synergizes With Tumor-Derived Granulocyte-Macrophage Colony-Stimulating Factor For Treatment Of An Experimental Mammary Carcinoma," Proc. Natl. Acad. Sci. USA 95:10067-10071.
Høyland-Kroghsbo, N.M. et al. (Feb. 19, 2013). "A Quorum-Sensing-Induced Bacteriophage Defense Mechanism," mBio 4(1):e00362-12, 8 pages.
International Search Report and The Written Opinion of the International Searching Authority for PCT/EP2018/066954, mailed Oct. 23, 2018, filed Jun. 25, 2018, 14 pages.
International Search Report and The Written Opinion of the International Searching Authority for PCT/EP2019/057453, mailed Aug. 16, 2019, filed Mar. 25, 2019, 21 pages.
International Search Report for PCT/EP2016/059803, mailed Jun. 30, 2016, filed May 3, 2016, 6 pages.
International Search Report for PCT/EP2018/082053, mailed Mar. 14, 2019, filed Nov. 21, 2018, 9 pages.
Invitation To Pay Additional Fees, mailed Feb. 4, 2022, for PCT Application No. PCT/EP2021/076360, filed Sep. 24, 2021, 13 pages.
Ivanov, I.I. et al. (May 2010). "Segmented Filamentous Bacteria Take The Stage," Mucosal Immunol. 3(3):209-212, 7 pages.
Jiang, W. et al. (Jan. 29, 2013). "RNA-Guided Editing of Bacterial Genomes Using CRISPR-Cas Systems," Nat. Biotechnology 31:233-241, 24 pages.
Jiang, W. et al. (Mar. 2013, e-pub. Sep. 1, 2013). "CRISPR-Assisted Editing Of Bacterial Genomes," Nat. Biotechnol. 31(3):233-239, 24 pages.
Jiang, W. et al. (Nov. 2013). "Demonstration Of CRISPR/Cas9/sgRNA-Mediated Targeted Gene Modification In *Arabidopsis*, Tobacco, Sorghum and Rice," Nucleic Acids Research 41(20):e188, 12 pages.
Jin, Y. et al. (2019, e-pub. Apr. 23, 2019). "The Diversity of Gut Microbiome is Associated With Favorable Responses to Anti-Programmed Death 1 Immunotherapy in Chinese Patients With NSCLC," Journal of Thoracic Oncology 14(8):1378-1389.
Jinek, M. et al. (Aug. 17, 2012). "A Programmable Dual-RNA-Guided DNA Endonuclease In Adaptive Bacterial Immunity," Science 337(6096):816-821.
Johnson, C. M. et al. (Nov. 23, 2015). "Integrative and Conjugative Elements (ICEs): What They Do and How They Work," Annual Review of Genetics 49(1):577-601, 33 pages.
Jones, R.B. et al. (2008). "Tim-3 Expression Defines A Novel Population Of Dysfunctional T Cells With Highly Elevated Frequencies In Progressive HIV-1 Infection," J. Exp. Med. 205(12):2763-2779.
Kaiser, J. (Nov. 2, 2017). "Your Gut Bacteria Could Determine How You Respond To Cutting-Edge Cancer Drugs," Science retrieved from Internet https://www.sciencemag.org/news/2017/11/your-gut-bacteria-could-dtermine- how-you-respond-cutting-edge-cancer-drugs, last visited Jul. 25, 2021, 4 pages.
Kalia, V.C. (2015). Quorum Sensing vs Quorum Quenching: A Battle with No End in Sight, Springer Publisher, 383 pages.
Karch, H. et al. (Jul. 1999). "Epidemiology and diagnosis of Shiga toxin-producing *Escherichia coli* infections," Diagnostic Microbiology and Infectious Disease 34(3):229-243.
Kaulich, M. et al. (2015, e-pub. Jan. 13, 2015). "Efficient CRISPR-rAAV Engineering of Endogenous Genes to Study Protein Function by Allele-Specific RNAi," Nucleic Acids Research 43(7):e45, 8 pages.
Keskin, H. et al. (Nov. 20, 2014). "Transcript-RNA-Templated DNA Recombination and Repair," Nature 515:436-439, 18 pages.
Khare, A. et al. (Dec. 8, 2015). "Multifactorial Competition and Resistance in a Two-Species Bacterial System," PLOS Genetics 11(12):e1005715, 21 pages.
Khoja, L. et al. (2015). "Pembrolizumab," Journal For ImmunoTherapy Of Cancer 3(36):1-13.
Kochenderfer, J.N. et al. (Sep. 2009). "Construction and Pre-clinical Evaluation Of An Anti-CD19 Chimeric Antigen Receptor," J. Immunother. 32(7):689-702, 26 pages.
Koonin, E.V. et al. (2017, e-pub. Jun. 9, 2017). "Diversity, Classification and Evolution of CRISPR-Cas Systems," Current Opinion in Microbiology 37:67-78.
Kosiewicz, M.M. et al. (2014, e-pub. Mar. 26, 2014). "Relationship Between Gut Microbiota and Development of T Cell Associated Disease," FEBS Lett. 588:4195-4206.
Kostic, A.D. et al. (Aug. 14, 2013). "Fusobacterium nucleatum Potentiates Intestinal Tumorigenesis and Modulates The Tumor-Immune Microenvironment," Cell Host Microbe. 14(2):207-215, 18 pages.
Krom, R.J. et al. (Jul. 5, 2015). "Engineered Phagemids for Nonlytic, Targeted Antibacterial Therapies," Nano Letters 15(7):4808-4813.
Kugelberg, E. et al. (Aug. 2005). "Establishment Of A Superficial Skin Infection Model In Mice By Using *Staphylococcus aureus* and *Streptococcus pyogenes*," Antimicrob Agents Chemother. 49(8):3435-3441.
Kutter, E. et al. (Jul. 21, 2018). "From Host To Phage Metabolism: Hot Tales of Phage T4's Takeover of *E. coli*," Viruses 10:387, 17 pages.
La Scola, B. et al. (Sep. 4, 2008). "The Virophage as a Unique Parasite of the Giant Mimivirus," Nature Letters 455:100-104.
Leshem, A. et al. (Sep. 29, 2020). "The Gut Microbiome and Individual-Specific Responses to Diet," mSystems 5(5):e00665-20, 12 pages.
Letter of Opposition, dated Aug. 18, 2022, 12 pages.
Letter of Patentee for 16719873.8, dated Apr. 10, 2018, 6 pages.
Letter of Patentee for 16719873.8, dated Apr. 27, 2021, 8 pages.
Letter of Patentee for 16719873.8, dated Apr. 30, 2021, 7 pages.
Letter of Patentee for 16719873.8, dated Aug. 9, 2019, 10 pages.
Letter of Patentee for 16719873.8, dated Feb. 18, 2020, 10 pages.
Letter of Patentee for 16719873.8, dated Feb. 8, 2021, 12 pages.
Letter of Patentee for 16719873.8, dated Feb. 8, 2021, 33 pages.
Letter of Patentee for 16719873.8, dated Oct. 23, 2019, 9 pages.
Lombardo, A. et al. (Nov. 2007, e-pub. Oct. 28, 2007). "Gene Editing in Human Steam Cells Using Zinc Finger Nucleases and Integrase-Defective Lentiviral Vector Delivery," Nature Biotechnology 25(11):1298-1306.
Lopez-Sanchez, M.-J. et al. (2012, e-pub. Jul. 27, 2012). "The Highly Dynamic CRISPR1 System Of *Streptococcus agalactiae* Controls The Diversity Of its Mobilome," Molecular Microbiology 85(6):1057-1071.
Lu, T.K. et al. (Jul. 3, 2007). "Dispersing Biofilms With Engineered Enzymatic Bacteriophage," PNAS 104 (27):11197-11202.
Lucchini, S. et al. (Aug. 18, 2006). "H-NS Mediates the Silencing of Laterally Acquire Genes in Bacteria," PLOS Pathogens 2(8):e81, 7 pages.
Ludwig, W.S. et al. (1985). "The Phylogenetic Position Of *Streptococcus* and Enterococcus," Journal of General Microbiology 131:543-551.
Luo, M.L. et al. (2015, e-pub. Oct. 17, 2014). "Repurposing Endogenous Type I CRISPR-Cas Systems For Programmable Gene Repression," Nucleic Acids Research 43(1):674-681.
Lutz, R. et al. (1997). "Independent and Tight Regulation of Transcriptional Units in *Escherichia coli* Via The LacR/O, The TetR/O and AraC/I1-I2 Regulatory Elements," Nucleic Acids Research 25(6):1203-1210.

(56) References Cited

OTHER PUBLICATIONS

López, P. et al. (Apr. 5, 2016). "Th17 Responses and Natural IgM Antibodies Are Related To Gut Microbiota Composition In Systemic Lupus Erythematosus Patients," Sci. Rep. 6:24072, 12 pages.

Macon, B.L. et al. (Jan. 2, 2018). "Acute Nephrities," retrieved from healthline, https://www.healthline.com/health/acute-nephritic-syndrome#types, last visited Jul. 20, 2018, 13 pages.

Magee, M.S. et al. (Nov. 2014). "Challenges To Chimeric Antigen Receptor (CAR)-T Cell Therapy For Cancer," Discov. Med. 18(100):265-271, 6 pages.

Mahoney, K.M. et al. (2015). "The Next Immune-Checkpoint Inhibitors: PD-1/PD-L1 Blockade In Melanoma," Clinical Therapeutics 37(4):764-782.

Makarova, K.S. et al. (Jun. 2011). "Evolution and Classification of the CRISPR-Cas Systems," Nat. Rev. Microbiol. 9(6):467-477, 23 pages.

Makarova, K.S. et al. (Nov. 2015, e-pub.May 11, 2017). "An Updated Evolutionary Classification of CRISPR-Cas Systems," Nature Rev. Microbiol. 13(11):722-736, 31 pages.

Mali, P. et al. (Oct. 2013, e-pub. Sep. 27, 2013). "Cas9 as a Versatile Tool for Engineering Biology," Nature Methods 10(10):957-963, 16 pages.

Mancha-Agresti, P. et al. (Mar. 2017). "A New Broad Range Plasmid for DNA Delivery in Eukaryotic Cells Using Lactic Acid Bacteria: In Vitro and In Vivo Assays," Molecular Therapy: Methods & Clinical Development 4:83-91.

Manica, A. et al. (2011, e-pub. Mar. 8, 2011). "In vivo Activity Of CRISPR-Mediated Virus Defence In a Hyperthermophilic Archaeon," Molecular Microbiology 80(2):481-491.

Manson, J.M. et al. (2008). "Chapter 2: The Commensal Microbiology of the Gastrointestinal Tract," in GL Microbiota and the Regulation of the Immune System, Advances in Experimental Medicine and Biology vol. 635, pp. 15-28.

Marin, M. et al. (May 2014). "Bloodstream Infections in Patients With Solid Tumors Epidemiology, Antibiotic Therapy, and Outcomes in 528 Episodes in a Single Cancer Center," Medicine 93:143-149.

Marraffini, L.A. et al. (Dec. 19, 2008, e-pub. Jun. 12, 2009). "CRISPR Interference Limits Horizontal Gene Transfer In *Staphylococci* By Targeting DNA," Science 322(5909):1843-1845, 7 pages.

Martel, B. et al. (2014, e-pub. Jul. 24, 2014). "CRISPR-Cas: An Efficient Tool For Genome Engineering of Virulent Bacteriophages," Nucleic Acids Research 42(14):9504-9513.

Martinez, R.M. et al. (Aug. 12, 2016). "Bloodstream Infections," Microbial Spectrum 4(4):DMIH2-0031-2016, 34 pages.

Matson, V. et al. (Jan. 5, 2018). "The Commensal Microbiome Is Associated With Anti-PD-1 Efficacy In Metastatic Melanoma Patients," Science 359(6371):104-108.

Matsushiro, A. et al. (Apr. 1999). "Induction Of Prophages Of Enterohemorrhagic *Escherichia coli* 0157:H7 with Norfloxacin," Journal Of Bacteriology 181(7):2257-2260.

Mayo Clinic (2019). "Pulmonary Embolism," retrieved from https://www.nnayoclinic.org/diseases-conditions/pulnnonary-ennbolisnn/synnptonns-causes/syc-20354647, last visited Aug. 5, 2019, 8 pages.

Mayo Clinic (2020). "Infectious Diseases," retrieved from https://www.nnayoclinic.org/diseases-conditions/infectious-diseases/diagnosis-treatnnent/drc-20351179, last visited Jan. 17, 2020, 5 pages.

Mayo Clinic (2020). "Malaria," retrieved from https://www.nnayoclinic.org/diseases-conditions/nnalaria/diagnosis-treatnnent/drc-20351190, last visited Jan. 17, 2020, 3 pages.

Mayo Clinic (2020). "Sexually Transmitted Diseases (STDs)," retrieved from https://www.nnayoclinic.org/diseases-conditions/sexually-transnnitted-diseases-stds/diagnosis-treatnnent/drc-20351246, last visited Jan. 17, 2020, 5 pages.

Mayo Clinic (Jul. 20, 2018). "Bacterial Vaginosis," retrieved from https://www.mayoclinic.org/diseases-conditions/bacterial-vaginosis/symptoms-causes/syc-20352279, last visited Jul. 20, 2018, 3 pages.

Mayo Clinic (Jul. 20, 2018). "Cystitis," retrieved from https://www.mayoclinic.org/diseases-conditions/cystitis/symptoms-causes/syc-20371306, last visited Jul. 20, 2018, 10 pages.

Mayo Clinic (Jul. 20, 2018). "Meningitis," retrieved from https://www.mayoclinic.org/diseases-conditions/meningitis/symptoms-causes/syc-20350508, last visited Jul. 20, 2018, 6 pages.

Mayo Clinic (Jul. 20, 2018). "Pneumonia," retrieved from https://www.mayoclinic.org/diseases-conditions/pneumonia/symptoms-causes/syc-20354204, last visited Jul. 20, 2018, 5 pages.

Mayo Clinic (Mar. 29, 2020). "Liver Disease," retrieved from https://www.mayoclinic.org/diseases-conditions/liver-problems/diagnosis-treatment/drc-20374507, last visited Mar. 29, 2020, 8 pages.

Medina-Aparicio, L. et al. (May 2011, e-pub. Mar. 11, 2011). "The CRI SPR/Cas Immune System Is an Operon Regulated by LeuO, H-NS, and Leucine-Responsive Regulatory Protein in *Salmonella enterica* Serovar Typhi," Journal of Bacteriology 193(10):2396-2407.

Mei, J.-M. et al. (1997). "Identification of *Staphylococcus aureus* Virulence Genes in a Murine Model of Bacteraemia Using Signature-Tagged Mutagenesis," Molecular Microbiology 26(2):399-407.

Mercenier, A. (1990). "Molecular Genetics Of *Streptococcus thermophiles*," FEMS Microbiology Letters 87(1-2):61-77.

Meredith, H.R. et al. (Mar. 2015, e-pub. Feb. 17, 2015). "Collective Antibiotic Tolerance: Mechanisms, Dynamics, and Intervention," Nat. Chem. Biol. 11(3):182-188, 20 pages.

Michelsen, C.F. et al. (Nov. 2014, e-pub. Sep. 2, 2014). "*Staphylococcus aureus* Alters Growth Activity, Autolysis, and Antibiotic Tolerance in a Human Host-Adapted Pseudomonas aeruginosa Lineage," Journal of Bacteriology 196(22):3903-3911.

Mick, E. et al. (May 2013). "Holding a Grudge: Persisting Anti-Phage CRISPR Immunity In Multiple Human Gut Microbiomes," RNA Biology 10(5):900-906.

Miller, E.S. et al. (Sep. 2003). "Complete Genome Sequence of the Broad-Host-Range Vibriophage KVP40: Comparative Genomics of a T4-Related Bacteriophage," Journal of Bacteriology 185(17):5220-5233.

Mills, S. et al. (Jan./Feb. 2013). "Movers and Shakers: Influence Of Bacteriophages In Shaping The Mammalian Gut Microbiota," Gut Microbes 4(1):4-16.

Mitri, S. et al. (2013, e-pub. Aug. 30, 2013). "The Genotypic View of Social Interactions in Microbial Communities," Annu. Rev. Genet. 47:247-273.

Mitsuhashi, K. et al. (Mar. 13, 2015). "Association of *Fusobacterium* Species in Pancreatic Cancer Tissues With Molecular Features and Prognosis," Oncotarget 6(9):7209-7220.

Moons, P. et al. (2009, e-pub. Mar. 20, 2009). "Bacterial Interactions in Biofilms," Crit. Rev. Microbiol. 35(3):157-168.

Nakamura, S. et al. (Nov. 2008). "Metagenomic Diagnosis Of Bacterial Infections," Emerging Infectious Diseases 14(11):1784-1786.

Nale, J.Y. et al. (2012). "Diverse Temperate Bacteriophage Carriage In Clostridium Difficile 027 Strains," PloS One 7(5):e37263, 9 pages.

Navarre, W.W. et al. (2007). "Silencing of Xenogeneic DNA by H-NS—Facilitation Of Lateral Gene Transfer In Bacteria By A Defense System That Recognizes Foreign DNA," Genes & Development 21:1456-1471.

Nelson, M.H. et al. (2015). "Harnessing The Microbiome To Enhance Cancer Immunotherapy," Journal of Immunology Research 2015:Article 368736, 12 pages.

News (May 22, 2018). "UK Government and Bill & Melinda Gates Foundation Join Carb-X Partnership in Fight Against Superbugs: Millions Earmarked to Boost Research Into New Life-Saving Products to Address the Global Rise of Drug-Resistant Bacteria," Combating Antibiotic Resistant Bacteria, 7 pages.

Norris, J.S. et al. (2000). "Prokaryotic Gene Therapy To Combat Multidrug Resistant Bacterial Infection," Gene Therapy 7:723-725.

Notice of Intent to Issue Ex Parte Reexamination Certificate, mailed Aug. 12, 2019, for U.S. Appl. No. 90/014,184, filed Aug. 10, 2018, 26 pages.

Nowak, P. et al. (Nov. 28, 2015). "Gut Microbiota Diversity Predicts Immune Status In HIV-1 Infection," AIDS 29(18):2409-2418.

(56) References Cited

OTHER PUBLICATIONS

Ochoa, S. et al. (2021). "Virulence Assessment of Enterohepatic *Helicobacter* Species Carried by Dogs Using the Wax Moth Larvae *Galleria mellonella* as Infection Model," *Helicobacter* 26:e12808, 8 pages.
Office Action, mailed Nov. 4, 2021 for U.S. Appl. No. 90/014,705, filed Mar. 23, 2021, 7 pages.
Okazaki, T. et al. (2007). "PD-1 and PD-1 Ligands: From Discovery To Clinical Application," Intern. Immun. 19(7):813-824.
Onozawa, M. et al. (May 27, 2014). "Repair of DNA Double-Strand Breaks by Templated Nucleotide Sequence Insertions Derived From Distant Regions of the Genome," PNAS 111(21):7729-7734.
O'Reilly, D. et al. (2019, e-pub. Dec. 4, 2018). "Extensive CRISPR RNA Modification Reveals Chemical Compatibility and Structure-Activity Relationships For Cas9 Biochemical Activity," Nucleic Acid Research 47(2):546-558.
P1-GB1507773.8, (Jun. 17, 2015), 75 pages.
P2-GB1507774.6, (Jun. 17, 2015), 71 pages.
P3-GB1507775.3, (Jun. 17, 2015), 70 pages.
P4-GB1507776.1, (Jun. 17, 2015), 77 pages.
Pardoll, D.M. (Apr. 2012, e-pub. Mar. 22, 2012). "The Blockade Of Immune Checkpoints In Cancer Immunotherapy," Nat. Rev. Cancer 12(4): 252-264.
Park, A. (Oct. 18, 2011). "A Surprising Link Between Bacteria and Colon Cancer," Cancer retrieved from http://healthlande.time.com/2011/10/18/a-surprising-link-between-bacteria-and-colon-cancer/, last visited Aug. 27, 2019, 3 pages.
Park, H. et al. (2005). "A Distinct Lineage Of CD4 T Cells Regulates Tissue Inflammation By Producing Interleukin 17," Nat. Immunol. 6(11):1133-1141, 24 pages.
Pastagia, N. et al. (Feb. 2011). "A Novel Chimeric Lysin Shows Superiority to Mupirocin for Skin Decolonization of Methicillin-Resistant and -Sensitive *Staphylococcus aureus* Strains," Antimicrobial Agents and Chemotherapy 55(2):738-744.
Patterson, A.G. et al. (2017, e-pub. Mar. 27, 2017). "Regulation of CRISPR-Cas Adaptive Immune Systems," Current Opinion in Microbiology 37:1-7.
Pawluk, A. et al. (Apr. 15, 2014). "A New Group Of Phage Anti-CRISPR Genes Inhibits The Type I-E CRISPR-Cas System Of Pseudomonas aeruginosa," mBio. 5(2):e00896.
Perez-Chanona, E. et al. (2016, e-pub. Jan. 26, 2016). "The Role of Microbiota in Cancer Therapy," Current Opinion in Immunology 39:75-81.
Pires, D.P. et al. (Sep. 2016, e-pub. Jun. 1, 2016). "Genetically Engineered Phages: A Review of Advances Over the Last Decade," Microbiology and Molecular Biology Reviews 80(3):523-543.
Pul, Ü. et al. (2010, e-pub. Feb. 17, 2010). "Identification and Characterization of *E. coli* CRISPR-cas Promoters and Their Silencing by H-NS," Molecular Microbiology 75(6):1495-1512.
Purdy, D. et al. (2002). "Conjugative Transfer Of Clostridial Shuttle Vectors From *Escherichia coli* To Clostridium difficile Through Circumvention Of The Restriction Barrier," Molec. Microbiology 46(2):439-452.
Ramalingam, S.S. et al. (2014). "LB2-Metastatic Non-Small Cell Lung Cancer: Phase II Study Of Nivolumab (Anti-PD-1, BMS-936558, ONO-4538) In Patients With Advanced, Refractory Squamous Non-Small Cell Lung Cancer," International Journal Of Radiation Oncology Biology Physics Late Breaking Abstract (LB2), 90(5):1266-1267.
Ran, F.A. et al. (Apr. 9, 2015). "In Vivo Genome Editing Using *Staphylococcus aureus* Cas9," Nature 570(7546):186-191, 28 pages.
Rashid, T. et al. (2013). "The Role of Klebsiella in Crohn's Disease With a Potential for the Use of Antimicrobial Measures," International Journal of Rheumatology 2013(Article ID 610393):1-9.
Ray, K. (Jan. 2020). "Manipulating the Gut Microbiota to Combat Alcoholic Hepatitis," Nature Reviews Gastroenterology & Hepatology 17:3, 1 page.
Rea, K. et al. (2020, e-pub. Nov. 14, 2019). "Gut Microbiota: A Perspective for Psychiatrists," Neuropsychobiology 79:50-62.
Regulating with RNA in Bacteria and Archaea Conference (Dec. 5-8, 2015), 185 pages.
Request for Ex Parte Reexamination mailed Aug. 10, 2018, for U.S. Appl. No. 15/160,405, now U.S. Pat. No. 9,701,964, 42 pages.
Request for Ex Parte Reexamination mailed Nov. 1, 2018, for U.S. Appl. No. 15/160,405, now U.S. Pat. No. 9,701,964, 35 pages.
Request for Ex Parte Reexamination under 35 U.S. C. § 302 and 37 C.F.R. § 1.510, dated Feb. 16, 2021, 72 pages.
Richter, C. et al. (2012, e-pub. Oct. 19, 2012). "Function and Regulation of Clustered Regularly Interspaced Short Palindromic Repeats (CRISPR) / CRISPR Associated (Cas) Systems," Viruses 4(12):2291-2311.
Ridaura, V.K. et al. (Sep. 6, 2013). "Cultured Gut Microbiota From Twins Discordant For Obesity Modulate Adiposity and Metabolic Phenotypes In Mice," Science 341(6150):1241214, 22 pages.
Rinninella, E. et al. (Jan. 10, 2019). "What is the Healty Gut Microbiota Composition? A Changing Ecosystem Across Age, Environment, Diet, and Diseases," Microorganisms 7(1):14, 22 pages.
Roberts, A.P. et al. (Dec. 1, 2003). "Development of An Integrative Vector For the Expression of Antisense RNA in Clostridium difficile," Journal of Microbiological Methods 55(3):617-624.
Roberts, A.P. et al. (Jun. 2009, e-pub. May 20, 2009). "A Modular Master On The Move: The Tn916 Family Of Mobile Genetic Elements," Trends Microbiol. 17(6):251-258. Abstract Only.
Rogers, L. et al. (2016). "*Escherichia coli* and Other Enterobacteriaceae: Occurrence and Detection," Encyclopedia of Food and Health pp. 545-551.
Rong, Z. et al. (Mar. 14, 2014). "Homologous Recombination in Human Embryonic Stem Cells Using CRISPR/Cas9 Nickase and a Long DNA Donor Template," Protein & Cell 5(4):258-260.
Rosselló-Mora, R. et al. (Jan. 2001). "The Species Concept for Prokaryotes," FEMS Microbiol. Rev. 25(1):39-67.
Roy, S. et al. (May 2017, e-pub. Mar. 17, 2017). "Microbiota: A Key Orchestrator Of Cancer Therapy," Nat. Rev. Cancer 17(5):271-285.
Rutherford, S.T. et al. (Nov. 1, 2012). "Bacterial Quorum Sensing: Its Role in Virulence and Possibilities for its Control," Cold Spring Harb. Perspect Med. 2(11):a012427, 25 pages.
Ryan, R.P. et al. (2008). "Diffusible Signals and Interspecies Communication in Bacteria," Microbiology 154:1845-1858.
Safdar, N. et al. (Jun. 4, 2002). "The Commonality Of Risk Factors For Nosocomial Colonization and infection With Antimicrobial-Resistant *Staphylococcus aureus*, Enterococcus, Gram-Negative Bacilli, Clostridium difficile, and Candida," Ann. Intern. Med. 136(11):834-844.
Saito, H. et al. (Jun. 15, 2016, e-pub. Apr. 12, 2016). "Adoptive Transfer of CD8+ T Cells Generated From Inducted Pluripotent Stem Cells Triggers Regressions of Large Tumors Along With Immunological Memory," Cancer Research 76(12):3473-3483.
Samaržija, D. et al. (2001). "Taxonomy, Physiology and Growth Of Lactococcus Lactis: A Review," Mljekarstvo 51(1):35-48.
Samonis, G. et al. (Sep. 2013, e-pub. Apr. 27, 2013). "A Prospective Study Of Characteristics And Outcomes Of Bacteremia In Patients With Solid Organ Or Hematologic Malignancies," Support Care Cancer 21(9):2521-2526.
Sapranauskas, R. et al. (Nov. 1, 2011, e-pub. Aug. 3, 2011). "The *Streptococcus thermophilus* CRISPR/ Cas System Provides Immunity In *Escherichia coli*," Nucleic Acids Research 39(21):9275-9282.
Schnabi, B.G. (2020), "The Role of Enterococcus Faecalis in Alcoholic Liver Disease," retrieved from https://grantome.com/grant/NIH/O01-BX004594-01A2, last visited Oct. 20, 2020, 2 pages.
Seed, K.D. et al. (Feb. 28, 2013). "A Bacteriophage Encodes Its Own CRISPR/Cas Adaptive Response To Evade Host Innate Immunity," Nature 494(7438):489-491, 9 pages.
Selle, K. et al. (Apr. 1, 2015). "Harnessing CRISPR-Cas Systems For Bacterial Genome Editing," Trends in Microbiology 23(4):225-232.
Sepsis Alliance. (Dec. 14, 2017). "What Are Vaccines," Retrieved from https://www.sepsis.org/sepsisand/prevention-vaccinations/; last visited Jul. 8, 2019, 3 pages.

(56) References Cited

OTHER PUBLICATIONS

Sepsis Alliance. (Jul. 8, 2019). "Prevention," Retrieved from https://www.sepsis.org/sepsisand/prevention/; accessed last visited Jul. 8, 2019, 5 pages.
Shalem, O. et al. (May 2015, e-pub. Apr. 9, 2015). "High-Throughput Functional Genomics Using CRISPR-Cas9," Nature Reviews Genetics 16:299-311.
Shank, E.A. et al. (Apr. 2009. e-pub. Apr. 1, 2010). "New Developments in Microbial Interspecies Signaling," Curr. Opin. Microbiol. 12(2):205-214, 15 pages.
Sharan, S.K. et al. (2009). "Recombineering: A Homologous Recombination-Based Method of Genetic Engineering," Nat. Protoc. 4(2):206-223, 37 pages.
Shoemaker, N.B. et al. (Feb. 2001). "Evidence For Extensive Resistance Gene Transfer Among *Bacteroides* spp. And Among *Bacteroides* and Other Genera In The Human Colon," Appl. Environ. Microbiol. 67(2):561-68.
Sivan, A. et al. (Nov. 27, 2015, e-pub Nov. 5, 2015). "Commensal Bifidobacterium Promotes Antitumor Immunity and Facilitates Anti-PD-L1 Efficacy," Science 350(6264):1084-1089, 13 pages.
Sivan, A. et al. (Nov. 6, 2014). "Evidence Implicating the Commensal Microbiota in Shaping Anti-Tumor Immunity in Melanoma," Journal for Immuno Therapy of Cancer 2(Suppl. 3):O11, 1 page.
Skennerton, C.T. et al. (May 2011). "Phage Encoded H-NS: A Potential Achilles Heel in the Bacterial Defence System," PLoS One 6(5):e20095, 7 pages.
Slutsker, L. et al. (Apr. 1998). "A Nationwide Case-Control Study Of *Escherichia coli* O157:H7 Infection In The United States," J. Infect. Dis. 177(4):962-966.
Somkuti, G. A. et al. (Apr. 1988). "Genetic Transformation Of *Streptococcus thermophilus* By Electroporation," Biochimie 70(4):579-585. Abstract Only.
Sorek, R. et al. (2013, e-pub. Mar. 11, 2013). "CRISPR-Mediated Adaptive Immune Systems in Bacteria and Archaea," Annual Review of Biochemistry 82:237-266.
Sorg, R. A. et al. (2014). "Gene Expression Platform For Synthetic Biology In The Human Pathogen *Streptococcus pneumoniae*," ACS Synthetic Biology 4(3):228-239. Abstract Only, 2 pages.
Soucy, S.M. et al. (Aug. 2015). "Horizontal Gene Transfer: Building the Web of Life," Nature Reviews Genetics 16:472-482.
Soutourina, O.A. et al. (May 9, 2013). "Genome-Wide Identification of Regulatory RNAs in the Human Pathogen Clostridium difficile," PLos Genet. 9(5):e1003493, 20 pages.
Srivastava, S. (2013). "Genetics of Bacteria," Springer, India, 207 pages.
Stanford, E.H. & S. (2022). "Decontamination," Retrieved from the Internet; https://ehs.stanford.edu/manual/biosafety-manual/decontamination, last visited Nov. 29, 2022, 2 pages.
Stecher, B. et al. (2011). "Gut Inflammation Can Boost Horizontal Gene Transfer Between Pathogenic and Commensal Enterobacteriaceae," PNAS pp. 1-6, 17 pages.
Stern, A. et al. (2012). "CRISPR Targeting Reveals a Reservoir Of Common Phages Associated With The Human Gut Microbiome," Genome Research 22(10):1985-1994.
Stern, A. et al. (Aug. 2010), Self-Targeting By CRISPR: Gene Regulation Or Autoimmunity? Trends Genet. 26(8):335-340, 10 pages.
Stiefel, U. et al. (Aug. 2014, e-pub. May 27, 2014). "Gastrointestinal Colonization With a Cephalosporinase- Producing *Bacteroides* Species Preserves Colonization Resistance Against Vancomycin-Resistant Enterococcus and Clostridium Difficile In Cephalosporin-Treated Mice," Antimicrob. Agents Chemother. 58(8):4535-4542.
Stoebel, D.M. et al. (2008). "Anti-Silencing: Overcoming H-NS-Mediated Repression Of Transcription In Gramnegative Enteric Bacteria," Microbiology 154:2533-2545.
Suvorov, A. (1988). "Transformation Of Group A Streptococci By Electroporation," FEMS Microbiology Letters 56(1):95-100.
Svenningsen, S.L. et al. (Mar. 22, 2005). "On the Role of Cro in λ Prophage Induction," PNAS 102(12):4465-4469.
Takaishi, H. et al. (2008). "Imbalance In Intestinal Microflora Constitution Could Be Involved In The Pathogenesis of Inflammatory Bowel Disease," Int. J. Med. Microbiol.298:463-472.
Takeda, T. et al. (2011). "Distribution of Genes Encoding Nucleoid-Associated Protein Homologs in Plasmids," International Journal of Evolutionary Biology 2001:685015, 31 pages.
Tan, J. (Dec. 17, 2015). "Immunotherapy Meets Microbiota," Cell 163:1561.
Tao, P. et al. (2019, e-pub. Jul. 6, 2018). "Bacteriophage T4 Nanoparticles For Vaccine Delivery Against Infectious Diseases," Advance Drug Delivery Reviews 145:57-72.
Tarr, P.I. et al. (Mar. 19-25, 2005). "Shiga-Toxin-Producing *Escherichia coli* and Haemolytic Uraemic Syndrome," Lancet 365(9464):1073-1086.
Tiscornia, G. et al. (2006, e-pub. Jun. 27, 2006). "Production and Purification of Lentiviral Vectors," Nature Protocols 1(1):241-245.
Tlaskalová-Hogenová, H. et al. (2011, e-pub. Jan. 31, 2011). "The Role of Gut Microbiota (Commensal Bacteria) and the Mucosal Barrier in the Pathogenesis of Inflammatory and Autoimmune Diseases and Cancer: Contribution of Germ-Free and Gnotobiotic Animal Models of Human Diseases," Cellular & Molecular Immunology 8:110-120.
Todar, K. (2012). "The Normal Bacterial Flora of Humans," Todar's Online Textbook of Bacteriology, 8 pages.
Topalian, S.L. et al. (Jun. 28, 2012). "Safety, Activity, and Immune Correlates Of Anti-PD-1 Antibody In Cancer," N. Engl. J. Med. 366(26):2443-2454, 19 pages.
Turnbaugh, P.J. et al. (Dec. 2006). "An Obesity-Associated Gut Microbiome With Increased Capacity For Energy Harvest," Nature 444:1027-1131.
U.S. Appl. No. 62/168,355, filed May 29, 2015, Barrangou, R. et al.(Copy not submitted herewith pursuant to the waiver of 37 C.F.R. 1.98(a)(2)(iii) issued by the Office on Sep. 21, 2004).
U.S. Appl. No. 62/296,853, filed Feb. 18, 2016, Barrangou, R. et al. (Copy not submitted herewith pursuant to the waiver of 37 C.F.R. 1.98(a)(2)(iii) issued by the Office on Sep. 21, 2004).
Uchiyama, J. et al. (2013, e-pub. Mar. 8, 2013). "Characterization of Helicobacter pylori Bacteriophage KHP30," Applied and Environmental Microbiology 79(10):3176-3184.
USPTO (2021). Engineered Phagmids, U.S. Appl. No. 15/780,668, 1 page.
USPTO Interference 106,123—Declaration to Declare Interference Jun. 11, 2020, 11 pages.
USPTO Interference 106,123—Junior Party Annotated Copy of Claims Jul. 9, 2020, 31 pages.
USPTO Interference 106,123—Junior Party List of Motions Jul. 16, 2020, 6 pages.
USPTO Interference 106,123—Redeclaration Jul. 21, 2020, 6 pages.
USPTO Interference 106,123—Rockefeller Clean Copy of Claims Jun. 25, 2020, 7 pages.
USPTO Interference 106,123—Rockefeller Motion 2 (Indefiniteness), Oct. 16, 2020, 24 pages.
USPTO Interference 106,123—Rockefeller Notice of Lead and Backup Counsel Jun. 25, 2020, 3 pages.
USPTO Interference 106,123—Rockefeller Notice of Real Party in Interest Jun. 25, 2020, 3 pages.
USPTO Interference 106,123—Rockefeller Notice of Related Proceedings Jun. 25, 2020, 3 pages.
USPTO Interference 106,123—Rockefeller Power of Attorney Jun. 25, 2020, 3 pages.
USPTO Interference 106,123—Rockefeller Request for File Copies Jun. 25, 2020, 10 pages.
USPTO Interference 106,123—Rockefeller Revised List of Proposed Motions Aug. 13, 2020, 4 pages.
USPTO Interference 106,123—Senior Party List of Proposed Motions Jul. 16, 2020, 5 pages.
USPTO Interference 106,123—SNIPR Clean Copy of Claims Jun. 25, 2020, 27 pages.
USPTO Interference 106,123—SNIPR Motion 2 (Lack of Enablement and Written Description), Oct. 16, 2020, 32 pages.
USPTO Interference 106,123—SNIPR Motion 4 (Deny Benefit to Count 1), Oct. 16, 2020, 16 pages.

(56) References Cited

OTHER PUBLICATIONS

USPTO Interference 106,123—SNIPR Motion 5 (Substitute Count), Oct. 16, 2020, 41 pages.
USPTO Interference 106,123—SNIPR Motion 6 (Motion to Designate Claims as Not Corresponding to Count 1 or Proposed Count 2), Oct. 16, 2020, 24 pages.
USPTO Interference 106,123—SNIPR Notice of Lead and Backup Counsel Jun. 25, 2020, 4 pages.
USPTO Interference 106,123—SNIPR Notice of Related Proceedings Jun. 25, 2020, 4 pages.
USPTO Interference 106,123—SNIPR Real Party in Interest Jun. 25, 2020, 3 pages.
USPTO Interference 106,123—SNIPR Request for File Copies Jun. 25, 2020, 10 pages.
USPTO Interference 106,123—Standing Order Jun. 11, 2020, 81 pages.
USPTO Interference 106,123—Decision on Motions, Sep. 7, 2021, 18 pages.
USPTO Interference 106,123—Joint Stipulated Extension of Time, Sep. 4, 2020, 4 pages.
USPTO Interference 106,123—Judgement, Nov. 19, 2021, 3 pages.
USPTO Interference 106,123—Junior Party Revised List of Motions Aug. 13, 2020, 6 pages.
USPTO Interference 106,123—Memorandum, Jan. 19, 2021, 6 pages.
USPTO Interference 106,123—Notice of Cross Examination—van der Oost, Dec. 1, 2020, 3 pages.
USPTO Interference 106,123—Order Additional Applications 37 C.F.R. § 41.104(a), Sep. 3, 2020, 6 pages.
USPTO Interference 106,123—Order Authorizing Motions and Setting Times 37 C.F.R. 11.104(c) and 121 Aug. 24, 2020, 10 pages.
USPTO Interference 106,123—Order—Additional Applications, Jan. 13, 2021, 6 pages.
USPTO Interference 106,123—Order—Bd.R. 109(b)—Authorizing Copies of Office Records Jul. 21, 2020, 3 pages.
USPTO Interference 106,123—Order—Video Dispositions 37 C.F.R. § 41.104(a), Sep. 25, 2020, 3 pages.
USPTO Interference 106,123—Rockefeller List of Exhibits, Oct. 16, 2020, 4 pages.
USPTO Interference 106,123—Rockefeller List Of Exhibits, Nov. 13, 2020, 4 pages.
USPTO Interference 106,123—Rockefeller List Of Exhibits, Feb. 19, 2021, 5 pages.
USPTO Interference 106,123—Rockefeller Motion 1 (Lack of Written Description), Oct. 16, 2020, 30 pages.
USPTO Interference 106,123—Rockefeller Motion 3 (To Add A Claim), Nov. 13, 2020, 36 pages.
USPTO Interference 106,123—Rockefeller Notice of Settlement Discussions, Oct. 21, 2020, 3 pages.
USPTO Interference 106,123—Rockefeller Order—Responsive Motion 37 C.F.R. § 41.121(a)(2), Nov. 2, 2020, 2 pages.
USPTO Interference 106,123—Rockefeller Reply 1, Feb. 19, 2021, 51 pages.
USPTO Interference 106,123—Rockefeller Reply 2, Feb. 2, 2021, 37 pages.
USPTO Interference 106,123—Rockefeller Reply 3, Feb. 19, 2021, 48 pages.
USPTO Interference 106,123—Rockefeller Updated Notice Of Related Proceedings, Nov. 13, 2020, 3 pages.
USPTO Interference 106,123—SNIPR Exhibit List, Oct. 16, 2020, 7 pages.
USPTO Interference 106,123—SNIPR Exhibit List, Feb. 2, 2021, 8 pages.
USPTO Interference 106,123—SNIPR Motion 1 (Terminate Interference As Contrary to AIA), Oct. 16, 2020, 20 pages.
USPTO Interference 106,123—SNIPR Notice of Appeal, Dec. 14, 2021, 28 pages.
USPTO Interference 106,123—SNIPR Request for Oral Argument, Mar. 12, 2021, 4 pages.
USPTO Interference 106,123—Order—Show Cause, Aug. 19, 2021, 4 pages.
USPTO Interference 106,123—Rockefeller Notice, Aug. 13, 2021, 3 pages.
USPTO Interference 106,123—Rockefeller Request for Oral Argument, Mar. 12, 2021, 3 pages.
USPTO Interference 106,123—Rockefeller Response To Show Cause, Sep. 7, 2021, 7 pages.
USPTO Interference 106,123—Rockefeller Updated Notice of Related Proceedings, Jul. 15, 2021, 3 pages.
USPTO Interference 106,123—SNIPR Reply 1, Feb. 19, 2021, 19 pages.
USPTO Interference 106,123—SNIPR Reply 2, Feb. 19, 2021, 42 pages.
USPTO Interference 106,123—SNIPR Reply 4, Feb. 19, 2021, 28 pages.
USPTO Interference 106,123—SNIPR Reply 5, Feb. 19, 2021, 44 pages.
USPTO Interference 106,123—SNIPR Reply 6, Feb. 19, 2021, 27 pages.
Vaisman, A. et al. (2013). "Prevalence and Incidence of Antimicrobial-Resistant Organisms Among Hospitalized Inflammatory Bowel Disease Patients," Can. J. Infect. Dis. Med. Microbiol. 24(4):e117-e121.
Veeranagouda, Y. et al. (Jun. 4, 2014). "Identification Of Genes Required For The Survival Of B. fragilis Using Massive Parallel Sequencing Of a Saturated Transposon Mutant Library," BMC Genomics 15:429, 11 pages.
Vega, N.M. et al. (Oct. 2014). "Collective Antibiotic Resistence: Mechanisms and Implications," Curr. Opin. Microbiol. 21:28-34, 14 pages.
Velasco, E. et al. (2006). "Comparative Study Of Clinical Characteristics Of Neutropenic and Non-Neutropenic Adult Cancer Patients With Bloodstream Infections," Eur. J. Clin. Microbiol. Infect. Dis. 25:1-7.
Vercoe, R.B. et al. (Apr. 18, 2013). "Cytotoxic Chromosomal Targeting by CRISPR/Cas Systems Can Reshape Bacterial Genomes and Expel Or Remodel Pathogenicity Islands," PLOS Genetics 9(4):e1003454, 13 pages.
Villarino, N.F. et al. (Feb. 23, 2016, e-pub. Feb. 8, 2016). "Composition Of The Gut Microbiota Modulates The Severity Of Malaria," Proc. Natl. Acad. Sci. USA 113(8):2235-2240.
Vétizou, M. et al. (Nov. 27, 2015, e-pub Nov. 5, 2015). "Anticancer Immunotherapy By CTLA-4 Blockade Relies On The Gut Microbiota," Science 350(6264):1079-1084, 13 pages.
Waegeman, H. et al. (2011, e-pub. Sep. 8, 2011). "Increasing Recombinant Protein Production in *Escherichia coli* Through Metabolic and Genetic Engineering," J. Ind. Microbiol. Biotechnol. 38:1891-1910.
Wagner, P.L. (2002). "Bacteriophage Control Of Shiga Toxin 1 Production and Release By *Escherichia coli*," Molecular Microbiology 44(4):957-970.
Walters, W.A. et al. (Nov. 17, 2014). "Meta-Analyses Of Human Gut Microbes Associated With Obesity and IBD," FEBS Letters 588(22):4223-4233, 34 pages.
Wang, I.-N. et al. (2000). "HOLINS: The Protein Clocks of Bacteriophage Infections," Annu. Rev. Microbiol. 54:799-825, 33 pages.
Wang, J. et al. (2019). "Core Gut Microbiota Analysis of Feces in Healthy Mouse Model," Supplementary Information, 12 pages.
Wang, J. et al. (Apr. 24, 2019). "Core Gut Bacteria Analysis of Healthy Mice," Frontiers in Microbiology 10(887):1-14.
Waters, J. L. et al. (Nov./Dec. 2013). "Regulation of CTnDOT Conjugative Transfer is a Complex and Highly Coordinated Series of Events," MBIO 4(6):e00569-13, 8 pages.
Wegmann, U. et al. (Apr. 2007). "Complete Genome Sequence Of The Prototype Lactic Acid Bacterium *Lactococcus lactis* Subsp. Cremoris MG1363," Journal Of Bacteriology, 189(8):3256-3270.
Wei, Y. et al. (2015, e-pub. Jan. 14, 2015). "Sequences Spanning The Leader-Repeat Junction Mediate CRISPR Adaptation To Phage In *Streptococcus thermophiles*," Nucleic Acids Research 43(3):1749-1758.

(56) References Cited

OTHER PUBLICATIONS

Weir, T.L. et al. (Aug. 6, 2013). "Stool Microbiome and Metabolome Differences Between Colorectal Cancer Patients and Healthy Adults," PLOS One 8(8):e70803, 10 pages.

Westra, E.R. et al. (Jun. 8, 2012). "CRISPR Immunity Relies on the Consecutive Binding and Degradation of Negatively Supercoiled Invader DNA by Cascade and Cas3," Molecular Cell 46:595-605.

Westra, E.R. et al. (Sep. 1, 2010, e-pub. Aug. 18, 2010). "H-NS—Mediated Repression of CRISPR-Based Immunity in *Escherichia coli* K12 Can Be Relieved By The Transcription Activator LeuO," Molecular Microbiology 77(6):1380-1393.

Westwater, C. et al. (2002). "Development of a P1 Phagemid System for the Delivery of DNA Into Gram-Negative Bacteria," Microbiology 148:943-950.

Westwater, C. et al. (Apr. 2003). "Use of Genetically Engineered Phage To Deliver Antimicrobial Agents To Bacteria: An Alternative Therapy For Treatment of Bacterial Infections," Antimicrobial Agents and Chemotherapy 47(4):1301-1307.

Wexler, H.M. (Oct. 2007). "Bacteroides: the Good, the Bad, and the Nitty-Gritty," Clinical Microbiology Reviews 20(4):593-621.

Wikipedia (2023). "Mobile Genetic Elements," retrieved from the Internet: https://en.wikipedia.org/wiki/Mobile_genetic_elements, last visited Feb. 27, 2023, 9 pages.

Wong, C.S. et al. (Jun. 29, 2000). "The Risk Of The Hemolytic-Uremic Syndrome After Antibiotic Treatment Of *Escherichia coli* O157:H7 Infections," N. Engl. J. Med. 342(26):1930-1936, 13 pages.

Written Opinion for PCT Application No. PCT/EP2016/059803, mailed Jun. 30, 2016, filed May 3, 2016, 6 pages.

Written Opinion for PCT/EP2018/082053, mailed Mar. 14, 2019, filed Nov. 21, 2018, 6 pages.

Wu, J. et al. (Jun. 2019). "Fusobacterium nucleatum Contributes to the Carcinogenesis of Colorectal Cancer by Inducting Inflammation and Suppressing Host Immunity," Translational Oncology 12(6):846-851.

Xavier, K.B. et al. (Sep. 29, 2005). "Interference With AI-2-Mediated Bacterial Cell-Cell Communication," Nature 437(7059):750-753, 10 pages.

Xie, Z. et al. (Oct. 2013, e-pub. Aug. 9, 2013). "Development Of a Tunable Wide-Range Gene Induction System Useful For The Study Of Streptococcal Toxin-Antitoxin Systems," Applied And Environmental Microbiology 79(20):6375-6384.

Xu, K. et al. (2015, e-pub. Jul. 20, 2014). "Efficient Genome Engineering in Eukaryotes Using Cas9 From *Streptococcus thermophilus*," Cell Mol. Life Sci. 72:383-399.

Xu, T. et al. (Jul. 2015, e-pub. Apr. 24. 2015). "Efficient Genome Editing in Clostridium cellulolyticum via CRISPR-Cas9 Nickase," Applied and Environmental Microbiology 81(13):4423-4431.

Yang, Y. et al. (Jun. 5, 2014, e-pub. Apr. 13, 2014). "Focused Specificity Of Intestinal Th17 Cells Towards Commensal Bacterial Antigens," Nature 510(7503):152-156, 29 pages.

Yosef, I. et al. (Dec. 13, 2011). "High-Temperature Protein G Is Essential For Activity Of The *Escherichia coli* Clustered Regularly Interspaced Palindromic Repeats (CRISPR)/Cas System," Proc. Natl. Acad. Sci. USA 108(50):20136-20141.

Yosef, I. et al. (Jun. 9, 2015). "Temperate and Lytic Bacteriophages Programmed To Sensitize and Kill Antibiotic-Resistant Bacteria," Proc. Natl. Acad. Sci. USA 112(23):7267-7272.

Young, R. et al. (1995). "Holins: Form and Function in Bacteriophage Lysis," FEMS Microbiology Reviews 17:191-205.

YourGenome: CRISPR/CAS9, retrieved from https://www.yourgenonne.org/facts/what-is-crispr-cas9, last visited Jan. 6, 2020, 8 pages.

Yu, Z. et al. (Mar. 21, 2014). "Various Applications of TALEN- and CRISPR/Cas9-Mediated Homologous Recombination to Modify the *Drosophila* Genome," Biology Open 3(4):271-280.

Zembower, T.R. (2004). "Epidemiology of Infections in Cancer Patients," in Infectious Complications in Cancer Patients, Springer International Publishing Switzerland, 48 pages.

Zhang, R. et al. (2009, e-pub. Oct. 30, 2008). "DEG 5.0, A Database of Essential Genes in Both Prokaryotes and Eukaryotes," Nucleic Acids Research 37:D455-D458.

Zhang, T. et al. (Sep. 24, 2016). "The Efficacy and Safety Of Anti-PD-1/PD-L1 Antibodies For Treatment Of Advanced Or Refractory Cancers: A Meta-Analysis," Oncotarget 7(45):73068-73079.

Zhang, X.Z. (2011). "Simple, Fast and High-Efficiency Transformation System For Directed Evolution Of Cellulase In Bacillus Subtilis," Microbial Biotechnology 4(1):98-105.

Zhang, Y. et al. (2017). "LsrB-Based and Temperature-Dependent Identification of Bacterial AI-2 Receptor," AMB Expr. 7:188, 10 pages.

Zimmerhackl, L.B. (Jun. 29, 2000). "*E. coli*, Antibiotics, and The Hemolytic-Uremic Syndrome," N. Engl. J. Med. 342(26):1990-1991, 6 pages.

Zitvogel, L. et al. (Jan. 2015), "Cancer and The Gut Microbiota: An Unexpected Link," Sci. Transl. Med. 7 (271):271ps1, 10 pages.

Zitvogel, L. et al. (Mar. 2018). "The Microbiome In Cancer Immunotherapy: Diagnostic Tools and Therapeutic Strategies," Science 359(6382):1366-1370.

Fukushima, M. et al. (Aug. 2002). "Phylogenetic Analysis of *Salmonella, Shigella,* and *Escherichi coli* Strains on the bases of the gyrB Gene Sequence," Journal of Clinical Microbiology 40(8):2779-2785.

Perez-Rodriguaz, R. et al. (2010, e-pub. Dec. 13, 2010). "Envelope Stress is a Trigger of CRISPR RNA-Mediated DNA Silencing in *Escherichia coli*," Molecular Microbiology 79:584-599.

Admella, J. et al. (2023). "Investigating Bacterial Infections in *Galleria mellonella* Larvae: Insights into Pathogen Dissemination and Behavior," Journal of Invertebrate Pathology 200:107975, 8 pages.

Senior, N.J. et al. (2011). "Galleria mellonella as an Infection Model for Campylobacter jejuni Virulence," Journal of Medical Microbiology 60:661-669.

Annex 1 filed by Patentee (Apr. 27, 2021), 2 pages.

Annex 1 filed by Patentee (Aug. 2, 2021), 6 pages.

Bacillota (Apr. 30, 2024). (synonym Firmicutes), Wikipedia, 7 pages.

Burmølle, M. et al. (Jun. 2006). "Enhanced Biofilm Formation and Increased Resistance to Antimicrobial Agents and Bacterial Invasion are Caused by Synergistic Interactions in Multispecies Biofilms," Applied and Environmental Microbiology 72(6):3916-3923.

CGV Generation (No Date), 15 pages.

Champagne, C.P. et al. (2009). "Interactions Between *Lactococcus lactis* and *Streptococcus thermophilus* Strains in Cheddar Cheese Processing Conditions," International Dairy Journal 19:669-674.

D66 (Dec. 20, 2019). Remarks, 11 pages.

Declaration of Hinton, dated Jan. 23, 2023, 43 pages.

Declaration of Hoyland-Kroghsbo, dated Jan. 26, 2023, 9 pages.

EP Opposition, dated Apr. 11, 2024, for European Patent Application No. 16719873.8, 237 pages.

Ex Parte Re-Exam Communication Transmittal Form, dated May 22, 2024, for U.S. Appl. No. 90/019,229, for U.S. Pat. No. 10,463,049, 106 pages.

Giaouris, E. et al. (Aug. 20, 2015). "Intra- and Inter-Species Interactions Within Biofilms of Important Foodborne Bacterial Pathogens," Frontiers in Microbiology 6(841):1-26.

Hansen, J.J. et al. (Mar. 2015). "Therapeutic Manipulation of the Microbiome in IBD: Current Results and Future Approaches," Curr. T. Options Gastroentrol. 13(1):105-120.

International Search Report and Written Opinion, mailed May 12, 2022, for PCT Application No. PCT/EP2021/076360, 23 pages.

Kara, D. et al. (2006). "Differences Between Single- and Dual-Species Biofilms of *Streptococcus* and *Veillonella parvula* in Growth Acidogenicity and Susceptibility to Chlorhexidine," Eur. J. Oral. Sci. 114:5-63.

Milho, C. et al. (2019). "*Escherichia coli* and *Salmonella Enteritidis* Dual-Species Biofilms: Interspecies Interactions and Antibiofilm Efficacy of Phages," Scientific Reports 9:18183, 15 pages.

Noonan, K.A. et al. (May 20, 2015). "Adoptive Transfer of Activated Marrow-Infiltrating Lymphocytes Induces Measurable Antiumor Immunity in the Bone Marrow in Multiple Myeloma," Science Translational Medicine 7(228):288ra78, 14 pages.

(56) References Cited

OTHER PUBLICATIONS

O'Flynn, G. et al. (Jun. 2004). "Evaluation of a Cocktail of Three Bacteriophages for Biocontrol of *Escherichia coli* O157:H7," Applied and Environmental Microbiology 70(6):3417-3424.

*Staphylococcus aureaus* (Apr. 30, 2024). Wikipedia, 33 pages.

Summons to Attend Oral Proceedings Pursuant to Rule 115(1) EPC, dated Apr. 11, 2024, for European Patent Application No. 16719873.8, 47 pages.

Borges, A.L. et al. (May 2020). "Bacterial Alginate Regulators and Phage Homologs Repress CRISPR-Cas Immunity," Nat. Microbiol. 5(5):679-687, 27 pages.

Egan, M. et al. (2014). "Cross-Feeding by Bifidobacterium breve UCC2003 During Co-Cultivation with Bifidobacterium bifidum PRL2010 in a Mucin-Based Medium," BMC Microbiology 14:282, 14 pages.

Fritts, R.K. et al. (Mar. 2021, e-pub. Jan. 13, 2021). "Extracellular Metabolism Sets the Table for Microbial Cross-Feeding," Microbiology and Molecular Biology Reviews 85(1):e001325-20, 29 pages.

Heilmann, S. et al. (Jul. 31, 2012). "Coexistence of Phage and Bacteria on the Boundary of Self-Organized Refuges," PNAS 109(31):12828-12833.

Henke, J.M. et al. (Oct. 2004). "Three Parallel Quorum-Sensing Systems Regulate Gene Expression in Vibrio harveyi," Journal of Bacteriology 186(20):6902-6914.

Hofer, U. (2016, e-pub. Nov. 28, 2016). "Quorum Sensing Controls the Cost of CRISPR-Cas," Nature Reives Micorbiology, 1 page.

Høyland-Kroghsbo, N.M. et al. (Jan. 3, 2017). "Quorum Sensing Controls the Pseudomonas aeruginosa CRISPR-Cas Adaptive Immune System," PNAS 114(1):131-135.

Król, J.E. et al. (Jul. 2013). "Invasion of *E. coli* Biofilms by Antibiotic Resistance Plasmids," Plasmid 70(1):110-119, 17 pages.

Marraffini, L.A. (Jan. 3, 2017). "Sensing Danger," PNAS 114(1):15-16.

Mayorga-Ramos, A. et al. (Jun. 22, 2023). "CRISPR-Cas-Based Antimicrobials: Design, Challenges, and Bacterial Mechanisms of Resistance," ACS Infect. Dis. 9:1283-1302.

Mumford, R. et al. (2017, e-pub. Dec. 20, 2016). "Bacterial Competition and Quorum-Sensing Signalling Shape the Eco-Evolutionary Outcomes of Model in vitro Phage Therapy," Evolutionary Application 10:161-169.

Navarre, W.W. (2016, e-pub. Sep. 16, 2016). "Chapter Three—The Impact of Gene Silencing on Horizontal Gene Transfer and Bacterial Evolution," Adv. Microb. Physiol. 69:157-186.

Patterson, A.G. et al. (Dec. 15, 2016). "Quorum Sensing Controls Adaptive Immunity Through The Regulation Of Multiple CRISPR-Cas Systems," Mol. Cell 64(6):1102-1108.

Popa, O. et al. (2011, e-pub. Aug. 17, 2011). "Trends and Barriers to Lateral Gene Transfer in Prokaryotes," Current Opinion in Microbiology 14:615-623.

Samson, J.E. et al. (Oct. 2013, e-pub. Aug. 27, 2013). "Revenge of the Phages: Defeating Bacterial Defences," Nature Reviews Microbiology 11:675-687.

Van Houte, S. et al. (Sep. 2016, e-pub. Jul. 13, 2016). "Evolutionary Ecology of Prokaryotic Immune Mechanisms," Microbiology and Molecular Biology Reviews 80(3):745-763.

Westra, E.R. et al. (2012). "The CRISPRs, They are A-Changin: How Prokaryotes Generate Adaptive Immunity," Annu. Rev. Genet. 46:311-339.

Westra, E.R. et al. (May 2014). "CRISPR-Cas Systems: Beyond Adaptive Immunity," Nature Reviews Microbiology 12:317-326.

Wiedenbeck, J. et al. (2011, e-pub. Jul. 2011). "Origins of Bacterial Diversity Through Horizontal Genetic Transfer and Adaptation to New Ecological Niches," FEMS Microbiology Reviews 35:957-976.

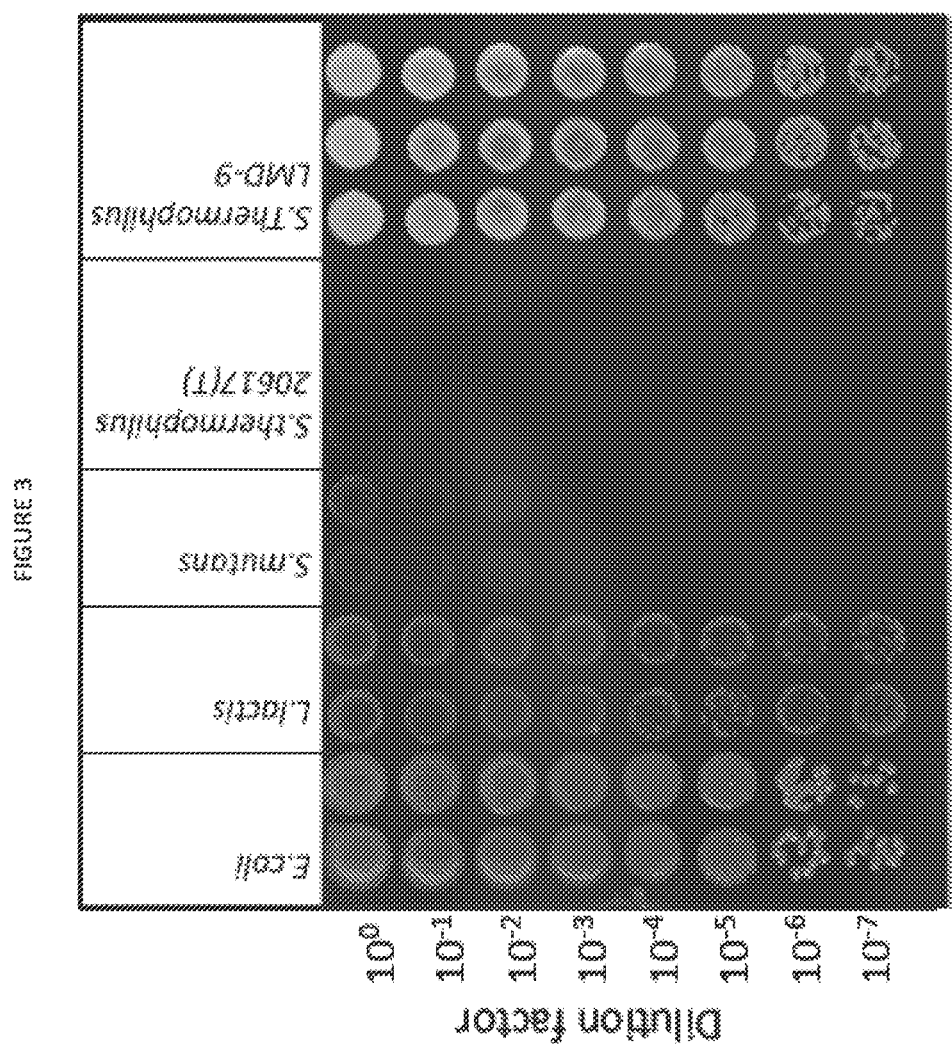

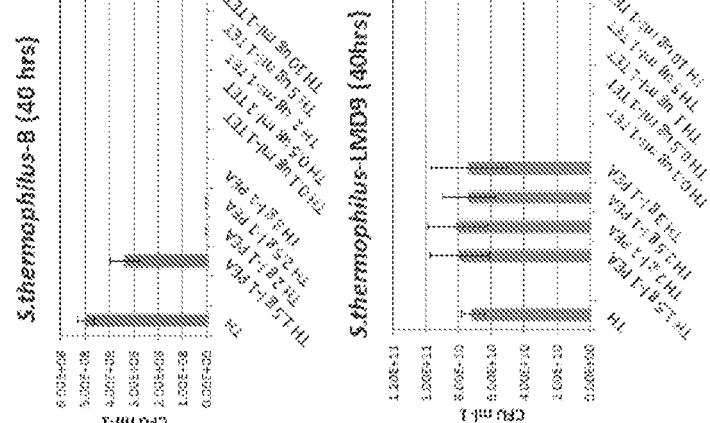
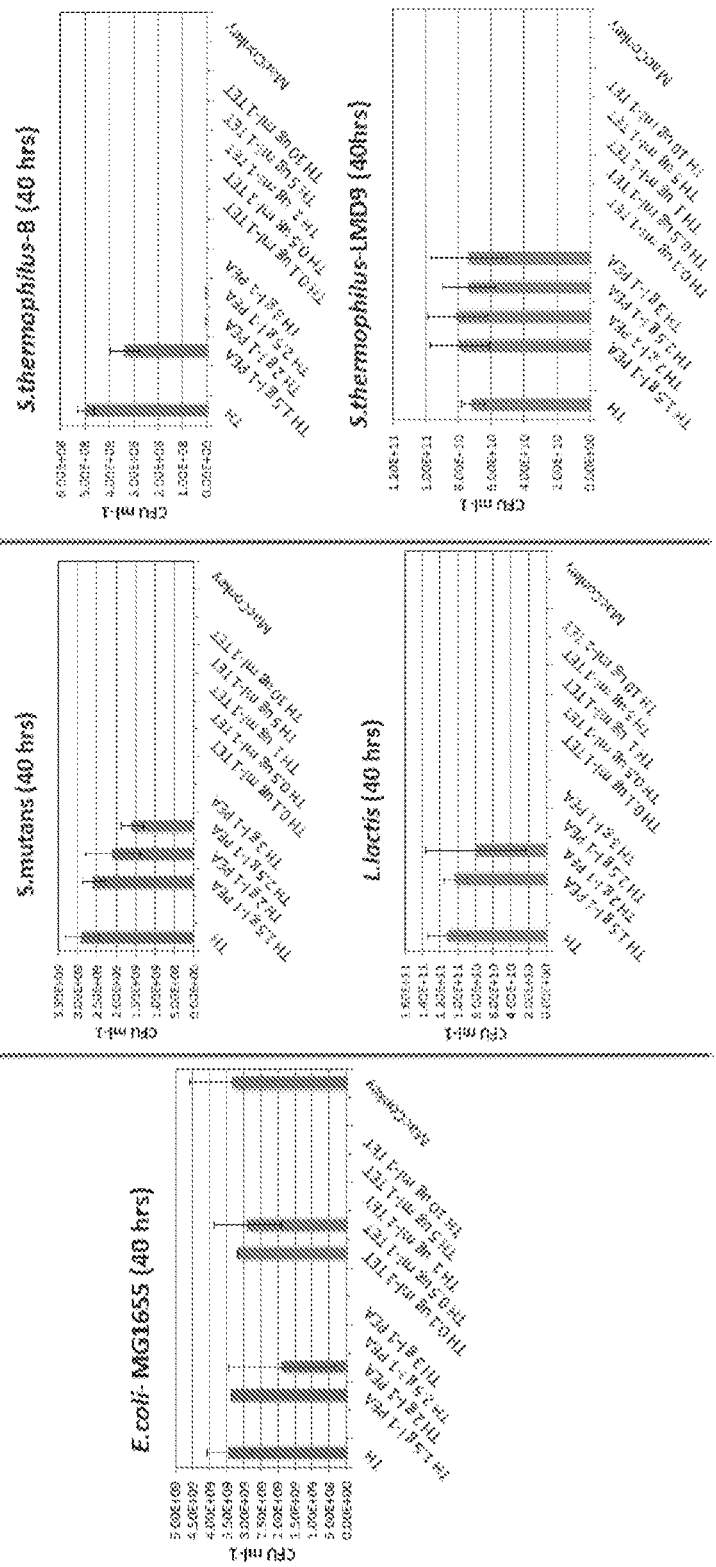

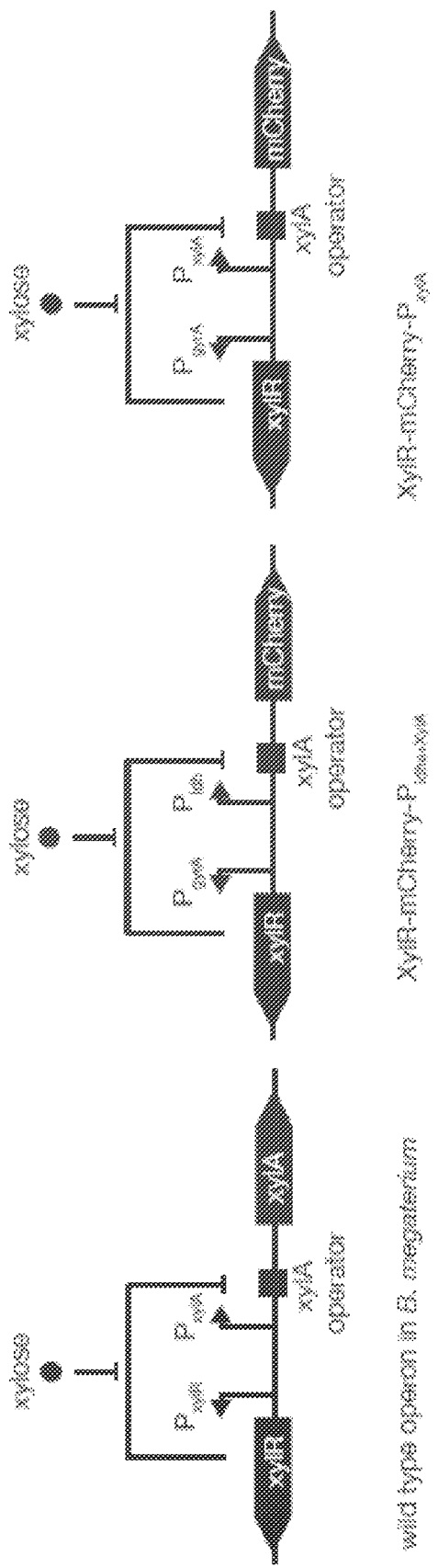

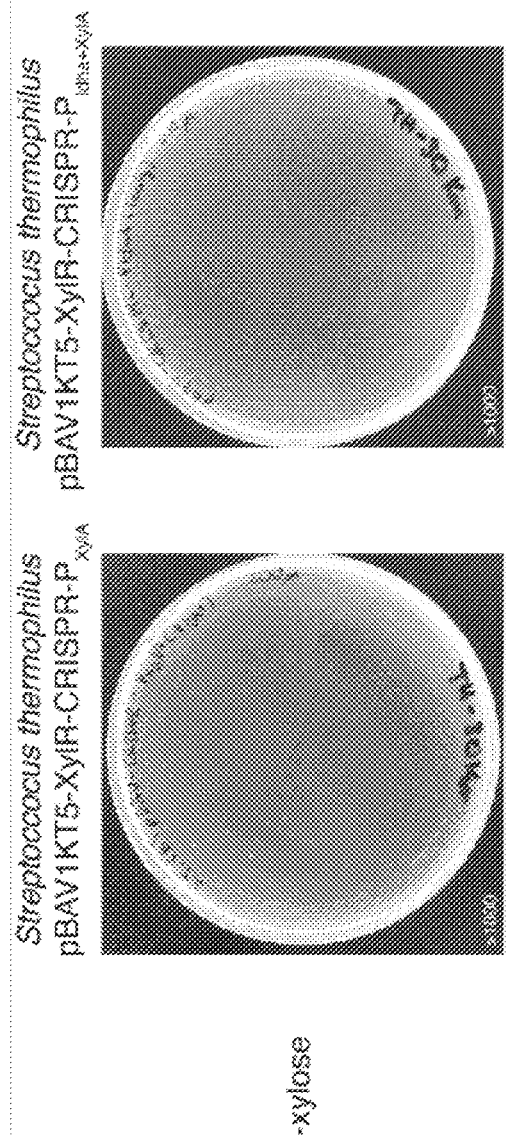
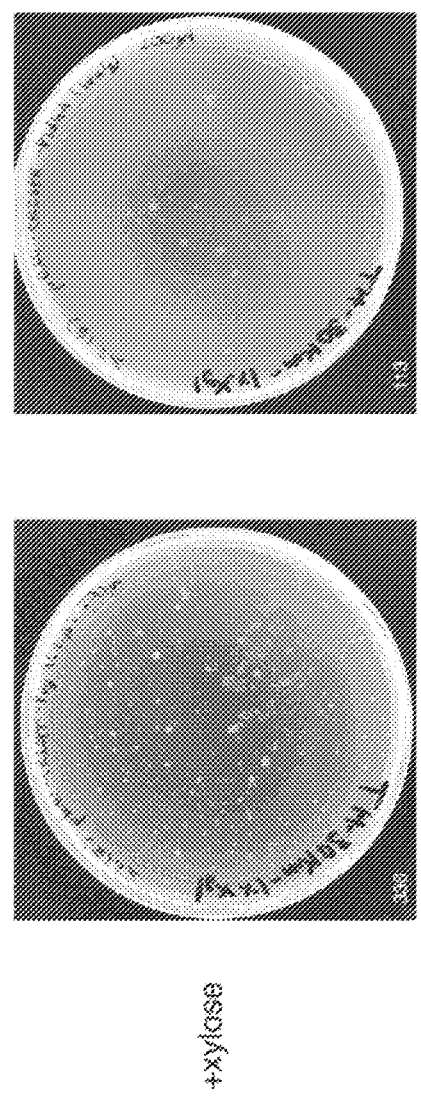
FIGURE 10A  FIGURE 10B  FIGURE 10C  FIGURE 10D

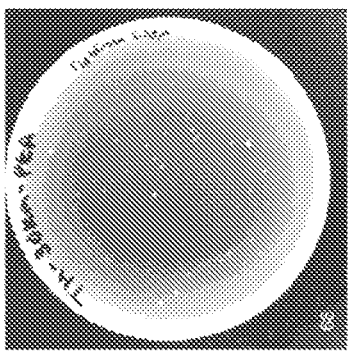
FIGURE 12A
Todd Hewitt agar
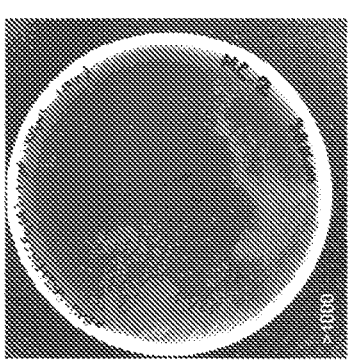
FIGURE 12B
MacConkey agar
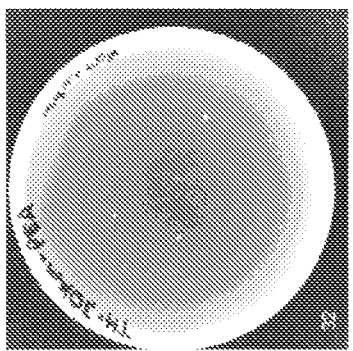
FIGURE 12C
Todd Hewitt agar supplemented with 2.5 g l⁻¹ PEA
*S.thermophilus, L.lactis and E.coli with plasmid pBAV1KT5-P$_{xylA}$*
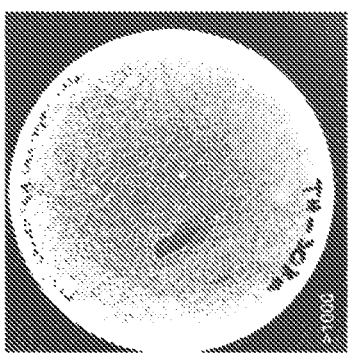
FIGURE 12D
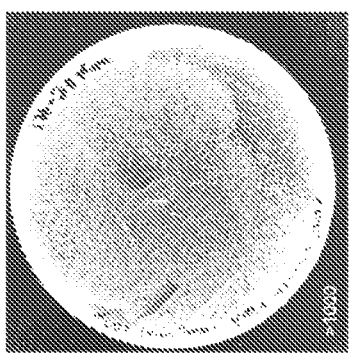
FIGURE 12E
FIGURE 12F
*S.thermophilus, L.lactis and E.coli with plasmid pBAV1KT5-P$_{ldhA}$*

SEQUENCE LISTING

Sequence total quantity: 128
SEQ ID NO: 1            moltype =    length =
SEQUENCE: 1
000

SEQ ID NO: 2            moltype =    length =
SEQUENCE: 2
000

SEQ ID NO: 3            moltype =    length =
SEQUENCE: 3
000

SEQ ID NO: 4            moltype =    length =
SEQUENCE: 4
000

SEQ ID NO: 5            moltype =    length =
SEQUENCE: 5
000

SEQ ID NO: 6            moltype =    length =
SEQUENCE: 6
000

SEQ ID NO: 7            moltype =    length =
SEQUENCE: 7
000

SEQ ID NO: 8            moltype =    length =
SEQUENCE: 8
000

SEQ ID NO: 9            moltype =    length =
SEQUENCE: 9
000

SEQ ID NO: 10           moltype =    length =
SEQUENCE: 10
000

SEQ ID NO: 11           moltype =    length =
SEQUENCE: 11
000

SEQ ID NO: 12           moltype =    length =
SEQUENCE: 12
000

```
SEQ ID NO: 13            moltype =     length =
SEQUENCE: 13
000

SEQ ID NO: 14            moltype =     length =
SEQUENCE: 14
000

SEQ ID NO: 15            moltype =     length =
SEQUENCE: 15
000

SEQ ID NO: 16            moltype =     length =
SEQUENCE: 16
000

SEQ ID NO: 17            moltype =     length =
SEQUENCE: 17
000

SEQ ID NO: 18            moltype =     length =
SEQUENCE: 18
000

SEQ ID NO: 19            moltype =     length =
SEQUENCE: 19
000

SEQ ID NO: 20            moltype = DNA   length = 10
FEATURE                  Location/Qualifiers
source                   1..10
                         mol_type = unassigned DNA
                         organism = Streptococcus sp.
SEQUENCE: 20
acgatttgag                                                                10

SEQ ID NO: 21            moltype =     length =
SEQUENCE: 21
000

SEQ ID NO: 22            moltype = DNA   length = 10
FEATURE                  Location/Qualifiers
source                   1..10
                         mol_type = unassigned DNA
                         organism = Streptococcus sp.
SEQUENCE: 22
ttcatttgag                                                                10

SEQ ID NO: 23            moltype = DNA   length = 10
FEATURE                  Location/Qualifiers
source                   1..10
                         mol_type = unassigned DNA
                         organism = Streptococcus sp.
SEQUENCE: 23
atcatttgag                                                                10

SEQ ID NO: 24            moltype = DNA   length = 11
FEATURE                  Location/Qualifiers
source                   1..11
                         mol_type = unassigned DNA
                         organism = Streptococcus sp.
SEQUENCE: 24
tttcatttga g                                                              11

SEQ ID NO: 25            moltype = DNA   length = 11
FEATURE                  Location/Qualifiers
source                   1..11
                         mol_type = unassigned DNA
                         organism = Streptococcus sp.
SEQUENCE: 25
aatcatttga g                                                              11

SEQ ID NO: 26            moltype = DNA   length = 12
FEATURE                  Location/Qualifiers
source                   1..12
                         mol_type = unassigned DNA
                         organism = Streptococcus sp.
SEQUENCE: 26
```

```
aattcatttg ag                                                                    12

SEQ ID NO: 27              moltype = DNA   length = 12
FEATURE                    Location/Qualifiers
source                     1..12
                           mol_type = unassigned DNA
                           organism = Streptococcus sp.

SEQUENCE: 27
aaatcatttg ag                                                                    12

SEQ ID NO: 28              moltype = DNA   length = 13
FEATURE                    Location/Qualifiers
source                     1..13
                           mol_type = unassigned DNA
                           organism = Streptococcus sp.

SEQUENCE: 28
aaattcattt gag                                                                   13

SEQ ID NO: 29              moltype = DNA   length = 13
FEATURE                    Location/Qualifiers
source                     1..13
                           mol_type = unassigned DNA
                           organism = Streptococcus sp.

SEQUENCE: 29
aaaatcattt gag                                                                   13

SEQ ID NO: 30              moltype = DNA   length = 14
FEATURE                    Location/Qualifiers
source                     1..14
                           mol_type = unassigned DNA
                           organism = Streptococcus sp.

SEQUENCE: 30
aaaattcatt tgag                                                                  14

SEQ ID NO: 31              moltype =       length =
SEQUENCE: 31
000

SEQ ID NO: 32              moltype =       length =
SEQUENCE: 32
000

SEQ ID NO: 33              moltype =       length =
SEQUENCE: 33
000

SEQ ID NO: 34              moltype =       length =
SEQUENCE: 34
000

SEQ ID NO: 35              moltype =       length =
SEQUENCE: 35
000

SEQ ID NO: 36              moltype =       length =
SEQUENCE: 36
000

SEQ ID NO: 37              moltype =       length =
SEQUENCE: 37
000

SEQ ID NO: 38              moltype = DNA   length = 10
FEATURE                    Location/Qualifiers
source                     1..10
                           mol_type = unassigned DNA
                           organism = Streptococcus sp.

SEQUENCE: 38
gttttttgtac                                                                      10

SEQ ID NO: 39              moltype = DNA   length = 11
FEATURE                    Location/Qualifiers
source                     1..11
                           mol_type = unassigned DNA
                           organism = Streptococcus sp.

SEQUENCE: 39
gtttttgtac t                                                                     11

SEQ ID NO: 40              moltype = DNA   length = 12
```

| | | |
|---|---|---|
| FEATURE | Location/Qualifiers | |
| source | 1..12<br>mol_type = unassigned DNA<br>organism = Streptococcus sp. | |
| SEQUENCE: 40 | | |
| gtttttgtac tc | | 12 |
| SEQ ID NO: 41 | moltype = DNA   length = 13 | |
| FEATURE | Location/Qualifiers | |
| source | 1..13<br>mol_type = unassigned DNA<br>organism = Streptococcus sp. | |
| SEQUENCE: 41 | | |
| gtttttgtac tct | | 13 |
| SEQ ID NO: 42 | moltype = DNA   length = 14 | |
| FEATURE | Location/Qualifiers | |
| source | 1..14<br>mol_type = unassigned DNA<br>organism = Streptococcus sp. | |
| SEQUENCE: 42 | | |
| gtttttgtac tctc | | 14 |
| SEQ ID NO: 43 | moltype = DNA   length = 15 | |
| FEATURE | Location/Qualifiers | |
| source | 1..15<br>mol_type = unassigned DNA<br>organism = Streptococcus sp. | |
| SEQUENCE: 43 | | |
| gtttttgtac tctca | | 15 |
| SEQ ID NO: 44 | moltype = DNA   length = 16 | |
| FEATURE | Location/Qualifiers | |
| source | 1..16<br>mol_type = unassigned DNA<br>organism = Streptococcus sp. | |
| SEQUENCE: 44 | | |
| gtttttgtac tctcaa | | 16 |
| SEQ ID NO: 45 | moltype = DNA   length = 63 | |
| FEATURE | Location/Qualifiers | |
| source | 1..63<br>mol_type = unassigned DNA<br>organism = Streptococcus thermophilus | |
| SEQUENCE: 45 | | |
| caaggacagt tattgatttt ataatcacta tgtgggtata aaaacgtcaa aatttcattt | | 60 |
| gag | | 63 |
| SEQ ID NO: 46 | moltype = DNA   length = 103 | |
| FEATURE | Location/Qualifiers | |
| source | 1..103<br>mol_type = unassigned DNA<br>organism = Escherichia coli | |
| SEQUENCE: 46 | | |
| aaacaaagaa ttagctgatc tttaataata aggaaatgtt acattaaggt tggtgggttg | | 60 |
| tttttatggg aaaaaatgct ttaagaacaa atgtatactt aga | | 103 |
| SEQ ID NO: 47 | moltype = AA   length = 1053 | |
| FEATURE | Location/Qualifiers | |
| source | 1..1053<br>mol_type = protein<br>organism = Staphylococcus aureus | |
| SEQUENCE: 47 | | |
| MKRNYILGLD IGITSVGYGI IDYETRDVID AGVRLFKEAN VENNEGRRSK RGARRLKRRR | | 60 |
| RHRIQRVKKL LFDYNLLTDH SELSGINPYE ARVKGLSQKL SEEEFSAALL HLAKRRGVHN | | 120 |
| VNEVEEDTGN ELSTKEQISR NSKALEEKYV AELQLERLKK DGEVRGSINR FKTSDYVKEA | | 180 |
| KQLLKVQKAY HQLDQSFIDT YIDLLETRRT YYEGPGEGSP FGWKDIKEWY EMLMGHCTYF | | 240 |
| PEELRSVKYA YNADLYNALN DLNNLVITRD ENEKLEYYEK FQIIENVFKQ KKKPTLKQIA | | 300 |
| KEILVNEEDI KGYRVTSTGK PEFTNLKVYH DIKDITARKE IIENAELLDQ IAKILTIYQS | | 360 |
| SEDIQEELTN LNSELTQEEI EQISNLKGYT GTHNLSLKAI NLILDELWHT NDNQIAIFNR | | 420 |
| LKLVPKKVDL SQQKEIPTTL VDDFILSPVV KRSFIQSIKV INAIIKKYGL PNDIIIELAR | | 480 |
| EKNSKDAQKM INEMQKRNRQ TNERIEEIIR TTGKENAKYL IEKIKLHDMQ EGKCLYSLEA | | 540 |
| IPLEDLLNNP FNYEVDHIIP RSVSFDNSFN NKVLVKQEEN SKKGNRTPFQ YLSSSDSKIS | | 600 |
| YETFKKHILN LAKGKGRISK TKKEYLLEER DINRFSVQKD FINRNLVDTR YATRGLMNLL | | 660 |
| RSYFRVNNLD VKVKSINGGF TSFLRRKWKF KKERNKGYKH HAEDALIIAN ADFIFKEWKK | | 720 |
| LDKAKKVMEN QMFEEKQAES MPEIETEQEY KEIFITPHQI KHIKDFKDYK YSHRVDKKPN | | 780 |
| RELINDTLYS TRKDDKGNTL IVNNLNGLYD KDNDKLKKLI NKSPEKLLMY HHDPQTYQKL | | 840 |
| KLIMEQYGDE KNPLYKYYEE TGNYLTKYSK KDNGPVIKKI KYYGNKLNAH LDITDDYPNS | | 900 |
| RNKVVKLSLK PYRFDVYLDN GVYKFVTVKN LDVIKKENYY EVNSKCYEEA KKLKKISNQA | | 960 |

```
EFIASFYNND LIKINGELYR VIGVNNDLLN RIEVNMIDIT YREYLENMND KRPPRIIKTI   1020
ASKTQSIKKY STDILGNLYE VKSKKHPQII KKG                                1053

SEQ ID NO: 48              moltype = AA  length = 1368
FEATURE                    Location/Qualifiers
source                     1..1368
                           mol_type = protein
                           organism = Streptococcus pyogenes
SEQUENCE: 48
MDKKYSIGLD IGTNSVGWAV ITDEYKVPSK KFKVLGNTDR HSIKKNLIGA LLFDSGETAE   60
ATRLKRTARR RYTRRKNRIC YLQEIFSNEM AKVDDSFPHR LEESFLVEED KKHERHPIFG   120
NIVDEVAYHE KYPTIYHLRK KLVDSTDKAD LRLIYLALAH MIKFRGHFLI EGDLNPDNSD   180
VDKLFIQLVQ TYNQLFEENP INASGVDAKA ILSARLSKSR RLENLIAQLP GEKKNGLFGN   240
LIALSLGLTP NFKSNFDLAE DAKLQLSKDT YDDDLDNLLA QIGDQYADLF LAAKNLSDAI   300
LLSDILRVNT EITKAPLSAS MIKRYDEHHQ DLTLLKALVR QQLPEKYKEI FFDQSKNGYA   360
GYIDGGASQE EFYKFIKPIL EKMDGTEELL VKLNREDLLR KQRTFDNGSI PHQIHLGELH   420
AILRRQEDFY PFLKDNREKI EKILTFRIPY YVGPLARGNS RFAWMTRKSE ETITPWNFEE   480
VVDKGASAQS FIERMTNFDK NLPNEKVLPK HSLLYEYFTV YNELTKVKYV TEGMRKPAFL   540
SGEQKKAIVD LLFKTNRKVT VKQLKEDYFK KIECFDSVEI SGVEDRFNAS LGTYHDLLKI   600
IKDKDFLDNE ENEDILEDIV LTLTLFEDRE MIEERLKTYA HLFDDKVMKQ LKRRRYTGWG   660
RLSRKLINGI RDKQSGKTIL DFLKSDGFAN RNFMQLIHDD SLTFKEDIQK AQVSGQGDSL   720
HEHIANLAGS PAIKKGILQT VKVVDELVKV MGRHKPENIV IEMARENQTT QKGQKNSRER   780
MKRIEEGIKE LGSQILKEHP VENTQLQNEK LYLYYLQNGR DMYVDQELDI NRLSDYDVDH   840
IVPQSFLKDD SIDNKVLTRS DKNRGKSDNV PSEEVVKKMK NYWRQLLNAK LITQRKFDNL   900
TKAERGGLSE LDKAGFIKRQ LVETRQITKH VAQILDSRMN TKYDENDKLI REVKVITLKS   960
KLVSDFRKDF QFYKVREINN YHHAHDAYLN AVVGTALIKK YPKLESEFVY GDYKVYDVRK   1020
MIAKSEQEIG KATAKYFFYS NIMNFFKTEI TLANGEIRKR PLIETNGETG EIVWDKGRDF   1080
ATVRKVLSMP QVNIVKKTEV QTGGFSKESI LPKRNSDKLI ARKKDWDPKK YGGFDSPTVA   1140
YSVLVVAKVE KGKSKKLKSV KELLGITIME RSSFEKNPID FLEAKGYKEV KKDLIIKLPK   1200
YSLFELENGR KRMLASAGEL QKGNELALPS KYVNFLYLAS HYEKLKGSPE DNEQKQLFVE   1260
QHKYHLDEII EQISEFSKRV ILADANLDKV LSAYNKHRDK PIREQAENII HLFTLTNLGA   1320
PAAFKYFDTT IDRKRYTSTK EVLDATLIHQ SITGLYETRI DLSQLGGD              1368

SEQ ID NO: 49              moltype = DNA  length = 28
FEATURE                    Location/Qualifiers
source                     1..28
                           mol_type = unassigned DNA
                           organism = Desulfovibrio gigas
SEQUENCE: 49
gttcactgcc gcataggcag ctcagaaa                                      28

SEQ ID NO: 50              moltype = DNA  length = 23
FEATURE                    Location/Qualifiers
source                     1..23
                           mol_type = unassigned DNA
                           organism = Desulfovibrio desulfuricans
SEQUENCE: 50
cctggcctgc cccaagtgca agg                                           23

SEQ ID NO: 51              moltype = DNA  length = 32
FEATURE                    Location/Qualifiers
source                     1..32
                           mol_type = unassigned DNA
                           organism = Desulfovibrio desulfuricans
SEQUENCE: 51
gtcgccccccc acgcggggc gtggattgaa ac                                 32

SEQ ID NO: 52              moltype = DNA  length = 28
FEATURE                    Location/Qualifiers
source                     1..28
                           mol_type = unassigned DNA
                           organism = Desulfovibrio desulfuricans
SEQUENCE: 52
tggagcggga aacgggattt gaacccgc                                      28

SEQ ID NO: 53              moltype = DNA  length = 29
FEATURE                    Location/Qualifiers
source                     1..29
                           mol_type = unassigned DNA
                           organism = Desulfovibrio desulfuricans
SEQUENCE: 53
gtgttcccca cgggcgtggg gatgaaccg                                     29

SEQ ID NO: 54              moltype = DNA  length = 25
FEATURE                    Location/Qualifiers
source                     1..25
                           mol_type = unassigned DNA
                           organism = Desulfovibrio gigas
SEQUENCE: 54
```

-continued

```
aacctttctg caaaaaggtt tcccc                                          25

SEQ ID NO: 55            moltype = DNA   length = 23
FEATURE                  Location/Qualifiers
source                   1..23
                         mol_type = unassigned DNA
                         organism = Desulfovibrio gigas
SEQUENCE: 55
ccgctggatc cggctgcagc gcc                                            23

SEQ ID NO: 56            moltype = DNA   length = 28
FEATURE                  Location/Qualifiers
source                   1..28
                         mol_type = unassigned DNA
                         organism = Desulfovibrio gigas
SEQUENCE: 56
gttcactgcc gcataggcag ctcagaaa                                       28

SEQ ID NO: 57            moltype = DNA   length = 32
FEATURE                  Location/Qualifiers
source                   1..32
                         mol_type = unassigned DNA
                         organism = Desulfovibrio gigas
SEQUENCE: 57
cacccgacta ttgaagtcgg gcctcattga ag                                  32

SEQ ID NO: 58            moltype = DNA   length = 36
FEATURE                  Location/Qualifiers
source                   1..36
                         mol_type = unassigned DNA
                         organism = Desulfovibrio hydrothermalis
SEQUENCE: 58
gtcaaaaccc ataccgatat ggatacctct tttgag                              36

SEQ ID NO: 59            moltype = DNA   length = 36
FEATURE                  Location/Qualifiers
source                   1..36
                         mol_type = unassigned DNA
                         organism = Desulfovibrio hydrothermalis
SEQUENCE: 59
gtcaaaaccc ataccgatat ggatacctct tttgag                              36

SEQ ID NO: 60            moltype = DNA   length = 36
FEATURE                  Location/Qualifiers
source                   1..36
                         mol_type = unassigned DNA
                         organism = Desulfovibrio hydrothermalis
SEQUENCE: 60
gtcaaaaccc ataccgatat ggatacctct tttgag                              36

SEQ ID NO: 61            moltype = DNA   length = 36
FEATURE                  Location/Qualifiers
source                   1..36
                         mol_type = unassigned DNA
                         organism = Desulfovibrio hydrothermalis
SEQUENCE: 61
gtcaaaaccc ataccgatat ggatacctct tttgag                              36

SEQ ID NO: 62            moltype = DNA   length = 36
FEATURE                  Location/Qualifiers
source                   1..36
                         mol_type = unassigned DNA
                         organism = Desulfovibrio hydrothermalis
SEQUENCE: 62
ctcaaaagag gtatccatat cggtatgggt tttgac                              36

SEQ ID NO: 63            moltype = DNA   length = 28
FEATURE                  Location/Qualifiers
source                   1..28
                         mol_type = unassigned DNA
                         organism = Desulfovibrio hydrothermalis
SEQUENCE: 63
gttcactgcc ggataggcag cttagaaa                                       28

SEQ ID NO: 64            moltype = DNA   length = 32
FEATURE                  Location/Qualifiers
source                   1..32
                         mol_type = unassigned DNA
                         organism = Desulfovibrio magneticus
```

```
SEQUENCE: 64
gtcgcccct gcgcgggggc gtggattgaa ac                                         32

SEQ ID NO: 65           moltype = DNA   length = 29
FEATURE                 Location/Qualifiers
source                  1..29
                        mol_type = unassigned DNA
                        organism = Desulfovibrio magneticus
SEQUENCE: 65
ttttctgagc tgcctatgcg gcagtgaac                                            29

SEQ ID NO: 66           moltype = DNA   length = 46
FEATURE                 Location/Qualifiers
source                  1..46
                        mol_type = unassigned DNA
                        organism = Desulfovibrio vulgaris
SEQUENCE: 66
catcgacgac gaacccgggc accgcctgat ggtccacgcc gtcatg                         46

SEQ ID NO: 67           moltype = DNA   length = 32
FEATURE                 Location/Qualifiers
source                  1..32
                        mol_type = unassigned DNA
                        organism = Desulfovibrio vulgaris
SEQUENCE: 67
gtcgcccctc acgcggggc gtggatagaa ac                                         32

SEQ ID NO: 68           moltype = DNA   length = 32
FEATURE                 Location/Qualifiers
source                  1..32
                        mol_type = unassigned DNA
                        organism = Desulfovibrio vulgaris
SEQUENCE: 68
gtttcaatcc acgccccgc acgggggcg ac                                          32

SEQ ID NO: 69           moltype = DNA   length = 28
FEATURE                 Location/Qualifiers
source                  1..28
                        mol_type = unassigned DNA
                        organism = Desulfurispirillum indicum
SEQUENCE: 69
tttctgagct gcctatgcgg cagtgaac                                             28

SEQ ID NO: 70           moltype = DNA   length = 36
FEATURE                 Location/Qualifiers
source                  1..36
                        mol_type = unassigned DNA
                        organism = Desulfurispirillum indicum
SEQUENCE: 70
gaccgaagac ctgtcggaaa cgacggggat tgagac                                    36

SEQ ID NO: 71           moltype = DNA   length = 29
FEATURE                 Location/Qualifiers
source                  1..29
                        mol_type = unassigned DNA
                        organism = Desulfurivibrio alkaliphilus
SEQUENCE: 71
cggttcatcc ccgcgagtgc ggggaacat                                            29

SEQ ID NO: 72           moltype = DNA   length = 28
FEATURE                 Location/Qualifiers
source                  1..28
                        mol_type = unassigned DNA
                        organism = Desulfurivibrio alkaliphilus
SEQUENCE: 72
tttctgagct gcctgtgcgg cagtgaac                                             28

SEQ ID NO: 73           moltype = DNA   length = 29
FEATURE                 Location/Qualifiers
source                  1..29
                        mol_type = unassigned DNA
                        organism = Desulfurobacterium thermolithotrophum
SEQUENCE: 73
gttttatctg aacgtagtgg gatataaag                                            29

SEQ ID NO: 74           moltype = DNA   length = 29
FEATURE                 Location/Qualifiers
source                  1..29
                        mol_type = unassigned DNA
```

```
                        organism = Desulfovibrio desulfuricans
SEQUENCE: 74
cggttcatcc ccgcgggtgc ggggaacac                                    29

SEQ ID NO: 75           moltype = RNA   length = 28
FEATURE                 Location/Qualifiers
misc_feature            1..28
                        note = Synthetic oligonucleotide
source                  1..28
                        mol_type = other RNA
                        organism = synthetic construct
SEQUENCE: 75
gttagcagcc gcataggctg cttaaata                                     28

SEQ ID NO: 76           moltype = DNA   length = 33
FEATURE                 Location/Qualifiers
source                  1..33
                        mol_type = unassigned DNA
                        organism = Vibrio cholerae
CDS                     1..33
                        protein_id = 78
                        translation = NLNREDKQRVD
SEQUENCE: 76
aatttaaata gggaagataa gcaaagggtt gac                               33

SEQ ID NO: 77           moltype = DNA   length = 31
FEATURE                 Location/Qualifiers
source                  1..31
                        mol_type = unassigned DNA
                        organism = Vibrio cholerae
SEQUENCE: 77
tttaaatagg gaagataagc aaagggttga c                                 31

SEQ ID NO: 78           moltype = AA    length = 11
FEATURE                 Location/Qualifiers
source                  1..11
                        mol_type = protein
                        organism = Vibrio cholerae
SEQUENCE: 78
NLNREDKQRV D                                                       11

SEQ ID NO: 79           moltype = DNA   length = 32
FEATURE                 Location/Qualifiers
misc_feature            1..32
                        note = Synthetic oligonucleotide
source                  1..32
                        mol_type = other DNA
                        organism = synthetic construct
SEQUENCE: 79
cattgcaact atgcaaaatg atgaagctaa aa                                32

SEQ ID NO: 80           moltype = DNA   length = 32
FEATURE                 Location/Qualifiers
misc_feature            1..32
                        note = Synthetic oligonucleotide
source                  1..32
                        mol_type = other DNA
                        organism = synthetic construct
SEQUENCE: 80
tgttagagtc ggtagtatct ggatgatcga ta                                32

SEQ ID NO: 81           moltype = DNA   length = 32
FEATURE                 Location/Qualifiers
misc_feature            1..32
                        note = Synthetic oligonucleotide
source                  1..32
                        mol_type = other DNA
                        organism = synthetic construct
SEQUENCE: 81
ttatgtattg accccgacac gccccccgac tg                                32

SEQ ID NO: 82           moltype = DNA   length = 32
FEATURE                 Location/Qualifiers
misc_feature            1..32
                        note = Synthetic oligonucleotide
source                  1..32
                        mol_type = other DNA
                        organism = synthetic construct
SEQUENCE: 82
```
ttacagacga cctaactctt cagtaccatg at                                       32

SEQ ID NO: 83          moltype = DNA   length = 32
FEATURE                Location/Qualifiers
misc_feature           1..32
                       note = Synthetic oligonucleotide
source                 1..32
                       mol_type = other DNA
                       organism = synthetic construct
SEQUENCE: 83
tacataagct gcaacacggt gttcgtttaa gt                                       32

SEQ ID NO: 84          moltype = DNA   length = 32
FEATURE                Location/Qualifiers
misc_feature           1..32
                       note = Synthetic oligonucleotide
source                 1..32
                       mol_type = other DNA
                       organism = synthetic construct
SEQUENCE: 84
aaaatacgcc ttttcccttt catcgtttaa ag                                       32

SEQ ID NO: 85          moltype = DNA   length = 32
FEATURE                Location/Qualifiers
misc_feature           1..32
                       note = Synthetic oligonucleotide
source                 1..32
                       mol_type = other DNA
                       organism = synthetic construct
SEQUENCE: 85
accaacaaat cccataaact gataaccacg tt                                       32

SEQ ID NO: 86          moltype = DNA   length = 32
FEATURE                Location/Qualifiers
misc_feature           1..32
                       note = Synthetic oligonucleotide
source                 1..32
                       mol_type = other DNA
                       organism = synthetic construct
SEQUENCE: 86
gtcaaccctt tgcttatctt ccctatttaa at                                       32

SEQ ID NO: 87          moltype = DNA   length = 32
FEATURE                Location/Qualifiers
misc_feature           1..32
                       note = Synthetic oligonucleotide
source                 1..32
                       mol_type = other DNA
                       organism = synthetic construct
SEQUENCE: 87
tgttaaccac cgcttgaaat aatcatgatg ca                                       32

SEQ ID NO: 88          moltype = DNA   length = 32
FEATURE                Location/Qualifiers
misc_feature           1..32
                       note = Synthetic oligonucleotide
source                 1..32
                       mol_type = other DNA
                       organism = synthetic construct
SEQUENCE: 88
tgtgtctata ctcaaccaat ttaagcgccg ca                                       32

SEQ ID NO: 89          moltype = DNA   length = 32
FEATURE                Location/Qualifiers
misc_feature           1..32
                       note = Synthetic oligonucleotide
source                 1..32
                       mol_type = other DNA
                       organism = synthetic construct
SEQUENCE: 89
ctactctccc caatattagc cattcctaat tc                                       32

SEQ ID NO: 90          moltype = DNA   length = 32
FEATURE                Location/Qualifiers
misc_feature           1..32
                       note = Synthetic oligonucleotide
source                 1..32
                       mol_type = other DNA
                       organism = synthetic construct

```
SEQUENCE: 90
gtcaccttac cgtaagacag gcagtaaaat ta                                  32

SEQ ID NO: 91            moltype = DNA   length = 32
FEATURE                  Location/Qualifiers
misc_feature             1..32
                         note = Synthetic oligonucleotide
source                   1..32
                         mol_type = other DNA
                         organism = synthetic construct
SEQUENCE: 91
aaactagtgg acgtaatgca gtattcacgg tt                                  32

SEQ ID NO: 92            moltype = DNA   length = 32
FEATURE                  Location/Qualifiers
misc_feature             1..32
                         note = Synthetic oligonucleotide
source                   1..32
                         mol_type = other DNA
                         organism = synthetic construct
SEQUENCE: 92
atccacacta caaatagaac actcaaccgt ga                                  32

SEQ ID NO: 93            moltype = DNA   length = 32
FEATURE                  Location/Qualifiers
misc_feature             1..32
                         note = Synthetic oligonucleotide
source                   1..32
                         mol_type = other DNA
                         organism = synthetic construct
SEQUENCE: 93
tgtgtctata ctcaaccaat ttaagcgccg ca                                  32

SEQ ID NO: 94            moltype = DNA   length = 32
FEATURE                  Location/Qualifiers
misc_feature             1..32
                         note = Synthetic oligonucleotide
source                   1..32
                         mol_type = other DNA
                         organism = synthetic construct
SEQUENCE: 94
ctactctccc caatattagc cattcctaat tc                                  32

SEQ ID NO: 95            moltype = DNA   length = 32
FEATURE                  Location/Qualifiers
misc_feature             1..32
                         note = Synthetic oligonucleotide
source                   1..32
                         mol_type = other DNA
                         organism = synthetic construct
SEQUENCE: 95
aaactagtgg acgtaatgca gtattcacgg tt                                  32

SEQ ID NO: 96            moltype = DNA   length = 32
FEATURE                  Location/Qualifiers
misc_feature             1..32
                         note = Synthetic oligonucleotide
source                   1..32
                         mol_type = other DNA
                         organism = synthetic construct
SEQUENCE: 96
ataatcgttt tgagtctcac cagcttttag gc                                  32

SEQ ID NO: 97            moltype = DNA   length = 32
FEATURE                  Location/Qualifiers
misc_feature             1..32
                         note = Synthetic oligonucleotide
source                   1..32
                         mol_type = other DNA
                         organism = synthetic construct
SEQUENCE: 97
atccacacta caaatagaac actcaaccgt ga                                  32

SEQ ID NO: 98            moltype = DNA   length = 32
FEATURE                  Location/Qualifiers
misc_feature             1..32
                         note = Synthetic oligonucleotide
source                   1..32
                         mol_type = other DNA
```

```
                        organism = synthetic construct
SEQUENCE: 98
tattgattgg tctctaacct tgggatgatt aa                                 32

SEQ ID NO: 99           moltype = DNA  length = 32
FEATURE                 Location/Qualifiers
misc_feature            1..32
                        note = Synthetic oligonucleotide
source                  1..32
                        mol_type = other DNA
                        organism = synthetic construct
SEQUENCE: 99
ttcacgggta gcaacagggt aataaaccaa ta                                 32

SEQ ID NO: 100          moltype = DNA  length = 32
FEATURE                 Location/Qualifiers
misc_feature            1..32
                        note = Synthetic oligonucleotide
source                  1..32
                        mol_type = other DNA
                        organism = synthetic construct
SEQUENCE: 100
cattgcaact atgcaaaatg atgaagctaa aa                                 32

SEQ ID NO: 101          moltype = DNA  length = 32
FEATURE                 Location/Qualifiers
misc_feature            1..32
                        note = Synthetic oligonucleotide
source                  1..32
                        mol_type = other DNA
                        organism = synthetic construct
SEQUENCE: 101
tgttagagtc ggtagtatct ggatgatcga ta                                 32

SEQ ID NO: 102          moltype = DNA  length = 32
FEATURE                 Location/Qualifiers
misc_feature            1..32
                        note = Synthetic oligonucleotide
source                  1..32
                        mol_type = other DNA
                        organism = synthetic construct
SEQUENCE: 102
tagaagagta ataggagcta ctgcaaactt gt                                 32

SEQ ID NO: 103          moltype = DNA  length = 32
FEATURE                 Location/Qualifiers
misc_feature            1..32
                        note = Synthetic oligonucleotide
source                  1..32
                        mol_type = other DNA
                        organism = synthetic construct
SEQUENCE: 103
taactatgtg tggtttatat tttgtgtgca ag                                 32

SEQ ID NO: 104          moltype = DNA  length = 32
FEATURE                 Location/Qualifiers
misc_feature            1..32
                        note = Synthetic oligonucleotide
source                  1..32
                        mol_type = other DNA
                        organism = synthetic construct
SEQUENCE: 104
ttttgaaact attgacagaa ggttgggaac ct                                 32

SEQ ID NO: 105          moltype = DNA  length = 32
FEATURE                 Location/Qualifiers
misc_feature            1..32
                        note = Synthetic oligonucleotide
source                  1..32
                        mol_type = other DNA
                        organism = synthetic construct
SEQUENCE: 105
ttgaggttga acctcttccg gttcctcttc tg                                 32

SEQ ID NO: 106          moltype = DNA  length = 32
FEATURE                 Location/Qualifiers
misc_feature            1..32
                        note = Synthetic oligonucleotide
source                  1..32
```

```
                        mol_type = other DNA
                        organism = synthetic construct
SEQUENCE: 106
gtgtattgct tgcagtgggt tacacacaag aa                                     32

SEQ ID NO: 107          moltype = DNA   length = 47
FEATURE                 Location/Qualifiers
source                  1..47
                        mol_type = unassigned DNA
                        organism = Bacteroides fragilis
SEQUENCE: 107
gttgtgattt gctttcaaat tagtatcttt gaaccattgg aaacagc                     47

SEQ ID NO: 108          moltype = DNA   length = 29
FEATURE                 Location/Qualifiers
source                  1..29
                        mol_type = unassigned DNA
                        organism = Bacteroides fragilis
SEQUENCE: 108
atttcaattc cataaggtac aattaatac                                         29

SEQ ID NO: 109          moltype = DNA   length = 32
FEATURE                 Location/Qualifiers
source                  1..32
                        mol_type = unassigned DNA
                        organism = Bacteroides helcogenes
SEQUENCE: 109
gtttcaatcc acacaccegt atagggtgtg ac                                     32

SEQ ID NO: 110          moltype = DNA   length = 47
FEATURE                 Location/Qualifiers
source                  1..47
                        mol_type = unassigned DNA
                        organism = Bacteroides sp.
SEQUENCE: 110
actgtttctg atatgtcaaa gataaaattt tgaaagcaaa tcacaac                     47

SEQ ID NO: 111          moltype = DNA   length = 23
FEATURE                 Location/Qualifiers
source                  1..23
                        mol_type = unassigned DNA
                        organism = Bacteroides thetaiotaomicron
SEQUENCE: 111
gaaaaaatac agtttcgctc tca                                               23

SEQ ID NO: 112          moltype = DNA   length = 32
FEATURE                 Location/Qualifiers
source                  1..32
                        mol_type = unassigned DNA
                        organism = Prevotella dentalis
SEQUENCE: 112
gtcgcgtctc acgtaggcgc gtggattgaa ac                                     32

SEQ ID NO: 113          moltype = DNA   length = 47
FEATURE                 Location/Qualifiers
source                  1..47
                        mol_type = unassigned DNA
                        organism = Prevotella denticola
SEQUENCE: 113
attgtgcttg ctactgcaaa gatacacatt ttgaagcaat tcacaac                     47

SEQ ID NO: 114          moltype = DNA   length = 37
FEATURE                 Location/Qualifiers
source                  1..37
                        mol_type = unassigned DNA
                        organism = Prevotella denticola
SEQUENCE: 114
ctcaatgagt atcttccatt aaaacaagga ttaagac                                37

SEQ ID NO: 115          moltype = DNA   length = 36
FEATURE                 Location/Qualifiers
source                  1..36
                        mol_type = unassigned DNA
                        organism = Prevotella intermedia
SEQUENCE: 115
gttgttttta ccttgcaaac agcaggcaga tacaac                                 36

SEQ ID NO: 116          moltype = DNA   length = 47
FEATURE                 Location/Qualifiers
```

```
source                  1..47
                        mol_type = unassigned DNA
                        organism = Prevotella intermedia
SEQUENCE: 116
gttgtatttg ccaatgcaaa gatactaatt ttaaagctaa tcacaac                    47

SEQ ID NO: 117          moltype = DNA  length = 36
FEATURE                 Location/Qualifiers
source                  1..36
                        mol_type = unassigned DNA
                        organism = Prevotella ruminicola
SEQUENCE: 117
gttgtatatc attcctttcc tacatcaaac cacaac                                36

SEQ ID NO: 118          moltype = DNA  length = 29
FEATURE                 Location/Qualifiers
source                  1..29
                        mol_type = unassigned DNA
                        organism = Clostridium difficile
SEQUENCE: 118
atttacatac cacttagtta atataaaac                                        29

SEQ ID NO: 119          moltype = DNA  length = 29
FEATURE                 Location/Qualifiers
source                  1..29
                        mol_type = unassigned DNA
                        organism = Clostridium difficile
SEQUENCE: 119
gttttatatt aactaagtgg tatgtaaat                                        29

SEQ ID NO: 120          moltype = DNA  length = 112
FEATURE                 Location/Qualifiers
misc_feature            1..112
                        note = Synthetic polynucleotide
source                  1..112
                        mol_type = other DNA
                        organism = synthetic construct
SEQUENCE: 120
ttaaataacg aaaacaccct gccataaaat gacagggtgt tgatttcggc atgaagcctt      60
atctttgtag cttctgcaag atttaagtaa ctgtgtaagg cgtcccttac ac             112

SEQ ID NO: 121          moltype = DNA  length = 30
FEATURE                 Location/Qualifiers
misc_feature            1..30
                        note = Synthetic oligonucleotide
source                  1..30
                        mol_type = other DNA
                        organism = synthetic construct
SEQUENCE: 121
tgtcctatga atcagctcct tttctcggcc                                       30

SEQ ID NO: 122          moltype = DNA  length = 30
FEATURE                 Location/Qualifiers
misc_feature            1..30
                        note = Synthetic oligonucleotide
source                  1..30
                        mol_type = other DNA
                        organism = synthetic construct
SEQUENCE: 122
ggctataaga taaactacgg gcaagtttga                                       30

SEQ ID NO: 123          moltype = DNA  length = 974
FEATURE                 Location/Qualifiers
misc_feature            1..974
                        note = Synthetic polynucleotide
source                  1..974
                        mol_type = other DNA
                        organism = synthetic construct
SEQUENCE: 123
gcggataaca attactagag aaagaggaga aatactattc ttctcctctt taaataacga      60
aaacaccctg ccataaaatg acagggtgtt gatttcggca tgaagcctta tctttgtagc    120
ttctgcaaga tttaagtaac tgtgtaaggc gtcccttaca cttgcatgta gcggataaca    180
attactagag aaagaggaga aatactattc ttctcctctt taaataacga aaacaccctg    240
ccataaaatg acagggtgtt gatttcggca tgaagcctta tctttgtagc ttctgcaaga    300
tttaagtaac tgtgtaaggc gtcccttaca cttgcatgta tagttattat accagggga     360
cagtgcaatg tcaagaataa actgtagaat gactagtgac ttaaatcttg agagtacaaa    420
aacccgttgg aatcgtgatt aatagtaact gttgttgtac agttacttaa atcttgagag    480
tacaaaaacg gccgagaaaa ggagctgatt cataggacag ttgtacagtt acttaaatct    540
tgagagtaca aaaactcaaa cttgcccgta gtttatctta tagccgttgt acagttactt    600
```

-continued

```
aaatcttgag agtacaaaaa catttacctc ctttgattta agtgaacaag tttatcctag  660
ttattatacc aggggacag tgcaatgtca agaataaact gtagaatgac tagtgactta  720
aatcttgaga gtacaaaaac ccgttggaat cgtgattaat agtaactgtt gttgtacagt  780
tacttaaatc ttgagagtac aaaaacggcc gagaaaagga gctgattcat aggacagttg  840
tacagttact taaatcttga gagtacaaaa actcaaactt gcccgtagtt tatcttatag  900
ccgttgtaca gttacttaaa tcttgagagt acaaaaacat ttacctcctt tgatttaagt  960
gaacaagttt atcc                                                     974

SEQ ID NO: 124          moltype = DNA  length = 221
FEATURE                 Location/Qualifiers
misc_feature            1..221
                        note = Synthetic polynucleotide
source                  1..221
                        mol_type = other DNA
                        organism = synthetic construct
SEQUENCE: 124
ttaaatcttg agagtacaaa aacccgttgg aatcgtgatt aatagtaact gttgttgtac   60
agttacttaa atcttgagag tacaaaaacg gccgagaaaa ggagctgatt cataggacag  120
ttgtacagtt acttaaatct tgagagtaca aaaactcaaa cttgcccgta gtttatctta  180
tagccgttgt acagttactt aaatcttgag agtacaaaaa c                      221

SEQ ID NO: 125          moltype = DNA  length = 32
FEATURE                 Location/Qualifiers
source                  1..32
                        mol_type = unassigned DNA
                        organism = Desulfovibrio vulgaris
SEQUENCE: 125
gtcgccccc acgcgggggc gtggattgaa ac                                   32

SEQ ID NO: 126          moltype = DNA  length = 32
FEATURE                 Location/Qualifiers
source                  1..32
                        mol_type = unassigned DNA
                        organism = Desulfobulbus propionicus
SEQUENCE: 126
gtcgccccc acgcgggggc gtggattgaa ac                                   32

SEQ ID NO: 127          moltype = DNA  length = 25
FEATURE                 Location/Qualifiers
source                  1..25
                        mol_type = unassigned DNA
                        organism = Desulfurispirillum indicum
SEQUENCE: 127
aacctttctg caaaaggtt tcccc                                           25

SEQ ID NO: 128          moltype = DNA  length = 28
FEATURE                 Location/Qualifiers
source                  1..28
                        mol_type = unassigned DNA
                        organism = Desulfovibrio gigas
SEQUENCE: 128
tttctgagct gcctatgcgg cagtgaac                                       28
```

ALTERING MICROBIAL POPULATIONS AND MODIFYING MICROBIOTA

CROSS REFERENCE TO RELATED APPLICATIONS

This application is a Continuation of U.S. application Ser. No. 16/813,615 filed Mar. 9, 2020, now U.S. Pat. No. 11,844,760, which is a Divisional of U.S. application Ser. No. 15/460,962 filed Mar. 16, 2017, now U.S. Pat. No. 10,582,712, which is a Continuation of U.S. application Ser. No. 15/160,405 filed May 20, 2016, now U.S. Pat. No. 9,701,964, which is a Continuation Application under 35 U.S.C. § 120 of International Patent Application No. PCT/EP2016/059803 filed on May 3, 2016, which claims priority to GB Application Numbers 1507773.8, filed on May 6, 2015; 1507774.6, filed on May 6, 2015; 1507775.3, filed on May 6, 2015; 1507776.1, filed on May 6, 2015; 1508461.9, filed on May 17, 2015; 1509366.9, filed on May 31, 2015; 1510891.3, filed on Jun. 20, 2015; 1518402.1, filed on Oct. 17, 2015; 1600417.8, filed on Jan. 10, 2016; and 1600418.6, filed on Jan. 10, 2016, the contents of which are incorporated herein by reference in their entirety.

REFERENCE TO AN ELECTRONIC SEQUENCE LISTING

The content of the electronic sequence listing (786212500106SEQLIST.xml; Size: 114,171 bytes; and Date of Creation: Oct. 31, 2023) is herein incorporated by reference in its entirety.

FIELD OF THE INVENTION

The invention relates to methods of inhibiting bacterial population growth, altering the relative ratio of sub-populations of first and second bacteria in a mixed population of bacteria, nucleic acid arrays for this purpose and vectors comprising the arrays. The invention relates to engineered systems for modifying host cell nucleic acid, components of such systems and application of these in industry and medicine. The invention is particularly useful, for example, for treatment of microbes such as for environmental, food and beverage use. The invention relates inter alia to methods of controlling microbiologically influenced corrosion (MIC) or biofouling of a substrate or fluid in an industrial or domestic system. The invention also relates to treated fluids and vectors for use in the methods. In embodiments, the methods use horizontal transfer of arrays. The invention also provides arrays comprised by mobile genetic elements (MGEs) for this purpose and vectors comprising these arrays.

BACKGROUND OF THE INVENTION

Inhibiting bacterial population growth and altering the relative ratios of different bacterial species in a mixture finds application in a wide range of industries and settings, for example for treatment of waterways, drinking water or in other environmental settings. Application is also found in altering bacteria in humans and non-human animals, eg, livestock, for reducing pathogenic infections or for re-balancing gut or oral microbiota. Recently, there has been interest in analysing the relative proportions of gut bacteria in humans with differing body mass or obesity profiles, or in investigating possible bacterial influence in disease contexts such as Crohn's disease.

Although bacterial innate immune mechanisms against phage abound, an extensively documented bacterial adaptive immune system is the CRISPR/Cas system. Engineered CRISPR/Cas systems have been used for precise modification of nucleic acid in various types of prokaryotic and eukaryotic cells, ranging from bacterial to animal and plant cells (eg, see Jiang W et al (2013)). Prokaryotes, such as bacteria and archaea, encode adaptive immune systems, called CRISPR/Cas (clustered regularly interspaced short palindromic repeats/CRISPR associated), to provide resistance against mobile invaders, such as viruses (eg, bacteriophage) and plasmids. Reference is made to Seed et al (2013), which explains that bacteriophages (or phages) are the most abundant biological entities on earth, and are estimated to outnumber their bacterial prey by tenfold. The constant threat of phage predation has led to the evolution of a broad range of bacterial immunity mechanisms that in turn result in the evolution of diverse phage immune evasion strategies, leading to a dynamic co-evolutionary arms race.

Host immunity is based on incorporation of invader DNA sequences in a memory locus (CRISPR array), the formation of guide RNAs from this locus, and the degradation of cognate invader DNA (protospacer) situated adjacent a protospacer adjacent motif (PAM). See, for example WO2010/075424. The host CRISPR array comprises various elements: a leader (including a promoter) immediately 5' of one or more repeat-spacer-repeat units where the repeats are identical and the spacers differ. By acquiring spacer sequence from invading virus or plasmid nucleic acid, the host defence system is able to incorporate new spacers into the CRISPR array (each spacer flanked by repeats) to act as a memory to tackle future invasion by the virus or plasmid. It has been observed that recently-acquired spacers tend to be inserted into the host array directly after the leader.

Reference is made to Heler et al (2014), which explains that CRISPR loci and their associated genes (Cas) confer bacteria and archaea with adaptive immunity against phages and other invading genetic elements. A fundamental requirement of any immune system is the ability to build a memory of past infections in order to deal more efficiently with recurrent infections. The adaptive feature of CRISPR-Cas immune systems relies on their ability to memorize DNA sequences of invading molecules and integrate them in between the repetitive sequences of the CRISPR array in the form of 'spacers'. The transcription of a spacer generates a small antisense RNA that is used by RNA-guided Cas nucleases to cleave the invading nucleic acid in order to protect the cell from infection. The acquisition of new spacers allows the CRISPR-Cas immune system to rapidly adapt against new threats and is therefore termed 'adaptation' (ie, vector sequence spacer acquisition).

Seed et al (2013) reported a remarkable turn of events, in which a phage-encoded CRISPR/Cas system was used to counteract a phage inhibitory chromosomal island of the bacterial host. A successful lytic infection by the phage reportedly was dependent on sequence identity between CRISPR spacers and the target chromosomal island. In the absence of such targeting, the phage-encoded CRISPR/Cas system could acquire new spacers to evolve rapidly and ensure effective targeting of the chromosomal island to restore phage replication. Bondy-Denomy et al (2012) describe the early observed examples of genes that mediate the inhibition of a CRISPR/Cas system. Five distinct 'anti-CRISPR' genes were found in the genomes of bacteriophages infecting *Pseudomonas aeruginosa*. Mutation of the anti-CRISPR gene of a phage rendered it unable to infect bacteria with a functional CRISPR/Cas system, and the addition of the same gene to the genome of a CRISPR/Cas-targeted phage allowed it to evade the CRISPR/Cas system.

Immature RNAs are transcribed from CRISPR arrays and are subsequently matured to form crRNAs. Some CRISPR/Cas systems also comprise sequences encoding trans-activating RNAs (tracrRNAs) that are able to hybridise to repeats in the immature crRNAs to form pre-crRNAs, whereby further processing produces mature, or crRNAs. The architecture of cRNAs varies according to the type (Type I, II or III) CRISPR/Cas system involved.

CRISPR-associated (cas) genes are often associated with CRISPR arrays. Extensive comparative genomics have identified many different cas genes; an initial analysis of 40 bacterial and archaeal genomes suggested that there may be 45 cas gene families, with only two genes, cas1 and cas2, universally present. Cas1 and Cas2 are believed to be essential for new spacer acquisition into arrays, thus are important in mechanisms of developing resistance to invader nucleic acid from phage or plasmids. Nunez et al (2015) reportedly demonstrated the Cas1-Cas2 complex to be the minimal machinery that catalyses spacer DNA acquisition and apparently explain the significance of CRISPR repeats in providing sequence and structural specificity for Cas1-Cas2-mediated adaptive immunity.

CRISPR/Cas systems also include sequences expressing nucleases (eg, Cas9) for cutting invader nucleic acid adjacent cognate recognition motifs (PAMs) in invader nucleotide sequences. PAM recognition of nucleases is specific to each type of Cas nuclease. The PAMs in the invader sequences may lie immediately 3' of a protospacer sequence, with nucleases typically cutting 3-4 nucleotides upstream of (5' of) the PAM. The conservation of the PAM sequence differs between CRISPR-Cas systems and appears to be evolutionarily linked to cas1 and the leader sequence. Fineran et al (2014) observed that Invaders can escape type I-E CRISPR-Cas immunity in *Escherichia coli* K12 by making point mutations in a region (the "seed region") of the protospacer or its adjacent PAM, but hosts quickly restore immunity by integrating new spacers in a positive-feedback process involving acquisition ("priming"). To date, the PAM has been well characterized in a number of type I and type II systems and the effect of mutations in the protospacer has been documented (see references 5, 14, 23, 46, 47 in Fineran et al (2014)). Fineran et al (2014) concluded that their results demonstrated the critical role of the PAM and the seed sequence, in agreement with previous work.

Semenova et al (2011) investigated the role of the seed sequence and concluded that that in the case of *Escherichia coli* subtype CRISPR/Cas system, the requirements for crRNA matching are strict for the seed region immediately following the PAM. They observed that mutations in the seed region abolish CRISPR/Cas mediated immunity by reducing the binding affinity of the crRNA-guided Cascade complex to protospacer DNA.

The stages of CRISPR immunity for each of the three major types of adaptive immunity are as follows:—
 (1) Acquisition begins by recognition of invading DNA by Cas1 and Cas2 and cleavage of a protospacer;
 (2) A protospacer sequence is ligated to the direct repeat adjacent to the leader sequence; and
 (3) Single strand extension repairs the CRISPR and duplicates the direct repeat.

The crRNA processing and interference stages occur differently in each of the three major types of CRISPR systems. The primary CRISPR transcript is cleaved by Cas to produce crRNAs. In type I systems Cas6e/Cas6f cleave at the junction of ssRNA and dsRNA formed by hairpin loops in the direct repeat. Type II systems use a trans-activating (tracr) RNA to form dsRNA, which is cleaved by Cas9 and RNaseIII. Type III systems use a Cas6 homolog that does not require hairpin loops in the direct repeat for cleavage. In type II and type III systems secondary trimming is performed at either the 5' or 3' end to produce mature crRNAs. Mature crRNAs associate with Cas proteins to form interference complexes. In type I and type II systems, base-pairing between the crRNA and the PAM causes degradation of invading DNA. Type III systems do not require a PAM for successful degradation and in type III-A systems base-pairing occurs between the crRNA and mRNA rather than the DNA, targeted by type III-B systems.

STATEMENTS OF INVENTION

First Configuration of the Invention

The inventors believe that they have demonstrated for the first time inhibition of population growth of a specific bacterial strain in a mixed consortium of bacteria that naturally occur together in microbiota (human, animal or environmental microbiota) with one or more of the following features:—
 Population growth inhibition by
 targeting wild-type cells;
 harnessing of wild-type endogenous Cas nuclease activity;
 targeting essential and antibiotic resistance genes;
 wherein the targets are wild-type sequences.

The inventors have demonstrated this in a mixed bacterial population with the following features:—
 targeting bacterial growth inhibition in a mixed population of human microbiota (such as gut microbiota) species;
 wherein the population comprises three different species;
 comprising selective killing of one of those species and sparing cells of the other species;
 targeting cell growth inhibition in the presence of a phylogenetically-close other species, which is spared such inhibition;
 targeting cell growth inhibition in a mixed population comprising target Firmicutes species and non-firmicutes species;
 targeting cell growth inhibition of a specific Firmicutes strain whilst sparing a different Firmicutes species in a mixed population;
 targeting cell growth inhibition of a specific gram positive bacterial strain whilst sparing a different gram positive bacterial species in a mixed population;
 targeting a pathogenic (in humans) bacterial species whilst sparing a commensul human gut bacterial species;
 targeting a pathogenic bacterial species whilst sparing a probiotic human gut bacterial species;
 targeting cell growth inhibition in a mixed bacterial population on a surface;
 achieving at least a 10-fold growth inhibition of a specific bacterial species alone or when mixed with a plurality of other bacterial species in a consortium; and
 achieving at least a 10-fold growth inhibition of two different strains of a specific bacterial species.

The ability to harness endogenous Cas activity in wild-type cells is very useful for in situ treatment of host cell infections in organisms (humans and animals, for example) and the environment. Treatment of wild-type (ie, non-engineered or pre-manipulated) bacterial populations, such as human, animal or plant microbiota can also be addressed using the invention. The ability to effect selective growth inhibition in a mixed population is useful for addressing bacterial populations, such as human, animal or plant microbiota, or for addressing environmental microbiomes. This feature is also useful for producing medicaments (eg, bacterial cell transplants for administration to a human or animal subject for any treatment or prevention disclosed herein; or for producing a herbicide or insecticide composition comprising the product bacterial population of the invention), wherein the selective killing can be used to selectively alter the ratio of different bacteria in a mixed population to produce an altered bacterial population which is the medicament, herbicide or insecticide; or from which the medicament, herbicide or insecticide is produced. For example, the medicament can be intranasally transplanted into a human or animal recipient to effect such treatment or prevention.

In the worked Example below, growth inhibition was addressed in a bacterial population (a gram positive Firmicutes population) on a solid surface. A >10-fold population growth inhibition was achieved. Targeting was directed to an antibiotic resistance gene. The invention will be useful in inhibiting the growth of antibiotic-resistant bacteria, wherein the target sequence is a sequence of an antibiotic resistance gene. In an example, co-administration of the engineered nucleotide sequence with the antibiotic may be effective. This may provide more complete treatment or prevention of host cell infection in human or animal subjects and/or enable the reduction of therapeutically-effective antibiotic dose for administration to a human or animal. This is useful in view of the increasing worry regarding over-administration of antibiotics and the development of resistance in human and animal populations. The invention also finds application ex vivo and in vitro for treating an industrial or medical fluid, surface, apparatus or container (eg, for food, consumer goods, cosmetics, personal healthcare product, petroleum or oil production); or for treating a waterway, water, a beverage, a foodstuff or a cosmetic, wherein the host cell(s) are comprised by or on the fluid, surface, apparatus, container, waterway, water, beverage, foodstuff or cosmetic. The invention finds application also in control of corrosion, biofilms and biofouling. The first configuration thus provides the following concepts:—

Use of a host modifying (HM) CRISPR/Cas system for altering the relative ratio of sub-populations of first and second bacteria in a mixed population of bacteria, the second bacteria comprising host cells,
  for each host cell the system comprising components according to (i) to (iv):—
  (i) at least one nucleic acid sequence encoding a Cas nuclease;
  (ii) a host cell target sequence and an engineered host modifying (HM) CRISPR array comprising a spacer sequence (HM-spacer) and repeats encoding a HM-crRNA, the HM-crRNA comprising a sequence that hybridises to the host cell target sequence to guide said Cas to the target in the host cell to modify the target sequence;
  (iii) an optional tracrRNA sequence or a DNA sequence expressing a tracrRNA sequence;
  (iv) wherein said components of the system are split between the host cell and at least one nucleic acid vector that transforms the host cell, whereby the HM-crRNA guides Cas to the target to modify the host CRISPR/Cas system in the host cell; and wherein the target sequence is modified by the Cas whereby the host cell is killed or host cell growth is reduced.

A host modifying (HM) CRISPR/Cas system for the use of claim 1 for modifying a target nucleotide sequence of a bacterial host cell, the system comprising components according to (i) to (iv):—
  (i) at least one nucleic acid sequence encoding a Cas nuclease;
  (ii) a host cell target sequence and an engineered host modifying (HM) CRISPR array comprising a spacer sequence (HM-spacer) and repeats encoding a HM-crRNA, the HM-crRNA comprising a sequence that is capable of hybridising to the host target sequence to guide said Cas to the target in the host cell to modify the target sequence;
  (iii) an optional tracrRNA sequence or a DNA sequence for expressing a tracrRNA sequence;
  (iv) wherein said components of the system are split between the host cell and at least one nucleic acid vector that can transform the host cell, whereby the HM-crRNA guides Cas to the target to modify the host CRISPR/Cas system in the host cell.

This is exemplified by the worked Examples herein where we show selective host cell growth inhibition by at least 10-fold in a mixed and non-mixed cell population. The mixture simulates a combination of species and strains found in human microbiota.

Use of wild-type endogenous Cas nuclease activity of a bacterial host cell population to inhibit growth of the population, wherein each host cell has an endogenous CRISPR/Cas system having wild-type Cas nuclease activity, the use comprising transforming host cells of the population, wherein each transformed host cell is transformed with an engineered nucleotide sequence for providing host modifying (HM) cRNA or guide RNA (gRNA) in the host cell, the HM-cRNA or gRNA comprising a sequence that is capable of hybridising to a host cell target protospacer sequence for guiding endogenous Cas to the target, wherein the cRNA or gRNA is cognate to an endogenous Cas nuclease of the host cell that has said wild-type nuclease activity and following transformation of the host cells growth of the population is inhibited.

Use (optionally the use is according to the use of the immediately preceding paragraph above) of a host modifying (HM) CRISPR/Cas system for killing or reducing the growth of bacterial host cells, for each host cell the system comprising components according to (i) to (iv):—
  (i) at least one nucleic acid sequence encoding a Cas nuclease;
  (ii) an engineered host modifying (HM) CRISPR array comprising a spacer sequence (HM-spacer) and repeats encoding a HM-crRNA, the HM-crRNA comprising a sequence that hybridises to a host cell target sequence to guide said Cas to the target in the host cell to modify the target sequence;
  (iii) an optional tracrRNA sequence or a DNA sequence expressing a tracrRNA sequence;
  (iv) wherein said components of the system are split between the host cell and at least one nucleic acid vector that transforms the host cell, whereby the HM-crRNA guides Cas to the target to modify the target sequence in the host cell;
  Wherein the Cas nuclease is endogenous to the host cell; and wherein the target sequence is modified by the Cas whereby the host cell is killed or host cell growth is reduced.

Thus, the HM-cRNA is capable of hybridising to the host cell target sequence to guide said Cas to the target in the host cell to modify the target sequence.

In an alternative, HM-crRNA and tracrRNA are comprised by a single guide RNA (gRNA).

By harnessing endogenous Cas nuclease, embodiments of the invention use endogenous Cas nuclease activity (ie, without the need for prior genetic modification of the host cell to activate or enhance the nuclease activity). Thus, in an example, the Cas nuclease is encoded by a wild-type gene of the host cell. In an example, the nuclease is active to achieve the cell killing or growth inhibition without inactivation of an endogenous Cas nuclease (or Cas nuclease gene) repressor in the host cell. Thus, the invention can address wild-type bacterial populations without the need for prior manipulation to bring about effective Cas-mediated cell killing or growth reduction. Thus, the population can be exposed to the cRNA when the population is in its wild-type environment (such as a waterway or comprised by a human or animal microbiome).

In an example, the first bacteria are Bacteroidetes (eg, *Bacteroides*) cells. In an example, the second bacteria are Firmicutes cells. The method is, for example, used to alter the ratios in a gut microbiota population (eg, ex vivo or in vivo), which is for example for treating or preventing increased body mass or obesity (eg, wherein the first bacteria are Firmicutes cells).

The first configuration also provides: A method of altering the relative ratio of sub-populations of first and second bacteria in a mixed population of bacteria comprising said sub-populations, wherein the first bacteria are host cells (eg, Bacteroidetes cells) infected by a phage and the second bacteria are not infected by said phage (or not Bacteroidetes bacteria), the method comprising combining the mixed population with a plurality of vectors in one or more steps for introduction of vector nucleic acid into host cells and allowing bacterial growth in the mixed population, wherein the relative ratios of said first and second bacteria is altered;

wherein each vector comprises an engineered phage-modifying (PM) CRISPR array for introduction into a phage-infected host cell for modifying a target nucleotide sequence of said phage in the cell,
(a) wherein the PM-CRISPR array comprises one or more sequences for expression of a PM-crRNA and a promoter for transcription of the sequence(s) in a phage-infected host cell; and
(b) wherein the PM-crRNA is capable of hybridising to the phage target sequence to guide Cas (eg, a Cas nuclease) in the infected host cell to modify the target sequence.

In a second configuration, the invention provides:—

A host modifying (HM) CRISPR/Cas system for modifying a target nucleotide sequence of a host cell (eg, for the use of the first configuration), the system comprising components according to (i) to (iv):
(i) at least one nucleic acid sequence encoding a Cas nuclease;
(ii) an engineered host modifying (HM) CRISPR array comprising a spacer sequence (HM-spacer) and repeats encoding a HM-crRNA, the HM-crRNA comprising a sequence that is capable of hybridising to a host target sequence to guide said Cas to the target in the host cell to modify the target sequence;
(iii) an optional tracrRNA sequence or a DNA sequence for expressing a tracrRNA sequence;
(iv) wherein said components of the system are split between the host cell and at least one nucleic acid vector that can transform the host cell, whereby the HM-crRNA guides Cas to the target to modify the target sequence in the host cell;
wherein optionally component (i) is endogenous to the host cell.

The second configuration also provides: An engineered phage-modifying (PM) CRISPR array for use in the method of the first configuration for modifying the genome of said phage,
(a) wherein the PM-CRISPR array comprises one or more sequences for expression of a PM-crRNA and a promoter for transcription of the sequence(s) in a phage-infected host cell; and
(b) wherein the PM-crRNA is capable of hybridising to a phage genome target sequence to guide Cas (eg, a Cas nuclease) in the infected host cell to modify the target sequence.

In an example, the phage is a Bacteroidetes (eg, *Bacteroides*) phage, eg, crAssphage.

In an example, the array comprises CRISPR repeats that are functional with a host cell CRISPR/Cas system. This is beneficial to increase selectivity of the array for the desired cell in a bacterial mixture. This also simplifies production of the array and vectors containing the array of the invention as it may not be necessary to include bulky nucleotide sequences encoding one or more Cas proteins (and/or tracrRNA) required for functioning of the array in the host cell. In an alternative, the array is provided with a cognate Cas9-encoding sequence and optionally a cognate tracrRNA-encoding sequence.

In a third configuration, the invention provides:—

An engineered nucleic acid vector for modifying a bacterial host cell comprising an endogenous CRISPR/Cas system, the vector
(a) comprising nucleic acid sequences for expressing a plurality of different crRNAs (eg, single guide RNAs, ie, gRNAs) for use in a CRISPR/Cas system or use according to the invention; and
(b) lacking a nucleic acid sequence encoding a Cas nuclease, wherein a first of said crRNAs is capable of hybridising to a first nucleic acid sequence in said host cell; and a second of said crRNAs is capable of hybridising to a second nucleic acid sequence in said host cell, wherein said second sequence is different from said first sequence; and
(c) the first sequence is comprised by an antibiotic resistance gene (or RNA thereof) and the second sequence is comprised by an antibiotic resistance gene (or RNA thereof); optionally wherein the genes are different;
(d) the first sequence is comprised by an antibiotic resistance gene (or RNA thereof) and the second sequence is comprised by an essential or virulence gene (or RNA thereof);
(e) the first sequence is comprised by an essential gene (or RNA thereof) and the second sequence is comprised by an essential or virulence gene (or RNA thereof); or
(f) the first sequence is comprised by a virulence gene (or RNA thereof) and the second sequence is comprised by an essential or virulence gene (or RNA thereof).

The third configuration also provides: A nucleic acid vector (eg, a plasmid, phage or phagemid) for use in the method of the invention, the vector comprising a CRISPR array of the invention.

In a fourth configuration, the invention provides:—

A nucleic acid vector (eg, a plasmid, virus, phage or phagemid) comprising an engineered CRISPR array for modifying a target sequence of the genome of a host bacterial cell (eg, pathogenic bacterial cell, such as described above) or the genome of a virus (eg, phage) in a host cell,
- (a) wherein the CRISPR array comprises one or more sequences for expression of a crRNA (eg, provided as a gRNA) and a promoter for transcription of the sequence(s) in the host cell;
- (b) wherein the crRNA is capable of hybridising to the target sequence to guide Cas (eg, a Cas nuclease) in the host cell to modify the target sequence;
- (c) wherein the array is comprised by a transposon that is capable of horizontal transfer between first and second bacterial cells of different species.

In a fifth configuration, the invention provides:—

An engineered CRISPR nucleic acid vector comprising or consisting of a mobile genetic element (MGE), wherein the MGE comprises an origin of transfer (oriT) and a CRISPR array for modifying a target sequence of the genome of a host cell (eg, pathogenic bacterial cell) or the genome of a virus (eg, prophage) in a host cell,
- (a) wherein the CRISPR array comprises one or more sequences for expression of a crRNA and a promoter for transcription of the sequence(s) in the host cell;
- (b) wherein the crRNA is capable of hybridising to the target sequence to guide Cas (eg, a Cas nuclease) in the host cell to modify the target sequence;
- (c) wherein the vector is capable of transfer between (i) first and second nucleic acid positions of a first host cell, wherein each position is a position on a chromosome or a plasmid and the target sequence is comprised by the host cell, or (ii) first and second host cells, wherein the target sequence is comprised by the first and/or second host cell.

In a sixth configuration, the invention provides:—

A method of controlling microbiologically influenced corrosion (MIC) or biofouling of a substrate in an industrial or domestic system, wherein a surface of the substrate is in contact with a population of first host cells of a first microbial species that mediates MIC or biofouling of the substrate, the method comprising
- (i) contacting the population with a plurality of vectors that are capable of transforming or transducing the cells, each vector comprising a CRISPR array whereby CRISPR arrays are introduced into the host cells, wherein
- (a) each CRISPR array comprises one or more nucleotide sequences for expression of a crRNA and a promoter for transcription of the sequence(s) in a host cell; and
- (b) each crRNA is capable of hybridising to a target sequence of a host cell to guide Cas (eg, a Cas nuclease) in the host cell to modify the target sequence (eg, to cut the target sequence); the target sequence being a gene sequence for mediating host cell viability; and
- (ii) allowing expression of said cRNAs in the presence of Cas in host cells, thereby modifying target sequences in host cells, resulting in reduction of host cell viability and control of MIC or biofouling of said substrate.

In another embodiment, there is provided:—

A method of controlling microbiologically influenced corrosion (MIC) or biofouling of a substrate comprised by a crude oil, gas or petrochemicals recovery, processing, storage or transportation equipment, wherein a surface of the substrate is in contact with a population of first host cells, wherein the first host cells are sulphur- or sulphate-reducing bacteria (SRB), extracellular polymeric substance-producing bacteria (EPSB), acid-producing bacteria (APB), sulphur- or sulphide-oxidizing bacteria (SOB), iron-oxidising bacteria (IOB), manganese-oxidising bacteria (MOB), ammonia producing bacteria (AmPB) or acetate producing bacteria (AcPB) of a first species that mediates MIC or biofouling of the substrate, wherein the surface and cell population are in contact with a liquid selected from sea water, fresh water, a fracking liquid or liquid in a well, the method comprising
- (i) contacting the cell population with vectors by mixing the liquid with a plurality of vectors that are capable of transforming or transducing first host cells, each vector comprising a CRISPR array whereby CRISPR arrays are introduced into the host cells, wherein
  - (a) each CRISPR array comprises one or more sequences for expression of a crRNA and a promoter for transcription of the sequence(s) in a host cell;
  - (b) each crRNA is capable of hybridising to a target sequence of a host cell to guide Cas (eg, a Cas nuclease) in the host cell to modify the target sequence (eg, to cut the target sequence); the target sequence being a gene sequence for mediating host cell viability;
  - (c) wherein each sequence of (a) comprises a sequence R1-S1-R1' for expression and production of the respective crRNA in a first host cell, wherein R1 is a first CRISPR repeat, R1' is a second CRISPR repeat, and R1 or R1' is optional; and S1 is a first CRISPR spacer that comprises or consists of a nucleotide sequence that is 80% or more identical to a target sequence of a said first host cell and
- (ii) allowing expression of said cRNAs in the presence of Cas in host cells, thereby modifying target sequences in host cells, resulting in reduction of host cell viability and control of MIC or biofouling of said substrate.

Other embodiments provide:—

A vector for use in the method, wherein the first cells are sulphate reducing bacteria (SRB) cells, eg, *Desulfovibrio* or *Desulfotomaculum* cells, the vector comprising one or more CRISPR arrays for targeting the SRB, wherein each array is as defined in (a)-(c).

In another embodiment, there is provided: A method of controlling microbial biofouling of a fluid in an industrial or domestic system, wherein the fluid comprises a population of first host cells of a first microbial species that mediates said biofouling, the method comprising
- (i) contacting the population with a plurality of vectors that are capable of transforming or transducing the cells, each vector comprising a CRISPR array whereby CRISPR arrays are introduced into the host cells, wherein
- (a) each CRISPR array comprises one or more nucleotide sequences for expression of a crRNA and a promoter for transcription of the sequence(s) in a host cell; and
- (b) each crRNA is capable of hybridising to a target sequence of a host cell to guide Cas (eg, a Cas nuclease) in the host cell to modify the target sequence (eg, to cut the target sequence); the target sequence being a gene sequence for mediating host cell viability; and
- (ii) allowing expression of said cRNAs in the presence of Cas in host cells, thereby modifying target sequences in host cells, resulting in reduction of host cell viability and control of said biofouling.

For example, there is provided: A method of controlling bacterial biofouling in ballast water of a ship or boat, wherein the water comprises a population of first host cells of a first microbial species that mediates said biofouling, the method comprising (i) contacting the population with a plurality of vectors that are capable of transforming or transducing the cells, each vector comprising a CRISPR array whereby CRISPR arrays are introduced into the host cells, wherein (a) each CRISPR array comprises one or more sequences for expression of a crRNA and a promoter for transcription of the sequence(s) in a host cell; and (b) each crRNA is capable of hybridising to a target sequence of a host cell to guide Cas (eg, a Cas nuclease) in the host cell to modify the target sequence (eg, to cut the target sequence); the target sequence being a gene sequence for mediating host cell viability; and (ii) allowing expression of said cRNAs in the presence of Cas in host cells, thereby modifying target sequences in host cells, resulting in reduction of host cell viability and control of said biofouling.

Other embodiments provide: Ballast sea water (for example, a sample of sea water or sea water in a container) comprising CRISPR arrays, wherein the ballast water is obtained or obtainable by the method. A ship, boat, sea container or rig comprising the ballast sea water. A vector for use in the method, wherein the first cells are Cholera (eg, vibrio, eg, O1 or O139), *E coli* or Enterococci sp cells, the vector comprising one or more CRISPR arrays for targeting the cells, wherein each array is as defined in (a) and (b) of the method.

The invention also provides vectors and CRISPR arrays suitable for use in this sixth configuration or for other applications, such as for medical use, or for food or beverage treatment. To this end, there is provided: A vector comprising a CRISPR array for introduction into a bacterial host cell, wherein the bacterium is capable of water-borne transmission, wherein (a) the CRISPR array comprises a sequence for expression of a crRNA and a promoter for transcription of the sequence in a said host cell;

(b) the crRNA is capable of hybridising to a host cell target sequence to guide a Cas (eg, a Cas nuclease) in the host cell to modify the target sequence (eg, to cut the target sequence); the target sequence being a nucleotide sequence for mediating host cell viability;

(c) wherein the sequence of (a) comprises a sequence R1-S1-R1' for expression and production of the crRNA, wherein R1 is a first CRISPR repeat, R1' is a second CRISPR repeat, and R1 or R1' is optional; and S1 is a first CRISPR spacer that comprises or consists of a nucleotide sequence that is 80% or more identical to the host cell target sequence.

Also provided are: A water or food treatment composition comprising a plurality of such vectors. A medicament for treatment or prevention of a bacterial infection (eg, a *Vibrio cholerae* infection) in a human, the medicament comprising a plurality of such vectors. The invention also provides bacterial populations, compositions, foodstuffs and beverages. For example, the foodstuff or beverage is a dairy product.

In a seventh configuration, the invention provides:—

In a first aspect:—

A method of modifying an expressible gene encoding a first Cas, the method comprising (a) combining a guide RNA (gRNA1) with the Cas gene in the presence of first Cas that is expressed from said gene; and (b) allowing gRNA1 to hybridise to a sequence of said Cas gene (eg, a promoter or a first Cas-encoding DNA sequence thereof) and to guide first Cas to the gene, whereby the Cas modifies the Cas gene.

A first nucleic acid vector or combination of vectors, eg, for use in the method, wherein (a) the first vector or a vector of said combination comprises an expressible nucleotide sequence that encodes a guide RNA (gRNA1, eg, a single gRNA) that is complementary to a predetermined protospacer sequence (PS1) for guiding a first Cas to modify PS1 at a first site (CS1), wherein PS1 is adjacent a PAM (P1) that is cognate to the first Cas; or the expressible sequence encodes a crRNA that forms gRNA1 with a tracrRNA; and (b) PS1 and P1 are sequences of an expressible first Cas-encoding gene and PS1 is capable of being modified at CS1 by the first Cas.

These aspects of the invention are useful for regulating Cas activity, eg, in a cell or in vitro. The invention involves targeting a Cas-encoding gene to restrict Cas activity, which is advantageous for temporal regulation of Cas. The invention may also be useful in settings where increased stringency of Cas activity is desirable, eg, to reduce the chances for off-target Cas cutting in when modifying the genome of a cell. Applications are, for example, in modifying human, animal or plant cells where off-target effects should be minimised or avoided, eg, for gene therapy or gene targeting of the cell or a tissue or an organism comprising the cell. For example, very high stringency is required when using Cas modification to make desired changes in a human cell (eg, iPS cell) that is to be administered to a patient for gene therapy or for treating or preventing a disease or condition in the human. The disclosure provides these applications as part of the methods and products of the invention.

The invention also addresses the problem of restricted insert capacity in vectors, particularly in viral vectors.

Thus, an eighth configuration of the invention provides:—

A nucleic acid vector comprising more than 1.4 kb of exogenous DNA sequence encoding components of a CRISPR/Cas system, wherein the sequence comprises an engineered array or engineered sequence (optionally as described herein) for expressing one or more HM- or PM-crRNAs or gRNAs in host cells (any cell herein, eg, human, animal or bacterial or archael host cells), wherein the array or engineered sequence does not comprise a nucleotide sequence encoding a Cas nuclease that is cognate to the cRNA(s) or gRNA(s); optionally wherein at least 2, 3 or 4 cRNAs or gRNAs are encoded by the exogenous DNA.

A nucleic acid vector comprising more than 1.4 kb or more than 4.2 kb of exogenous DNA sequence, wherein the exogenous DNA encodes one or more components of a CRISPR/Cas system and comprises an engineered array or sequence (eg, any such one described herein) for expressing one or more HM-crRNAs or gRNAs in host cells, wherein the exogenous sequence is devoid of a nucleotide sequence encoding a Cas nuclease that is cognate to the cRNA(s) or gRNA(s); optionally wherein at least 2 different cRNAs or gRNAs are encoded by the exogenous DNA.

Herein in any configurations, for example the cRNA(s) are provided by one or more single guide RNAs (gRNAs), and in this case "CRISPR array" may refer to one or more expressible nucleotide sequences that encode said gRNA(s). Thus, the sequences are capable of being expressed in host cell(s) for expressing the gRNA(s) inside the cell(s).

The invention is mainly described in terms of bacteria, but it is also applicable mutatis mutandis to archaea.

Any features on one configuration herein are, in an example, combined with a different configuration of the invention for possible inclusion of such combination in one or more claims herein.

BRIEF DESCRIPTION OF THE FIGURES

FIG. 3 shows a spot assay on TH-agar of the strains used in this work. All strains were grown on TH-agar at 37° C. for 20 hours. Serial dilutions of overnight cultures were done in duplicate for E. coli, L lactis and S. mutans, and triplicate for both strains of S. thermophilus in order to count individual colonies.

FIGS. 4A-4C show selective growth of S. thermophilus, S. mutans, L. lactis and E. coli under different culture conditions. Tetracycline cannot be used to selectively grown S. thermophilus LMD-9. However, 3 g l$^{-1}$ of PEA proved to selectively grow S. thermophilus LMD-9 while limiting growth of E. coli. FIG. 4A shows commencal gut bacteria. FIG. 4B shows relative of target species and FIG. 4C shows a target species.

FIGS. 5A-5C illustrate construction of two xylose induction cassettes (FIGS. 5B and 5C are based on the wild type B. megaterium operon is illustrated in FIG. 5A. (Xie et al. 2013).

FIG. 5B: Construction of two xylose induction cassettes (middle, right) based on the wild type B. megaterium operon (left). (Xie et al. 2013).

FIGS. 10A-10D show growth inhibition of Streptococcus thermophilus DSM 20617(T) with the plasmid pBAV1KT5-XylR-CRISPR-PXylA (FIGS. 10A and 10C) or pBAV1KT5-XylR-CRISPR-Pldha+XylA (FIGS. 10B and 10D). Not induced (FIGS. 10A and 10B) and induced (FIGS. 10C and 10D). Picture taken after 63H of incubation. Colony counts in bottom left corner (top row: >1000, >1000, bottom row: 336, 113).

FIGS. 12A-12F shows the selective S thermophilus growth inhibition in a co-culture of E. coli, L. lactis and S. thermophiles harboring either the pBAV1KT5-XylR-CRISPR-PxylA or the pBAV1KT5-XylR-CRISPR-PldhA+XylA plasmid. No growth difference is observed between E. coli harboring the pBAV1KT5-XylR-CRISPR-PxylA or the pBAV1KT5-XylR-CRISPR-PldhA+XylA plasmid (FIGS. 12B and 12E). However, S. thermophiles (selectively grown on TH agar supplemented with 2.5 gl-1 PEA, FIGS. 12C and 12F) shows a decrease in transformation efficiency between the pBAV1KT5-XylR-CRISPR-PxylA (strong) or the pBAV1KT5-XylR-CRISPR-PldhA+XylA (weak) plasmid as we expected. We thus demonstrated a selective growth inhibition of the target S. thermophilus sub-population in the mixed population of cells. Colony counts in bottom left corner (top row: >1000, >1000, 68, bottom row: >1000, >1000, 32).

DETAILED DESCRIPTION

Figure 1:
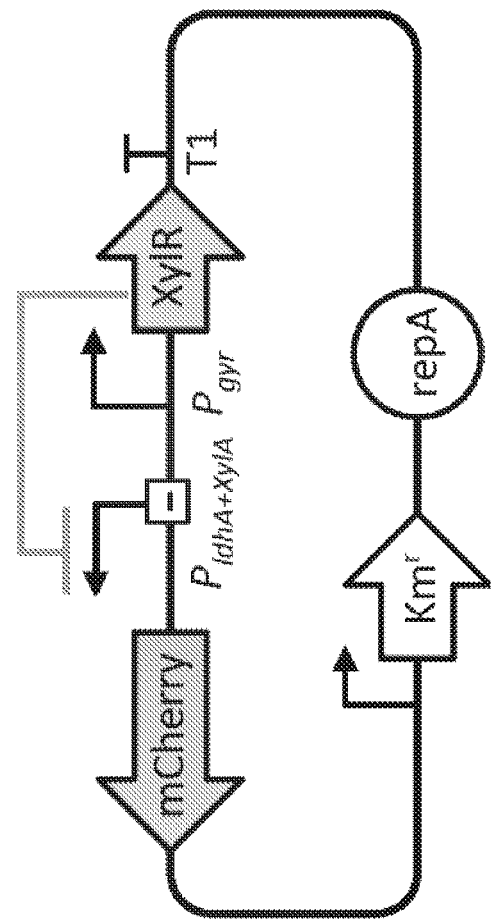
FIG. 1 shows a Xylose inducible system.

Inhibiting Microbial Population Growth & Altering Microbial Ratios

The invention relates to methods, uses, systems, arrays, cRNAs, gRNAs and vectors for inhibiting bacterial population growth or altering the relative ratio of sub-populations of first and second bacteria in a mixed population of bacteria, eg, for altering human or animal microbiomes, such as for the alteration of the proportion of Bacteroidetes (eg, Bacteroides), Firmicutes and/or gram positive or negative bacteria in microbiota of a human. See, for example, the first to third configurations described herein. The invention, for example, involves modifying one or more target nucleotide sequences of a host bacterial cell, eg, a Bacteroidetes cell or Firmicutes cell.

There have been a number of studies pointing out that the respective levels of the two main intestinal phyla, the Bacteroidetes and the Firmicutes, are linked to obesity, both in humans and in germfree mice. The authors of the studies deduce that carbohydrate metabolism is the important factor. They observe that the microbiota of obese individuals are more heavily enriched with bacteria of the phylum Firmicutes and less with Bacteroidetes, and they surmise that this bacterial mix may be more efficient at extracting energy from a given diet than the microbiota of lean individuals (which have the opposite proportions). In some studies, they found that the relative abundance of Bacteroidetes increases as obese individuals lose weight and, further, that when the microbiota of obese mice are transferred to germfree mice, these mice gain more fat than a control group that received microbiota from lean mice. See, eg, Turnbaugh, P. J., R. E. Ley, M. A. Mahowald, V. Magrini, E. R. Mardis, and J. I. Gordon. 2006, "An obesity-associated gut microbiome with increased capacity for energy harvest", Nature 444:1027-1131.

Concepts

The invention provides the following concepts involving a host cell target:—

1. Use of a host modifying (HM) CRISPR/Cas system for killing or reducing the growth of bacterial host cells, for each host cell the system comprising components according to (i) to (iv):—
   (i) at least one nucleic acid sequence encoding a Cas nuclease;
   (ii) an engineered host modifying (HM) CRISPR array comprising a spacer sequence (HM-spacer) and repeats encoding a HM-crRNA, the HM-crRNA comprising a sequence that hybridises to a host cell target sequence to guide said Cas to the target in the host cell to modify the target sequence;
   (iii) an optional tracrRNA sequence or a DNA sequence expressing a tracrRNA sequence;
   (iv) wherein said components of the system are split between the host cell and at least one nucleic acid vector that transforms the host cell, whereby the HM-crRNA guides Cas to the target to modify the target sequence in the host cell;
   wherein the Cas nuclease is endogenous to the host cell; and wherein the target sequence is modified by the Cas whereby the host cell is killed or host cell growth is reduced.

Concept 1 alternatively provides:

Use of a host modifying (HM) CRISPR/Cas system for altering the relative ratio of sub-populations of first and second bacteria in a mixed population of bacteria, the second bacteria comprising host cells, for each host cell the system comprising components according to (i) to (iv):—
   (i) at least one nucleic acid sequence encoding a Cas nuclease;
   (ii) an engineered host modifying (HM) CRISPR array comprising a spacer sequence (HM-spacer) and repeats encoding a HM-crRNA, the HM-crRNA comprising a sequence that hybridises to a host cell target sequence to guide said Cas to the target in the host cell to modify the target sequence;
   (iii) an optional tracrRNA sequence or a DNA sequence expressing a tracrRNA sequence;
   (iv) wherein said components of the system are split between the host cell and at least one nucleic acid vector that transforms the host cell, whereby the HM-crRNA guides Cas to the target to modify the target sequence in the host cell; wherein optionally the Cas nuclease is endogenous to the host cell; and wherein the target sequence is modified by the Cas whereby the host cell is killed or host cell growth is reduced.

Concept 1 also provides: A method of altering the relative ratio of sub-populations of first and second bacteria in a mixed population of bacteria, the second bacteria comprising host cells, and the method comprising combining the mixed population with of a host modifying (HM) CRISPR/Cas system whereby second bacteria host cells are killed or the growth of said cells is reduced thereby altering said ratio, wherein for each host cell the system comprises components according to (i) to (iv):—
   (i) at least one nucleic acid sequence encoding a Cas nuclease;
   (ii) an engineered host modifying (HM) CRISPR array comprising a spacer sequence (HM-spacer) and repeats encoding a HM-crRNA, the HM-crRNA comprising a sequence that hybridises to a host cell target sequence to guide said Cas to the target in the host cell to modify the target sequence;
   (iii) an optional tracrRNA sequence or a DNA sequence expressing a tracrRNA sequence;
   (iv) wherein said components of the system are split between the host cell and at least one nucleic acid vector that transforms the host cell, whereby the HM-crRNA guides Cas to the target to modify the target sequence in the host cell;
   wherein optionally the Cas nuclease is endogenous to the host cell; and
   wherein the target sequence is modified by the Cas whereby the host cell is killed or host cell growth is reduced.

Concept 1 also provides:—

Use of a host modifying (HM) CRISPR/Cas system for altering the relative ratio of sub-populations of first and second bacteria in a mixed population of bacteria, the second bacteria comprising a plurality of host cells each comprising a target protospacer sequence, for each host cell the system comprising components (ii) and (iii) defined above, the system further comprising at least one nucleic acid sequence encoding a Cas nuclease; wherein said component (ii) and said Cas-encoding sequence are comprised by at least one nucleic acid vector that transforms the host cell, whereby the HM-crRNA encoded by (i) guides Cas to the target to modify the target sequence in the host cell; wherein the Cas nuclease is endogenous to the host cell; and wherein the target sequence is modified by the Cas whereby the host cell is killed or host cell growth is reduced.

In an embodiment, the growth of first bacteria is not inhibited; or the growth inhibition of said host cells is at least 2×, 3×, 4×, 5×, 6×, 7×, 8×, 9×, 10×, 50×, 100× or 1000× the growth inhibition of the first cells. The growth inhibition can be calculated as a fold-inhibition or as a percentage inhibition (as described herein). In another example, inhibition is measured in a culture sample by a spectrophotometer, wherein light absorbance (eg, at $OD_{600}$) is determined at the start and end of a predetermined crRNA/gRNA treatment period (see the description of such a period herein when determining inhibition by fold or percentage). In an example, the increase in absorbance (comparing the absorbance at the beginning of the predetermined period with absorbance at the end of that period) for the host cell sample is less than for the control sample (which has not been exposed to said cRNA or gRNA), eg, the increase for the former is at least 10, 100, 1000, 10000 or 100000 times lower than for the latter (eg, determined as $OD_{600}$). In an example, the determination of growth inhibition (ie, the end of the predetermined period) is made at the mid-exponential growth phase of each sample (eg, 6-7 hours after the start of the predetermined period).

In an example, the host cells are comprised by a microbiota population comprised by an organism or environment (eg, a waterway microbiota, water microbiota, human or animal gut microbiota, human or animal oral cavity microbiota, human or animal vaginal microbiota, human or animal skin or hair microbiota or human or animal armpit microbiota), the population comprising first bacteria that are symbiotic or commensal with the organism or environment and second bacteria comprising said host cells, wherein the host cells are detrimental (eg, pathogenic) to the organism or environment. In an embodiment, the population is ex vivo.

The ratio of the first bacteria sub-population to the second bacteria sub-population is increased.

Concept 1 also provides a use for inhibiting host cell growth as described further below.

2. A host modifying (HM) CRISPR/Cas system for modifying a target nucleotide sequence of a host cell (eg, for the use of concept 1), the system comprising components according to (i) to (iv):—
  (i) at least one nucleic acid sequence encoding a Cas nuclease;
  (ii) an engineered host modifying (HM) CRISPR array comprising a spacer sequence (HM-spacer) and repeats encoding a HM-crRNA, the HM-crRNA comprising a sequence that is capable of hybridising to a host target sequence to guide said Cas to the target in the host cell to modify the target sequence;
  (iii) an optional tracrRNA sequence or a DNA sequence for expressing a tracrRNA sequence;
  (iv) wherein said components of the system are split between the host cell and at least one nucleic acid vector that can transform the host cell, whereby the HM-crRNA guides Cas to the target to modify the target sequence in the host cell;
  wherein optionally component (i) is endogenous to the host cell.

In an alternative, HM-crRNA and tracrRNA are comprised by a single guide RNA (gRNA).

By harnessing endogenous Cas nuclease, embodiments of the invention use endogenous Cas nuclease activity (ie, without the need for prior genetic modification of the host cell to activate or enhance the nuclease activity). Thus, in an example, the Cas nuclease is encoded by a wild-type gene of the host cell. In an example, the nuclease is active to achieve the cell killing or growth reduction without inhibition of an endogenous Cas nuclease (or Cas nuclease gene) repressor in the host cell. Thus, the invention can address wild-type bacterial populations without the need for prior manipulation to make bring about effective Cas-mediated cell killing or growth reduction. Thus, the population can be exposed to the cRNA when the population is in its wild-type environment (such as a waterway or comprised by a human or animal microbiome).

In an example, the second bacteria are Bacteroidetes (eg, *Bacteroides*) cells. In an example, the second bacteria are Firmicutes cells. The use, system or method is, for example, used to alter the ratios in a gut microbiota population (eg, ex vivo or in vivo), which is for example for treating or preventing increased body mass or obesity (eg, wherein the second bacteria are Firmicutes cells).

In an example, the use, method, system, vector, engineered nucleotide sequence, cRNA or gRNA is for therapeutically or prophylactically rebalancing microbiota of a human or non-human animal comprising the mixed population, eg for treating or preventing obesity, diabetes IBD, a GI tract condition or an oral cavity condition.

In an example, the microbiota mentioned herein is microbiota of a human or animal microbiome (eg, gut, vaginal, scalp, armpit, skin bloodstream, throat or oral cavity microbiome).

In an example, the microbiota mentioned herein is an armpit microbiota and the use, method, system, vector, engineered nucleotide sequence, cRNA or gRNA is for preventing or reducing body odour of a human.

In an example, the host cell population or mixed population is harboured by a beverage or water (eg, a waterway or drinking water) for human consumption.

In an example, the use, method, system, vector, engineered nucleotide sequence, cRNA or gRNA is for reducing pathogenic infections or for re-balancing gut or oral microbiota eg, for treating or preventing obesity or disease in a human or animal. For example, the use, method, system, vector, engineered nucleotide sequence, cRNA or gRNA is for knocking-down *Clostridium dificile* bacteria in a gut microbiota.

In an example, the first bacteria are *Bacteroides* bacteria and the second bacteria are Firmicutes or pathogenic bacteria, eg, gut bacteria. In an example, the host cells or second bacteria are Firmicutes cells, eg, selected from *Streptococcus* (eg, *thermophilus* and/or *pyogenes*), *Bacillus*, *Lactobacillus*, *Listeria*, *Clostridium*, *Heliobacterium* and *Staphylococcus* cells. In an example, the mixed population contains *Bacteroides* and metronidazole (MTZ)-resistant *C dificile* strain 630 sub-populations, wherein the host cells comprise said *C dificile* cells.

In an example, the host cell population, mixed population or system is comprised by a composition (eg, a beverage, mouthwash or foodstuff) for administration to a human or non-human animal for populating and rebalancing the gut or oral microbiota thereof.

In an example, the product of the use or method, or the system, vector, engineered nucleotide sequence, cRNA or gRNA is for administration to a human or non-human animal by mucosal, gut, oral, intranasal, intrarectal, intravaginal, ocular or buccal administration.

In an example of any configuration herein, the mixed population (prior to combining with the array, gRNA, crRNA or engineered sequence) is a sample of a microbiota of a human or animal subject, eg, a gut or any other microbiota disclosed herein or a microbiota of any microbiome disclosed herein. In an example, in this instance the product of the use of the invention is a modified microbiota population that is useful for an treatment or therapy of a human or animal subject, as disclosed herein.

3. The system of concept 2, wherein the vector or vectors lack a Cas (eg, a Cas9) nuclease-encoding sequence.

4. The use, method or system of any preceding concept, wherein each host cell is of a strain or species found in human microbiota, optionally wherein the host cells are mixed with cells of a different strain or species, wherein the different cells are Enterobacteriaceae or bacteria that are probiotic, commensal or symbiotic with humans (eg, in the human gut. In an example, the host cell is a Firmicutes, eg, *Streptococcus*, cell.

5. The use, method or system of any preceding concept for the alteration of the proportion of Bacteroidetes (eg, *Bacteroides*) bacteria in a mixed bacterial population (eg, in a human, such as in human microbiota).

6. The use, method or system of concept 5 for increasing the relative ratio of Bacteroidetes versus Firmicutes.

7. The use, method or system of any preceding concept, wherein said Cas nuclease is provided by an endogenous Type II CRISPR/Cas system of the cell.

8. The use, method or system of any preceding concept, wherein component (iii) is endogenous to the host cell.

9. The use, method or system of any preceding concept, wherein the target sequence is comprised by an antibiotic resistance gene, virulence gene or essential gene of the host cell.

10. The use, method or system of any preceding concept, the array being comprised by an antibiotic composition, wherein the array is in combination with an antibiotic agent.

11. The use, method or system of any preceding concept, wherein alternatively HM-crRNA and tracrRNA are comprised by a single guide RNA (gRNA), eg provided by the vector.

12. The use, method or system of any preceding concept, wherein the host cell comprises a deoxyribonucleic acid strand with a free end (HM-DNA) encoding a HM-sequence of interest and/or wherein the system comprises a sequence encoding the HM-DNA, wherein the HM-DNA comprises a sequence or sequences that are homologous respectively to a sequence or sequences in or flanking the target sequence for inserting the HM-DNA into the host genome (eg, into a chromosomal or episomal site).

13. An engineered nucleic acid vector for modifying a bacterial host cell comprising an endogenous CRISPR/Cas system, the vector
   (a) comprising nucleic acid sequences for expressing a plurality of different crRNAs (eg, gRNAs) for use in a CRISPR/Cas system, method or use according to any preceding concept; and
   (b) optionally lacking a nucleic acid sequence encoding a Cas nuclease, wherein a first of said crRNAs is capable of hybridising to a first nucleic acid sequence in said host cell;
   and a second of said crRNAs is capable of hybridising to a second nucleic acid sequence in said host cell, wherein said second sequence is different from said first sequence; and
   (c) the first sequence is comprised by an antibiotic resistance gene (or RNA thereof) and the second sequence is comprised by an antibiotic resistance gene (or RNA thereof); optionally wherein the genes are different;
   (d) the first sequence is comprised by an antibiotic resistance gene (or RNA thereof) and the second sequence is comprised by an essential or virulence gene (or RNA thereof);
   (e) the first sequence is comprised by an essential gene (or RNA thereof) and the second sequence is comprised by an essential or virulence gene (or RNA thereof); or
   (f) the first sequence is comprised by a virulence gene (or RNA thereof) and the second sequence is comprised by an essential or virulence gene (or RNA thereof).

14. The vector of concept 13 inside a host cell comprising one or more Cas that are operable with cRNA (eg, single guide RNA) encoded by the vector.

15. The use, method, system or vector of any preceding concept, wherein the HM-CRISPR array comprises multiple copies of the same spacer.

16. The use, method, system or vector of any preceding concept, wherein the vector(s) comprises a plurality of HM-CRISPR arrays.

17. The use, method, system or vector of any preceding concept, wherein each vector is a plasmid, cosmid, virus, a virion, phage, phagemid or prophage.

18. The use, method, system or vector of any preceding concept, wherein the system or vector comprises two, three or more of copies of nucleic acid sequences encoding crRNAs (eg, gRNAs), wherein the copies comprise the same spacer sequence for targeting a host cell sequence (eg, a virulence, resistance or essential gene sequence).

19. The use, method, system or vector of concept 18, wherein the copies are split between two or more vector CRISPR arrays.

20. A bacterial host cell comprising a system or vector recited in any preceding concept.

21. The system, vector or cell of any one of concepts 2 to 20 in combination with an antibiotic agent (eg, a beta-lactam antibiotic).

22. The use, method, system, vector or cell of any preceding concept, wherein the or each host cell is a *Staphylococcus, Streptococcus, Pseudomonas, Salmonella, Listeria, E coli, Desulfovibrio* or *Clostridium* host cell. In an example, the or each host cell is a Firmicutes cell, eg, a *Staphylococcus, Streptococcus, Listeria* or *Clostridium* cell.

In an example, each CRISPR array comprises a sequence R1-S1-R1' for expression and production of the respective crRNA (eg, comprised by a single guide RNA) in the host cell, (i) wherein R1 is a first CRISPR repeat, R1' is a second CRISPR repeat, and R1 or R1' is optional; and (ii) S1 is a first CRISPR spacer that comprises or consists of a nucleotide sequence that is 95% or more identical to said target sequence.

In an example, R1 and R1' are at least 95% identical respectively to the first and second repeat sequences of a CRISPR array of the second host cell species. In an example, R1 and R1' are at least 95% (eg, 96, 97, 98, 99 or 100%) identical respectively to the first (5'-most) and second (the repeat immediately 3' of the first repeat) repeat sequences of a CRISPR array of said species, eg, of a said host cell of said species. In an example, R1 and R1' are functional with a Type II Cas9 nuclease (eg, a *S thermophilus, S pyogenes* or *S aureus* Cas9) to modify the target in a said host cell.

An alternative Concept 1 use of invention provides the following, as demonstrated by the worked experimental Example:

The use of wild-type endogenous Cas nuclease activity of a bacterial host cell population to inhibit growth of the population, wherein each host cell has an endogenous CRISPR/Cas system having wild-type Cas nuclease activity, the use comprising transforming host cells of the population, wherein each transformed host cell is transformed with an engineered nucleotide sequence for providing host modifying (HM) cRNA or guide RNA (gRNA) in the host cell, the HM-cRNA or gRNA comprising a sequence that is capable of hybridising to a host cell target protospacer sequence for guiding endogenous Cas to the target, wherein the cRNA or gRNA is cognate to an endogenous Cas nuclease of the host cell that has said wild-type nuclease activity and following transformation of the host cells growth of the population is inhibited.

In the worked Example below, inhibition was addressed in a bacterial population (a gram positive Firmicutes) on a solid surface. A >10-fold inhibition of host cell population growth was achieved. Targeting was directed to an antibiotic resistance gene and an essential gene. The invention will be useful in inhibiting the growth of antibiotic-resistant bacteria, wherein the target sequence is a sequence of an antibiotic resistance gene. In an example, co-administration of the engineered nucleotide sequence with the antibiotic may be effective. This may provide more complete treatment or prevention of host cell infection in human or animal subjects and/or enable the reduction of therapeutically-effective antibiotic dose for administration to a human or animal. This is useful in view of the increasing worry regarding over-administration of antibiotics and the development of resistance in human and animal populations.

The demonstration of the invention's ability to inhibit host cell growth on a surface is important and desirable in embodiments where the invention is for treating or preventing diseases or conditions mediated or caused by microbiota as disclosed herein in a human or animal subject. Such microbiota are typically in contact with tissue of the subject (eg, gut, oral cavity, lung, armpit, ocular, vaginal, anal, ear, nose or throat tissue) and thus we believe that the demonstration of activity to inhibit growth of a microbiota bacterial species (exemplified by *Streptococcus*) on a surface supports this utility.

In an example, wild-type host cell endogenous Cas9 or cfp1 activity is used. The engineered nucleotide sequence may not be in combination with an exogenous Cas nuclease-encoding sequence.

In an example, the host cells are wild-type (eg, non-engineered) bacterial cells. In another example, the host cells are engineered (such as to introduce an exogenous nucleotide sequence chromosomally or to modify an endogenous nucleotide sequence, eg, on a chromosome or plasmid of the host cell), and wherein the host cells comprise an endogenous CRISPR/Cas system having wild-type Cas nuclease activity that is operable with the crRNA or gRNA. In an example, the formation of bacterial colonies of said host cells is inhibited following said transformation. In an example, proliferation of host cells is inhibited following said transformation. In an example, host cells are killed following said transformation.

By "cognate to" it is intended that the endogenous Cas is operable with crRNA or gRNA sequence to be guided to the target in the host cell. The skilled addressee will understand that such Cas guiding is generally a feature of CRISPR/Cas activity in bacterial cells, eg, wild-type CRISPR/Cas activity in bacterial cells having endogenous active wild-type CRISPR/Cas systems.

By "wild-type" Cas activity it is intended, as will be clear to the skilled addressee, that the endogenous Cas is not an engineered Cas or the cell has not been engineered to de-repress the endogenous Cas activity. This is in contrast to certain bacteria where Cas nuclease activity is naturally repressed (ie, there is no wild-type Cas nuclease activity or none that is useful for the present invention, which on the contrary is applicable to addressing wild-type host cells in situ for example where the endogenous Cas activity can be harnessed to effect cell population growth inhibition).

In an example, inhibition of host cell population growth is at least 2, 3, 4, 5, 6, 7, 8, 9 or 10-fold compared to the growth of said host cells not exposed to said engineered nucleotide sequence. For example, growth inhibition is indicated by a lower bacterial colony number of a first sample of host cells (alone or in a mixed bacterial population) by at least 2, 3, 4, 5, 6, 7, 8, 9 or 10-fold compared to the colony number of a second sample of the host cells (alone or in a mixed bacterial population), wherein the first cells have been transformed by said engineered nucleotide sequence but the second sample has not been exposed to said engineered nucleotide sequence. In an embodiment, the colony count is determined 12, 24, 36 or 48 hours after the first sample has been exposed to the engineered sequence. In an embodiment, the colonies are grown on solid agar in vitro (eg, in a petri dish). It will be understood, therefore, that growth inhibition can be indicated by a reduction (<100% growth compared to no treatment, ie, control sample growth) in growth of cells or populations comprising the target sequence, or can be a complete elimination of such growth. In an example, growth of the host cell population is reduced by at least 10, 20, 30, 40, 50, 60, 70, 80, 90 or 95%, ie, over a predetermined time period (eg, 24 hours or 48 hours following combination with the cRNA or gRNA in the host cells), ie, growth of the host cell population is at least such percent lower than growth of a control host cell population that has not been exposed to said cRNA or gRNA but otherwise has been kept in the same conditions for the duration of said predetermined period. In an example, percent reduction of growth is determined by comparing colony number in a sample of each population at the end of said period (eg, at a time of mid-exponential growth phase of the control sample). For example, after exposing the test population to the crRNA or gRNA a time zero, a sample of the test and control populations is taken and each sample is plated on an agar plate and incubated under identical conditions for said predetermined period. At the end of the period, the colony number of each sample is counted and the percentage difference (ie, test colony number divided by control colony number and then times by 100, and then the result is subtracted from 100 to give percentage growth reduction). The fold difference is calculated by dividing the control colony number by the test colony number.

Inhibition of population growth can be indicated, therefore, by a reduction in proliferation of host cell number in the population. This may be due to cell killing by the nuclease and/or by downregulation of host cell proliferation (division and/or cell growth) by the action of the nuclease on the target protospacer sequence. In an embodiment of a treatment or prevention as disclosed herein, host cell burden of the human or animal subject is reduced, whereby the disease or condition is treated (eg, reduced or eliminated) or prevented (ie, the risk of the subject developing the disease or condition) is reduced or eliminated.

The invention is useful for targeting wild-type bacterial populations found naturally in the environment (eg, in water or waterways, cooling or heating equipment), comprised by beverages and foodstuffs (or equipment for manufacturing, processing or storing these) or wild-type bacterial populations comprised by human or animal microbiota. Thus, the invention finds utility in situations when pre-modification of host cells to make them receptive to killing or growth inhibition is not possible or desirable (eg, when treatment in situ of microbiota in the gut or other locations of a subject is desired). In another application, the invention finds utility for producing ex vivo a medicament for administration to a human or animal subject for treating or preventing a disease or condition caused or mediated by the host cells, wherein the medicament comprises a modified mixed bacterial population (eg, obtained from faeces or gut microbiota of one or more human donors) which is the product of the use or method of the invention, wherein the population comprises a sub-population of bacteria of a species or strain that is different to the species or strain of the host cells. The former sub-population cells do not comprise the target and thus are not modified by the use or method. Thus, for example, the method can be used to reduce the proportion of a specific Firmicutes sub-population and spare Bacteroidetes in the mixed population, eg, for producing a medicament for treating or preventing a metabolic or GI condition or disease disclosed herein. In this way, the invention can provide a modified bacterial transplant (eg, a modified faecal transplant) medicament for such use or for said treatment or prevention in a human or animal. For example, the method can be used to modify one or more microbiota in vitro to produce a modified collection of bacteria for administration to a human or animal for medical use (eg, treatment or prevention of a metabolic condition (such as obesity or diabetes) or a GI tract condition (eg, any such condition mentioned herein) or a cancer (eg, a GI tract cancer)) or for cosmetic or personal hygiene use (eg, for topical use on a human, eg, for reducing armpit or other body odour by topical application to an armpit of a human or other relevant location of a human). In another example, the array, crRNA, gRNA or engineered nucleotide sequence is administered to a human or animal and the host cells are harboured by the human or animal, eg, comprised by a microbiota of the human or animal (such as a gut microbiota or any other type of micriobiota disclosed herein). In this way, a disease or condition mediated or caused by the host cells can be treated or prevented. In an example, the transformation is carried out in vitro and optionally the array, crRNA, gRNA or engineered nucleotide sequence is comprised by nucleic acid that is electroporated into host cells. In an example, the nucleic acid are RNA (eg, copies of the gRNA). In another example, the nucleic acid are DNA encoding the crRNA or gRNA for expression thereof in host cells.

Thus, in an example, the invention provides an engineered nucleotide sequence for providing host cell modifying (HM) cRNA or guide RNA (gRNA) in a population of wild-type bacterial host cells comprised by a microbiota of a human or animal subject for treating or preventing a disease or condition mediated or caused by host cells of the microbiota of the subject, the cRNA or gRNA comprising a sequence that is capable of hybridising to a host cell target protospacer sequence for guiding Cas to the target, wherein the cRNA or gRNA is cognate to an endogenous host cell Cas nuclease that has wild-type nuclease activity, wherein following transformation of host cells growth of the population is inhibited and the disease or condition is treated or prevented.

In an example, the engineered nucleotide sequence comprises a HM-CRISPR array as defined herein. In an example, the engineered nucleotide sequence encodes a single guide RNA. In an example, the engineered nucleotide sequence is a guide RNA (eg, a singe guide RNA) or crRNA. In an example, the engineered sequence is comprised by a bacteriophage that is capable of infecting the host cells, wherein the transformation comprises transduction of the host cells by the bacteriophage. The bacteriophage can be a bacteriophage as described herein. In an example, the engineered nucleotide sequence is comprised by a plasmid (eg, a conjugative plasmid) that is capable of transforming host cells. The plasmid can be a plasmid as described herein. In an example, the engineered nucleotide sequence is comprised by a transposon that is capable of transfer into and/or between host cells. The transposon can be a transposon as described herein.

Any use or method of the invention can comprise transforming host cells with nucleic acid vectors for producing cRNA or gRNA in the cells. For example, the vectors or nucleic acid comprising the engineered nucleotide sequence are administered orally, intravenously, topically, ocularly, intranasally, by inhalation, by rectal administration, in the ear, by vaginal administration or by any other route of administration disclosed herein or otherwise to a human or animal comprising the mixed bacterial population (eg, as part of microbiota of the human or animal), wherein the administration transforms the host cells with the vectors or nucleic acid.

In an example, the host cell population is ex vivo. In an example, the mixed population is comprised by a human or animal subject and a host cell infection in the subject is treated or prevented.

In an example, the first and second bacteria are comprised by a microbial consortium wherein the bacteria live symbiotically. In an example, the consortium is a human or animal microbiota; in an example the consortium is comprised by a human or animal (eg, wherein the use, system, engineered sequence, vector or cell is for treating infection by host cells of the consortium in the human or animal, eg, wherein the host cells mediate or cause antibiotic resistance or a deleterious disease or condition in the human or animal). The species (*E coli, L lactis* and *S thermophilus*) used in the worked Example below are strains that co-exist symbiotically in human and animal gut microbiota. The Example also addresses targeting in a mixed gram positive and gram negative bacterial population. Additionally, the Example addresses a population of Firmicutes (*S thermophilus*) and a population of Enterobacteriaceae (*E coli*), both of which are found in human microbiota. Other examples of Enterobacteriaceae are *Salmonella, Yersinia pestis, Klebsiella, Shigella, Proteus, Enterobacter, Serratia*, and *Citrobacter*.

In an example, the method, use, engineered nucleotide sequence, array, crRNA, gRNA, vector or system is for treating host cell infection in a human gut microbiota population, optionally the population also comprising first bacteria that are human commensal gut bacteria and/or Enterobacteriaceae, eg, wherein the host cells and commensal cells (first and second bacteria) live symbiotically in human gut microbiota.

In an example the use or system is for the alteration of the proportion of Bacteroidetes bacteria in a mixed bacterial population comprising Bacteroidetes bacteria and other bacteria. For example, for increasing the relative ratio of Bacteroidetes versus one, more or all Firmicutes (eg, versus *Streptococcus*) in the population. In this case, the host cells can be Firmicutes cells comprising the target(s). In an example, the population is a bacterial population of a microbiota comprised by a human or animal subject and the method, use, engineered nucleotide sequence, vector or system is for (i) treating an infection in the subject by said host cells comprised (eg, comprised by the mixed population); (ii) treating or preventing in the subject a condition or disease mediated by said host cells; (iii) reducing body odour of the human that is caused or mediated by said host cells; or (iv) personal hygiene treatment of the human. In an example, the engineered nucleotide sequence, array, crRNA, gRNA or vector of the invention is for use in such a system or use of the invention.

In an example, the condition or disease is a metabolic or gastrointestinal disease or condition, eg, obesity, IBD, IBS, Crohn's disease or ulcerative colitis. In an example, the condition or disease is a cancer, eg, a solid tumour or a GI cancer (eg, stomach cancer), liver cancer or pancreatic cancer. In an example, the condition is resistance or reduced responsiveness to an antibiotic (eg, any antibiotic disclosed herein).

In an example, the cell comprises an endogenous RNase III that is operable with component (ii) in the production of said HM-crRNA in the cell. In an alternative, one or more of the vectors comprises a nucleotide sequence encoding such a RNase III for expression of the RNase III in the host cell.

In an example, the essential gene (comprising the target) encodes a DNA polymerase of the cell. This is exemplified below.

In an example of the use, system, vector or cell, array, cRNA or gRNA comprises a sequence that is capable of hybridising to a host cell target protospacer sequence that is a adjacent a NGG, NAG, NGA, NGC, NGGNG, NNGRRT or NNAGAAW protospacer adjacent motif (PAM), eg, a AAAGAAA or TAAGAAA PAM (these sequences are written 5' to 3'). In an embodiment, the PAM is immediately adjacent the 3' end of the protospacer sequence. In an example, the Cas is a *S aureus, S thermophilus* or *S pyogenes* Cas. In an example, the Cas is Cpf1 and/or the PAM is TTN or CTA.

In an example the engineered nucleotide sequence, crRNA, gRNA or array is in combination with an antibiotic agent, eg, wherein the target is comprised by an antibiotic resistance gene wherein the antibiotic is said agent. In embodiment, the host cells are sensitive to the antibiotic. For example, there may be insufficient sensitivity to use the antibiotic to eradicate infection of presence of the host cells (eg, in a human or manufacturing vessel/equipment comprising the population), but the antibiotic can dampen down or reduce host cell sub-population size or growth whilst further killing or growth inhibition is effected using Cas modification (eg, target cutting) according to the invention.

The invention provides the use, system, array, crRNA, gRNA, engineered nucleotide sequence, vector or cell for a method of antibiotic (first antibiotic) treatment of an infection of said host cells in a human or animal subject, wherein an antibiotic resistance gene (for resistance to the first antibiotic) is Cas-targeted by the system or vector in host cells, wherein the method comprises administering the system, array, crRNA, gRNA, engineered nucleotide sequence, vector or cell and the antibiotic to the subject. The gene is downregulated, ie, expression of a protein product encoded by the gene is reduced or eliminated in the host cell, whereby antibiotic resistance is downregulated. The infection is reduced or prevented in the subject. In an example, the antibiotic is administered simultaneously with the system, array, crRNA, gRNA, engineered nucleotide sequence, vector or cell; in another example, the administration is sequential (eg, the antibiotic before the system, array, crRNA, gRNA, engineered nucleotide sequence, vector or cell). This feature of the invention can be useful for enhancing antibiotic treatment in the subject, eg, when antibiotic alone is not fully effective for treating such a host cell infection. The antibiotic can be any antibiotic disclosed herein, eg, tetracycline.

In an example, each engineered nucleotide sequence or vector comprises a said CRISPR array or a sequence encoding a said crRNA or gRNA and further comprises an antibiotic resistance gene (eg, kanamycin resistance), wherein the HM-crRNA or gRNA does not target the antibiotic resistance gene. In an example, the target sequence is comprised by an antibiotic resistance gene of the host cell, wherein the antibiotic is different from the first antibiotic (eg, kanamycin). In this way, the system, engineered sequence or vector is able to target the host without targeting itself. By exposing the host cells to the first antibiotic, one can promote retention of the engineered sequence or vector therein by positive selection pressure since cells containing the first antibiotic resistance gene will have a survival advantage in the presence of the first antibiotic (when host cells that are not transformed by the engineered sequence or vectors are not resistant to the first antibiotic). Thus, an example provides: The use of the invention comprising exposing the host cell or mixed population to said antibiotic (eg, kanamycin) and said engineered sequence or vector(s), for promoting maintenance of cRNA or gRNA-encoding sequences in host cells: or the system, engineered sequence, array or vector of the invention is in combination with said antibiotic.

In an example the sequence encoding the cRNA or gRNA or the component (ii) is under a constitutive promoter (eg, a strong promoter) operable in the host cell species, or an inducible promoter. In an example component (iii) is under a constitutive promoter operable in the host cell species, or an inducible promoter.

In an example, the or each host cell is a gram positive cell. In another example, the or each host cell is a gram positive cell.

In an example the method, use, system, engineered sequence or vector is for treating host cell infection in a human gut microbiota population, optionally the population comprising human commensal gut bacteria (ie, gut bacteria that are commensal with humans).

In an example of the method, use, system, array, crRNA, gRNA, engineered sequence or vector, the host cells are comprised by a mixed bacterial population comprised by a human or animal subject and the method, use, system, array, crRNA, gRNA, engineered sequence or vector is for (i) treating an infection in the subject by said host cells comprised by the mixed population; (ii) treating or preventing in the subject a condition or disease mediated by said host cells; (iii) reducing body odour of the human that is caused or mediated by said host cells; or (iv) personal hygiene treatment of the human.

In an example of the method, use, system, array, crRNA, gRNA, engineered sequence or vector is for in vitro treating an industrial or medical fluid, solid surface, apparatus or container (eg, for food, consumer goods, cosmetics, personal healthcare product, petroleum or oil production); or for treating a waterway, water, a beverage, a foodstuff or a cosmetic, wherein the host cell(s) are comprised by or on the fluid, surface, apparatus, container, waterway, water, beverage, foodstuff or cosmetic.

The invention also provides: An ex vivo mixed population of bacteria obtainable by the use or method of any concept herein.

In an example, the mixed population or the product of the use or method is in a container for medical or nutritional use. For example, the container is a sterilised container, eg, an inhaler or connected to a syringe or IV needle.

In an example, the product population of the use or method is useful for administration to a human or animal to populate a microbiome thereof.

The invention provides: A foodstuff or beverage for human or non-human animal consumption comprising the population product of the use or method.

Herein, in an example of any configuration, concept or aspect, the *Bacteroides* is a species selected from *caccae, capillosus, cellulosilyticus, coprocola, coprophilus, coprosuis, distasonis, dorei, eggerthii, faecis, finegoldii, fluxus, fragalis, intestinalis, melaninogenicus, nordii, oleiciplenus, oralis, ovatus, pectinophilus, plebeius, stercoris, thetaiotaomicron, uniformis, vulgatus* and *xylanisolvens*. For example, the *Bacteroides* is *thetaiotaomicron*, eg, wherein the host cell or mixed population is a gut microbiota population ex vivo or in vitro. In an example, the host cells, first or second bacteria sub-population comprises a plurality of different Bacteroidetes species, or a plurality of *Bacteroides* species (eg, comprising *B thetaiotaomicron* and *B fragalis*), or *Bacteroides* and *Prevotella* species. Herein, in an example, the *Prevotella* is a species selected from *bergensis, bivia, buccae, buccalis, copri, melaninogenica, oris, ruminicola, tannerae, timonensis* and *veroralis*. In an alternative, the host cells, first or second bacteria are Firmicutes cells. In an example, the host cells, first or second sub-population comprises or consists of one or more Firmicutes selected from *Anaerotruncus, Acetanaerobacterium, Acetitomaculum, Acetivibrio, Anaerococcus, Anaerofilum, Anaerosinus, Anaerostipes, Anaerovorax, Butvrivibrio, Clostridium, Capracoccus, Dehalobacter, Dialister, Dorea, Enterococcus, Ethanoligenens, Faecalibacterium, Fusobacterium, Gracilibacter, Guggenheimella, Hespellia, Lachnobacterium, Lachnospira, Lactobacillus, Leuconostoc, Megamonas, Moryella, Mitsuokella, Oribacterium, Oxobacter, Papillibacter, Proprionispira, Pseudobutyrivibrio, Pseudoramibacter, Roseburia, Ruminococcus, Sarcina, Seinonella, Shuttleworthia, Sporobacter, Sporobacterium, Strepto-* coccus, Subdoligranulum, Syntrophococcus, Thermobacillus, Turibacter and Weisella. In an example, the host cells, or the first or second sub-population consists of Clostridium cells (and optionally the other sub-population consists of Bacteroides (eg, thetaiotaomicron) cells). In an example, the host cells, or the first or second sub-population consists of Enterococcus cells (and optionally the other sub-population consists of Bacteroides (eg, thetaiotaomicron) cells). In an example, the host cells, or the first or second sub-population consists of Ruminococcus cells (and optionally the other sub-population consists of Bacteroides (eg, thetaiotaomicron) cells). In an example, the host cells, or the first or second sub-population consists of Streptococcus cells (and optionally the other sub-population consists of Bacteroides (eg, thetaiotaomicron) cells). In an example, the host cells, or the first or second sub-population consists of Faecalibacterium cells (and optionally the other sub-population consists of Bacteroides (eg, thetaiotaomicron) cells). For example, the Faecalibacterium is a Faecalibacterium prausnitzii (eg, A2-165, L2-6, M21/2 or SL3/3).

In an example, the host cells, or the first or second sub-population comprises or consists of one or more Firmicutes selected from Anaerotruncus, Acetanaerobacterium, Acetitomaculum, Acetivibrio, Anaerococcus, Anaerofilum, Anaerosinus, Anaerostipes, Anaerovorax, Butyrivibrio, Clostridium, Capracoccus, Dehalobacter, Dialister, Dorea, Enterococcus, Ethanoligenens, Faecalibacterium, Fusobacterium, Gracilibacter, Guggenheimella, Hespellia, Lachnobacterium, Lachnospira, Lactobacillus, Leuconostoc, Megamonas, Moryella, Mitsuokella, Oribacterium, Oxobacter, Papillibacter, Proprionispira, Pseudobutyrivibrio, Pseudoramibacter, Roseburia, Ruminococcus, Sarcina, Seinonella, Shuttleworthia, Sporobacter, Sporobacterium, Streptococcus, Subdoligranulum, Syntrophococcus, Thermobacillus, Turibacter and Weisella. In an example, the host cells, or the first or second sub-population consists of Clostridium (eg, dificile) cells (and optionally the other sub-population consists of Bacteroides (eg, thetaiotaomicron) cells). In an example, the host cells, or the first or second sub-population consists of Enterococcus cells (and optionally the other sub-population consists of Bacteroides (eg, thetaiotaomicron) cells). In an example, the host cells, or the first or second sub-population consists of Ruminococcus cells (and optionally the other sub-population consists of Bacteroides (eg, thetaiotaomicron) cells). In an example, the host cells, or the first or second sub-population consists of Streptococcus cells (and optionally the other sub-population consists of Bacteroides (eg, thetaiotaomicron) and/or Enterobacteriaceae (eg, E coli) cells). In an example, the host cells, or the first or second sub-population consists of Faecalibacterium cells (and optionally the other sub-population consists of Bacteroides (eg, thetaiotaomicron) cells). In an example, the host cells, or the first or second sub-population consists of Streptococcus cells (optionally S thermophilus and/or pyogenes cells) and the other sub-population consists of Bacteroides (eg, thetaiotaomicron) and/or Enterobacteriaceae (eg, E coli) cells.

The population product of the use or method of the invention is, in an embodiment, for administration to a human or non-human animal by mucosal, gut, oral, intranasal, intrarectal, intravaginal, ocular or buccal administration.

Optionally the host cells, or the first or second sub-population bacteria are B fragalis bacteria and the population is harboured by water.

A suitable beverage comprising an array, system, engineered sequence, vector or gRNA of the invention is, for example, a probiotic drink, eg, an adapted Yakult (trademark), Actimel (trademark), Kevita (trademark), Activia (trademark), Jarrow (trademark) or similar drink for human consumption.

Phage Sequence Targets

In aspects of the invention, the target sequence is a sequence of a phage that infects a host bacterial cell. Desired modification of phage genomes, as achieved by the invention, not only relates to phage killing or knock-down, but instead can be desired phage gene or regulatory element activation in the host cell (eg, when the phage expresses a desired protein or other product that is associated with increased host cell viability or proliferation). Alternatively, modification may be inducible phage gene expression regulation, eg, by use of an inducible Cas that is targeted according to the invention to the phage target site. In an embodiment, the invention provides for modifying the phage target site by cutting with a Cas nuclease in the host cell. This may be useful for various reasons, for example:—
  A. to mutate the target site to activate or inactivate it (eg, for gene knock-down or inactivation of an anti-host gene; or for killing the host cell when the phage target is integrated in the host chromosome);
  B. to delete the target sequence or a larger sequence comprising the target sequence (eg, when the invention is used with first and second PM-crRNAs that target spaced sites in the phage genome, wherein cuts in each site result in deletion of phage nucleic acid between the cuts);
  C. to insert a desired PM-DNA sequence into the host cell genome (eg, by providing one or more PM-crNA-guided cuts in a host nucleic acid for homologous recombination insertion of the desired PM-DNA).

The invention provides the following aspects:—

1. A method of altering the relative ratio of sub-populations of first and second bacteria in a mixed population of bacteria comprising said sub-populations, wherein the first bacteria are host cells (eg, Bacteroidetes host cells) (wherein the first bacteria are optionally infected by a phage and the second bacteria are not infected by said phage (or not Bacteroidetes)), the method comprising combining the mixed population with a plurality of vectors in one or more steps for introduction of vector nucleic acid (eg, a PM-containing transposon thereof) into host cells and allowing bacterial growth in the mixed population, wherein the relative ratios of said first and second bacteria is altered;
  wherein each vector comprises an engineered phage-modifying (PM) CRISPR array for introduction into host cell for modifying a target nucleotide sequence (eg, of said phage) in the cell,
  (a) wherein the PM-CRISPR array comprises one or more sequences for expression of a PM-crRNA respectively and a promoter for transcription of the sequence(s) in a host cell; and
  (b) wherein the PM-crRNA is capable of hybridising to the target sequence to guide Cas (eg, a Cas nuclease) in the host cell to modify the target sequence.

By targeting phage sequence(s) to inactivate gene(s) required for phage viability, propagation or infectivity, in one aspect the invention provides the array with a positive selective advantage that may promote its uptake and retention by host cells infected with the phage. When host cells are killed or growth is reduced, the relative ratio of first to second bacteria in the population is reduced. The invention provides such a product population, eg, for use as a medicament for treatment or prevention (reducing the risk) of a disease or condition in a human or animal subject, wherein the medicament is administered to the subject. The disease or condition can be any disease or condition disclosed herein. In an example, a single guide RNA (gRNA) is expressed in the host cells to provide the crRNA and each vector comprises an expressible engineered nucleotide sequence encoding such a gRNA.

In an example using a PM-array, the target sequence is a *Bacteroides thetaiotaomicron* sequence. Optionally the target sequence is not comprised by *B fragalis*. This is useful, for example, where the modifying cuts or otherwise renders the target sequence non-functional, whereby the ratio of *B thetaiotaomicron* host cells is increased without targeting *B fragalis*, eg, where the mixed population is a gut microbiota population as described herein. *B fragalis* is in some settings associated with abscesses and thus this example reduces the risk of this, whilst enabling alteration of ratios (increase of *B thetaiotaomicron* cell proportion) as per the invention that is useful for example to re-balance gut microbiota, eg, for treating or preventing obesity or diabetes or IBD.

The promoter (or a HM- or PM-array) is operable in a host cell. In an example, the promoter is a viral or phage promoter, eg, a T7 promoter. In another example, the promoter is a bacterial promoter (eg, a promoter of the host cell species).

2. The method of aspect 1, wherein the first bacteria are *Bacteroides* (eg, *thetaiotamicron* or *fragalis*), *Alistipes, Alkaliflexus, Parabacteroides, Tannerella, Xylanibacter* and/or *Prevotella* bacteria.

3. The method of aspect 1 or 2, wherein the second bacteria are Firmicutes bacteria (eg, when the first bacteria are Bacteroidetes or *Bacteroides*).

4. The method of any preceding aspect, wherein the ratio of the first bacteria sub-population to the second bacteria sub-population is increased, ie, is greater after said method has been carried out than before.

5. The method of aspect 4, wherein the mixed population is comprised by a composition (eg, a beverage, mouthwash or foodstuff) for administration to a human or non-human animal for populating and rebalancing the gut or oral microbiota thereof, eg, wherein the mixed population is in vitro, or in vivo in the human or non-human animal. The method of aspect 1, 2 or 3, wherein the ratio of the first bacteria sub-population to the second bacteria sub-population is decreased, ie, is less after said method has been carried out than before.

6. The method of aspect 6, wherein the mixed population is harboured by a beverage or water (eg, a waterway or drinking water) for human consumption.

7. The method of any preceding aspect, wherein each vector is a plasmid, phage (eg, a packaged phage) or phagemid.

8. The method of aspect 8, wherein each vector is a phage (eg, a packaged phage) and vector nucleic acid is introduced into host cells by phage vector nucleic acid transduction into host cells, ie, by infection of host cells by phage vectors. In an example, the phage comprises one or more transposons as described herein.

9. The method of aspect 8, wherein each vector is a plasmid and vector nucleic acid is introduced into host cells by transformation or horizontal plasmid transfer from bacteria harbouring the vectors. In an example, the plasmid comprises one or more transposons as described herein. In an example, the bacteria harbouring the vectors is a non-Bacteroidetes or non-*Bacteroides* species.

Additionally or alternatively, the bacteria harbouring the vectors is a non-Firmicutes species. In an example, the bacteria harbouring the vectors are bacteria of one or more species selected from the group consisting of a *Lactobacillus* species (eg, *acidophilus* (eg, La-5, La-14 or NCFM), *brevis, bulgaricus, plantarum, rhammosus, fermentum, caucasicus, helveticus, lactis, reuteri* or *casei* eg, *casei* Shirota), a *Bifidobacterium* species (eg, *bifidum, breve, longum* or *infantis*), *Streptococcus thermophilus* and *Enterococcus faecium*. For example, the bacteria are *L acidophilus* or *lactis* bacteria.

10. An engineered Bacteroidetes phage-modifying (PM) CRISPR array for use in the method of any preceding aspect for modifying the genome of said Bacteroidetes phage,
(a) wherein the PM-CRISPR array comprises one or more sequences for expression of a PM-crRNA and a promoter for transcription of the sequence(s) in a Bacteroidetes phage-infected host cell; and
(b) wherein the PM-crRNA is capable of hybridising to a Bacteroidetes phage genome target sequence to guide Cas (eg, a Cas nuclease) in the infected host cell to modify the target sequence.

11. A nucleic acid vector (eg, a plasmid, phage or phagemid) for use in the method of any one of aspects 1 to 10, the vector comprising a PM-CRISPR array of aspect 11.

In a General Embodiment of the Invention, there is Alternatively Provided for Aspect 12:—

A nucleic acid vector (eg, a plasmid, virus, phage or phagemid) comprising an engineered HM-CRISPR array for modifying a target sequence of the genome of a host bacterial cell (eg, pathogenic bacterial cell, such as described above) or the genome of a virus (eg, phage) in a host cell,
(a) wherein the CRISPR array comprises one or more sequences for expression of a crRNA and a promoter for transcription of the sequence(s) in the host cell; and
(b) wherein the crRNA is capable of hybridising to the target sequence to guide Cas (eg, a Cas nuclease) in the host cell to modify the target sequence.

The promoter is operable in a host cell. In an example, the promoter is a viral or phage promoter, eg, a T7 promoter. In another example, the promoter is a bacterial promoter (eg, a promoter of the host cell species).

In an example, the array is comprised by a transposon described herein. In an example, the array is comprised by a carrier bacterium as described herein. In an example, a plurality of the arrays is provided for targeting one or more target nucleotide sequences of the phage or host cell, wherein the plurality of arrays are comprised by bacterial cells, eg, carrier, first recipient or second recipient cells as described herein. In an example, the carrier cells are comprised by a beverage (eg, a probiotic drink for human consumption) or foodstuff as described herein. In an example, the array or carrier bacteria are for administration to a human or non-human animal for treating or preventing an infection of the human or animal, eg wherein the host cell is pathogenic. In an example, the array or carrier bacteria are for administration to the gut of a human or non-human animal for treating or preventing obesity, diabetes or IBD of the human or animal.

12. The array or vector of aspect 11 or 12 wherein the array or vector is comprised by a bacterial cell, eg, a probiotic cell for human or non-human animal consumption.

13. The method, array or vector of any preceding aspect, wherein the vectors are comprised by a third bacterial population (eg, carrier bacteria described herein) that is used for said combining with the mixed population or is for combination with the mixed population, whereby vector nucleic acid is introduced into host cells by transformation (eg, by horizontal plasmid vector or transposon transfer from the third bacteria to the first bacteria host cells) or transduction (eg, by phage vector infection of first bacteria host cells).

14. The method, array or vector of any preceding aspect, wherein the or each array or vector is comprised by a human or non-human animal gut commensal or symbiotic bacterial cell (eg, a carrier bacterial cell as described herein). Thus, the cell is of a gut bacterial species that is commensal or symbiotic with the human or non-human animal.

15. The method or vector of any one of aspects 12 to 15, wherein the or each vector is a plasmid, phage or phagemid comprising an origin of replication that is operable in a Firmicutes host cell or in a Bacteroidetes phage-infected host cell (eg, a *Bacteroides* cell), and optionally operable in a commensal or symbiotic bacterial cell as defined in aspect 15. In an example, the origin of replication is oriT or any other origin of replication described herein.

16. The method or vector of any one of aspects 12 to 16, wherein the or each vector is a plasmid or phagemid comprising a sequence (eg, a transposon described herein) that is capable of horizontal transfer between (1) a human or non-human animal commensal or symbiotic bacterial cell that is not a *Bacteroides* cell and (2) a said phage-infected cell which is a *Bacteroides* cell; or between (3) a human or non-human animal commensal or symbiotic bacterial cell that is not a Firmicutes cell and (4) a Firmicutes cell comprising the target sequence.

17. The method or vector of any one of aspects 12 to 17, wherein the or each vector is a plasmid or phagemid sequence (eg, a transposon described herein) that is capable of horizontal transfer between (1) a said phage-infected cell which is a *Bacteroides* cell and (2) a bacterial cell that is suitable for probiotic administration to a human or non-human animal gut; or between (3) a Firmicutes cell comprising the target sequence and (4) a bacterial cell that is suitable for probiotic administration to a human or non-human animal gut.

18. The method or vector of any one of aspects 15 to 18, wherein the commensal, symbiotic or probiotic species is selected from the group consisting of a *Lactobacillus* species (eg, *acidophilus* (eg, La-5, La-14 or NCFM), *brevis, bulgaricus, plantarum, rhammosus, fermentum, caucasicus, helveticus, lactis, reuteri* or *casei* eg, *casei* Shirota), a *Bifidobacterium* species (eg, *bifidum, breve, longum* or *infantis*), *Streptococcus thermophilus* and *Enterococcus faecium*.

The method, array or vector of any preceding aspect, wherein the promoter is operable for transcription of said sequence(s) in a said phage-infected Bacteroidetes host cell and in a commensal, symbiotic or probiotic bacterial cell as defined in any one of aspects 15 to 19; or in a Firmicutes cell comprising the target sequence and in a commensal, symbiotic or probiotic bacterial cell as defined in any one of aspects 15 to 19. For example, the promoter is a viral or bacterial promoter, eg, a T7 promoter. In an example, the promoter is a host cell promoter, eg, a promoter of a host CRISPR/Cas array.

19. The method, array or vector of any preceding aspect, or any use herein, wherein the modifying is (i) cutting of the target sequence, (ii) downregulating transcription of a gene comprising the target sequence, (iii) upregulating transcription of a gene comprising the target sequence, or (iv) adding, deleting or substituting a nucleic acid sequence at the target.

20. The method, array or vector of any preceding aspect, wherein the Bacteroidetes phage is a *Bacteroides* phage selected from a crAssphage, a GB-124 phage, a GA-17 phage, a HB-13 phage, a H16-10 phage, a B40-8 phage and *B fragalis* phage ATCC51477-Bl. Reference is made to Nat Commun. 2014 Jul. 24; 5:4498. doi: 10.1038/ncomms5498, "A highly abundant bacteriophage discovered in the unknown sequences of human faecal metagenomes", Dutilh B E et al. The crAssphage ~97 kbp genome is six times more abundant in publicly available metagenomes than all other known phages together; it comprises up to 90% and 22% of all reads in virus-like particle (VLP)-derived metagenomes and total community metagenomes, respectively; and it totals 1.68% of all human faecal metagenomic sequencing reads in the public databases. Using a new co-occurrence profiling approach, Dutilh et al predicted a *Bacteroides* host for this phage, consistent with *Bacteroides*-related protein homologues and a unique carbohydrate-binding domain encoded in the phage genome.

21. The method, array or vector of any preceding aspect, or any use herein, wherein the target sequence is comprised by a phage gene required for host cell infectivity, the phage lysogenic or lytic cycle, or phage viability, eg. an essential gene or coat protein gene.

22. The method, array or vector of any preceding aspect, wherein the target sequence is comprised by a BACON (Bacteroidetes-associated carbohydrate-binding) domain-encoding sequence (eg, wherein the host is a *Bacteroides* host) or an endolysin-encoding sequence. Reference is made to FEBS Lett. 2010 Jun. 3; 584(11):2421-6, doi:10.1016/j.febslet.2010.04.045. Epub 2010 Apr. 21, "Mining metagenomic data for novel domains: BACON, a new carbohydrate-binding module", Mello L et al. The presence of the BACON domain in a phage-structural protein might be explained by the proposed bacteriophage adherence to mucus model. According to this model, phage adhere to the mucin glycoproteins composing the intestinal mucus layer through capsid-displayed carbohydrate-binding domains (such as the immunoglobulin-like fold or the BACON domain), facilitating more frequent interactions with the bacteria that the phage infects.

25. The method, array or vector of any preceding aspect, or any use herein, wherein the CRISPR array comprises a sequence R1-S1-R1' for expression and production of the crRNA in the host cell,
  (i) wherein R1 is a first CRISPR repeat, R1' is a second CRISPR repeat, and R1 or R1' is optional; and
  (ii) S1 is a first CRISPR spacer that comprises or consists of a nucleotide sequence that is 95% or more identical to said target sequence. For example, the target sequence comprises a protospacer or is comprised by a protospacer sequence that is immediately adjacent to a protospacer adjacent motif (PAM) that is cognate to a Cas when the array of the invention is in the host cell, wherein the Cas is also cognate to the crRNA expressed from the array. In an embodiment, the Cas is endogenous to the cell. In another example, the Cas is exogenous to the host cell, eg, provided by a vector of the invention.

26. The method, array or vector of aspect 25, wherein R1 and R1' are at least 95% (eg, 96, 97, 98, 99 or 100%) identical to repeat sequences of a CRISPR array of a cell of the same species as the host cell.

27. The method, array or vector of aspect 25, wherein R1 and R1' is each at least 95% (eg, 96, 97, 98, 99 or 100%) identical to a repeat sequence of a CRISPR array (eg, a Type II-C array) of a *Bacteroides* species selected from *thetaiotamicron* and *fragalis* (eg, *Bacteroides fragalis* NCTC 9343), wherein the host cells comprise a CRISPR/Cas system that is functional with the repeat sequence and are *Bacteroides* cells, eg, of said species.

28. The method, array, use or vector of aspect 27, wherein R1 and R1' are at least 95% (eg, 96, 97, 98, 99 or 100%) identical respectively to the first (5'-most) and second (the repeat immediately 3' of the first repeat) repeat sequences of a CRISPR array of said species, eg, of a said host cell of said species. In an example, the array is a Type II-C array. In an example, the array or vector further comprises R2-S2-R2', wherein the spacer S2 is the same or different from the spacer S1 (eg, for targeting a different target site in the host cell or phage genome), wherein R2 and R2' are functional in the host cell and are optionally the same as R1. For example, each of R1, R1', R2 and R2' is a *B fragalis* CRISPR repeat.

29. The method, array, use or vector of aspect 25, wherein (iii) each of R1 and R1' is identical to a repeat sequence of a CRISPR array (eg, a Type II-C array) of a *Bacteroides* species cell, wherein the species is selected from the group consisting of *caccae, capillosus, cellulosilyticus, coprocola, coprophilus, coprosuis, distasonis, dorei, eggerthii, faecis, finegoldii, fluxus, fragalis* (eg, *fragalis* NCTC 9343), *intestinalis, melaninogenicus, nordii, oleiciplenus, oralis, ovatus, pectinophilus, plebeius, stercoris, thetaiotaomicron, uniformis, vulgatus* and *xylanisolvens*, and (iv) wherein the host cell comprises a CRISPR/Cas system that is functional with the repeat sequence and is a *Bacteroides* cell of a species selected from said group (eg, the same species as the selected species of (iii)).

30. The method, array, use or vector of aspect 25, wherein R1 and R1' are functional with a CRISPR/Cas system of a said host Bacteroidetes or Firmicutes cell for modification of the target sequence. In an example, R1, R1', R2 and R2' are Type II (eg, Type II-C) CRISPR/Cas system repeats of the same bacterial species, eg, a *Bacteroides*, such as *thetaiotamicron* or *fragalis* or *Streptococcus*, such as *thermophilus* or *pyogenes*.

31. The method, array, use or vector of aspect 25, wherein R1 and R1' are at least 95% (eg, 96, 97, 98, 99 or 100%) identical to repeat sequences of a CRISPR array (eg, a Type II-C array) of a Bacteroidetes (eg, *Bacteroides* or *Prevotella*) or Firmicutes (eg, *Streptococcus*) cell.

32. The method, array, use or vector of aspect 25, wherein each of R1 and R1' is at least 95% (eg, 96, 97, 98, 99 or 100%) identical to a sequence selected from SEQ ID NOs: 1 to 5 of Table 2 and optionally the first bacterial cells are *Bacteroides* cells, eg, of a species or strain (eg, the species or strain listed against the selected sequence) in Table 2.

33. The method, array, use or vector of aspect 25, wherein each of R1 and R1' is at least 95% (eg, 96, 97, 98, 99 or 100%) identical to a sequence selected from SEQ ID NOs: 6 to 11 Table 2 of and optionally the first bacterial cells are *Prevotella* cells, eg, of a species or strain (eg, the species or strain listed against the selected sequence) in Table 2.

34. The method, array or vector of any preceding aspect, wherein the or each array is in combination with one or more Cas nuclease(s) that function with the crRNA in a said host cell to modify the target sequence. For example, the target sequence comprises a protospacer sequence immediately adjacent to a Protospacer Adjacent Motif (PAM), optionally wherein the PAM is cognate to a Cas nuclease comprised by the Bacteroidetes host cells. In an example, the Cas is a Type II-C Cas nuclease.

35. The method, array or vector of any preceding aspect, wherein the or each array is in combination with nucleic acid sequence(s) encoding one or more Cas nuclease(s) that function with the crRNA in a said host cell to modify the target sequence.

36. The method, array, use or vector of aspect 25, wherein R1 and R1' are functional with a Type II Cas9 nuclease (eg, a *S pyogenes, S thermophilus* or *S aureus* Cas9) to modify the target in a said host cell, optionally wherein the method, array or vector is further according to aspect 34 or 35 wherein the Cas is said Cas9.

37. An ex-vivo mixed population of bacteria obtainable by the method of any one of aspects 1 to 10 or 14 to 36 or a use herein. For example, the mixed population is in a container for medical or nutritional use. For example, the container is a sterilised container.

38. A composition for administration to a human or non-human animal for therapeutic, prophylactic, cosmetic, human or non-human animal body mass reduction (eg, cosmetic reduction) or nutritional use, the composition comprising the mixed population of aspect 37. In an example, the composition is for oral, systemic, inhaled, intrarectal, ocular, buccal or intravaginal administration. In an example, the composition is for administration to the gut or oral cavity of a human or non-human animal.

39. A foodstuff or beverage for human or non-human animal consumption comprising the mixed population of aspect 37 or the composition of aspect 38.

40. The foodstuff or beverage of aspect 39, which is a nutritional supplement or a probiotic beverage or foodstuff.

41. An antibiotic composition for treating or preventing a Bacteroidetes infection in a human or non-human animal or in drinking water, wherein the composition comprises an array or vector of any one of aspects 11 to 36, optionally wherein the modifying is according to aspect 21 (iii) or (iv).

42. A probiotic composition for increasing the proportion of gut Bacteroidetes (eg, to treat or prevent obesity, diabetes (eg, Type I) or a GI inflammatory condition) in a human or non-human animal, wherein the composition comprises an array or vector of any one of aspects 11 to 36, optionally wherein the modifying is according to aspect 21 (iii) or (iv).

43. The composition of aspect 38, 41 or 42 for increasing the relative proportions of gut *Bacteroides* to Firmicutes in the human or animal, eg for treating or preventing obesity, diabetes (eg, Type I diabetes) or a GI condition (eg, Crohn's disease, IBD, IBS or ulcerative colitis).

In an alternative, "array" in any configuration of the invention can instead by an engineered nucleotide sequence encoding a HM-crRNA or gRNA for expression in a host cell. The features of any of the aspects herein relating to an array can, therefore, in the alternative apply mutatis mutandis to such an engineered sequence.

Mobile Genetic Elements & Crispr Systems

44. A nucleic acid vector (eg, a plasmid, virus, phage or phagemid) comprising an engineered CRISPR array for modifying a target sequence of the genome of a host bacterial cell (eg, Firmicutes or pathogenic bacterial cell, such as described above) or the genome of a virus (eg, phage) in a host cell,
  (a) wherein the CRISPR array comprises one or more sequences for expression of a crRNA (eg, comprised by a gRNA) and a promoter for transcription of the sequence(s) in the host cell;
  (b) wherein the crRNA is capable of hybridising to the target sequence to guide Cas (eg, a Cas nuclease) in the host cell to modify the target sequence;
  (c) wherein the array is comprised by a transposon that is capable of horizontal transfer between first and second bacterial cells of different species.

Optionally, the Cas nuclease is a wild-type endogenous Cas nuclease of the host cell.

45. The vector of aspect 44, wherein the array is for administration to a human or non-human animal; and the first cell species is non-pathogenic to the human or animal and the second cell species is pathogenic to the human or animal, wherein the array is comprised by the first cell.

46. The vector of aspect 45, wherein the first cell species is a species that is commensal or symbiotic with the human or animal, eg, a gut microbiota species.

47. The vector of aspect 45 or 46, wherein the first cell species is selected from the group consisting of a *Lactobacillus* species (eg, *acidophilus* (eg, La-5, La-14 or NCFM), *brevis, bulgaricus, plantarum, rhammosus, fermentum, caucasicus, helveticus, lactis, reuteri* or *casei* eg, *casei* Shirota), a *Bifidobacterium* species (eg, *bifidum, breve, longum* or *infantis*), *Streptococcus thermophilus* and *Enterococcus faecium*.

48. The vector of any one of aspects 44 to 47, wherein the vector is comprised by a beverage (eg, a probiotic drink) or foodstuff for human or animal consumption.

49. The vector of any one of aspects 44 to 48, wherein the vector comprises at least one repeat-spacer-repeat unit for targeting the target sequence, wherein the repeats are at least 95% (eg, 96, 97, 98, 99 or 100%) identical to repeats of a CRISPR/Cas system of the host cell, whereby the repeats of the vector are operable in the host cell to guide Cas of the host system to modify the target nucleotide sequence.

50. The vector of aspect 49, wherein the vector lacks a Cas (eg, Cas nuclease)-encoding sequence.

Targeting of a nucleotide sequence of the host CRISPR/Cas system according to the invention is useful for removing host cell resistance to a vector (eg, invading virus) or reducing the development or increase of resistance. For example, the invention thereby provides the advantage of targeting and knocking down the activity of an endogenous CRISPR/Cas system so that new vector (eg, phage) spacer acquisition is inhibited.

A feature of mobilisation is the presence of a cis-acting region (oriT) that is required for transfer. This region is the initiation site of DNA processing at which a site- and strand-specific nick is made in the plasmid to start the transfer event. The invention provides further embodiments employing mobile genetic elements (MGEs) as follows:—

1. An engineered CRISPR nucleic acid vector comprising or consisting of a mobile genetic element (MGE), wherein the MGE comprises an origin of transfer (oriT) and a CRISPR array for modifying a target sequence of the genome of a host cell (eg, pathogenic bacterial cell) or the genome of a virus (eg, prophage) in a host cell,
   (a) wherein the CRISPR array comprises one or more sequences for expression of a crRNA and a promoter for transcription of the sequence(s) in the host cell;
   (b) wherein the crRNA is capable of hybridising to the target sequence to guide Cas (eg, a Cas nuclease) in the host cell to modify the target sequence;
   (c) wherein the vector is capable of transfer between (i) first and second nucleic acid positions of a first host cell, wherein each position is a position on a chromosome or a plasmid and the target sequence is comprised by the host cell, or (ii) first and second host cells, wherein the target sequence is comprised by the first and/or second host cell.

Examples of MGEs are ICEs, transposons, plasmids and bacteriophage. An origin of transfer (oriT) is a short sequence (eg, up to 500 bp) that is necessary for transfer of the DNA that contains it from a bacterial host to recipient during conjugation. The oriT is cis-acting—it is found on the same DNA that is being transferred, and it is transferred along with the DNA. A typical origin of transfer comprises three functionally defined domains: a nicking domain, a transfer domain, and a termination domain.

Optionally, the promoter is operable for transcription of said sequence(s) in the first and second (and optionally the third) cells.

Optionally the target sequence is comprised by the second cell. Optionally the target sequence is not comprised by the second cell.

In an example, the first and second cells are of different bacterial species (eg, species found in a human microbiome population, eg, of the gut, armpit, vagina or mouth). In an example, the first and second cells are ex vivo. In another example, the first and second cells are comprised by a human gut, vaginal, armpit or oral microbiome in vivo or ex vivo.

2. The vector of embodiment 1, wherein the MGE is or comprises an integrative and conjugative element (ICE). Alternatively, the MGE is a mobilisable MGE (ie, able to use factors encoded by genes not carried by the MGE, in order to be mobilised). The terms "mobilisable" and "conjugative" in relation to MGEs are readily apparent to the skilled addressee.

Reference is made to the ICEberg database (db-mml.sjtu.edu.cn/ICEberg/), which provides examples of suitable ICEs for the invention and sources for suitable oriT. In an example, the ICE is a member of an ICE family comprising an ICE selected from the group 1 to 28, or the oriT is an oriT of a member of such a family: 1=SXT/R391; 2=Tn916; 3=Tn4371; 4=CTnDOT/ERL; 5=ICEclc; 6=ICEBs1; 7=ICEHin1056; 8=PAPI-1; 9=ICEMISym(R7A); 10=ICESt1; 11=SPI-7; 12=ICE6013; 13=ICEKp1; 14=TnGBS1; 15=Tn5253; 16=ICESa2603; 17=ICEYe1; 18=10270-RD.2; 19=Tn1207.3; 20=Tn1806; 21=ICEA5632; 22=ICEF-I/II; 23=ICEAPG2; 24=ICEM; 25=10270-RD.1; 26=Tn5801; 27=PPI-1; 28=ICEF-III. Family descriptions are found in the ICEberg database. For example, the Tn916 family was defined by Roberts et al (2009) (Trends Microbiol. 2009 June; 17(6):251-8. doi: 10.1016/j.tim.2009.03.002. Epub 2009 May 20; "A modular master on the move: the Tn916 family of mobile genetic elements", Roberts A, Mullany P). Elements belonging to the Tn916 family are defined by the following criteria: they must have the general organization shown in Roberts et al, and they must have a core region (conjugation and regulation module) that is similar in sequence and structure to the original Tn916 at the DNA level. Exceptions are some conjugative transposons, such as Tn1549 which have been previously classified in this family and those with a high degree of protein similarity as described in corresponding references.

3. The vector of embodiment 2, wherein the ICE is a transposon, eg, a conjugative transposon. In an example, the MGE is a mobilisable transposon that is mobilisable in the presence of a functional helper element, optionally wherein the transposon is in combination with a said helper element.

4. The vector of any preceding embodiment, wherein the vector is a plasmid, optionally wherein the MGE is a transposon comprised by the plasmid. For example, the transposon is a conjugative transposon. In an example the transposon is a mobilisable transposon (eg, mobilisable using one or more factors encoded by the plasmid, eg, by genes outside the transposon sequence of the plasmid). Optionally, the transposon is a Type I transposon. Optionally, the transposon is a Type II transposon.

5. The vector of any preceding embodiment, wherein oriT is functional in the first and second host cells. This is useful to promote spread and propogation across bacteria in a bacterial population, eg, when the first and second cells are of different species.

6. The vector of embodiment 5 when comprised by the first cell, wherein the first cell comprises nucleotide sequences encoding proteins operable to transfer the MGE to the second cell, wherein the sequences are not comprised by the MGE. This is useful to avoid using space in the MGE for such sequences. For example, this enables construction of a more compact MGE for transfer between cells or enables inclusion of larger or more CRISPR arrays, eg, to include a plurality of spacers to target respective sequences in a host cell or to target different sequences in the first and second host cells.

7. The vector of embodiment 6, wherein the sequences are not comprised by the vector. This is useful to avoid using space in the vector or MGE for such sequences. For example, this enables construction of a more compact vector or MGE for transfer between cells or enables inclusion of larger or more CRISPR arrays, eg, to include a plurality of spacers to target respective sequences in a host cell or to target different sequences in the first and second host cells, and/or to include one or more sequences for encoding Cas protein(s), eg a Cas9.

8. The vector of embodiment 6 or 7, wherein the sequences are comprised by a conjugative transposon of the first cell. This is useful since it enables harnessing of factors outside the MGE to effect conjugative transposition, for horizontal transfer of the MGE of the invention between first and second host cells (eg, of different bacterial species in a human microbiome).

9. The vector of embodiment 8, wherein the transposon is operable in trans to transfer the MGE to the second cell. This is useful since it enables harnessing of factors outside the MGE to effect conjugative transposition, for horizontal transfer of the MGE of the invention between first and second host cells (eg, of different bacterial species in a human microbiome). For example, the oriT of the MGE of the invention is the same as an oriT comprised by a conjugative transposon of the host cell. This is useful to enable the MGE of the invention to operate with factors encoded by the host cell for effecting horizontal transfer of the MGE between the first and second host cells (eg, bacterial cells of different species, eg, human microbiome species). This enables the MGE to be more compact or frees up space for CRISPR arrays and/or Cas gene(s) as discussed above.

The term "operable in trans" means that the MGE (ICE) is operable for horizontal transfer using proteins expressed from host nucleotide sequences outside the vector nucleotide sequences (eg, proteins expressed by a conjugative transposon of the host cell) to transfer the MGE (or the entire vector, such as a plasmid containing the MGE) into the second cell.

10. The vector of any preceding embodiment when comprised by the first cell, wherein the oriT of the MGE is the same as an oriT comprised by an ICE of the first cell, wherein the ICE is operable in trans to transfer the MGE to the second cell.

11. The vector of any preceding embodiment, wherein the vector oriT is an oriT of a Bacteroidetes (eg, Bacteroidales or *Bacteroides*) or *Prevotella* transposon. This useful when the first and/or second host cell is a Bacteroidetes (eg, Bacteroidales or *Bacteroides*) or *Prevotella* cell respectively. For example, the first cell is a cell of such a species and the second cell is a Firmicutes cell, the target sequence being comprised by the second cell but not the first cell, whereby the CRISPR array directs Cas in the second cell to cut the target sequence. In an example, the target sequence is comprised by an essential gene or antibiotic resistance gene of the second cell (and for the latter, optionally the vector is in combination with said antibiotic or administered to a human or non-human animal in combination with said antibiotic). Optionally, the transposon is a CTnDot or CTnERL transposon and the vector is in combination with tetracycline or administered to a human or non-human animal in combination with tetracycline.

12. The vector of any preceding embodiment, wherein the vector oriT is a CTnDot, CTnERL SXT/R391, Tn916 or Tn4371 family transposon oriT.

13. The vector of any preceding embodiment, wherein the MGE comprises first and second terminal repeat sequences and the CRISPR array between the repeat sequences.

14. The vector of any preceding embodiment, wherein the MGE leaves behind a transposon copy (1) at the first nucleic acid position when it has transferred to the second position; or (2) in the first cell when the it has transferred to the second cell. This is useful for promoting propagation and maintenance of the MGE in a bacterial population comprising the host cell(s). In an alternative, the MGE does not leave behind a transposon copy (i) at the first nucleic acid position when it has transferred to the second position; or (ii) in the first cell when the it has transferred to the second cell.

15. The vector of any preceding embodiment when comprised by the first and/or second cell (eg, first and second copies of the vector comprised by the first and second cells).

16. The vector of embodiment 15, wherein the first and second cells are cells of different species. For example, the first cell is a *Lactobacillus* cell (eg, as described herein) and/or the second cell is a Bacteroidetes (eg, *Bacteroides* cell, eg, such a cell described herein) or a Firmicutes cell (eg, such a cell described herein). In an example, the first cell is a Bacteroidetes (eg, *Bacteroides* cell, eg, such a cell described herein) and the second cell is a Firmicutes cell (eg, such a cell described herein), eg, for administration to a gut microbiome of a human for treating or preventing a GI condition or diabetes; or for treating or preventing obesity.

17. The vector of embodiment 15 or 16, wherein the first and second cells are bacterial or archaeal cells.

18. The vector of embodiment 16 or 17, wherein the first cell is non-pathogenic in a human (eg, a commensal or symbiotic bacterial cell) and optionally the second cell is a pathogenic cell in a human. In an alternative, the second cell is a non-pathogenic cell in a human. The term "non-pathogenic in a human" includes cells, such as certain bacterial species (eg, *Bacteroides* species, such as *fragalis*) that can reside in microbiomes of the human (eg, the gut, vaginal, armpit or oral microbiome) without pathogenicity or substantial pathogenicity, but in other environments of the human are pathogenic. The skilled person will readily understand that the first cell type can be retained in or on a human and the second cell type should be reduced in or on the human. For example, the CRISPR array modifies the genome of the second cell to kill or reduce cell viability or growth in or on the human. For example, the target site is comprised by the second cell and the site is cut by said Cas nuclease, thereby inactivating or down-regulating a gene comprising the target site. For example, the gene is an essential gene or antibiotic resistance gene of the second cell. In an example, the gene is a virulence gene.

19. The vector of any preceding embodiment, or any use herein, wherein the second cell (each host cell) is a cell selected from (i) a *Staphylococcus aureus* cell, eg, resistant to an antibiotic selected from methicillin, vancomycin-resistant and teicoplanin; (ii) a *Pseudomonas aeruginosa* cell, eg, resistant to an antibiotic selected from cephalosporins (eg, ceftazidime), carbapenems (eg, imipenem or meropenem), fluoroquinolones, aminoglycosides (eg, gentamicin or tobramycin) and colistin; (iii) a *Klebsiella* (eg, *pneumoniae*) cell, eg, resistant to carbapenem; (iv) a *Streptococcus* (eg, *pneumoniae* or *pyogenes*) cell, eg, resistant to an antibiotic selected from erythromycin, clindamycin, beta-lactam, macrolide, amoxicillin, azithromycin and penicillin; (v) a *Salmonella* (eg, serotype *Typhi*) cell, eg, resistant to an antibiotic selected from ceftriaxone, azithromycin and ciprofloxacin; (vi) a *Shigella* cell, eg, resistant to an antibiotic selected from ciprofloxacin and azithromycin; (vii) a *Mycobacterium tuberculosis* cell, eg, resistant to an antibiotic selected from Resistance to isoniazid (INH), rifampicin (RMP), fluoroquinolone, amikacin, kanamycin and capreomycin; (viii) an *Enterococcus* cell, eg, resistant to vancomycin; (ix) an Enterobacteriaceae cell, eg, resistant to an antibiotic selected from a cephalosporin and carbapenem; (x) an *E. coli* cell, eg, resistant to an antibiotic selected from trimethoprim, itrofurantoin, cefalexin and amoxicillin; (xi) a *Clostridium* (eg, *dificile*) cell, eg, resistant to an antibiotic selected from fluoroquinolone antibiotic and carbapenem; (xii) a *Neisseria gonnorrhoea* cell, eg, resistant to an antibiotic selected from cefixime (eg, an oral cephalosporin), ceftriaxone (an injectable cephalosporin), azithromycin and tetracycline; (xiii) an *Acinetobacter baumannii* cell, eg, resistant to an antibiotic selected from beta-lactam, meropenem and a carbapenem; or (xiv) a *Campylobacter* cell, eg, resistant to an antibiotic selected from ciprofloxacin and azithromycin. Such species can be pathogenic to humans.

20. The vector or use of embodiment 19, wherein the target site is comprised by an antibiotic resistance gene of the second cell, wherein the antibiotic is a respective antibiotic recited in embodiment 19.

21. The vector of any one of embodiments 15 to 20, wherein the first cell is a Bacteroidetes (eg, Bacteroidales or *Bacteroides*) cell; *Lactobacillus* (eg, *acidophilus* (eg, La-5, La-14 or NCFM), *brevis, bulgaricus, plantarum, rhammosus, fermentum, caucasicus, helveticus, lactis, reuteri* or *casei* eg, *casei* Shirota); *Bifidobacterium* (eg, *bifidum, breve, longum* or *infantis*); *Streptococcus thermophiles; Enterococcus faecium; Alistipes; Alkaliflexus; Parabacteroides; Tannerella*; or *Xylanibacter* cell.

22. The vector of any preceding embodiment, wherein the first and/or second nucleic acid positions of (i) are comprised by a Bacteroidetes (eg, Bacteroidales or *Bacteroides*) cell; or the first and/or second host cells of (ii) are Bacteroidetes (eg, Bacteroidales or *Bacteroides*) or *Prevotella* cells.

23. The vector of embodiment 22, wherein the first cell is a Bacteroidetes (eg, Bacteroidales or *Bacteroides*) cell and the second cell is a Firmicutes (eg, *Clostridium* or *Staphylococcus*) cell, eg, wherein the vector is for administration to a gut microbiome of a human for treating or preventing a GI condition or diabetes; or for treating or preventing obesity.

24. The vector of embodiment 16 or 17 (or any use herein), wherein the first cell (each first cell) is environmentally-acceptable in an environment (eg, in a water or soil environment) and optionally the second cell (each host cell) is not acceptable in the environment. The water environment will be readily apparent to the skilled person and can, for example, be a marine or waterway (eg, lake, canal, river or reservoir) environment. In an example, the water environment is drinking water intended for human consumption or sewage water. In an example, the soil environment is soil of farming land or soil at a mining site (eg, a mineral or metal mining site).

By "acceptable" and "not acceptable" the skilled person will readily understand that the first cell type can be retained in the environment and the second cell type should be reduced in the environment. For example, the CRISPR array modifies the genome of the second cell to kill or reduce cell viability or growth in the environment. For example, the target site is comprised by the second cell and the site is cut by said Cas nuclease, thereby inactivating or down-regulating a gene comprising the target site. For example, the gene is an essential gene or antibiotic resistance gene of the second cell. In an example, the gene is a virulence gene.

In an example, the environment is a microbiome of a human, eg, the oral cavity microbiome or gut microbiome or the bloodstream. In an example, the environment is not an environment in or on a human. In an example, the environment is not an environment in or on a non-human animal. In an embodiment, the environment is an air environment. In an embodiment, the environment is an agricultural environment. In an embodiment, the environment is an oil or petroleum recovery environment, eg, an oil or petroleum field or well. In an example, the environment is an environment in or on a foodstuff or beverage for human or non-human animal consumption.

In an example, the vector, system, vector, array, crRNA, gRNA, method or any use herein is for use in an industry or the environment is an industrial environment, wherein the industry is an industry of a field selected from the group consisting of the medical and healthcare; pharmaceutical; human food; animal food; plant fertilizers; beverage; dairy; meat processing; agriculture; livestock farming; poultry farming; fish and shellfish farming; veterinary; oil; gas; petrochemical; water treatment; sewage treatment; packaging; electronics and computer; personal healthcare and toiletries; cosmetics; dental; non-medical dental; ophthalmic; non-medical ophthalmic; mineral mining and processing; metals mining and processing; quarrying; aviation; automotive; rail; shipping; space; environmental; soil treatment; pulp and paper; clothing manufacture; dyes; printing; adhesives; air treatment; solvents; biodefence; vitamin supplements; cold storage; fibre retting and production; biotechnology; chemical; industrial cleaning products; domestic cleaning products; soaps and detergents; consumer products; forestry; fishing; leisure; recycling; plastics; hide, leather and suede; waste management; funeral and undertaking; fuel; building; energy; steel; and tobacco industry fields.

25. The vector of any preceding embodiment in combination with a nucleic acid (eg, a DNA) for incorporation at the modified target site.

In an example, the modification is cutting of the target site and the nucleic acid (eg DNA) is incorporated by homologous recombination in the host cell. This is useful for effecting precise targeted modification of the host cell genome using the vector of the invention.

26. The vector of embodiment 25, wherein the nucleic acid for incorporation is or comprises a regulatory element or exon sequence, eg a human sequence.

27. The vector of any preceding embodiment in combination with a transposase for mobilisation of the MGE.

28. The vector or any preceding embodiment, wherein the vector or MGE comprises a toxin-antioxin module that is operable in the first host cell; optionally wherein the toxin-antitoxin module comprises an anti-toxin gene that is not operable or has reduced operation in cells other than the first cell.

29. The vector or any preceding embodiment, wherein the vector or MGE comprises a toxin-antioxin module that is operable in the second host cell; optionally wherein the toxin-antitoxin module comprises an anti-toxin gene that is not operable or has reduced operation in cells other than the second cell.

30. The vector or any preceding embodiment, wherein the vector or MGE comprises a toxin-antioxin module that is operable in the first and second host cells; optionally wherein the toxin-antitoxin module comprises an anti-toxin gene that is not operable or has reduced operation in cells other than the first and second cells. The use of a toxin-antitoxin module is useful to confer selective advantages and thus MGE retention and spread. For example, the module is a Type I module, eg, a Hok-Sok module. For example, the module is a Type II module, eg, a HiCa-HicB module. For example, the module is a tad-ata-type toxin-antitoxin module. For example, the module is a plasmid addiction module. In an example, the first and/or second cell is a *Bacteroides* cell and the module is a module of a *Bacteroides* species, eg, the Txe/YoeB family addiction module (see, eg, uniprot.org/uniprot/F0R9D1); RelE/StbE family addiction module (see, eg, uniprot.org/uniprot/F0R9A0); HigA family addiction module (see, eg, uniprot.org/uniprot/D7J8V2 or uniprot.org/uniprot/D2ESD0); RelE/StbE family addiction module (see, eg, uniprot.org/uniprot/F0R5F4). Use of a toxin-antitoxin in the vector or MGE can be useful to allow for destruction of a vector-bearing cell other than a cell that is desired (eg, the first and second and/or third bacterial cell). In this example, the MGE or vector comprises a toxin gene of a bacterial toxin-antitoxin module and a cognate anti-toxin gene, wherein the expression of the toxin and anti-toxin genes are separately regulated, eg, from different promoters. For example, the toxin gene can comprise a promoter that is constitutively active in the first, second (and third) cells so that the toxin is always produced. The anti-toxin gene can comprise a promoter that is inducible by one or more factors (eg, a protein expressed) in the first and/or second cells, but not in non-target cells of different strain or species. As is known, the anti-toxin is inherently less stable than the toxin in a bacterial toxin/anti-toxin system, and thus transfer of the vector or MGE to a cell that is not a target cell (eg, not the first and/or second cell) will lead to toxin expression in the absence of anti-toxin expression or lower anti-toxin activity, thus leading to cell death of the non-target cell. This, therefore creates a selection pressure for the target cells (first, second and third cells) to take up and retain the vector of the invention so that it can have the desired CRISPR array activity therein and also be propagated across target cells in a population (such as the gut microbiota). This also limits the spread of the vector or MGE to non-target cells so that the effect of the array is controlled in the population—in this respect there will be a pressure for non-target cells not to take up the vector and if they do, the recipient cells will not survive in the population, thereby limiting replication of non-target cells with the MGE and array.

31. The vector of any preceding embodiment wherein the first and second cells are of the same phylum (eg, both bacterial cells) and the vector is replicable or operable (d) in the first cell and/or second cell but not in another cell of the same phylum; (e) in the first cell and/or second cell but not in another cell of the same order; (f) in the first cell and/or second cell but not in another cell of the same class; (g) in the first cell and/or second cell but not in another cell of the same order; (h) in the first cell and/or second cell but not in another cell of the same family; (i) in the first cell and/or second cell but not in another cell of the same genus; (j) in the first cell and/or second cell but not in another cell of the same species; (k) in the first cell and/or second cell but not in another cell of the same strain.

This affords selectivity of the vector of the invention (eg, for selective killing of the second host cell type in a mixed bacterial population) in a microbiome. This can be achieved, for example, by engineering the MGE or array (eg, the promoter thereof) so that it requires expression of a particular protein for replication or operation (eg, expression to produce crRNA). For example, the promoter can be selected from a promoter that operates in the first and/or second cell but not in other cells, or wherein the MGE is engineered so that one or more of the replication initiation sites thereof are dependent upon a protein or other factor produced in the first and/or second cell but in not other cells.

32. First and second copies of the vector of any preceding embodiment in a mixed population of cells, wherein the first vector is comprised by the first cell, the second vector is comprised by the second cell, the cells are cells of different species (eg, different bacterial species) and the one or both of the vector MGEs is capable of transferring to a third cell (eg, a bacterial cell), wherein the third cell species is the same as the species of the first or second cell or is a species that is different from the first and second cell species. This is useful, since the first cell can act as a carrier (eg, when it is non-pathogenic it can be adminstered to a huma or animal so that it populates the human or animal, such as a microbiome thereof). By horizontal transfer, the carrier can transfer and propagate CRISPR arrays of the invention to third cells (directly or via second cells, the latter acting as a reservoir for arrays). The arrays can then mediate Cas modification (eg, cutting) of the target sequence in the third cells, eg, to inactivate or down-regulate an essential or antibiotic resistance gene of the third cells.

Generally herein, when the target sequence is comprised by an antibiotic resistance gene of a cell, the vector, engineered sequence or array of the invention can be administered to a human or animal together with (simultaneously or sequentially) the antibiotic. This is useful to kill or reduce proliferation of cells comprising the target sequence. In this respect, the vector, engineered sequence or array is comprised by a composition comprising an antibiotic, wherein the target sequence is a sequence of a gene encoding for resistance to said antibiotic.

Optionally, the mixed population comprises the third cell.

In an example, there is a provided a plurality of the first cells, each comprising a vector of the invention. In an example, there is a provided a plurality of the second cells, each comprising a vector of the invention. In an example, there is a provided a plurality of the first cells in combination with a plurality of the second cells, each cell comprising a vector of the invention. In an example, there is a provided a plurality of the first cells in combination with a plurality of the second cells and a plurality of the third cells, cells of at least 2 (or all of) said pluralities comprising a vector of the invention.

33. The vectors of embodiment 32, wherein the vector or MGE comprises a toxin-antioxin module that is operable in the first, second and third host cells; optionally wherein the toxin-antitoxin module comprises an anti-toxin gene that is not operable or has reduced (ie, lesser) operation in cells other than the first, second and third cells.

34. The vector of any preceding embodiment, wherein the MGE is a conjugative transposon, oriT is functional in the first and second host cells, the MGE comprises first and second terminal repeat sequences and the CRISPR array between the repeat sequences, and wherein the first and second cells are bacterial cells, the second cell being of a human microbiota cell species (eg, a pathogenic species), wherein the target site is comprised by the second cell but not the first cell, and wherein said modifying inactivates or down-regulates a gene or regulatory sequence comprising said target in the second cell.

Usefully, the first cells can thereby act as carriers and reservoirs for the arrays of the invention, which can be transferred by horizontal transfer of the MGEs.

In an example, the MGE is a conjugative Bacteroidetes transposon, oriT is a Bacteroidetes oriT functional in the first and second host cells, the MGE comprises first and second terminal repeat sequences and the CRISPR array between the repeat sequences, and wherein the first and second cells are bacterial cells, the first cell being a Bacteroidetes cell and the second cell being a Firmicutes cell (eg, *Clostridium* or *Staphylococcus* cell), wherein the target site is comprised by the second cell but not the first cell, and wherein said modifying inactivates or down-regulates a gene or regulatory sequence comprising said target in the second cell.

35. The vector of embodiment 34 when comprised by the first or second cell.

36. The vector of any preceding embodiment, wherein the first and second cells are comprised by a mixed bacterial cell population, eg, a population of cells of human or non-human animal (eg, dog, cat or horse) gut, vaginal, armpit or oral microbiota species. As explained above, the population is useful for administration to a human or animal to populate a microbiome thereof.

37. An ex vivo composition comprising a plurality of cells as defined in embodiment 22, wherein each cell comprises a vector according to any one of embodiments 1 to 36. Alternatively, the composition is in vivo, eg, in a non-human animal.

38. A beverage or foodstuff for human or non-human animal consumption comprising a vector of any one of embodiments 1 to 36 or the composition of embodiment 37. The beverage can be, for example, a probiotic drink, eg, for consumption daily, once every two days or weekly by a human or animal, eg, to treat or prevent obesity or a GI condition in the human or animal.

39. A composition comprising a plurality of *Bacteroides* cells, wherein each cell comprises a vector according to any one of embodiments 1 to 36.

Usefully, the cells can act as carriers and a reservoir of arrays of the invention, for administration to a microbiome (eg, gut microbiome) of a human or animal, eg, to treat or prevent obesity or a GI condition in the human or animal, 40. A mixed population of bacterial cells comprising a sub-population of first cells and a sub-population of second cells, wherein the first cells comprise vectors according to any one of embodiments 1 to 36, wherein the vectors are capable of horizontal transfer between the first and second cell sub-populations. Such a population is useful as it can be adminstered (eg, intranasally) to a human or animal so that the bacteria populate one or more microbiomes (eg, gut microbiome) of the human or animal. The first (and optionally also the second) cells can act as carriers of the CRISPR arrays of the invention, especially when those cells are non-pathogenic to the human or animal (eg, non-pathogenic in the gut microbiome). The microbiome can be any other microbiome or microbiota population disclosed herein.

41. The population of embodiment 40, wherein one or both of the first and second bacterial species is capable of populating the gut microbiota of a human or non-human animal, and optionally the first bacteria are commensal or symbiotic with humans or animals. Usefully, the first bacteria can be safely administered to the human or animal and can act as a carrier of the arrays of the invention for transfer thereafter to other cells of the microbiota.

42. The population of embodiment 40, wherein the mixed population is harboured by a beverage or water (eg, a waterway or drinking water for human consumption) or soil.

Provision of the population in water or soil is useful for treating such in the environment or (for water) in heating, cooling or industrial systems, or in drinking water storage containers.

In an example of any embodiment, the second cell is a cholera cell comprising the target sequence, wherein when the target sequence is modified the cell is killed or cell proliferation is reduced. In an example, the second cell is comprised by water for human consumption (eg, such water before or after processing for human consumption). In an example, the vector is comprised by a pharmaceutical composition for administration to a human to treat or prevent cholera in the human.

43. A composition comprising a plurality of vectors according to any one of embodiments 1 to 36 in vitro. For example, the composition is mixed with a multi-species bacterial population in an industrial apparatus or container (eg, for food, consumer goods, cosmetics, personal healthcare product, petroleum or oil production).

44. The vector, composition, foodstuff, beverage or population of any preceding embodiment for administration to a human or non-human animal for therapeutically or prophylactically populating and rebalancing a microbiome thereof or for cosmetically changing the human or animal (eg, for cosmetic weight-loss).

45. A method of modifying a target nucleotide sequence in a host cell, the method comprising
   (1) combining the host cell with a carrier cell,
   (a) wherein the carrier cell comprises a CRISPR nucleic acid vector comprising a CRISPR array for modifying the target,
   (b) wherein the CRISPR array comprises one or more sequences for expression of a crRNA and a promoter for transcription of the sequence(s) in the host cell;
   (c) wherein the crRNA is capable of hybridising to the target sequence to guide Cas (eg, a Cas nuclease) in the host cell to modify the target sequence; and
   (2) culturing the cells together, wherein the vector is transferred from the carrier cell to the host cell, whereby the crRNA hybridises to the target sequence to guide Cas in the host cell and the target is modified.

In an example, the method is carried out ex vivo. In an example, the method is a cosmetic method and is not a therapeutic or prophylactic medical method.

46. The method of embodiment 45, wherein the vector is according to any one of embodiments 1 to 36.

47. The method of embodiment 45 or 46, wherein the host cell is a cell of a human or non-human animal microbiome bacterial species, optionally wherein the host cell is a cell of a pathogenic bacterial species. In an example, any microbiome herein is selected from a gut, vaginal, armpit, scalp, skin or oral microbiome.

48. The method of any one of embodiments 45 to 47, wherein the carrier cell is of a species that is a commensal or symbiotic human or non-human animal microbiome bacterial species. In an example, the carrier cell is non-pathogenic to humans, eg, when administered intranasally, topically or orally.

In any configuration, concept, aspect, embodiment or example etc herein the vector, composition, array or population of the invention is administered intranasally, topically or orally to a human or non-human animal, or is for such administration. The skilled person aiming to treat a microbiome of the human or animal will be able to determine the best route of administration, depending upon the microbiome of interest. For example, when the microbiome is a gut microbiome, administration can be intranasally or orally.

When the microbiome is a scalp or armpit microbiome, administration can be topically. When the microbiome is in the mouth or throat, the administration can be orally.

49. The method of any one of embodiments 45 to 48, wherein the host cell is of a gut microbiome bacterial species of a human or non-human animal.

50. A method of altering the relative ratio of sub-populations of first and second bacteria host cell species in a mixed population of bacteria comprising said sub-populations, the method comprising
  A: providing said first bacterial host cells;
  B: providing the second bacterial host cells, wherein the second cells are cells of a different species or strain to the first cells;
  C: introducing engineered CRISPR arrays into the first bacterial host cells, wherein each CRISPR array comprises one or more sequences for expression of a crRNA and a promoter for transcription of the sequence(s) in a said second host cell, wherein the crRNA is capable of hybridising to a target sequence comprised by said second cell to guide Cas (eg, a Cas nuclease) in the host cell to modify the target sequence;
  D: combining the first and second bacterial cells together to produce a mixed bacterial population; and
  E: allowing bacterial growth in the mixed population such that horizontal transfer of CRISPR arrays from first bacterial cells to second bacterial cells occurs, wherein target sequences in second cells are Cas modified, whereby the relative ratios of said first and second bacteria is altered.

51. The method of embodiment 50, wherein each CRISPR array is according to any one of embodiments 1 to 26.

52. The method of embodiment 50 or 51, further comprising obtaining a first sample of the mixed population of step E and optionally comparing the proportion of second cells in the first sample to the proportion of second cells in a second sample of cells, wherein the second sample is a sample of a mixed population of bacterial cells used to provide the second cells in step B and the comparison shows that the proportion of second cells has increased or decreased after step E.

53. The method of embodiment 52, wherein the second sample is a sample of a human or animal microbiome (eg, gut, vaginal, scalp, armpit, skin or oral cavity cells).

54. The method of any one of embodiments 50 to 53, wherein a sample of a human or animal microbiome (eg, gut, vaginal, scalp, armpit, skin or oral cavity cells) is used to provide the second cells of step B.

55. The method of any one of embodiments 50 to 54, wherein a recombinant, cultured population of the first cells is used for step A.

56. The method of any one of embodiments 50 to 55, wherein plasmid, ICE or transposon horizontal transfer is used in step E, wherein each plasmid, ICE or transposon comprises a said CRISPR array.

57. The method of any one of embodiments 50 to 56 for therapeutically or prophylactically rebalancing the microbiota of a human or non-human animal, eg, for treating or preventing obesity, diabetes IBD, a GI tract condition or an oral cavity condition. The diabetes can be Type I or II. In an example, the prophylaxis is medical. In an example, the prophylaxis herein is non-medical, eg, cosmetic or for hygiene purposes. For example, the microbiota is an armpit microbiota and the method is for preventing or reducing body odour of a human. For example, in this case the method down-regulates growth or viability of host bacterial cells that mediate the generation and/or persistence of human body odour.

58. The method of any one of embodiments 50 to 57, comprising providing third bacterial host cells of a species or strain that is different to the carrier and host cells, wherein the third cells are comprised by the mixed population in step E or combined with said population after step E, wherein horizontal transfer of CRISPR arrays to third host cells occurs.

59. The method of embodiment 58, wherein the third cells do not comprise a said target sequence.

In this way, the third cells can act as carriers of the arrays and are capable of horizontally transferring arrays to host cells comprising the target sequence.

60. The method of embodiment 58, wherein the third cells do comprise a target sequence for Cas modification.

61. The method of any one of embodiments 50 to 60, wherein the carrier (and optionally also the third) cells are of a species recited in embodiment 21, eg, Bacteroidetes cells.

62. The method of any one of embodiments 50 to 60, wherein the host cells are of a species recited in embodiment 19 or Firmicutes cells.

63. The vector, composition, foodstuff, beverage, population or method of any preceding embodiment wherein each vector is or is comprised by a plasmid, phage (eg, a packaged phage) or phagemid.

64. The vector, composition, foodstuff, beverage, population or method of any preceding embodiment, wherein the modifying is (i) cutting of the target sequence, (ii) down-regulating transcription of a gene comprising the target sequence, (iii) up-regulating transcription of a gene comprising the target sequence, or (iv) adding, deleting or substituting a nucleic acid sequence at the target.

65. The vector, composition, foodstuff, beverage, population or method of any preceding embodiment, wherein each target sequence is a sequence comprised by a regulatory element or gene of the host cell, wherein the gene is an essential gene, a CRISPR gene or an antibiotic resistance gene, optionally wherein the regulatory element is an element of such a gene. In an alternative, the gene is a virulence gene.

66. The vector, composition, foodstuff, beverage, population or method of any preceding embodiment, wherein each target sequence is a sequence comprised by a phage genome, wherein the phage is comprised by the host cell. In an example, the target sequence is comprised by a phage gene required for host cell infectivity, the phage lysogenic or lytic cycle, or phage viability, eg, an essential gene or coat protein gene.

In an example, the Bacteroidetes phage is a *Bacteroides* phage selected from a crAssphage, a GB-124 phage, a GA-17 phage, a HB-13 phage, a H16-10 phage, a B40-8 phage and *B fragalis* phage ATCC51477-B1. This is useful, for example, for providing a survival advantage to Bacteroidetes in the gut microbiome of a human or animal. In this way, the ratio of Bacteroidetes to Firmicutes can be altered to increase the proportion of the former versus the latter (eg, for treating or preventing obesity). In an example, the target sequence is comprised by a BACON (Bacteroidetes-associated carbohydrate-binding) domain-encoding sequence (eg, wherein the host is a *Bacteroides* host) or an endolysin-encoding sequence.

67. The vector, composition, foodstuff, beverage, population or method of any preceding embodiment, wherein each CRISPR array comprises a sequence R1-S1-R1' for expression and production of the respective crRNA in the host cell,
- (i) wherein R1 is a first CRISPR repeat, R1' is a second CRISPR repeat, and R1 or R1' is optional; and
- (ii) S1 is a first CRISPR spacer that comprises or consists of a nucleotide sequence that is 95% or more identical to said target sequence.

68. The vector, composition, foodstuff, beverage, population or method of embodiment 67, wherein R1 and R1' are at least 95% identical respectively to the first and second repeat sequences of a CRISPR array of the second host cell species.

69. The vector, composition, foodstuff, beverage, population or method of embodiment 67 or 68, wherein R1 and R1' are functional with a CRISPR/Cas system of said host cell for modification of the target sequence.

70. The vector, composition, foodstuff, beverage, population or method of any preceding embodiment, wherein the or each array is in combination with one or more Cas nuclease(s) that function with the respective crRNA in a host cell to modify the target sequence. The target sequence comprises a protospacer sequence immediately adjacent to a Protospacer Adjacent Motif (PAM).

71. The vector, composition, foodstuff, beverage, population or method of any preceding embodiment, wherein the or each array is in combination with nucleic acid sequence(s) encoding one or more Cas nuclease(s) that function with the respective crRNA in a host cell to modify the target sequence.

72. The vector, composition, foodstuff, beverage, population or method of any one of embodiments 67 to 71, wherein R1 and R1' are functional with a Type II Cas9 nuclease (eg, a *S pyogenes* or *S aureus* Cas9) to modify the target in a said host cell, optionally wherein the vector, composition, foodstuff, beverage, population or method is further according to embodiment 70 or 71 wherein the Cas is said Cas9.

73. An ex-vivo mixed population of bacteria obtainable by the method of any one of embodiments 50 to 72.

74. A composition for administration to a human or non-human animal for therapeutic, prophylactic, cosmetic, human or non-human animal body mass reduction (eg, cosmetic reduction) or nutritional use, the composition comprising the mixed population of embodiment 73.

75. A foodstuff or beverage for human or non-human animal consumption comprising the mixed population of embodiment 73 or the composition of embodiment 74.

76. The foodstuff or beverage of embodiment 75, which is a nutritional supplement or a probiotic beverage or foodstuff.

77. An antibiotic composition for treating or preventing a bacterial infection in a human or non-human animal or in drinking water or in soil, wherein the composition comprises a vector of any one of embodiments 1 to 36 and 63 to 72.

78. A probiotic composition for increasing the proportion of gut Bacteroidetes (eg, to treat or prevent obesity, diabetes or a GI inflammatory condition) in a human or non-human animal, wherein the composition comprises a vector of any one of embodiments 1 to 36 and 63 to 72.

79. The composition of embodiment 74, 77 or 78 for increasing the relative proportions of gut *Bacteroides* to Firmicutes in a human or animal, eg for treating or preventing obesity, diabetes or a GI condition.

80. The vector, composition, foodstuff, beverage, population or method of any preceding embodiment, wherein the vector does not comprise a Cas nuclease-encoding sequence operable with the array. This is useful to save space in the vector (eg, to allow for inclusion of larger arrays or more arrays for host cell targeting—this is useful to target multiple genome locations to reduce likelihood of evolution of resistance to the arrays of the invention).

81. The vector, composition, foodstuff, beverage, population or method of any preceding embodiment, wherein the MGE does not comprise a Cas nuclease-encoding sequence operable with the array. This is useful to save space in the MGE (eg, to allow for inclusion of larger arrays or more arrays for host cell targeting—this is useful to target multiple genome locations to reduce likelihood of evolution of resistance to the arrays of the invention). For example, it is possible to avoid including the large sequence encoding Cas9 endonuclease.

82. The vector, composition, foodstuff, beverage, population or method of embodiment 80 or 81, wherein the array is operable with a Cas endonuclease found in cells of the same species or strain as the first and/or second cell. In an example, the array is operable with a Cas endonuclease found in cells of the same species or strain as a host cell or third cell. This is useful to save space in the vector or MGE (eg, to allow for inclusion of larger arrays or more arrays for host cell targeting—this is useful to target multiple genome locations to reduce likelihood of evolution of resistance to the arrays of the invention).

83. The vector, composition, foodstuff, beverage or population of any preceding embodiment, wherein the first and second cells are bacterial cells of different species, wherein the second cell is of a human microbiota species and the first cell is of a species that is non-pathogenic in said human microbiota, wherein the target sequence is not comprised by the genome of the first cell, the MGE comprising an oriT that is operable in the first and second cells, wherein the MGE is capable of horizontal transfer from the first cell to the second cell.

In an alternative, there is provided:—

The method of any preceding embodiment, wherein the carrier and host cells are bacterial cells of different species, wherein the host cell is of a human microbiota species and the carrier cell is of a species that is non-pathogenic in said human microbiota, wherein the target sequence is not comprised by the genome of the carrier cell, the MGE comprising an oriT that is operable in the carrier and host cells, wherein the MGE is capable of horizontal transfer from the carrier cell to the host cell.

84. The vector, composition, foodstuff, beverage, population or method of claim 83, wherein the vector is comprised by a bacteriophage, the bacteriophage being capable of infecting the first cell (carrier) to introduce the MGE into the first (carrier) cell.

85. The vector, composition, foodstuff, beverage, population or method of embodiment 83 or 84, wherein the target sequence is comprised by the genome of the second (host) cell (eg comprised by an essential or antibiotic resistance gene of the genome).

86. The vector, composition, foodstuff, beverage, population or method of embodiment 85, wherein the second (host) cell species is pathogenic in said human microbiota, wherein the target sequence is modified by cutting of the target sequence or down-regulating a gene comprising said target sequence. In an example, the second (host) cell is a cell according to any one of features (i) to (xiv) of embodiment 19. In an example the second (host) cell is a Firmicutes cell, eg, wherein the vector is for treating or preventing obesity in a human.

87. The vector, composition, foodstuff, beverage, population or method of embodiment 83, 84 or 85, wherein the second (host) cell species is non-pathogenic in said human microbiota.

88. The vector, composition, foodstuff, beverage, population or method of any one of embodiment 83 to 87, wherein the second (host) cell is a Bacteroidetes or *Prevotella* cell; optionally wherein the MGE is capable of horizontal transfer from the second (host) cell species to Firmicutes species of said human microbiota. The latter is useful, for example, for treating or preventing obesity in a human when the target sequence is comprised by the Firmicutes, but not the first (carrier) or second (host) cell.

89. The vector, composition, foodstuff, beverage, population or method of any one of embodiment 83 to 88, wherein the MGE is capable of horizontal transfer from the second (host) cell species to a third bacterial cell species of said human microbiota, wherein the third cell species is pathogenic in said human microbiota and comprises said target sequence. In an example, the first (carrier) and second (host) cells do not comprise the target sequence.

90. The vector, composition, foodstuff, beverage, population or method of embodiment 89, wherein the third cell is a cell according to any one of features (i) to (xiv) of claim 19.

91. The vector, composition, foodstuff, beverage, population or method of any preceding embodiment, wherein the MGE is devoid of a sequence encoding a Cas endonuclease that is operable with repeat sequences of the array, and wherein the vector comprises such a sequence (eg, encoding a Cas9) outside the MGE.

Any of the general features also may apply to the present configuration. Any of the features of any other configuration, aspect, paragraph, example, embodiment or concept herein also may be combined with the present configurations employing MGEs.

Thus, the invention provides the following features, numbered as paragraphs; these paragraphs apply to any of the aspects as recited, or to any of embodiments 1 to 91, or to any other configuration herein:—

1. A vector of any one of aspects 44 to 50, wherein the target sequence is a nucleotide sequence of a host CRISPR/Cas system, whereby the crRNA guides Cas to the target to modify the host CRISPR/Cas system in the host cell.

2. The vector of paragraph 1, wherein the host CRISPR/Cas system is a Type I, II or III system and the target sequence is a nucleotide sequence conserved in said Type of system in at least one, two or three additional host strains or species, wherein said additional strains or species are different from said host.

3. The vector of any preceding paragraph, wherein the target sequence is identical to a *Streptococcus* species (eg, *S thermophilus* or *S pyogenes*) CRISPR/Cas system sequence.

4. The vector of any preceding paragraph, wherein the target sequence of the host CRISPR/Cas system comprises
   i. a CRISPR array leader or leader promoter sequence contiguous with the 5'-most nucleotide of the first repeat (and optionally comprising said 5'-most nucleotide of the repeat, eg, comprising the first 3 nucleotides at the 5' end of the first repeat);
   ii. a sequence of up to 20 (eg, 3, 5, 7, 9, 10, 12, 15, 20, 30 or 32) nucleotides contiguous nucleotides immediately 5' of the first repeat;
   iii. a sequence of up to 20 (eg, 3, 5, 7, 9, 10, 12, 15, 20, 30 or 32) contiguous nucleotides of the 5'-most nucleotides of the first repeat; or
   iv. a sequence of up to 20 (eg, 3, 5, 7, 9, 10, 12, 15, 20, 30 or 32) contiguous nucleotides immediately 3' of the first spacer repeat (and optionally wherein the sequence comprises the 3'-most nucleotide of the first spacer, eg, comprising the last 3 nucleotides at the 3' end of the first repeat).

5. The vector of paragraph 1, 2 or 3, wherein the array is comprised by a nucleic acid vector (eg, a virus, virion, phage, phagemid or prophage) and
   i. the crRNA comprises or consists of the structure R-S-R, wherein R=a CRISPR repeat and S=a CRISPR spacer, wherein S comprises, (in 5' to 3' direction) V-$H_R$ or $H_R$-V or, wherein V=a sequence identical to a DNA sequence of the vector and $H_R$=a DNA sequence of a repeat of a CRISPR array of said host cell CRISPR array;
   ii. wherein the sequence of $H_R$ is immediately contiguous with the sequence of V in the host CRISPR array; and
   iii. wherein the crRNA is capable of hybridising to a spacer of the host CRISPR array to guide Cas to the host target for modification of the host CRISPR array in the cell.

For example, V is a sequence of a phage vector coat protein-encoding sequence. In this respect Heler et al found in a study of bacterial resistance that three CRISPR-independent, bacteriophage-resistant mutants displayed a marked defect in phage adsorption (about 50%), indicating that most likely they carry envelope resistance mutations.

6. The vector of paragraph 5, wherein the first crRNA does not or does not substantially hybridise to the nucleic acid present in the vector. For example, the first crRNA does not hybridise to V in the vector or hybridises less strongly than it hybridises to the spacer of the host array. Hybridisation testing is routine for the skilled person. For example, it can be determined in vitro by isolating or synthesizing the vector DNA and incubating it with the crRNA. Standard techniques, eg, using PCR can be used to detect whether or not hybridisation has occurred (eg, tested under pH and temperature conditions that would be found in host cell).

7. The vector of paragraph 5 or 6, wherein V=one or up to 40 (eg, up to 15) contiguous nucleotides of vector DNA. The seed sequence immediately 5' of the PAM in the protospacer found in a target sequence is important for crRNA pairing and functioning of the CRISPR/Cas system to cut. This seed sequence includes around 15 or 12 contiguous nucleotides immediately 5' of the PAM.

8. The method, array or vector of any preceding aspect or paragraph, wherein the array is comprised by a vector and comprises (in 5' to 3' direction) a first repeat sequence, a first spacer sequence and a second repeat sequence, wherein the spacer sequence comprises a sequence that is capable of hybridising (eg, is identical to or has greater than 90% identity) to the target sequence in the host cell, the array further comprising a promoter for transcription of the repeats and spacer in the host cell, and optionally the vector comprises a Cas nuclease-encoding sequence and/or a tracrRNA-encoding sequence for encoding a functional Cas and/or tracrRNA sequence in the host cell, wherein the tracrRNA sequence comprises a sequence that is complementary to the first or second repeat.

9. The method, array or vector of any preceding aspect or paragraph, wherein the CRISPR array is comprised by a vector and comprises (in 5' to 3' direction) a first repeat sequence, a first spacer sequence and a second repeat sequence, wherein the spacer sequence comprises a sequence that is capable of hybridising (eg, is identical to or has greater than 90% identity) to the target sequence in the host cell, the array further comprising a promoter for transcription of the repeats and spacer in the host cell, and wherein the vector does not comprise a Cas nuclease-encoding sequence and/or a tracrRNA-encoding sequence for encoding a tracrRNA sequence in the host cell wherein the tracrRNA sequence comprises a sequence that is complementary to the first or second repeat, wherein the HM-CRISPR array is functional in the host cell to guide Cas (eg, endogenous host Cas nuclease) to the host target site, optionally using a host tracrRNA.

10. The method, array or vector of paragraph 8 or 9, wherein the repeats are identical to repeats in a host array, wherein the CRISPR array of the invention does not comprise a PAM recognised by a Cas (eg, a Cas nuclease, eg, Cas9) of a host CRISPR/Cas system. The ability to omit Cas sequences frees up space in the array of the invention.

An "essential gene" is a gene in the host whose presence or expression is required for host cell growth or for promoting or sustaining cell viability. A resistance gene is a gene in the host whose presence or expression is required for providing complete or partial resistance to an anti-host drug, eg, an antibiotic, eg, a beta-lactam antibiotic. A virulence gene is a gene in the host whose presence or expression is required for infectivity of an organism that the host cell is capable of infecting, eg, wherein the host is a pathogen (eg, of a plant, animal, human, livestock, companion pet, plant, bird, fish or insect).

11. The method, array or vector of any preceding aspect or paragraph, wherein the CRISPR array is in combination with a non-host cell Cas (eg, a Type I system Cas wherein the host system is a Type II or III; a Type II system Cas wherein the host system is a Type I or III; or a Type III system Cas wherein the host system is a Type I or II), optionally wherein the host cell does not comprise or express a Cas of a Type that is the same as the Type of the non-host Cas. This is useful since the CRISPR array does not target a sequence in itself (such as in the vector) or a vector-encoded Cas in the host.

12. The method, array or vector of any preceding aspect or paragraph, wherein the CRISPR array is in combination with a tracrRNA sequence or a sequence encoding a tracrRNA sequence (eg, on same nucleic acid as the array), optionally wherein the tracrRNA sequence and HM-crRNA are comprised by a single guide RNA (gRNA)).

13. The method, array or vector of any preceding aspect or paragraph, wherein the CRISPR array is in combination with a Cas or a sequence encoding a Cas, optionally wherein the array is integrated in a host cell genome and the Cas is endogenous to the host cell or encoded by an exogenous sequence. In an example, the Cas-encoding sequence is an exogenous sequence that has been introduced into the host, eg, from a plasmid or virus, such as a phage.

14. The method, array or vector of any preceding aspect or paragraph, wherein the CRISPR array is comprised by a nucleotide sequence of a plasmid, virus, virion, phage, phagemid or prophage. The phagemid is a packaged phage. The prophage is a phage integrated into the host chromosome or episomal in the cell.

15. The method, array or vector of any preceding aspect or paragraph, wherein the CRISPR array is integrated in a host cell genome, eg, in a chromosome or episomal nucleic acid.

In one example the array is in combination with a dead Cas (eg, dCas9) conjugated to a transcription or translation activator that acts on the target sequence or a gene comprising the target sequence. This is useful, for example, for switching on gene expression in the host cell (eg, of a desired gene, eg, an exogenous gene sequence that has previously been engineered into the host cell, eg, to encode an antibiotic where the host is a microbe, or to encode a desired exogenous protein for production in host culture, eg, for food, drink, medicine or any other application of the invention as disclosed herein).

16. A virus (eg, a virion, phage, phagemid or prophage) comprising a CRISPR array of any preceding aspect or paragraph, eg, for infecting a cell, eg, a microbe or for use in medicine or dentistry.

17. A population of virions according to paragraph 16, a first and a second virion thereof comprising different array leaders or promoters and/or for targeting different target sequences in the host cell or in different host strains.

18. A collection of CRISPR arrays, each array being according to any preceding aspect or paragraph, wherein a first array comprises a first promoter for crRNA transcription; a second array comprises a second promoter for crRNA transcription that is different from the first promoter; and wherein each promoter is identical to a host promoter or is a homologue thereof; optionally wherein the first or both promoters is identical to a host Cas (eg, Cas1, 2, 9 or Csn2) promoter or a host CRISPR array promoter. For example, the first promoter is an endogenous Cas nuclease promoter or endogenous Cas1 or Cas2 promoter; or the promoter of an endogenous gene that is highly or constitutively expressed or is an essential, virulence or resistance gene of the host cell. By using endogenous promoters, there will be pressure during evolution of the host to preserve the host promoters, and thus this decreases the likelihood of the host CRISPR/Cas defence system targeting one or more promoters of the arrays.

19. A collection of CRISPR arrays of the invention, wherein a first array comprises one or more spacers (eg, 2, 3, 4, 5, 6, 7, 8, 9, 10, 20, 30, 40, 50 or more spacers); and the second array comprises more than one spacer t eg, 2, 3, 4, 5, 6, 7, 8, 9, 10, 20, 30, 40, 50 or more spacers), wherein said spacers of the second array are identical to the one or more spacers of the first array. This is useful for evading host resistance by homologous recombination of HM-array spacers, as proving many of such spacers in the HM-array (or furthermore distributing the spacers across a plurality of arrays) increases the chances that some HM-array spacers will remain in the host cell even if the host cell does delete some of the spacers. The defence against deletion is also enhanced by using different repeats flanking identical copies of the spacers in different arrays. Thus the invention provides the following:—

20. The collection of paragraph 18 or 19, wherein spacers (or said spacers) of the first array are flanked by first repeats that are identical; spacers (or said spacers) of the second array are flanked by second repeats that are identical; and wherein the first repeats are different from the second repeats.

21. The collection of paragraph 20, wherein the first repeats are identical to repeats in a host cell CRISPR/Cas system.

22. The collection of paragraph 20, wherein the first repeats are different from repeats in a host CRISPR/Cas system.

23. The collection of any one of paragraphs 18 to 22, wherein the first and second arrays are contained in the same host cell or in the same vector (eg, plasmid, virus, virion, phage, phagemid or prophage).

24. The collection of any one of paragraphs 18 to 22, wherein the first array is contained in a first vector and the second array is contained in a second vector which does not contain the first array (eg, wherein the vectors are plasmids or virions (eg, of the same virus type) or packaged phage (eg, of the same phage type).

In an embodiment, the vectors used in the method of the invention are vectors comprised by an array of any one of paragraphs 18 to 24.

25. A host cell comprising an array, virus, virion, phage, phagemid, prophage, population or collection according to any preceding paragraph.

Any of the general features (see below) also may apply to the present configuration.

An example of the invention provides the following for reducing the risk of host adaptation and resistance to the array:—

The CRISPR array or vector of the invention for modifying a target nucleotide sequence of a host cell,
  a. wherein the host cell comprises a first endogenous promoter (first host promoter) for transcription of the target sequence;
  b. wherein the CRISPR array comprises a sequence encoding a crRNA and a first promoter for transcription of the crRNA, the crRNA being optionally comprised by a single guide RNA (gRNA) and capable of hybridising to the host target sequence to guide Cas to the target in the host cell to modify the target sequence;
  c. wherein the sequence of the first promoter is the sequence of a second endogenous host promoter that is different to the sequence of the first host promoter.

In an example, a promoter is used for each vector (eg, phage) CRISPR unit that is a promoter of an essential gene in the host—that way the host will express the crRNA well (and constitutively if the promoter is from a host gene that must always or often be switched on). The host will not easily adapt away from that promoter so will not easily gain resistance. Optionally it is possible to use different essential promoters for different vector CRISPR units to decrease the chance of host adaptation (resistance). One can use the promoter of the virulence or essential or resistance gene being targeted in the host by the array (or a different array). To gain resistance to the phage the host would need to mutate the endogenous gene promoter and the gene targeting site (which may, for example, be in an coding sequence that is essential for cell growth, viability or anti-host drug (eg, antibiotic) resistance) and thus risk inactivating the gene that way too.

The provision as per the invention of multiple copies of nucleic acid sequences encoding crRNAs, wherein the copies comprise the same spacer sequence for targeting a host cell sequence as per the invention is advantageous for reducing the chances of host removal (eg, by host cell homologous recombination) of useful targeting spacers from the vector. Multiple targeting spacers can be provided flexibly, on the same or multiple HM-arrays of the invention to provide alternative ways of evading resistance.

Thus, the invention provides the following concepts:—

1. A host modifying (HM) CRISPR/Cas system (eg, Type I, II or III) for modifying a target nucleotide sequence of a host cell, the system comprising components according to (i) to (iv):—
  (i) at least one nucleic acid sequence encoding a Cas nuclease (eg, a Cas9);
  (ii) an engineered host modifying (HM) CRISPR array (eg, an array as described above) comprising a spacer sequence (HM-spacer) and repeats encoding a HM-crRNA, the HM-crRNA comprising a sequence that is capable of hybridising to a host target sequence to guide Cas to the target in the host cell to modify the target sequence;
  (iii) an optional tracrRNA sequence or a DNA sequence for expressing a tracrRNA sequence;
  (iv) wherein said components of the system comprises two, three or more of copies (eg, 2, 3, 4, 5, 6, 7, 8, 9, 10, 20, 30, 40, 50 or more); of nucleic acid sequences encoding crRNAs, wherein the copies comprise the same spacer sequence for targeting a host cell sequence (eg, a host virulence, resistance or essential gene sequence or a sequence of a host CRISPR/Cas system component that mediates vector adaptation).

For example, the system comprises 4 or more; or 5 or more; of said copies of nucleic acid sequences encoding crRNAs comprising the same spacer. This is advantageous to increase the expression of desired cRNAs in the host. Additionally, this provides greater chance of avoiding host resistance as more than one sequence will need to be targeted (especially if there are may copies such as 5, 10, 15, 20, 30, 40, 50 or 100 or more). Distribution of the copies over different arrays, eg, the vector comprises these spaced on the same DNA strand, is useful to reduce the chances of recombination between spacers or between flanking repeats which could then lead to excision of the desired cRNA-encoding sequences. The chances of the host excising all copies is reduced by providing copies distributed across many vector arrays, it is also reduced by including many copies of the desired spacers (eg, many copies in a first vector array and many copies in a second vector array—it is possible to include at least 2, 3, 4, 5, 6, 10 or more such arrays, each comprising 2, 3, 4, 5, 6, 7, 8, 9, 10, 20, 30, 40, 50 or 100 or more copies of the desired spacer).

2. The system of concept 1, wherein said components of the system comprises 4, 5, 10, 15 or 20 more of said copies of nucleic acid sequences encoding crRNAs comprising the same spacer.

3. The system of concept 1 or 2, wherein the copies are split between two or more nucleic acid vector CRISPR arrays.

4. The system of concept 3, wherein the system comprises first and second HM-arrays, wherein first and second vector CRISPR arrays are contained in the same host cell or in the same vector (eg, a plasmid, virus, virion, phage, phagemid or prophage).

5. The system of concept 3 or 4, wherein the first array is contained in a first vector and the second array is contained in a second vector which does not contain the first array (eg, wherein the vectors are plasmids or virions (eg, of the same virus type) or phagemids (eg, of the same phage type).

6. The system of any preceding concept, wherein the repeats are identical to repeats in a host CRISPR array.

7. The system of any one of concepts 1 to 5, wherein the repeats are not identical to repeats in a host CRISPR array.

8. A host cell comprising a system, vector, virus, virion, phage, phagemid or prophage according to any preceding concept.

9. An antimicrobial composition (eg, an antibiotic, eg, a medicine, disinfectant or mouthwash), comprising a system, vector, virus, virion, phage, phagemid or prophage according to any one of concepts 1 to 8.

Any of the general features (see below) also may apply to the present concepts.

Split Crispr/Cas9 System

This configuration is advantageous to free up space in target vectors, for example viruses or phage that have restricted capacity for carrying exogenous sequence. By freeing up space, one is able to include more targeting spacers or arrays, which is useful for evading host resistance. It is advantageous, for example to harness the endogenous Cas endonuclease rather than encode it in the vector—especially for bulky Cas sequences such as sp or saCas9. Additionally, there is not chance of inferior compatibility as may be seen with some exogenous Cas from non-host sources. The ability to reduce virus, eg, phage genome size, may also be beneficial for promoting host cell uptake (infection and/or maintenance of the virus in host cells). In some examples, an advantage is that invasion of the host by the vector (eg, phage) may upregulate host CRISPR/Cas activity, including increased expression of host Cas nucleases—in an attempt of the host to combat invading nucleic acid. This, however, is also useful to provide endogenous Cas for use with the arrays, vectors, systems and other aspects of this configuration invention when these comprise one or more repeats that are recognised by the host Cas. In the case where the invention involves one or more spacers targeting a host CRISPR array (as per also the first configuration of the invention), this then promotes inactivation of the host CRISPR array itself, akin to a "suicidal" host cell which then uses its own Cas nuclease to inactivate its own CRISPR systems.

Thus, the invention provides the following features, numbered as examples:—

1. A host modifying (HM) CRISPR/Cas9 system (eg, Type I, II or III) for modifying a target nucleotide sequence of a host cell, the system comprising components according to (i) to (iv):—
    (i) at least one nucleic acid sequence encoding a Cas nuclease (eg, a Cas9);
    (ii) an engineered host modifying (HM) CRISPR array (eg, an array of the invention described above) comprising a spacer sequence (HM-spacer) and repeats encoding a HM-crRNA, the HM-crRNA comprising a sequence that is capable of hybridising to a host target sequence to guide said Cas to the target in the host cell to modify the target sequence;
    (iii) an optional tracrRNA sequence or a DNA sequence for expressing a tracrRNA sequence;
    (iv) wherein said components of the system are split between the host cell and at least one nucleic acid vector that can transform the host cell, whereby the HM-crRNA guides Cas to the target to modify the target sequence in the host cell.

By "split" here it is meant that the vector comprises one or more (but not all) of the components of the system and the host cell comprises one or more (but not all) of the components, and the vector comprises one or more components that are not comprised by the host cell. In an embodiment, the vector and host cell do not share in common any of the components, eg, the host cell comprises component (i) and the vector comprises component (ii), and either the vector comprises component (iii) and/or the host cell comprises component (iii). When the vector is inside the host cell (eg, as an integrated or episomal vector, eg, a prophage), it is intended that the vector is the nucleic acid that has been provided by a vector that has transformed the host cell (and components of the system provided by such nucleic acid are not in that case be construed as host cell components). This can readily be determined by sequencing of nucleic acid (eg, chromosome and episomal nucleic acid) of the transformed host and comparing this against the sequences from a non-transformed host of the same type (eg, from the same host parental colony or clone, eg, when the host is a microbe, eg, a bacterium or archaeon).

Optionally, the system is a CRISPR/Cas9 system. Optionally, the nuclease of (a) is a Type I Cas nuclease. Optionally, the nuclease of (a) is a Type II Cas nuclease (eg, a Cas9). Optionally, the nuclease of (a) is a Type III Cas nuclease.

2. The system of example 1, wherein at least one of the components is endogenous to the host cell.

3. The system of example 1 or 2, wherein component (i) is endogenous to the host cell.

4. The system of any one of examples 1 to 3, wherein component (iii) is endogenous to the host cell.

5. A host modifying (HM) CRISPR/Cas system (eg, Type I, II or III) for modifying a target nucleotide sequence of a host cell, the system comprising components according to (a) to (e):—
    a. at least one nucleic acid sequence encoding a Cas nuclease (eg, a Cas9);
    b. an engineered host modifying (HM) CRISPR array comprising a spacer sequence (HM-spacer) and repeats encoding a HM-crRNA, the HM-crRNA comprising a sequence that is capable of hybridising to a host target sequence to guide said Cas to the target in the host cell;
    c. an optional tracrRNA sequence or a DNA sequence for expressing a tracrRNA sequence;
    d. wherein said components of the system are split between at least a first and a second nucleic acid vector, wherein at the first vector comprises component (a) but the second vector lacks component (a); and
    e. wherein the vectors can co-transform simultaneously or sequentially the host cell, whereby the HM-crRNA guides Cas to the target to modify the target sequence in the host cell.

The definition of "split" provided above applies mutatis mutandis to the present example comprising first and second vectors.

In an embodiment a tracrRNA sequence is not provided by the vectors, but is a tracrRNA sequence of an endogenous host cell CRISPR/Cas system, wherein the tracrRNA is capable of hybridising with the HM-crRNA in the cell for subsequent processing into mature crRNA for guiding Cas to the target in the host cell.

6. The system of example 5, wherein the first vector comprises component (a) and the second vector comprises components (b) and (c).

7. The system of example 5 or 6, wherein the first and/or second vector each comprises one, two, three or more further engineered HM-CRISPR-arrays.

8. The system of any one of examples 5 to 7, wherein one of the first and second vectors is a phagemid and the other vector is a helper phage.

9. The system of any preceding example (eg, example 3 or 6), wherein the crRNA sequence and tracrRNA sequence are comprised by a single guide RNA (gRNA), eg provided by the vector.

10. The system of any preceding example, wherein each vector has a restricted capacity for insertion of exogenous nucleic acid.

11. The system of any preceding example, wherein the vector or vectors are viruses (eg, virions, packaged phage, phagemid or prophage).

12. The system of any preceding example, wherein the host cell comprises a deoxyribonucleic acid strand with a free end (HM-DNA) encoding a HM-sequence of interest and/or wherein the system comprises a sequence encoding the HM-DNA (eg, integrated in the vector or in the host cell genome or an episome thereof), wherein the HM-DNA comprises a sequence or sequences that are homologous respectively to a sequence or sequences in or flanking the target sequence.

The strand comprises a free end, ie, an end not integrated into the host or vector DNA such that the strand has one or two free ends, ie, the DNA is unbonded to a neighbouring nucleotide immediately 5' and or 3' respectively.

13. The system of example 12, wherein the target site is cut in the host cell by Cas (eg, by Cas9 when said Cas nuclease is a Cas9), and the HM-DNA comprise first and second sequences that are homologous 5' and 3' respectively flanking the cut for inserting the HM-DNA into the host genome (eg, into a chromosomal or episomal site).

14. The system of example 13, wherein the insertion is by homology directed recombination (HDR).

15. The system of example 13, wherein the insertion is by non-homologous end joining (NHEJ).

16. The system of any one examples 12 to 15, wherein the HM-sequence is or encodes a regulatory element (eg, a promoter, eg, an inducible promoter that replaces an endogenous promoter), a transcription inhibiting sequence, a transcription enhancing sequence, a label, or a sequence that encodes an exogenous protein or domain.

17. The system of any one of examples 12 to 16, wherein the system comprises first and second HM-DNAs wherein a sequence of the first HM-DNA is complementary to a sequence of the second DNA whereby the DNAs are able to combine in the host cell by homologous recombination to form a combined HM-DNA for insertion into the host cell genome (eg, into a chromosomal or episomal site).

18. The system of any preceding example, wherein the vector or vectors are capable of infecting the host cell to introduce vector nucleic acid comprising a system component into the cell.

19. The system of any preceding example, wherein said Cas nuclease is a nickase.

20. The system of any preceding example, wherein the cell is a bacteria or archaea and said Cas nuclease is provided by an endogenous Type II CRISPR/Cas system of the bacteria or archaea.

21. The system of any preceding example, wherein the vector or vectors are inside a said host cell, optionally integrated into a host DNA.

22. The system of any preceding example, wherein the vector or vectors lack a Cas nuclease (eg, aCas9)-encoding sequence.

23. An engineered nucleic acid viral vector (eg, a vector, virion or packaged phage as described above) for infecting a microbe host cell comprising an endogenous CRISPR/Cas system, the vector
  (a) comprising nucleic acid sequences for expressing a plurality of different crRNAs for use in a CRISPR/Cas system according to any preceding example; and
  (b) lacking a nucleic acid sequence encoding a Cas nuclease (eg, a Cas9), wherein a first of said crRNAs is capable of hybridising to a first nucleic acid sequence in said host cell;
  and a second of said crRNAs is capable of hybridising to a second nucleic acid sequence in said host cell, wherein said second sequence is different from said first sequence; and
  (c) the first sequence is comprised by an anti-microbe (eg, antibiotic) resistance gene (or RNA thereof) and the second sequence is comprised by an anti-microbe resistance gene (or RNA thereof); optionally wherein the genes are different;
  (d) the first sequence is comprised by an anti-microbe resistance gene (or RNA thereof) and the second sequence is comprised by an essential or virulence gene (or RNA thereof);
  (e) the first sequence is comprised by an essential gene (or RNA thereof) and the second sequence is comprised by an essential or virulence gene (or RNA thereof); or
  (f) the first sequence is comprised by a virulence gene (or RNA thereof) and the second sequence is comprised by an essential or virulence gene (or RNA thereof).

24. An engineered (directly engineered or isolated from a vector in a host cell, where that vector was derived from an engineered vector that transformed the host) nucleic acid vector for transforming a host cell comprising an endogenous CRISPR/Cas system, the vector optionally being a vector as described above and
  (a') comprising nucleic acid sequences for expressing a plurality of different crRNAs for use in a CRISPR/Cas system according to any preceding example; and
  (b') lacking a nucleic acid sequence encoding a Cas nuclease (eg, a Cas9), wherein a first of said crRNAs is capable of hybridising to a first nucleic acid sequence in said host cell;
  and a second of said crRNAs is capable of hybridising to a second nucleic acid sequence in said host cell, wherein said second sequence is different from said first sequence; and
  the first and/or second sequence is a target sequence of the host CRISPR/Cas system which sequence is or comprises
  (c') a repeat DNA or RNA sequence (eg, wherein the repeat is the 5'-most repeat (the first repeat) in said host CRISPR array;
  (d') a tracrRNA sequence or a tracrRNA-encoding DNA sequence;
  (e') a CRISPR array leader sequence;
  (f') a Cas gene promoter (eg, a Cas1, Cas2 or Csn2 promoter);
  (g') a CRISPR array leader promoter sequence; or
  (h') a Cas-encoding DNA or RNA sequence (eg, wherein the Cas is Cas9, Cas1, Cas2 or Csn2), eg, wherein a first of said crRNAs is capable of targeting a host Cas1 gene sequence (or a sequence of an RNA thereof) and a second of said crRNAs is capable of targeting a host Cas2 gene sequence (or a sequence of an RNA thereof).

25. The vector of example 24, wherein the first and/or second target sequence is or comprises
  i. a CRISPR array leader or leader promoter sequence contiguous with the 5'-most nucleotide of the first repeat (and optionally comprising said 5'-most nucleotide of the repeat), eg, comprising the first 3 nucleotides at the 5' end of the first repeat;
  ii. a sequence of up to 20 (eg, 3, 5, 7, 9, 10, 12, 15, 20, 30 or 32) contiguous nucleotides immediately 5' of the first repeat;
  iii. a sequence of up to 20 (eg, 3, 5, 7, 9, 10, 12, 15, 20, 30 or 32) contiguous nucleotides of the 5'-most nucleotides of the first repeat; or
  iv. a sequence of up to 20 (eg, 3, 5, 7, 9, 10, 12, 15, 20, 30 or 32) contiguous nucleotides immediately 3' of the first spacer (and optionally wherein the sequence comprises the 3'-most nucleotide of the first spacer), eg, comprising the last 3 nucleotides at the 3' end of the first repeat.

26. The vector of example 24 or 25, wherein the or each target sequence is comprised by a sequence selected from the group consisting of SEQ ID NO: 1 to 44, or a complement thereof.

27. The vector of any one of examples 24 to 26, wherein the first crRNA comprises or consists of the structure R-S-R, wherein R=a CRISPR repeat and S=a CRISPR spacer, wherein S comprises, (in 5' to 3' direction) V-$H_R$ or $H_R$-V or, wherein V=a sequence identical to a DNA sequence of the vector and $H_R$=a DNA sequence of a repeat of a CRISPR array of said host cell CRISPR/Cas system, wherein the first crRNA is capable of hybridising to a spacer of the host CRISPR array to guide Cas to the target of the crRNA for modification of the host CRISPR array in the cell.

28. The vector of example 27, wherein the first crRNA does not substantially hybridise to the nucleic acid present in the vector, eg, wherein the first crRNA does not hybridise to V in the vector or hybridises less strongly than it hybridises to the spacer of the host array. The discussion above on determining this applies to this example too.

29. The vector of example 27 or 28, wherein V=one or up to 40 (eg, up to 15) contiguous nucleotides of vector DNA. For example, V=1, 2, 3, 4, 5, 6, 7 8 9, 10, 11, 12, 13, 14, 15, 16, 17, 18, 19, 20, 21, 22, 23, 24, 25, 26, 27, 28. 29, 30, 31, 32, 33, 34, 35, 36, 37, 38, 39 or 40 contiguous nucleotides of vector DNA.

30. The vector of example 29, wherein
i. the host CRISPR/Cas system is able to recognise a cognate PAM;
j. wherein the vector DNA comprises such a PAM immediately 3' of a protospacer sequence;
k. wherein V=one or up to 40 (eg, up to 15) nucleotides of the protospacer; and
l. wherein $H_R$=a sequence identical to a contiguous sequence of the repeat of the host CRISPR array.

31. The vector of example 30, wherein said contiguous sequence of the repeat of the host array is a sequence of at least 50% of a host repeat (eg, including the 5'-most or 3'-most nucleotide of the host repeat).

32. The vector of example 30 or 31, wherein V=from 1 to 40 (eg, up to 15) of the 3'-most protospacer contiguous nucleotides; and optionally said contiguous sequence of the repeat includes the 5'-most nucleotide of the host repeat.

33. The vector of example 30 or 31, wherein V=from 1 to 40 (eg, up to 15) of the 5'-most protospacer contiguous nucleotides; and optionally said contiguous sequence of the repeat includes the 3'-most nucleotide of the host repeat.

34. The vector of any one of examples 27 to 33, wherein R=a repeat that is recognised by the host CRISPR/Cas system. Alternatively, R=a repeat that is not recognised by the host CRISPR/Cas system. In this case, preferably the vector comprises a nucleotide sequence of a Cas nuclease (and optionally a tracrRNA) that is cognate to R, ie, is capable of functioning with R in the host cell.

35. A vector according to any one of examples 24 to 34, wherein the first sequence is according to any one of (c') to (h) and the second sequence is selected from a host essential gene, virulence gene or resistance gene.

36. An engineered nucleic acid viral vector (eg, a virion or packaged phage) for use in the system of any one of examples 1 to 22 for infecting a microbe host cell comprising an endogenous CRISPR/Cas system,
a. the vector comprising a first nucleic acid sequence for expressing a first crRNA in the host; and
b. wherein the first sequence comprises (in 5' to 3' direction) R1a-S1-R1b, wherein R1a=a first CRISPR repeat, wherein R1a is optional; R1b=a second CRISPR repeat and S1=a CRISPR spacer complementary to a host sequence (eg, a host sequence recited in example 23 or 24), wherein R1a and R1b are recognised by a host Cas nuclease (eg, a Type II nuclease, eg, a Cas9);
c. wherein the vector lacks (i) a nucleic acid sequence encoding a Cas nuclease (eg, a Cas9) that recognises the repeat(s) of (b) and/or (ii) a nucleic acid sequence encoding a tracrRNA sequence that is complementary to a crRNA sequence encoded by the first sequence.

For example, the vector is a nucleic acid vector comprised by a phage.

37. The vector of example 36, wherein
d. the vector comprises a second nucleic acid sequence for expressing second crRNA in the host, wherein the second crRNA is different from the first crRNA;
e. wherein the second sequence comprises (in 5' to 3' direction) R2a-S2-R2b, wherein R2a=a first CRISPR repeat, wherein R2a is optional; R2b=a second CRISPR repeat and S2=a CRISPR spacer complementary to a host sequence (eg, a host sequence recited in example 23 or 24), wherein R2a and R2b are recognised by a host Cas nuclease (eg, a Type I or II nuclease, eg, a Cas6).

Thus, for example, the first and second nucleic acid sequences are comprised by the same packaged phagemid, eg, in the same or different CRISPR arrays.

38. The vector of example 37, wherein the vector lacks (iii) a nucleic acid sequence encoding a Cas (eg, a Cas6) that recognises the repeat(s) of (e) and/or (iv) a nucleic acid sequence encoding a tracrRNA sequence that is complementary to a crRNA sequence encoded by the second sequence.

39. A collection of engineered nucleic acid viral vectors (eg, vectors, virions or packaged phages as described above) for use in the system of any one of examples 1 to 22 for co-infecting a microbe host cell comprising an endogenous CRISPR/Cas system, the collection comprising a first vector and a second vector,
f. wherein the first vector is according to example 36;
g. wherein the second vector comprises a second nucleic acid sequence for expressing second crRNA in the host, wherein the second crRNA is different from the first crRNA;
h. wherein the second sequence comprises (in 5' to 3' direction) R2a-S2-R2b, wherein R2a=a first CRISPR repeat, wherein R2a is optional; R2b=a second CRISPR repeat and S2=a CRISPR spacer complementary to a host sequence, wherein R2a and R2b are recognised by a host Cas nuclease (eg, a Type I or II nuclease, eg, a Cas6).

For example, the first vector is comprised by a first packaged phagemid and the second vector is comprised by a second packaged phagemid.

40. The collection of example 39, wherein the second vector comprises (v) a nucleic acid sequence encoding a Cas (eg, a Cas9) that recognises the repeat(s) of (b) and/or (vi) a nucleic acid sequence encoding a tracrRNA sequence that is complementary to a crRNA sequence encoded by the first sequence.

For example, in this case the Cas functions are provided by the endogenous host system. This saves vector space (eg, for inclusion of more host-targeting HM-array spacers) and simplifies vector and array construction.

41. The collection of example 39 or 40, wherein the second vector lacks (vii) a nucleic acid sequence encoding a Cas (eg, a Cas6) that recognises the repeat(s) of (h) and/or (viii) a nucleic acid sequence encoding a tracrRNA sequence that is complementary to a crRNA sequence encoded by the second sequence.

For example, in this case the Cas functions are provided by the endogenous host system.

42. The collection of example 39, wherein the first and second vectors each lacks (ix) a nucleic acid sequence encoding a Cas (eg, a Cas9) that recognises the repeat(s) of (b) and (x) a nucleic acid sequence encoding a Cas (eg, a Cas6) that recognises the repeat(s) of (h); optionally wherein the collection is comprised by a host cell comprising one or more Cas that recognise the repeat(s) of (b) and (h).

43. The collection of example 42, further comprising a third vector (eg, a virion or a phage) comprising a nucleic acid sequence according to (ix) and/or (x).

44. The collection of any one of examples 39 to 43, wherein each vector is comprised by a respective packaged virion or phagemid, or a respective virion or phage nucleic acid.

45. The vector or collection of any one of examples 36 to 44, wherein R1a and R1b comprise the same repeat sequence.

46. The vector or collection of any one of examples 37 to 45, wherein R2a and R2b comprise the same repeat sequence.

47. The vector or collection of any one of examples 37 to 46, wherein the repeat(s) of (b) are recognised by a Cas nuclease that is different from the Cas nuclease that recognises the repeat(s) of (e).

48. The vector or collection of any one of examples 37 to 47, wherein the host comprises CRISPR/Cas systems of different types (eg, a Type I and a Type II system; a Type I and a Type III system; a Type II and a Type III system; or Type I, II and III systems).

49. The vector or collection of any one of examples 36 to 48, wherein the repeat(s) of (b) are recognised by a Type II Cas nuclease, eg, a Cas9.

50. The vector or collection of any one of examples 37 to 49, wherein the repeat(s) of (e) are recognised by a Type I or III Cas nuclease, eg, a Cas6.

51. The vector or collection of any one of examples 23 to 50, wherein the vector is a virus, a virion, phage, phagemid or prophage.

52. The vector or collection of any one of examples 23 to 51 inside a host cell comprising one or more Cas that are operable with cRNA encoded by the vector(s).

53. The vector or collection of any one of examples 23 to 52 inside a host cell comprising a Cas9.

54. The vector or collection of any one of examples 23 to 53, in combination with a HM-DNA (eg, integrated in the vector, on a plasmid or in the host cell genome or an episome thereof), wherein the HM-DNA is as recited in any of examples 12 to 17.

55. The system, vector or collection of any preceding example, comprising nucleic acid sequences for expressing a plurality of different crRNAs, wherein said crRNAs are capable of targeting at least 3, 4, 5, 6, 7, 8, 9, 10, 15, 20, 30, 40, 50 or 100 DNA sequences in the host cell.

56. The system, vector or collection of any preceding example, comprising a first crRNA or a nucleic acid sequence encoding a first cRNA that is capable of targeting a DNA sequence of a Cas nuclease (or sequence of an RNA thereof) which is not said Cas nuclease (eg, Cas9) but which mediates host vector adaptation; optionally comprising a second crRNA or nucleic acid sequence encoding a second cRNA that is capable of targeting a sequence of a resistance, virulence or essential host gene (or RNA thereof) in the host.

57. The system, vector or collection of any preceding example, comprising two, three or more of copies of nucleic acid sequences encoding crRNAs, wherein the copies comprise the same spacer sequence for targeting a host cell sequence (eg, a virulence, resistance or essential gene sequence or a sequence of a host CRISPR/Cas system component that mediates vector adaptation, but which is not said Cas nuclease).

58. The system, vector or collection of example 57, wherein the copies are split between two or more vector CRISPR arrays.

59. The system, vector or collection of any preceding example, wherein the vector repeats are identical to repeats in a or the host CRISPR array (eg, each vector repeat has at least 95% sequence identity to a host repeat).

60. The system, vector or collection of any one of examples 1 to 58, wherein the vector repeats are not identical to repeats in a or the host CRISPR array.

61. The system, vector or collection of any preceding example, comprising first and second vector CRISPR arrays which are contained in the same host cell or by the same vector (eg, plasmid or virus or virion or phage or prophage or phagemid).

62. The system, vector or collection of example 61, wherein the first array is contained in a first vector and the second array is contained in a second vector which does not contain the first array (eg, wherein the vectors are plasmids or virions (eg, of the same virus type) or phagemids (eg, of the same phage type).

63. A host cell comprising a system, vector, collection, virus, virion, phage, phagemid or prophage according to any preceding example.

64. An antimicrobial composition (eg, an antibiotic, eg, a medicine, disinfectant or mouthwash), comprising a system, vector, virus, virion, phage, phagemid or prophage according to any one of examples 1 to 62.

Conditioning Microbes Together

The invention provides for methods of producing microbes (eg, phage and/or bacterial populations) that involves conditioning hosts and viruses together to facilitate co-evolution and thus conditioning of the hosts to the viruses (eg, phage) and vice versa. Using repressible control of crRNA expression or activity the invention purposely modulates the co-evolution in a controllable manner where a desired spacer activity can be toggled on or off to enable tuning to occur with or without stress imposed by spacer-guided Cas action in the host, eg, with or without antibiotic resistance gene targeting. In this way, the bacterial populations can be tuned for use in situations (eg, dairy or food production cultures) where phage inactivation of desirable genes may be encountered; or for use in tuning phage to be used to kill or modulate bacteria, eg, to knock-down antibiotic resistance. This configuration further enables, in one embodiment, culturing of antibiotic-resistant bacterial host with virus, eg, phage, harbouring one or more CRISPR arrays of the invention that target the antibiotic resistance gene of the host, since the method purposely represses the antibiotic resistance gene inactivation activity of the array during culturing with the host. Thus, a resistant bacterial host population can be used to grow up phage in culture (eg, in an industrial culture vessel or plant) allowing the phage and host to co-evolve and mutually tune without the antibiotic resistance inactivation effect hampering the growth and thus culturing ability of the host cells (which would otherwise minimise phage expansion) and whilst still enabling all other components of the desired phage to tune to the cultured host population. Testing of a sample of the resultant phage population can be carried out, eg, at lab scale, using an antibiotic resistant host cell population but with the test phage de-repressed for the array targeting of the antibiotic resistance gene of the host cells. Naturally-occurring and synthetic repression of gene expression in prokaryotic cell and phage settings is well known to the skilled person, eg, tet systems or light-inducible systems.

Thus, the invention provides the following features, numbered as paragraphs:—

1. A microbe production method, the method comprising
   (a) providing a host cell that comprises a host CRISPR/Cas system for nucleotide sequence targeting in the host cell;
   (b) providing a virus that is capable of infecting the host cell, wherein
   (i) the virus comprises one or more engineered host modifying (HM) CRISPR arrays (eg, an array as described above) for modifying target nucleotide sequences of the host cell;
   (ii) a first said HM-array encodes a first HM-crRNA comprising a spacer sequence (HM-spacer) that is capable of hybridising to a first host target sequence to guide Cas to the target in the host cell to modify the target sequence, optionally wherein the modification of the first target sequence reduces host cell growth or viability; and
   (iii) the first HM-array is reversibly repressible for the transcription of the first HM-crRNA and/or first HM-crRNA activity is repressible;
   (c) infecting the host cell with the virus to introduce the one or more HM-CRISPR arrays into the cell;
   (d) repressing the transcription of the first HM-crRNA and/or first HM-crRNA activity in the cell;
   (e) culturing the infected host cell to produce a population (PH1) of host cells comprising a population (PV1) of virus; and
   (f) obtaining the virus population PV1 and/or the cultured host cell population.

In an example, the first HM-crRNA comprises a HM-spacer that is capable of hybridising to the first host target sequence to guide Cas to the target in the host cell to modify the target sequence, wherein the target sequence is a nucleotide sequence of the host CRISPR/Cas system, whereby the first HM-crRNA guides Cas to the target to modify the host CRISPR/Cas system in the host cell, wherein the modification of the target sequence reduces or eliminates functioning of the host CRISPR/Cas system.

In an alternative, the modification enhances or inhibits expression of a gene in the host. In an embodiment, the gene is an essential gene, virulence gene or resistance gene (eg, an antibiotic resistance gene). In an embodiment, the modification enhances the expression of a gene product that is endogenous or exogenous to the host. In an example, the host is an engineered host comprising an exogenous nucleotide sequence (eg, for producing a desired protein) and the modification enhances or inhibits expression of the desired protein in the host cell. In an example, the desired protein is an antibiotic and host cell is a microbe, eg, bacterial or archaeal cell. Thus, the method enables culturing of culturing of host cells to produce the viral population, wherein the antibiotic is not expressed which would otherwise hamper the expansion of the host cell population. Thereafter, one or more viruses of the isolated virus population can be used in an antimicrobial composition for reducing host cell growth or viability, since the first HM-crRNA repression can be removed after isolation, thereby providing an actively antibiotic virus composition. The invention therefore also provides such a method and such an antibiotic composition comprising virus that are capable of expressing an antibiotic in a host cell. Modification to activate the expression can be effected, for example, by providing a Cas (eg, Cas9) conjugated to a transcription activator, wherein the Cas is a cognate Cas for the first HM-crRNA and the activator activates the transcription of the desired exogenous or endogenous gene. Modification to inhibit the expression can be effected, for example, by providing a dead Cas (eg, dCas9), wherein the CAs is a cognate Cas for the first HM-crRNA and inhibits transcription of the desired exogenous or endogenous gene.

Repression of the crRNA transcription or activity can be partial or complete (ie, no activity or no transcription of the crRNA from the array in the host). Activity refers to the ability of the crRNA to hybridise to the cognate host sequence for guiding of Cas to the first host target site for modification.

In an example, the virus is not so repressed when introduced into the cell, the method comprising carrying out step (d) after the virus has infected the cell, eg, by using a chemical, physical, mechanical, magnetic, light or other agent to cause repression. In an embodiment, the first HM-array comprises a repressible promoter (HM-promoter) for transcription of the first HMcrRNA and the promoter is repressed (eg, by binding a repressor agent, eg, a chemical or protein, to the promoter) after the first HM-array is introduced into the cell.

In another example, the virus is so repressed before step (c) is carried out, eg, by using a chemical, physical, mechanical, magnetic, light or other agent to cause repression. In an embodiment, the first HM-array comprises a repressible promoter (HM-promoter) for transcription of the first HMcrRNA and the promoter is repressed (eg, by binding a repressor agent, eg, a chemical or protein to the promoter) before the first HM-array is introduced into the cell, wherein subsequently the repressed first HM-array is introduced into the cell.

In one embodiment, step (f) comprises isolating PV1. In an embodiment, the step comprised separating PV1 or a virus thereof from host cells of PH1.

2. The method of paragraph 1, further comprising de-repressing the transcription of first HM-crRNA and/or first HM-crRNA activity in the virus population after step (e) or (f), and optionally thereafter further culturing the host cells.

3. The method of any preceding paragraph, comprising
   A. obtaining a population (PH2) of host cells that are optionally identical to the host cell of (a), (f) or the further cultured cells of paragraph 2;
   B. infecting the host cells of A with virus from the population PV1;
   C. repressing the transcription of the first HM-crRNA and/or first HM-crRNA activity in the cells;
   D. culturing the infected host cells to produce a population (PH3) of host cells comprising a population of virus (PV2); and
   E. obtaining the virus population PV2 (or a virus thereof) and/or the cultured host cell population.

4. The method of paragraph 3, further comprising de-repressing the transcription of first HM-crRNA and/or first HM-crRNA activity in the virus population after step (D) or (E), and optionally thereafter further culturing the host cells.

5. The method of any preceding paragraph, comprising testing an isolated sample of the virus population PV1 or PV2 on a further host cell or population (PH4) of host cells, optionally wherein the further cell or population PH4 is identical to the cell of (a), the testing comprising infecting the further cell or population PH4 with virus of said sample, waiting a period of time to allow any host cell growth to occur, and determining if a predetermined activity of the further cell or population PH4 (eg, cell growth or viability) has been modified (eg, reduced, such as reduced host cell growth or viability*) or occurred, wherein virus inside the cell or cells have de-repressed transcription of first HM-crRNA and/or first HM-crRNA activity during said period of time.

*This can be tested using a standard assay for plaque formation when the virus of the sample are added to the cell or PH4 plated on agar).

6. The method of any preceding paragraph 5, wherein all of the host cells are microbial cells (eg, bacterial or archaeal cells) and the modification of the first target sequence reduces host cell growth or viability, and said determining determines that antimicrobial activity** has occurred.

**This can be determined using a standard plaque assay.

7. The method of paragraph 5 or 6, wherein the period of time is at least one, 5, 10, 30, 60 or 120 minutes.

8. The method of any one of paragraphs 5 to 7, wherein the cell of (a) and optionally PH1, PH2 and/or PH3 cells do not comprise the first target sequence, wherein the further cell or population PH4 cells comprise the first target sequence.

9. The method of any one of paragraphs 1 to 8, wherein the cell of (a) and optionally PH1, PH2 and/or PH3 cells do not comprise a gene that confers resistance to a first antibiotic, wherein the first target sequence is a target sequence of such a gene; optionally wherein the further cell or population PH4 cells comprise said gene.

10. The method of any one of paragraphs 1 to 7, wherein the cell of (a) and optionally PH1, PH2 and/or PH3 cells comprise a gene that confers resistance to a first antibiotic, wherein the first target sequence is a target sequence of such a gene.

11. The method of any preceding paragraph, wherein all of the host cells are microbial cells (eg, bacterial or archaeal cells) and the modification of the first target sequence reduces host cell growth or viability, or reduces host cell resistance to an antibiotic.

12. The method of any preceding paragraph, wherein all of the host cells are infectious disease pathogens of humans, an animal (eg, non-human animal) or a plant.

13. The method of any preceding paragraph, wherein all of the host cells are of the same species, eg, selected from a species of *Escherichia* (eg, *E coli* O157:H7 or O104: H4), *Shigella* (eg, *dysenteriae*), *Salmonella* (eg, *typhi* or *enterica*, eg, serotype *typhimurium*, eg, DT 104), *Erwinia*, *Yersinia* (eg, *pestis*), *Bacillus*, *Vibrio*, *Legionella* (eg, pneumophilia), *Pseudomonas* (eg, *aeruginosa*), *Neisseria* (eg, *gonnorrhoea* or *meningitidis*), *Bordetella* (eg, *pertussis*), *Helicobacter* (eg, *pylori*), *Listeria* (eg, *monocytogenes*), *Agrobacterium*, *Staphylococcus* (eg, *aureus*, eg, MRSA), *Streptococcus* (eg, *pyogenes* or *thermophilus*), *Enterococcus*, *Clostridium* (eg, *dificile* or *botulinum*), *Corynebacterium* (eg, *amycolatum*), *Mycobacterium* (eg, *tuberculosis*), *Treponema*, *Borrelia* (eg, *burgdorferi*), *Francisella*, *Brucella*, *Campylobacter* (eg, *jejuni*), *Klebsiella* (eg, *pneumoniae*), *Frankia*, *Bartonella*, *Rickettsia*, *Shewanella*, *Serratia*, *Enterobacter*, *Proteus*, *Providencia*, *Brochothrix*, *Bifidobacterium*, *Brevibacterium*, *Propionibacterium*, *Lactococcus*, *Lactobacillus*, *Pediococcus*, *Leuconostoc*, *Vibrio* (eg, cholera, eg, O139, or *vulnificus*), *Haemophilus* (eg, *influenzae*), *Brucella* (eg, *abortus*), *Franciscella*, *Xanthomonas*, *Ehrlichia* (eg, *chaffeensis*), *Chlamydia* (eg, *pneumoniae*), *Parachlamydia*, *Enterococcus* (eg, *faecalis* or faceim, eg, linezolid-resistant), *Oenococcus* and *Acinetobacter* (eg, *baumannii*, eg, multiple drug resistant).

14. The method of claim 13, wherein all of the host cells are *Staphylococcus aureus* cells, eg, resistant to an antibiotic selected from methicillin, vancomycin-resistant and teicoplanin.

15. The method of claim 13, wherein all of the host cells are *Pseudomonas aeruginosa* cells, eg, resistant to an antibiotic selected from cephalosporins (eg, ceftazidime), carbapenems (eg, imipenem or meropenem), fluoroquinolones, aminoglycosides (eg, gentamicin or tobramycin) and colistin.

16. The method of claim 13, wherein all of the host cells are *Klebsiella* (eg, *pneumoniae*) cells, eg, resistant to carbapenem.

17. The method of claim 13, wherein all of the host cells are *Streptococcus* (eg, *pneumoniae* or *pyogenes*) cells, eg, resistant to an antibiotic selected from erythromycin, clindamycin, beta-lactam, macrolide, amoxicillin, azithromycin and penicillin.

18. The method of claim 13, wherein all of the host cells are *Salmonella* (eg, serotype *Typhi*) cells, eg, resistant to an antibiotic selected from ceftriaxone, azithromycin and ciprofloxacin.

19. The method of claim 13, wherein all of the host cells are *Shigella* cells, eg, resistant to an antibiotic selected from ciprofloxacin and azithromycin.

20. The method of claim 13, wherein all of the host cells are *Mycobacterium tuberculosis* cells, eg, resistant to an antibiotic selected from Resistance to isoniazid (INH), rifampicin (RMP), fluoroquinolone, amikacin, kanamycin and capreomycin.

21. The method of claim 13, wherein all of the host cells are *Enterococcus* cells, eg, resistant to vancomycin.

22. The method of claim 13, wherein all of the host cells are Enterobacteriaceae cells, eg, resistant to an antibiotic selected from a cephalosporin and carbapenem.

23. The method of claim 13, wherein all of the host cells are *E. coli* cells, eg, resistant to an antibiotic selected from trimethoprim, itrofurantoin, cefalexin and amoxicillin.

24. The method of claim 13, wherein all of the host cells are *Clostridium* (eg, *dificile*) cells, eg, resistant to an antibiotic selected from fluoroquinolone antibiotic and carbapenem.

25. The method of claim 13, wherein all of the host cells are *Neisseria gonnorrhoea* cells, eg, resistant to an antibiotic selected from cefixime (eg, an oral cephalosporin), ceftriaxone (an injectable cephalosporin), azithromycin and tetracycline.

26. The method of claim 13, wherein all of the host cells are *Acinetobacter baumannii* cells, eg, resistant to an antibiotic selected from beta-lactam, meropenem and a carbapenem.

27. The method of claim 13, wherein all of the host cells are *Campylobacter* cells, eg, resistant to an antibiotic selected from ciprofloxacin and azithromycin.

28. The method of any preceding paragraph, wherein the host cells produce Beta (β)-lactamase.

29. The method of any preceding paragraph, wherein the host cells are resistant to an antibiotic recited in any one of paragraphs 14 to 27.

30. The method of paragraph 29, wherein the first target sequence is a sequence of a gene encoding a product conferring host cell resistance to said antibiotic.

31. The method of any preceding paragraph, wherein the first target sequence is a sequence of an antibiotic resistance gene (ie, for conferring host cell resistance to an antibiotic eg, methicillin resistance) and/or one, more or all of the population PH1, the population PH2, the population PH3 and the population PH4 is resistant to an antibiotic or said antibiotic (eg, an antibiotic recited in any one of paragraphs 13 to 27).

32. The method of any preceding paragraph, wherein de-repressed virus of the virus population PV1 or PV2 have antimicrobial activity (eg, antibacterial activity, such as when the virus are phage); optionally wherein the host cell or cells comprise the first target sequence as recited in paragraph 30, wherein modification of the first target provides said antimicrobial activity.

33. The method of any preceding paragraph when dependent from paragraph 5, wherein the cells of PH4 are resistant to an antibiotic (eg, an antibiotic recited in any one of paragraphs 13 to 27) and the cells of (a) and PH2 are not resistant to said antibiotic. This aids manufacturing of the virus for drug use, since culturing and expansion can be performed relatively safety without the risk of having to deal with antibiotic-resistant host cells (and risk of inadequate containment of these and escape from drug manufacturing plant, for example). Nevertheless, testing against PH4 can be performed in a containment lab or other facility that is set up for use of antibiotic-resistant host strains. When testing against PH4, the first HM-crRNA is de-repressed so that modification of the resistance gene in the host cells is possible by the HM-array of the invention.

34. The method of any preceding paragraph, wherein the host CRISPR/Cas system is a Type I, II or III system and the target sequence is a nucleotide sequence conserved in said Type of system in at least one, two or three additional host strains or species of the same genus as the host cell of (a).

35. The method of any preceding paragraph, wherein the virus is a phage or phagemid.

36. The method of paragraph 35, wherein the virus of (b) is a Corticoviridae, Cystoviridae, Inoviridae, Leviviridae, Microviridae, Myoviridae, Podoviridae, Siphoviridae, or Tectiviridae virus.

37. The method of paragraph 35 or 36, wherein the virus of (b) is a naturally occurring phage, eg, a phage induced from a cell that is of the same strain as the cell of (a).

38. The method of paragraph 35, 36 or 37, wherein the phage of (b) is a mutated phage obtained through selective pressure using a phage-resistant bacterium.

39. The method of any preceding paragraph, wherein in (b)
(iv) said one or more HM-arrays comprise a HM-array that encodes a second HM-crRNA comprising a HM-spacer that is capable of hybridising to a second host target sequence to guide Cas to the second target in the host cell to modify the target sequence, wherein the second target sequence is a nucleotide sequence of the host CRISPR/Cas system, whereby the second HM-crRNA guides Cas to the second target to modify the host CRISPR/Cas system in the host cell, wherein the modification of the second target sequence reduces or eliminates functioning of the host CRISPR/Cas system; and
(v) wherein the HM-array of (iv) is active in the cell of (a) for the transcription of second HM-crRNA capable of hybridising to the second host target sequence.

In an embodiment, the HM-array of (ii) and (iv) are the same HM-array. In another embodiment, they are different H M-arrays (eg, arrays of different CRISPR/Cas types, eg, Type I and II, or Type II and III, or Type I and III, or different Type II arrays).

40. The method of paragraph 39, wherein the cells of any one or all of PH1-4 comprise said second target sequence.

41. The method of paragraph 39 or 40, wherein the second target sequence is identical to a CRISPR/Cas system sequence of a genus or species of cell as recited in any one of paragraphs 11 to 24 (eg, S thermophilus or S pyogenes or S aureus).

42. The method of any one of paragraphs 39 to 41, wherein the second target sequence is comprised by a sequence selected from the group consisting of SEQ ID NO: 1 to 44, or a complement thereof.

43. The method of any one of paragraphs 39 to 42, wherein the second target sequence comprises
A. a repeat DNA or RNA sequence (eg, wherein the repeat is the 5'-most repeat (the first repeat) in said host CRISPR array;
B. a tracrRNA sequence or a tracrRNA-encoding DNA sequence; a CRISPR array leader sequence;
C. a Cas gene promoter (eg, a Cas1, Cas2 or Csn2 promoter);
D. a CRISPR array leader promoter sequence; or
E. a Cas-encoding DNA or RNA sequence (eg, wherein the Cas is Cas9, Cas1, Cas2 or Csn2).

44. The method of any one of paragraphs 39 to 43, wherein the second target sequence comprises
F. a CRISPR array leader or leader promoter sequence contiguous with the 5'-most nucleotide of the first repeat (and optionally comprising said 5'-most nucleotide of the repeat);
G. a sequence of up to 20 contiguous nucleotides immediately 5' of the first repeat;
H. a sequence of up to 20 contiguous nucleotides of the 5'-most nucleotides of the first repeat; or
I. a sequence of up to 20 contiguous nucleotides immediately 3' of the first spacer repeat (and optionally wherein the sequence comprises the 3'-most nucleotide of the first spacer).

45. The method of any one of paragraphs 39 to 44, wherein
J. the second HM-crRNA comprises or consists of the structure R-S-R, wherein R=a CRISPR repeat and S=a CRISPR spacer, wherein S comprises, (in 5' to 3' direction) V-$H_R$ or $H_R$-V or, wherein V=a sequence at least 95, 96, 97, 98 or 99% identical to a DNA sequence of the virus of (b) and HR=a DNA sequence of a CRISPR repeat of said host cell CRISPR/Cas system;
K. wherein the sequence of $H_R$ is immediately contiguous with the sequence of V in the host CRISPR/Cas system; and
L. wherein the second HM-crRNA is capable of hybridising to a spacer of the host CRISPR/Cas system to guide Cas to the spacer for modification (eg, cleavage or inactivation) of the host CRISPR/Cas system in the cell.

46. The method of paragraph 45, wherein V=one or up to 40 (eg, up to 15) contiguous nucleotides of virus DNA.

47. The method of any one of paragraphs 39 to 46, wherein the second HM-crRNA does not substantially hybridise to nucleic acid of the virus of (b).

48. The method of any one of paragraphs 45 to 47, wherein
a. the host CRISPR/Cas system is able to recognise a cognate PAM;
b. wherein the nucleic acid of the virus of (b) comprises such a PAM immediately 3' of a protospacer sequence;
c. wherein V=one or up to 40 (eg, up to 15) nucleotides of the protospacer; and d. wherein $H_R$=a sequence identical to a contiguous sequence of the repeat of the host CRISPR/Cas system.

49. The method of paragraph 48, wherein said contiguous sequence of the repeat of the host system is a sequence of at least 50% of a host repeat (eg, including the 5-most or 3'-most nucleotide of the host repeat).

50. The method of paragraph 45 or 46, wherein V=from 1 to 40 (eg, up to 15) of the 3'-most protospacer contiguous nucleotides; and optionally said contiguous sequence of the repeat includes the 5'-most nucleotide of the host repeat.

51. The method of paragraph 48 or 49, wherein V=from 1 to 40 (eg, up to 15) of the 5'-most protospacer contiguous nucleotides; and optionally said contiguous sequence of the repeat includes the 3'-most nucleotide of the host repeat.

52. The method of any one of paragraphs 45 to 51, wherein R=a repeat that is recognised by the host CRISPR/Cas system.

53. The method of any preceding paragraph, wherein the or each HM-CRISPR comprises (in 5' to 3' direction) a first repeat sequence, a first spacer sequence and a second repeat sequence, wherein the spacer sequence comprises a sequence that is capable of hybridising to the respective target sequence in the host cell, the array further comprising a promoter for transcription of the repeats and spacer in the host cell, and optionally the nucleic acid of the virus of (b) comprises a Cas nuclease-encoding sequence and/or a tracrRNA-encoding sequence for encoding a functional Cas and/or tracrRNA sequence in the host cell, wherein the tracrRNA sequence comprises a sequence that is complementary to the first or second repeat.

54. The method of any preceding paragraph, wherein the or each HM-CRISPR array comprises (in 5' to 3' direction) a first repeat sequence, a first spacer sequence and a second repeat sequence, wherein the spacer sequence comprises a sequence that is capable of hybridising to the respective target sequence in the host cell, the array further comprising a promoter for transcription of the repeats and spacer in the host cell, and wherein the vector does not comprise a Cas nuclease-encoding sequence and/or a tracrRNA-encoding sequence for encoding a tracrRNA sequence in the host cell wherein the tracrRNA sequence comprises a sequence that is complementary to the first or second repeat, wherein the HM-CRISPR array is functional in the host cell to guide Cas (eg, endogenous host Cas nuclease) to the respective host target site, optionally using a host tracrRNA.

55. The method of paragraph 53 or 54, wherein the repeats are identical to repeats in the host CRISPR/Cas system, wherein the or each HM-CRISPR array does not comprise a PAM recognised by a Cas (eg, a Cas nuclease, eg, Cas9) of the host CRISPR/Cas system.

56. The method of any preceding paragraph, wherein the or each HM-CRISPR array comprises more than one copy of a HM-spacer (eg, at least 2, 3 or 4 copies).

57. The method of any preceding paragraph, encoding a second or third HM-crRNA (further HM-crRNA), wherein the further HM-crRNA comprises a nucleotide sequence that is capable of hybridising to a host target sequence to guide Cas to the target in the host cell; optionally wherein the target sequence is a nucleotide sequence of an essential, virulence or resistance gene of the host cell, or of an essential component of the CRISPR/Cas system of the host cell.

58. The method of any preceding paragraph, wherein the or each HM-CRISPR array comprises CRISPR repeat sequences that are identical to endogenous CRISPR repeat sequences of the host cell for producing the respective HM-crRNA in the host cell.

59. The method of any preceding paragraph, wherein the virus of (b) comprises a nucleotide sequence encoding a Cas (non-host Cas) that is functional in the host cell of (a) (eg, wherein the non-host Cas is a Type I system Cas wherein the host system is a Type II or III; a Type II system Cas wherein the host system is a Type I or III; or a Type III system Cas wherein the host system is a Type I or II), optionally wherein the host cell does not comprise or express a Cas of a Type that is the same as the Type of the non-host Cas.

60. The method of any preceding paragraph, wherein the virus of (b) comprises a nucleotide sequence encoding a tracrRNA sequence, optionally wherein the tracrRNA sequence and first HM-crRNA are comprised by a single guide RNA (gRNA)).

61. The method of any preceding paragraph, wherein the or each HM-crRNA is comprised by a respective single guide RNA (gRNA).

62. The method of any preceding paragraph, wherein the first HM-array is operable to cause Cas cleavage in the first target sequence, activation of the first target sequence (or gene comprising the first target sequence), knock-down of the first target sequence (or gene comprising the first target sequence) or mutation of the first target sequence.

63. A virus, host cell or virus population obtainable by the method of any preceding paragraph, optionally wherein the population is identical to PV1 or PV2 or the virus is obtainable from such a population.

64. A host cell (eg, bacterial cell) population obtainable by the method of any preceding paragraph, optionally wherein the population is identical to PH1, PH2, PH3 or PH4 or a cultured cell population recited in any preceding paragraph.

65. The host cell population of paragraph 64 wherein the population does not comprise nucleic acid of a virus of (b), or does not comprise said first HM-array or said second HM-array (eg, as determined by PCR).

66. The virus, host cell or population of any one of paragraphs 63 to 65, for medical or dental or ophthalmic use (eg, for treating or preventing an infection in an organism or limiting spread of the infection in an organism.

67. A composition comprising a virus, host cell or population according to any one of paragraphs 63 to 66 for food, beverage, dairy or cosmetic use (eg, use in a cosmetic product, eg, make-up), or for hygiene use (eg, use in a hygiene product, eg, soap).

68. Use of a composition a virus, host cell or population according to any one of paragraphs 63 to 67, in medicine or for dental therapeutic or prophylactic use.

69. Use of a composition a virus, host cell or population according to any one of paragraphs 63 to 68, in cosmetic use (eg, use in a cosmetic product, eg, make-up), or for hygiene use (eg, use in a hygiene product, eg, a soap).

70. The use, virus, host cell or population of any one of paragraphs 63 to 69 for modifying a microbial host cell (eg, for killing or reducing growth of the cell or a culture of microbe cells).

71. The method, virus or virus population of any one of paragraphs 1 to 63 and 66 to 70, wherein the virus or virus in said population express a holin and/or an endolysin for host cell lysis, optionally wherein the endolysin is a phage phi11, phage Twort, phage P68, phage phiWMY or phage K endolysin (eg, MV-L endolysin or P-27/HP endolysin).

72. The method, virus or virus population of any one of paragraphs 1 to 63 and 66 to 70, wherein the virus or virus in said population does no express a holin and/or an endo-lysin for host cell lysis.

73. The method, virus or virus population of any one of paragraphs 1 to 63 and 66 to 70, wherein the virus (eg, virus of (b)) or virus in each said population is in combination with an antimicrobial functional in the host cell of (a), eg, antibiotic agent, eg, a beta-lactam antibiotic (eg, an antibiotic recited in any one of paragraphs 13 to 27).

Control of Corrosion, Biofilms & Biofouling

The invention relates inter alia to methods of controlling microbiologically influenced corrosion (MIC) or biofouling of a substrate or fluid in an industrial or domestic system. The invention also relates to treated fluids and vectors for use in the methods.

Corrosion is the result of a series of chemical, physical and (micro) biological processes leading to the deterioration of materials such as metal (eg, steel or iron), plastic and stone. It is a world-wide problem with great societal and economic consequences. Current corrosion control strategies based on chemically produced products are under increasing pressure of stringent environmental regulations. Furthermore, they are rather inefficient and may be hampered by microbial (eg, bacterial) resistance to the agents used. Therefore, there is an urgent need for environmentally friendly and sustainable corrosion control strategies. Corrosion is influenced by the complex processes of different microorganisms performing different electrochemical reactions and secreting proteins and metabolites that can have secondary effects.

The severity of microbial corrosion processes is evident from the fact that many of the industrially and domestically used metals and alloys such as stainless steels, nickel and aluminium-based alloys and materials such as concrete, asphalt and polymers are readily degraded by microorganisms. Protective coatings, inhibitors, oils and emulsions are also subject to microbial degradation.

Microbially influenced corrosion (MIC) is a costly problem that impacts hydrocarbon production and processing equipment, water distribution systems, ships, railcars, and other types of metallic and non-metallic industrial and domestic systems. In particular, MIC is known to cause considerable damage to hydrocarbon fuel infrastructure including production, transportation, and storage systems, oftentimes with catastrophic environmental contamination results. Around 40% of pipe corrosion in the oil industry is attributed to microbiological corrosion and leads to huge financial losses in production, transportation and storage of oil every year. Pipe biofilms can cause the reduction in fluid velocity in equipment due to the process of incrustation on walls. Furthermore, pipe leaks are generated as a result of the corrosion, with consequent impacts on the environment and productivity.

MIC takes place in environments such as soil, fresh water and sea water and is estimated to be responsible for more than 30 percent of all corrosion damage. MIC occurs due to the fixation of microbes such as bacteria, release of metabolites and usually formation of biofilms that induce or accelerate the corrosion process. Among the groups of bacteria involved in the corrosion process are included: sulphur- or sulphate-reducing bacteria (SRB), extracellular polymeric substance-producing bacteria (EPSB), acid-producing bacteria (APB), sulphur- or sulphide-oxidising bacteria (SOB); iron- or manganese-oxidising bacteria (IOB), ammonia producing bacteria (AmPB) and acetate producing bacteria (AcPB). Small subunit ribosomal RNA gene pyrosequencing surveys indicate that acetic-acid-producing bacteria (*Acetobacter* spp. and *Gluconacetobacter* spp.) are prevalent in environments exposed to fuel-grade ethanol and water.

Microbial growth under environmental conditions influences electrochemical reactions directly or indirectly. Microbe-substrate interactions lead to initial adhesion and biofilm formation. The attachment of microbes such as bacteria to substrate, release of metabolites and formation of biofilms influences the electrochemical conditions at substrate surfaces, inducing or accelerating the corrosion process, thereby mediating the process of MIC. The formation of a bacterial biofilm on a metallic substrate comprises the following stages: I—formation of a film, through the adsorption of organic and inorganic molecules on the metal, which modifies the load distribution on the metallic surface and, also serves as a nutritional source for the bacteria, facilitating the adherence of free-floating microorganisms present in the liquid; II—adhesion and multiplication of aerobic bacteria forming microcolonies; III—production of extracellular polymeric substances (EPS) by some sessile bacteria; IV—colonisation by aerobic free-floating microbial cells, that will consume the oxygen by respiration, creating a local anaerobic environment in the biofilm as required by strict anaerobic bacteria and; V—increase of biofilm thickness, which may favour the shedding of the outer layers. The EPS produced by the bacteria adhered to the biofilm capture essential ions for their growth; they are used as a means of attachment and protect bacteria against biocides interfering with the mechanisms of corrosion by favouring the creation of differential aeration areas, besides serving as a nutritional source in case of low nutrient availability. The process of corrosion by differential aeration occurs due to uneven distribution of the biofilm on the metal substrate with aerated regions (surrounding the biofilm) and non-aerated regions (below the biofilm). The biofilm formation on the metal surface decreases the oxygen content, reaching levels of almost total anaerobiosis. *Pseudomonas* is the main EPS producer genus.

An example of a MIC biocorrosion process mediated by corrosive bacteria is as follows: (A) Aerobic corrosive bacteria from fresh water, sea water, industrial/domestic systems or storage tanks reach out equipment and pipelines of industrial or domestic systems, that have a conditioning film on the surface. (B) EPS-producing bacteria attach to equipment/pipeline walls and produce EPS, which creates a favourable environment for adhesion by other microorganisms. (C) Adhesion of other groups of corrosive bacteria to pipeline walls takes place, which release their metabolites, developing into a microcolony through cell division, consuming oxygen available. Action of iron-oxidising bacteria results in a large accumulation of ferric precipitation leading to blockage in the equipment/pipeline; sulphuric acid released by sulphur-oxidising bacteria promotes the acidification of the environment. (D) The low oxygen concentration and organic acids released by acid-producing bacteria favour attachment and development of sulphate-reducing bacteria producing hydrogen sulphide ($H_2S$), thereby accelerating the corrosion process and reducing the local pH. (E) A corroded equipment/pipeline results, which is partially blocked by iron precipitates with micro-leaks and containing a bacterial biofilm. The $H_2S$ poses a serious health risk to personnel operating the system affected. Furthermore, the production of thick biofilms and sludges lead to biofouling and hampering of the functioning of the system.

Similarly, bacterial populations may propagate in fluids, such as water stores or reservoirs (eg, in drinking water or in water of cooling systems), thereby mediating biofouling of the fluid. This may also be referred to as souring of the fluid. An example is waterway or drinking water reservoir souring.

The invention addresses such problems of MIC and biofouling by providing the following Aspects 1 et seq:—

1. A method of controlling microbiologically influenced corrosion (MIC) or biofouling of a substrate in an industrial or domestic system, wherein a surface of the substrate is in contact with a population of first host cells of a first microbial species that mediates MIC or biofouling of the substrate, the method comprising
   (i) contacting the population with a plurality of vectors that are capable of transforming or transducing the cells, each vector comprising a CRISPR array whereby CRISPR arrays are introduced into the host cells, wherein
   (a) each CRISPR array comprises one or more nucleotide sequences for expression of a crRNA and a promoter for transcription of the sequence(s) in a host cell; and
   (b) each crRNA is capable of hybridising to a target sequence of a host cell to guide Cas (eg, a Cas nuclease, eg, a Cas9 or Cpf1) in the host cell to modify the target sequence (eg, to cut the target sequence); the target sequence being a gene sequence for mediating host cell viability; and
   (ii) allowing expression of said cRNAs in the presence of Cas in host cells, thereby modifying target sequences in host cells, resulting in reduction of host cell viability and control of MIC or biofouling of said substrate.

In an example, the system comprises equipment (eg, for use in an industrial process) and the surface is a surface of said equipment. In an example, each array is an engineered array, eg, any engineered array disclosed herein. In an embodiment, the vector is an engineered CRISPR nucleic acid vector as described herein. In an example, the biofouling comprises microbial biofilm and/or sludge formation, proliferation or maintenance. In an example, the first host cells are sessile. In an example of Aspect 1 or 4 (below), "controlling" comprises preventing, reducing or eliminating said MIC or biofouling, or reducing spread of said MIC or biofouling in the system. Non-limiting examples of how bacteria mediate MIC or biofouling are described above. Cell growth or proliferation or maintenance is, for example, a characteristic of cell viability. Thus, in an example, the method reduces host cell proliferation and/or maintenance. In an example, the method kills host cells.

2. The method of Aspect 1, wherein said host cells are comprised by a microbial biofilm that is in contact with said substrate.

3. The method of any preceding Aspect, wherein said surface and host cells are in contact with a fluid, such as an aqueous liquid (eg, sea water, fresh water, stored water or potable water).

Fresh water is naturally occurring water on the Earth's surface in ice sheets, ice caps, glaciers, icebergs, bogs, ponds, lakes, rivers and streams, and underground as groundwater in aquifers and underground streams. Fresh water is generally characterized by having low concentrations of dissolved salts and other total dissolved solids. The term specifically excludes sea water and brackish water, although it does include mineral-rich waters such as chalybeate springs. In an example said fresh water is any of these fresh water types. Potable water is water for human or animal (eg, livestock) consumption. In an example, the fluid is selected from industrial cooling water wherein the system is a cooling system; sewage water wherein the system is a sewage treatment or storage system; drinking water wherein the system is a drinking water processing, storage, transportation or delivery system; paper making water wherein the system is a paper manufacture or processing system; swimming pool water wherein the system is a swimming pool or swimming pool water treatment or storage system; fire extinguisher water wherein the system is a fire extinguishing system; or industrial process water in any pipe, tank, pit, pond or channel.

4. A method of controlling microbial biofouling of a fluid in an industrial or domestic system (eg, for controlling bacterial souring of a liquid in a reservoir or container), wherein the fluid comprises a population of first host cells of a first microbial species that mediates said biofouling, the method comprising
   (i) contacting the population with a plurality of vectors that are capable of transforming or transducing the cells, each vector comprising a CRISPR array whereby CRISPR arrays are introduced into the host cells, wherein
   (a) each CRISPR array comprises one or more sequences for expression of a crRNA and a promoter for transcription of the sequence(s) in a host cell; and
   (b) each crRNA is capable of hybridising to a target sequence of a host cell to guide Cas (eg, a Cas nuclease) in the host cell to modify the target sequence (eg, to cut the target sequence); the target sequence being a gene sequence for mediating host cell viability; and
   wherein the method comprises allowing expression of said cRNAs in the presence of Cas in host cells, thereby modifying target sequences in host cells, resulting in reduction of host cell viability and control of said biofouling.

In an example, the fluid is a liquid. In an example, the fluid is a gaseous fluid.

Systems: An example system for any Aspect is selected from the group consisting of a:—Petrochemical recovery, processing, storage or transportation system; hydrocarbon recovery, processing, storage or transportation system; crude oil recovery, processing, storage or transportation system; natural gas recovery, processing, storage or transportation system, (eg, an oil well, oil rig, oil drilling equipment, oil pumping system, oil pipeline, gas rig, gas extraction equipment, gas pumping equipment, gas pipeline, oil tanker, gas tanker, oil storage equipment or gas storage equipment); Water processing or storage equipment; water reservoir (eg, potable water reservoir); Air or water conditioning (eg, cooling or heating) equipment, eg, a coolant tube, condenser or heat exchanger; Medical or surgical equipment; Environmental (eg, soil, waterway or air) treatment equipment; Paper manufacturing or recycling equipment; Power plant, eg, a thermal or nuclear power plant; Fuel (eg, hydrocarbon fuel, eg, petroleum, diesel or LPG) storage equipment; Mining or metallurgical, mineral or fuel recovery system, eg, a mine or mining equipment; Engineering system; Shipping equipment; Cargo or goods storage equipment (eg, a freight container); Food or beverage manufacturing, processing or packaging equipment; Cleaning equipment (eg, laundry equipment, eg, a washing machine or dishwasher); Catering (eg, domestic or commercial catering) equipment; Farming equipment; Construction (eg, building, utilities infrastructure or road construction) equipment; Aviation equipment; Aerospace equipment; Transportation equipment (eg, a motor vehicle (eg, a car, lorry or van); a railcar; an aircraft (eg, an aeroplane) or a marine or waterway vehicle (eg, a boat or ship, submarine or hovercraft)); Packaging equipment, eg, consumer goods packaging equipment; or food or beverage packaging equipment; Electronics (eg, a computer or mobile phone or an electronics component thereof); or electronics manufacture or packaging equipment; Dentistry equipment; Industrial or domestic piping (eg, a sub-sea pipe) or storage vessel (eg, a water tank or a fuel tank (eg, gasoline tank, eg, a gasoline tank of a vehicle)); Underground equipment; Building (eg, a dwelling or office or commercial premises or factory or power station); Roadway; Bridge; Agricultural equipment; Factory system; Crude oil or natural gas exploration equipment; Office system; and a Household system.

In an example, the system is used in an industry or business selected from the group consisting of agriculture, oil or petroleum industry, food or drink industry, clothing industry, packaging industry, electronics industry, computer industry, environmental industry, chemical industry, aerospace industry, automotive industry, biotechnology industry, medical industry, healthcare industry, dentistry industry, energy industry, consumer products industry, pharmaceutical industry, mining industry, cleaning industry, forestry industry, fishing industry, leisure industry, recycling industry, cosmetics industry, plastics industry, pulp or paper industry, textile industry, clothing industry, leather or suede or animal hide industry, tobacco industry and steel industry. In an example, the surface or fluid to be treated is a surface or fluid of equipment used in said selected industry. In an example, the system is used in the crude oil industry. In an example, the system is used in the natural gas industry. In an example, the system is used in the petroleum industry. In an example, the system is a sea container, platform or rig (eg, oil or gas platform or rig for use at sea or at sea), ship or boat. In an embodiment, such a system is anchored at sea; eg, non-temporarily anchored at sea, eg, has been anchored at sea for 1, 2, 3, 4, 5, 6, 7, 8, 9, 10, 11, 12, 13, 14, 15, 16, 17, 18, 19, 20, 21, 22, 23, 24 or more months (eg, contiguous months). In an embodiment, such a system is in the waters of a country or state; eg, non-temporarily at sea in such waters, eg, has been in waters of said country for 1, 2, 3, 4, 5, 6, 7, 8, 9, 10, 11, 12, 13, 14, 15, 16, 17, 18, 19, 20, 21, 22, 23, 24 or more months (eg, contiguous months).

In an example, the substrate surface to be treated comprises stainless steel, carbon steel, copper, nickel, brass, aluminium, concrete, a plastic or wood. In an example, the substrate is a metal weld or join. In an example, the surface is a metallic (eg, steel or iron) or non-metallic (eg, plastic, concrete, asphalt, wood, rubber or stone) surface. In an example, the metal is an alloy (eg, stainless steel, brass or a nickel-, zinc-, copper-, nickel- or aluminium-alloy). In an example, the surface is a man-made polymer surface. In an example, the surface is a substrate coating. In an example, the substrate is in contact with soil, fresh water or sea water. In an example, the fluid is potable water; a waterway; brackish water; or a liquid fuel, eg, gasoline or diesel (eg, for a car or motorised vehicle), LPG, kerosine, an alcohol (eg, ethanol, methanol or butanol), liquid hydrogen or liquid ammonia), in an example, the fuel is stored liquid fuel. In an example the fluid is an oil or non-aqueous liquid. In an example, the fluid is a liquid comprised by a waterway or body of water, eg, sea water, fresh water, potable water, a river, a stream, a pond, a lake, a reservoir, stored water (eg, in a water storage tank or cooling equipment), groundwater, well water, water in a rock formation, soil water or rainwater. In an example, the liquid is sea water. In an example, the substrate is in contact with a liquid mentioned in this paragraph. In an example, the fluid or liquid is selected from the group consisting of an oil, an aqueous solution, a hydraulic fracturing fluid, a fuel, carbon dioxide, a natural gas, an oil/water mixture, a fuel/water mixture, water containing salts, ocean or sea water, brackish water, sources of fresh water, lakes, rivers, stream, bogs, ponds, marshes, runoff from the thawing of snow or ice, springs, groundwater, aquifers, precipitation, any substance that is a liquid at ambient temperature (eg, at rtp) and is hydrophobic but soluble in organic solvents, hexanes, benzene, toluene, chloroform, diethyl ether, vegetable oils, petrochemical oils, crude oil, refined petrochemical products, volatile essential oils, fossil fuels, gasoline, mixtures of hydrocarbons, jet fuel, rocket fuel, biofuels. In an example the fluid is an oil/water mixture.

The terms "microbiologically influenced corrosion" or "MIC" as used herein, unless otherwise specified, refer to processes in which any element (substrate) of a system is structurally compromised due to the action of at least one member of a microbial population, eg, bacterial or archaeal population. The term "biofouling" as used herein, unless otherwise specified, refers to processes in which microorganisms (such as bacteria and/or archaea) accumulate on a substrate surface in contact with a fluid (eg, water or an aqueous liquid, or a hydrocarbon, or a petrochemical). Also included is the undesirable accumulation and proliferation of microorganisms (such as bacteria and/or archaea) in a fluid (eg, water or an aqueous liquid, or a hydrocarbon, or a petrochemical), ie, "souring" of the fluid. In an example, the bacteria are comprised by ship or boat ballast water and the bacteria are environmentally undesirable. The term "substrate" as used herein refers to any type of surface on which cells can attach and a biofilm can form and grow or on which biofouling (eg slime or sludge formation) can occur. The substrate may be an "industrial" substrate such as the surface of equipment in an petrochemical, fuel, crude oil or gas piping system, or a "non-industrial" (eg, domestic, eg, household or office) substrate such as a kitchen counter or a shower substrate or a garden substrate.

In an alternative of any of the Aspects, instead of a population of host bacterial cells, the population is a population of archaeal cells of a first species.

5. The method of Aspect 4, wherein said fluid is an aqueous liquid (eg, sea water, fresh water, stored water or potable water).

6. The method of any one of Aspects 3 to 5, wherein the method comprises mixing the fluid with the vectors, thereby contacting the host cells with vectors. For example, the vectors can be pre-mixed with a liquid (optionally with an antibiotic or biocide too) and the mixture then added to the fluid that is in contact with the surface (Aspect 1) or the fluid of Aspect 4.

7. The method of any one of Aspects 1-6, wherein each target sequence is a host cell virulence, resistance or essential gene sequence, eg, an exon or regulatory sequence thereof. Resistance can be antibiotic resistance. In an example, the host cells are contacted with said antibiotic and said vectors to reduce host cell viability.

8. The method of any one of Aspects 1-7, wherein the modification of target sequences results in host cell killing and/or a reduction in host cell growth or proliferation. Proliferation is, for example, cell expansion or cell distribution in contact with the surface.

9. The method of any one of Aspects 1-8, wherein the vectors comprise identical CRISPR arrays.

10. The method of any one of Aspects 1-9, wherein the host cells are bacterial or archaeal cells. In an alternative, instead the first cells are algal cells.

11. The method of any one of Aspects 1-10, wherein the first host cells are sulphate reducing bacteria (SRB) cells (eg, *Desulfovibrio* or *Desulfotomaculum* cells). In an example, the cells are selected from the group consisting of *Desulfotomaculum nigrificans, Desulfacinum infernum, Thermodesulfobacterium mobile, Thermodesulforhabdus norvegicus, Archaeoglobus fulgidus, Desulfomicrobium apsheronun,*

*Desulfovibrio gabonensis, Desulfovibrio longus, Desulfovibrio vietnamensis, Desulfobacterium cetonicum, Desulphomaculum halophilum, Desulfobacter vibrioformis* and *Desulfotomaculum thermocisternum* cells. In an example, the population comprises a mixture of two or more of these cell species.

12. The method of Aspect 11, wherein the surface or fluid is comprised by a crude oil, gas or petrochemicals recovery, processing, storage or transportation equipment. Crude oil is one of the most important energetic resources in the world. It is used as raw material in numerous industries, including the refinery-petrochemical industry, where crude oil is refined through various technological processes into consumer products such as gasoline, oils, paraffin oils, lubricants, asphalt, domestic fuel oil, vaseline, and polymers. Oil-derived products are also commonly used in many other chemical processes. In an alternative, the fluid is a said consumer product or the surface is in contact with such a consumer product.

13. The method of Aspect 11 or 12, wherein the surface is in contact with sea water, a fracking liquid or liquid in a well; or wherein the fluid is sea water, a fracking liquid or liquid in a well.

14. The method of any one of Aspects 1-13, wherein step (i) of the method comprises providing a population of microbial cells of a second species (second host cells), the second cells comprising said vectors, wherein the vectors are capable of transfer from the second host cells to the first host cells; and combining the second host cells with the first host cells, whereby vectors are introduced into the first host cells. In an example, the second cell(s) are environmentally-, industrially-, or domestically-acceptable in an environment (eg, in a water or soil environment) and the first host cell(s) are not acceptable in the environment.

15. The method of 14, wherein the first host cells are comprised by a mixture of microbial cells (eg, comprised by a microbial biofilm) before contact with said vectors, wherein the mixture comprises cells of said second species.

16. The method of Aspect 14 or 15, wherein said second species is a species of *Bacillus* or nitrate-reducing bacteria or nitrate reducing sulfide oxidizing bacteria (NRB).

17. The method of Aspect 16, wherein the NRB is selected from the group consisting of *Campylobacter* sp., *Nitrobacter* sp., *Nitrosomonas* sp., *Thiomicrospira* sp., *Sulfurospirillum* sp., *Thauera* sp., *Paracoccus* sp., *Pseudomonas* sp., *Rhodobacter* sp. and *Desulfovibrio* sp; or comprises at least 2 of said species.

18. The method of Aspect 17 wherein NRB is selected from the group consisting of *Nitrobacter vulgaris, Nitrosomonas europea, Pseudomonas stutzeri, Pseudomonas aeruginosa, Paracoccus denitrificans, Sulfurospirillum deleyianum,* and *Rhodobacter sphaeroides.*

19. The method of any one of Aspects 1-18, wherein the method comprises contacting the host cells of said first species with a biocide simultaneously or sequentially with said vectors. In an example, the vectors and biocide are provided pre-mixed in a composition that is contacted with the host cells.

20. The method of Aspect 19, wherein the biocide is selected from the group consisting of tetrakis hydroxymethyl phosphonium sulfate (THPS), glutaraldehyde, chlorine monoxide, chlorine dioxide, calcium hypochlorite, potassium hypochlorite, sodium hypochlorite, dibromonitrilopropionamide (DBNPA), methylene bis(thiocyanate) (MBT), 2-(thiocyanomethylthio) benzothiazole (TCMTB), bronopol, 2-bromo-2-nitro-1,3-propanediol (BNPD), tributyl tetradecyl phosphonium chloride (TTPC), taurinamide and derivatives thereof, phenols, quaternary ammonium salts, chlorine-containing agents, quinaldinium salts, lactones, organic dyes, thiosemicarbazones, quinones, carbamates, urea, salicylamide, carbanilide, guanide, amidines, imidazolines, acetic acid, benzoic acid, sorbic acid, propionic acid, boric acid, dehydroacetic acid, sulfurous acid, vanillic acid, p-hydroxybenzoate esters, isopropanol, propylene glycol, benzyl alcohol, chlorobutanol, phenylethyl alcohol, formaldehyde, iodine and solutions thereof, povidone-iodine, hexamethylenetetramine, noxythiolin, 1-(3-chloroallyl)-3,5,7-triazo-1-azoniaadamantane chloride, taurolidine, taurultam, N-(5-nitro-2-furfurylidene)-1-amino-hydantoin, 5-nitro-2-furaldehyde semicarbazone, 3,4,4'-trichlorocarbanilide, 3,4', 5-tribromosalicylanilide, 3-trifluoromethyl-4,4'-dichlorocarbanilide, 8-hydroxyquinoline, 1-cyclopropyl-6-fluoro-1, 4-dihydro-4-oxo-7-(1-piperazinyl)-3-quinolinecarboxylic acid, 1,4-dihydro-1-ethyl-6-fluoro-4-oxo-7-(1-piperazinyl)-3-quinolinecarboxylic acid, hydrogen peroxide, peracetic acid, sodium oxychlorosene, parachlorometaxylenol, 2,4,4'-trichloro-2'-hydroxydiphenol, thymol, chlorhexidine, benzalkonium chloride, cetylpyridinium chloride, silver sulfadiazine, silver nitrate, bromine, ozone, isothiazolones, polyoxyethylene (dimethylimino) ethylene (dimethylimino) ethylene dichloride, 2-(tert-butylamino)-4-chloro-6-ethylamino-5'-triazine (terbutylazine), and combinations thereof. In an example the biocide is tetrakis hydroxymethyl phosphonium sulfate (THPS). In an example, the biocide is a quaternary ammonium compound.

21. The method of any one of Aspects 1-20, wherein the system is used in an industry operation selected from the group consisting of mining; shipping; crude oil, gas or petrochemicals recovery or processing; hydraulic fracturing; air or water heating or cooling; potable water production, storage or delivery; transportation of hydrocarbons; and wastewater treatment.

22. The method of Aspect 21, wherein the surface is a surface of equipment used in said selected industry; or wherein the fluid is a fluid comprised by equipment used in said selected industry.

23. The method of any one of Aspects 1-22, wherein the surface is a surface of kitchen, bathing or gardening equipment; or wherein the fluid is comprised by kitchen, bathing or gardening equipment. For example, the equipment is used in a domestic setting.

24. The method of any one of Aspects 1-23 when dependent from Aspect 3, wherein the fluid is a potable liquid contained in a container (eg, water tank or bottle) and the surface is a surface of the container in contact with the liquid.

25. The method of any one of Aspects 1-24, wherein each vector comprises a mobile genetic element (MGE), wherein the MGE comprises an origin of transfer (oriT) and a said CRISPR array; wherein the MGE is capable of transfer between a host cell of said first species and a further microbial host cell in said industrial or domestic system. For example, the further cell(s) are environmentally-, industrially-, or domestically-acceptable in an environment (eg, in a water or soil environment) and the first host cell(s) are not acceptable in the environment.

26. The method of Aspect 25, wherein oriT is functional in the first and further host cells.

27. The method of Aspect 25 or 26, wherein said first and further host cells are comprised by a biofilm of fluid in contact with said surface; or wherein said cells are comprised by said fluid.

28. The method of Aspect 25, 26 or 27, wherein said further cell is a cell of a species as recited in any one of Aspects 16 to 18. In an example, the MGE is capable of transfer from the further cell to the first host cell and/or vice versa.

29. The method of any one of Aspects 25 to 27, wherein the further cell is a cell of said first species.

For example, in this embodiment the MGE is capable of transfer amongst first cells in a population in said system. When the MGE leaves a copy of itself in the transfer process to the other cell, this then provides means for propagating and spreading the MGE and thus CRISPR arrays through cell populations in the system, thereby spreading the target sequence modifying effect of the arrays. This can be effective, for example, to create spread of arrays in a biofilm in contact with the surface or in the fluid, and is useful as penetration of biofilms with conventional biocides can be sub-optimal.

30. The method of any one of Aspects 25 to 29, wherein each MGE is or comprises an integrative and conjugative element (ICE); or wherein each vector is a phage that is capable of infecting host cells of said first species and each MGE is a phage nucleic acid that is capable of said transfer between the cells.

31. The method of Aspect 30, wherein each ICE is a transposon, eg, a conjugative transposon.

32. The method of any one of Aspects 1-31, wherein each vector is a plasmid, optionally comprising an MGE according to any one of Aspects 25 to 31.

33. The method of any one of Aspects 25 to 32, wherein the first and/or further cell comprises nucleotide sequences encoding proteins operable to transfer the MGE to the other cell, wherein the sequences are not comprised by the MGE.

34. The method of Aspect 33, wherein the sequences are not comprised by the vector.

35. The method of Aspect 33, wherein the sequences are comprised by a conjugative transposon of the first cell and/or further cell.

36. The method of Aspect 35, wherein the transposon is operable in trans to transfer the MGE between the first and further cells.

37. The method of any one of Aspects 25 to 36, wherein the oriT of the MGE is the same as an oriT comprised by an ICE of the first cell and/or further cells, wherein the ICE is operable in trans to transfer the MGE between the first and further cells.

38. The method of any one of Aspects 25 to 37, wherein the vector oriT is an oriT of a SRB or NRB transposon.

39. The method of any one of Aspects 25 to 38, wherein each MGE comprises first and second terminal repeat sequences and a said CRISPR array between the repeat sequences.

40. The method of any one of Aspects 25 to 39, wherein the MGE leaves behind a CRISPR array copy (1) in the genome of a first host cell when it has transferred to a said further host cell; or (2) in a said further host cell when it has transferred to a first host cell. For example, the copy is comprised by a transposon or prophage left in the genome of the cell from which transfer takes place.

41. The method of any one of Aspects 25 to 40, wherein the first and further cells are bacterial cells of different species (eg, SRB and NRB; or SRB and *Bacillus* cells respectively).

42. The method of any one of Aspects 25 to 41 when dependent from Aspect 30 in combination with a transposase for mobilisation of the MGE.

43. The method of any one of Aspects 1-42, wherein the vector or MGE comprises a toxin-antioxin module that is operable in a host cell of said first species; optionally wherein the toxin-antitoxin module comprises an anti-toxin gene that is not operable or has reduced operation in cells of another species. These embodiments are useful to create a selective pressure that favours retention of the vector/MGE (and thus CRISPR arrays) in the first host cells comprising the target sequences.

44. The method of any one of Aspects 1-43, wherein the vector or MGE comprises a toxin-antioxin module that is operable in a said second or further cell; optionally wherein the toxin-antitoxin module comprises an anti-toxin gene that is not operable or has reduced operation in cells other than the second or further cell. This is useful to maintain a population of CRISPR arrays in the second or further cells (eg, when such cells are present in a biofilm also comprising the first cells), but wherein the toxin-antitoxin module provides additional killing (over and above the action of the target sequence modification) in first host cells. In an example, the vector or MGE comprises a toxin-antioxin module that is operable in a first host cell and in said second or further cell.

45. The method of any one of Aspects 43 or 44, wherein the toxin-antitoxin module is not operable or has reduced operation in cells other than the first and second or further cells. Thus, there can be a selective pressure in both the first and second (or further) cells to maintain the CRISPR arrays. Usefully, this then provides a reservoir for horizontal transfer of the arrays in MGEs between cells in a mixed population (eg, a biofilm contacting the surface or a population comprised by the fluid).

46. The method of any one of Aspects 25-45 wherein the first and second cells (or first and further cells) are of the same phylum (eg, both bacterial cells) and the vector is replicable or operable (A) in the first cell and/or second (or further) cell but not in another cell of the same phylum; (B) in the first cell and/or second (or further) cell but not in another cell of the same order; (C) in the first cell and/or second (or further) cell but not in another cell of the same class; (D) in the first cell and/or second (or further) cell but not in another cell of the same order; (E) in the first cell and/or second (or further) cell but not in another cell of the same family; (F) in the first cell and/or second (or further) cell but not in another cell of the same genus; or (G) in the first cell and/or second (or further) cell but not in another cell of the same species.

47. The method of Aspect 25 or any one of Aspects 26 to 46 when dependent from Aspect 25, wherein each MGE is a conjugative transposon, oriT is functional in the first and further (or second) host cells, the MGE comprises first and second terminal repeat sequences and a said CRISPR array between the repeat sequences, and wherein the first and further (or second) cells are bacterial cells, wherein the target site is comprised by the first cells but not the further (or second) cells, and wherein said modifying inactivates or down-regulates a gene or regulatory sequence comprising said target in the first cells, resulting in reduction of first host cell viability and control of said MIC or biofouling.

48. The method of any one of Aspects 1-47, wherein each CRISPR array comprises a sequence R1-S1-R1' for expression and production of the respective crRNA in a first host cell,
  (i) wherein R1 is a first CRISPR repeat, R1' is a second CRISPR repeat, and R1 or R1' is optional; and
  (ii) S1 is a first CRISPR spacer that comprises or consists of a nucleotide sequence that is 95% or more identical to a target sequence of a said first host cell.

49. The method of Aspect 48, wherein R1 and R1' are at least 95, 96, 97, 98 or 99% identical respectively to the first and second repeat sequences of a CRISPR array of the first host cell species. In an embodiment, both R1 and R1' are present.

50. The method of Aspect 48 or 49, wherein R1 and R1' are functional with a CRISPR/Cas system of said host cells of said first species for modification of target sequences.

51. The method of any one of Aspects 48 to 50, wherein the first host cells are sulphate reducing bacteria (SRB) cells and R1 and R1' are least 95, 96, 97, 98 or 99% identical respectively to a repeat sequence (eg, the first repeat) of a CRISPR array of the first host cell species.

52. The method of Aspect 51, wherein R1 and R1' are least 95, 96, 97, 98 or 99% identical respectively to a repeat sequence selected from the group consisting of SEQ ID NOs: 50-74, 125-128 and 49. See Table 1. In an embodiment, both R1 and R1' are present.

53. The method of Aspect 51, wherein R1 and R1' are least 95, 96, 97, 98 or 99% identical respectively to a repeat sequence selected from the group consisting of SEQ ID NOs: 51 and 125-126, 54 and 127, 69 and 128. SEQ ID NOs: 51 and 125-126, 54 and 127, 69 and 128 are found in more than one SRB species. This is particularly useful for targeting more than one SRB type with the CRISPR array of the invention, eg, when the SRB types co-exist in the industrial or domestic system to be treated, for example co-existing in a population or biofilm that is in contact with the substrate or in the fluid to be treated. In an embodiment, both R1 and R1' are present.

54. The method of any one of Aspects 48 to 53, wherein the sequences of R1 and R1' are identical.

55. The method of any one of Aspects 1-54, wherein each array introduced into a first host cell is introduced in combination with one or more Cas nuclease(s) (eg, a Cas9 and/or Cfp1) that function with the respective crRNA in a host cell to modify a target sequence thereof.

In an example, Cas herein in any configuration is deactivated for nuclease activity and optionally comprises a target sequence activator or depressor. A Cas 9 herein is, for example *S pyogenes* or *S aureus* Cas9. 56. The method of any one of Aspects 1-55, wherein each array introduced into a first host cell is introduced in combination with nucleic acid sequence(s) encoding one or more Cas nuclease(s) (eg, a Cas9 and/or Cfp1) that function with the respective crRNA in a host cell to modify the target sequence.

57. The method of any one of Aspects 48 to 56, wherein R1 and R1' are functional with a Type II Cas9 nuclease to modify a target sequence in a said first host cell, optionally wherein the method is further according to Aspect 55 or 56 wherein the Cas is said Cas9.

58. The method of any one of Aspects 1-57, wherein all or some of said vectors or MGEs do not comprise a Cas nuclease-encoding sequence operable with the respective array.

59. The method of Aspect 58, wherein each said respective array is operable with a Cas endonuclease found in cells of the first species.

60. The method of Aspect 25, or any one of Aspects 26 to 59 when dependent from Aspect 25, wherein each MGE is devoid of a sequence encoding a Cas endonuclease that is operable with repeat sequences of the array, and wherein the respective vector comprises such a sequence (eg, encoding a Cas9 of Cfp1) outside the MGE.

61. A method of controlling microbiologically influenced corrosion (MIC) or biofouling of a substrate comprised by a crude oil, gas or petrochemicals recovery, processing, storage or transportation equipment (eg, a crude oil tanker, oil rig or oil drilling equipment), wherein a surface of the substrate is in contact with a population of first host cells, wherein the first host cells are sulphur- or sulphate-reducing bacteria (SRB), extracellular polymeric substance-producing bacteria (EPSB), acid-producing bacteria (APB), sulphur- or sulphide-oxidizing bacteria (SOB), iron-oxidising bacteria (JOB), manganese-oxidising bacteria (MOB), ammonia producing bacteria (AmPB) or acetate producing bacteria (AcPB) of a first species that mediates MIC or biofouling of the substrate, wherein the surface and cell population are in contact with a liquid selected from sea water, fresh water, a fracking liquid or liquid in a well (eg, oil or natural gas well), the method comprising
  (i) contacting the cell population with vectors by mixing the liquid with a plurality of vectors that are capable of transforming or transducing first host cells, each vector comprising a CRISPR array whereby CRISPR arrays are introduced into the host cells, wherein
    (a) each CRISPR array comprises one or more sequences for expression of a crRNA and a promoter for transcription of the sequence(s) in a host cell;
    (b) each crRNA is capable of hybridising to a target sequence of a host cell to guide Cas (eg, a Cas nuclease, eg, a Cas9 or Cfp1) in the host cell to modify the target sequence (eg, to cut the target sequence); the target sequence being a gene sequence for mediating host cell viability;
    (c) wherein each sequence of (a) comprises a sequence R1-S1-R1' for expression and production of the respective crRNA in a first host cell, wherein R1 is a first CRISPR repeat, R1' is a second CRISPR repeat, and R1 or R1' is optional; and S1 is a first CRISPR spacer that comprises or consists of a nucleotide sequence that is 70, 75, 80, 85, 90 or 95% or more identical to a target sequence of a said first host cell and
  (ii) allowing expression of said cRNAs in the presence of Cas in host cells, thereby modifying target sequences in host cells, resulting in reduction of host cell viability and control of MIC or biofouling of said substrate. In an embodiment, both R1 and R1' are present.

62. The method of Aspect 61, wherein the method is according to Aspect 1 or any preceding Aspect when dependent from Aspect 1.

63. The method of Aspect 61 or 62, wherein each vector is a phage capable of infecting a first host cell or is a vector comprising a MGE (eg, a transposon) that comprises a said CRISPR array, wherein the MGE is capable of transfer into a first host cell.

64. The method of Aspect 61, 62 or 63, wherein the first cells are sulphate reducing bacteria (SRB) cells, eg, *Desulfovibrio* or *Desulfotomaculum* cells.

65. The method of Aspect 64, wherein R1 and R1' are at least 95, 96, 97, 98 or 99% identical respectively to a repeat sequence (eg, the first repeat) of a CRISPR array of the first host cell species and the vector arrays are operable with a Cas endonuclease found in cells of the first species. In an example, R1 and R1' are identical sequences.

66. The method of Aspect 65, wherein R1 and R1' are at least 95, 96, 97, 98 or 99% identical respectively to a repeat sequence selected from the group consisting of SEQ ID NOs: 50-74, 125-128 and 49. In an example, R1 and R1' are identical sequences.

67. The method of Aspect 66, wherein R1 and R1' are at least 95, 96, 97, 98 or 99% identical respectively to a repeat sequence selected from the group consisting of SEQ ID NOs: 51 and 125-126, 54 and 127, 69 and 128. See Table 1 This is particularly useful for targeting more than one SRB type with the CRISPR array of the invention, eg, when the SRB types co-exist in the industrial or domestic system to be treated, for example co-existing in a population or biofilm that is in contact with the substrate or in the fluid to be treated. In an example, R1 and R1' are identical sequences.

68. The method of any one of Aspects 1-67, wherein said plurality of vectors comprise additional vectors, wherein each additional vector comprises one or more CRISPR arrays for targeting additional host cells comprised by said population, wherein the additional host cell species is different from the first host cell species, wherein in step (i) said additional cells of the population are contacted with a plurality of said additional vectors that are capable of transforming or transducing the additional cells, each vector comprising a CRISPR array whereby CRISPR arrays are introduced into the additional host cells, wherein
   (a) each CRISPR array comprises one or more sequences for expression of a crRNA and a promoter for transcription of the sequence(s) in a host cell; and
   (b) each crRNA is capable of hybridising to a target sequence of a said additional host cell to guide Cas (eg, a Cas nuclease) in the host cell to modify the target sequence (eg, to cut the target sequence); the target sequence being a gene sequence for mediating host cell viability; and step (ii) comprises allowing expression of said cRNAs in the presence of Cas in said additional host cells, thereby modifying target sequences in additional host cells.

69. The method of Aspect 68, wherein the additional host cells mediate MIC or biofouling of said substrate or fluid, wherein step (ii) results in reduction of additional host cell viability and control of MIC or biofouling of said substrate or fluid.

70. A method of controlling bacterial biofouling in ballast water of a ship or boat, wherein the water comprises a population of first host cells of a first microbial species that mediates said biofouling, the method comprising
   (i) contacting the population with a plurality of vectors that are capable of transforming or transducing the cells, each vector comprising a CRISPR array whereby CRISPR arrays are introduced into the host cells, wherein
      (a) each CRISPR array comprises one or more sequences for expression of a crRNA and a promoter for transcription of the sequence(s) in a host cell; and
      (b) each crRNA is capable of hybridising to a target sequence of a host cell to guide Cas (eg, a Cas nuclease) in the host cell to modify the target sequence (eg, to cut the target sequence); the target sequence being a gene sequence for mediating host cell viability; and
   (ii) allowing expression of said cRNAs in the presence of Cas in host cells, thereby modifying target sequences in host cells, resulting in reduction of host cell viability and control of said biofouling.

71. The method of Aspect 70, wherein the first host cells are *Vibrio cholerae, E coli* or Enterococci sp cells.

72. The method of Aspect 70 or 71, wherein step (i) comprises mixing the ballast water with the vectors, eg, in the hull of a ship or boat.

73. The method of any one of Aspects 70 to 72, wherein the ship or boat is a marine vehicle and the water is sea water.

74. The method of any one of Aspects 70 to 72, wherein instead of a ship or boat, the ballast water is comprised by a container or a drilling platform at sea, eg, an oil platform or oil rig. In an example, the ship, boat, container, platform or rig is anchored at sea (ie, not temporarily in its location).

75. A method of discharging ballast water from a ship or boat, wherein the discharged ballast water comprises water treated by the method of any one of Aspects 70 to 74.

76. The method of Aspect 75, wherein the water is discharged into a body of water, eg, a sea, ocean or waterway (eg, a river, canal, lake or reservoir) or into a container.

77. Ballast sea water comprising CRISPR arrays, wherein the ballast water is obtained or obtainable by the method of any one of Aspects 70 to 76.

78. A ship, boat, container or rig comprising the ballast sea water of Aspect 77.

79. A vector for use in the method of any one of Aspects 61 to 69, wherein the first cells are sulphate reducing bacteria (SRB) cells, eg, *Desulfovibrio* or *Desulfotomaculum* cells, each vector comprising one or more CRISPR arrays for targeting the SRB, wherein each array is as defined in (a)-(c) of Aspect 61.

80. The vector of Aspect 79, wherein R1 and R1' are according to any one of Aspects 65 to 67.

81. A vector for use in the method of any one of Aspects 70 to 76, wherein the first cells are Cholera (eg, *vibrio*, eg, O1 or O139), *E coli* or Enterococci sp cells, the vector comprising one or more CRISPR arrays for targeting the cells, wherein each array is as defined in (a) and (b) of Aspect 70.

82. The vector of any one of Aspects 79 to 81, wherein the vector is a bacteriophage capable of infecting a said cell.

83. The vector of any one of Aspects 79 to 81, wherein the vector is a transposon or MGE capable of transfer into a said cell.

84. A plurality vectors, wherein each vector is according to Aspect 82 or 83, optionally in combination with a biocide or antibiotic that is capable of reducing viability of said cells.

Bacteria that Mediate MIC or Biofouling: In an example, the first host cells are selected from the group consisting of sulphur- or sulphate-reducing bacteria (SRB), extracellular polymeric substance-producing bacteria (EPSB, eg, *Pseudomonas*), acid-producing bacteria (APB), sulphur- or sulphide-oxidising bacteria (SOB); iron- or manganese-oxidising bacteria (IOB), ammonia producing bacteria (AmPB) and acetate producing bacteria (AcPB). For example, the first host cells are AcPB (eg, *Acetobacter* spp. and/or *Gluconacetobacter* spp) and the surface is in contact with a hydrocarbon fuel (eg, fuel-grade ethanol) and/or water.

The following are examples of relevant bacteria for the present invention (in an example, the first host cells are cells of any of the following species). *Acidithiobacillus* bacteria produce sulphuric acid. *Acidithiobacillus* thiooxidans, a subgenus of *Acidithiobacillus* bacteria, frequently damages sewer pipes. *Ferrobacillus ferrooxidans* directly oxidises iron to iron oxides and iron hydroxides. Other bacteria produce various acids, both organic and mineral, or ammonia. In the presence of oxygen, aerobic bacteria like *Thiobacillus thiooxidans, Thiobacillus thioparus*, and *Thiobacillus concretivorus*, all three widely present in the environment, are the common corrosion-causing factors resulting in biogenic sulphide corrosion. Without presence of oxygen, anaerobic bacteria, especially *Desulphovibrio* and *Desulphotomaculum*, are common. *Desulphovibrio salixigens* requires at least 2.5% concentration of sodium chloride, but *D. vulgaris* and *D. desulphuricans* can grow in both fresh and salt water. *D. africanus* is another common corrosion-causing microorganism. The *Desulphotomaculum* genus comprises sulphate-reducing spore-forming bacteria. *Desulphotomaculum orientis* and *nigrificans* are involved in corrosion processes. Sulphate-reducers require a reducing environment, and an electrode potential of at least −100 mV is required for them to thrive. However, even a small amount of produced hydrogen sulphide can achieve this shift, so the growth, once started, tends to accelerate.

In an Example the first host cells are *Serratia marcescens, Gallionella* sp., *Pseudomonas* sp., *Bacillus* sp. (eg, *B. subtilis, B. cereus, B. pumilus* or *B. megaterium*), *Thiobacillus* sp., *Sulfolobus* sp., *Klebsiella oxytoca, Pseudomonas aeruginosa, P. stutzeri, Micrococcus, Enterococcus, Staphylococcus* (eg, *S. aureus*), *E. faecalis* or *M. luteus* cells. In an example, the first host cells comprise a mixture of two or more of said species. These species have been isolated from diesel and naphtha-transporting pipelines located in the northwest and southwest regions in India; the association with localized corrosion of the pipeline steel in the presence of these consortia was corroborated. A joint project of different european aircraft manufacturers confirmed the involvement of isolates from genera *Micrococcus, Enterococcus, Staphylococcus* and *Bacillus* in strong corrosion damage in aluminium alloy, commonly used in aircraft construction. These bacteria may create a microacidic environment (acid producing bacteria), which favours the development of other bacteria, or produce EPS, favouring the formation of biofilm (EPS-producing bacteria). Thus, in an embodiment of the invention, the surface (eg, steel surface) of the system to be treated is in contact with diesel or naptha, or the fluid to be treated is diesel or naptha (and optionally the first host cells are of one or more species defined in this paragraph). In an embodiment of the invention, the surface (eg, aluminium-containing surface, eg, an aircraft surface) of the system to be treated is in contact with one, two, three or all genera: *Micrococcus, Enterococcus, Staphylococcus* and *Bacillus* (first host cells). In an example of any embodiment in this paragraph, the surface is a surface of a steel or aluminium component of the system.

Acid-producing bacteria: Aerobic bacteria are able to produce short-chain organic acids such as acetic, formic, lactic, propionic and butyric acids as products of their metabolism from the fermentative metabolism of organic materials. They are also initial colonizers due to aerobic metabolism. These microorganisms are present in a variety of environments, including gas stands and oils. Organic acids serve as substrates for the SRB, accelerating the corrosion process, besides reducing the pH of the surrounding medium. Furthermore, the large amount of organic acid produced acts in metal depolarisation, starting the local corrosive process.

Sulphur-oxidising bacteria: The sulphur-oxidising bacteria are aerobic and facultative anaerobic microorganisms which obtain the energy necessary for growth from the oxidation of inorganic sulphur compounds such as sulphide, sulphite, thiosulphate and, in some cases the sulphur. Oxidative metabolism results in the production of sulphuric acid which promotes environment acidification. This group encompasses many genera, the *Acidithiobacillus* genus being the most studied. The group also includes bacterial species from the genera *Sulfolobus, Thiomicrospira, Beggiatoa, Acidithiobacillus,* and *Thiothrix* as well as the species *Thiosphaera pantotropha* and *Paracoccus denitrificans*. In an example, the first host cells are cells of any one of these species.

Iron-oxidising bacteria: Iron oxidising bacteria are aerobic microorganisms, belonging to a large and diverse group, that get energy necessary for their metabolism from iron oxidation. Consequently, there is the formation of iron hydroxides that generally form insoluble precipitate on substrate surfaces, promoting regions with different oxygen levels. They are widely found in water from rivers, lakes and oil production. They have mostly a locomotor sheath and their presence can be detected by a large accumulation of ferric precipitated as corrosion product. This accumulation or inorganic fouling leads to problems to industrial equipment such as blockages in oil pipelines. Among the most common are: *Thiobacillus ferrooxidans* and the genera *Crenothrix, Gallionella, Leptothrix* and *Spherotillus*. In an example, the first host cells are cells of any one of these species.

Sulphur- or sulphate-reducing bacteria (SRB): The SRB form a morphological- and phylogenetically heterogenous group that includes bacteria and restricted anaerobic archaebacteria, although some species have significant tolerance to oxygen. They are mainly gram-negative bacteria, mesophilic and some thermophilic generally spore-forming. These microorganisms are capable of oxidising various organic compounds of low molecular weight, including mono- or dicarboxylic aliphatic acids, alcohols, hydrocarbons and aromatic compounds, using sulphate ions or other sulphur compounds (thiosulphate, sulphite, etc.) as electron acceptors. Acetate, lactate, pyruvate and ethanol are among the most commonly used substrates by SRB. The stimulation of SRB growth is due to existing anaerobic conditions in biofilms explained by the deposition of corrosion products combined with microorganisms and, during oil recovery, where there is injection of aqueous media such as sea water, rich in sulphate. Large amounts of biogenic hydrogen sulphide can be produced; most of the $H_2S$ formed in pipelines and other oil, gas or petrochemicals recovery, processing, storage or transportation equipment originates from the metabolic activity of SRB. Another economic impact on the oil industry is the acidification of oil and gas by $H_2S$.

Considering the numerous economic losses related to metabolic activity of SRB, efforts have been directed to the use of environmentally-harmful and toxic metabolic inhibitors such as molybdate, nitrate and nitrite, and application of biocides, which help the control of metabolic activity of SRB and subsequent inhibition of biogenic $H_2S$ production.

Several mechanisms contribute to contain the formation process of biogenic $H_2S$ by using metabolic inhibitors: I—competition between SRB and heterotrophic bacteria that are reducers of nitrite or nitrate by ordinary electron donors, resulting in competitive SRB exclusion; II—increased redox potential due to the presence of intermediaries of nitrate reduction (nitrous oxide and nitric oxide), since the biological production of $H_2S$ occurs only at low redox potential (below −100 mV); III—Change of energy metabolism of some SRB, reducing nitrate instead of sulphate; IV—sulphide oxidising bacteria and nitrate or nitrite reducing bacteria that use the nitrate or nitrite to re-oxidise $H_2S$, resulting in $H_2S$ removal; V-inhibition of the dissimilatory sulphite reductase by nitrite to inhibit the final enzymatic step via sulphate reduction in SRB.

In certain embodiments of the present invention, the host cell population in contact with the substrate to be treated or comprised by the fluid to be treated is also contacted with one or more nitrate and/or one or more nitrite in the presence of the vectors of the invention. For example, in step (i) simultaneously or sequentially with the vectors, the nitrate/nitrite and vectors are combined with (eg, injected into) oil, gas, petrochemical, water or other fluid comprised by the industrial or domestic system. Similarly, additionally or alternatively, molybdates also may also be used in these systems as a control mechanism for SRB. Thus, in one embodiment, the host cell population in contact with the substrate to be treated or comprised by the fluid to be treated is also contacted with one or more molybdate in the presence of the vectors of the invention. For example, in step (i) simultaneously or sequentially with the vectors, the molybdate(s) and vectors are combined with (eg, injected into) oil, gas, petrochemical or other fluid comprised by the industrial or domestic system.

In other embodiments, the population is contacted with nitrate-reducing bacteria and/or nitrate reducing sulphide oxidising bacteria (NRSOB) (herein collectively, "NRB") in the presence of the vectors of the invention. For example, simultaneously or sequentially with the vectors, the NRB are combined with (eg, injected into) oil, gas, petrochemical, water or other fluid comprised by the industrial or domestic system. In an example, the NRB comprise vectors of the invention, wherein the vectors are capable of transfer from the NRB cells to the first host cells (SRB cells); and following combining the NRB and SRB cells, the vectors are introduced into the SRB cells. In an example, the SRB cells are comprised by a mixture of microbial cells (eg, comprised by a microbial biofilm) before contact with said vectors, wherein the mixture comprises cells of the NRB species. Thus, in this case the invention involves contacting the SRB cells with NRB cells (containing vectors) where the NRB cell species are already co-existing with the SRB in the biofilm to be targeted, which thus increases compatibility and chance of uptake of the vector-containing NRB into the biofilm cell population. This is useful for increasing the chances of the vectors being taken into the biofilm, thereby increasing chances of efficacy to modify SRB cells and chances of propagation of the CRISPR arrays of the invention within the biofilm (especially when the arrays are comprised by mobile genetic elements, such as transposons or comprised by phage, as herein described).

SRB and NRB typically compete for the same non-polymer carbon source (such as acetates) present in certain oilfield and industrial water systems needed for growth of bacteria. By increasing the growth rate of the NRB in comparison to the SRB, the NRB may out compete the SRB in consumption of the available non-polymer carbon source, depriving the SRB of its ability to grow and create the undesirable sulphides and reduce corrosion rates. Further, by inhibiting the growth rate of the SRB, the NRB may predominate, again out competing the SRB for the available non-polymer carbon in the system, eg, oilfield or industrial water system. Thus, contacting the SRB cells in the population with NRB can help to reduce SRB cell viability by increasing the ratio of NRB to SRB in the population.

In an embodiment, the invention comprises contacting the population comprising the first host cell (eg, SRB) with organic and/or inorganic nitrates and nitrite. These serve to stimulate the growth of the NRB present, thus helping the NRB to outcompete SRB. Organic and inorganic nitrates or inorganic nitrites may be used injected into the certain oilfield and industrial water systems. Inorganic nitrates and inorganic nitrites available for use in the present disclosure include, for instance, potassium nitrate, potassium nitrite, sodium nitrate, sodium nitrite, ammonium nitrate, and mixtures thereof. These organic and inorganic nitrates and inorganic nitrites are commonly available, but are non-limiting and any appropriate nitrate or nitrite may be used.

The amount of organic or inorganic nitrate or nitrite used is dependent upon a number of factors, including the amount of sulphate and/or organic acids present in the population in the system, and the expected amount of NRB needed to counteract the SRB. In certain embodiment, for treating MIC of a substrate in contact with a liquid, or for treating biofouling of a liquid according to the invention, the concentration of organic or inorganic nitrate or nitrite used is less than 2000 ppm by weight of the liquid, alternatively 500 to 1600 ppm by weight or alternatively between about 900 and 1100 ppm by weight when applied using a batch application method. When applied through continuous operation, the concentration of the organic or inorganic nitrate or nitrite may be less than 500 ppm by weight, alternatively between 10 and 500 ppm, or alternatively between 10 and 100 ppm of the liquid.

In an embodiment, the population is contacted with the vectors of the invention and simultaneously or sequentially with NRB (eg, that comprise the vectors) and nitrate and/or nitrite.

Suitable NRB include any type of bacteria capable of performing anaerobic nitrate reduction, such as heterotrophic nitrate-reducing bacteria, and nitrate-reducing sulphide-oxidising bacteria. In an example, the NRB comprises one, two, three or more (eg, one or more) NRB selected from the group consisting of *Campylobacter* sp. *Nitrobacter* sp., *Thiobacillus* sp., *Nitrosomonas* sp., *Thiomicrospira* sp., *Sulfurospirillum* sp., *Thauera* sp., *Paracoccus* sp., *Pseudomonas* sp. and *Rhodobacter* sp. For example, the NRB is selected from one or more of *Nitrobacter vulgaris, Nitrosomonas europea, Pseudomonas stutzeri, Pseudomonas aeruginosa, Paracoccus denitrificans, Sulfurospirillum deleyianum*, and *Rhodobacter sphaeroides*.

In certain embodiments, the NRB is a NRB strain that is found in a crude oil, gas, petrochemical or water recovery, processing, transportation or storage system (eg, in equipment thereof), or is found in a subterranean formation, such as a water or oil well. The NRB may be optimized to metabolize under the system conditions. The NRB are, for example, selected from a library of NRB strains or may be cultured from the system to be treated or a similar system.

The amount of NRB contacted with the SRB cells in the system may depend upon a number of factors including the amount of SRB expected, as well as any biocide that may be present. When injected into subterranean formation, the permeability and porosity of the subterranean formation may be considered as well. In certain embodiments of the present disclosure, the amount of NRB injected into the liquid is between 1 and 108 bacteria count/ml of the liquid, or alternatively between 10 and $10^4$ bacteria count/ml of the liquid.

In addition to stimulating the NRB to out compete the SRB, it may be desirable to introduce additional SRB inhibitors in certain embodiments of the present disclosure together with the nitrates. In an example, the SRB are contacted with one or more SRB inhibitors selected from the group consisting of 9,10-anthraquinone, molybdates (such as sodium molybdate and/or lithium molybdate) and mixtures thereof. In certain embodiments of the present disclosure, molybdate is added to the liquid in the range of 5 to 100 ppm by weight of liquid.

In an example, vectors of the invention and one or more biocides (ie, biocides of the first host cells, such as SRB biocides) are mixed prior to contacting the first cells with the mixture, eg, by injection of the mixture into liquid that is in contact with the surface to be treated or injection of the mixture into the fluid to be treated.

Additionally or alternatively to NRB cells containing vectors, the invention contemplates use of a species of *Bacillus* cells comprising vectors of the invention.

In an embodiment, the vectors are bacteriophage that are capable of infecting the SRB and the phage are contacted with the first host cells (eg, SRB), whereby CRISPR arrays comprised by the phage are introduced into first host cells for modification thereof according to the invention. In an embodiment, when the first cells are SRB, the SRB are also contacted with the phage vectors of the invention and simultaneously or sequentially with NRB. Instead of, or in addition to contacting with NRB, the SRB are contacted with nitrate and/or nitrite.

Example mechanisms involved in MIC are as follows; in an embodiment, the "controlling" using the method comprises reducing a mechanism selected from:

Microbial (eg, bacterial) promotion of bio-mineralisation due to deposition of iron hydroxides on the metal surface, modifying the electrochemical processes at the interface metal/solution, inducing corrosion;

Production of EPS that favours the formation of biofilm;

Microbial (eg, bacterial) promotion of the degradation of petroleum products due to the release of the enzyme aryl hydrocarbon hydroxylase (AHH) that acts on the corrosion of metals;

Production of sulphuric acid, which increases the corrosion process; and

Oxidation of sulphur.

In an embodiment, the method comprises reducing a mechanism selected from:

Bacterial promotion of bio-mineralisation due to deposition of iron hydroxides on the surface, wherein the surface is a metallic surface;

Production of EPS;

Bacterial promotion of the degradation of petroleum products in the system due to the release of the enzyme aryl hydrocarbon hydroxylase (AHH), wherein the surface is a metallic surface;

Production of sulphuric acid; and

Oxidation of sulphur.

Examples Applicable to Mic or Bifouling Control

There are specific example applications envisioned by the present invention to reduce the corrosion and/or biofouling associated with bacteria. The applications described below are not intended to limit the concept of the present invention, and are merely illustrative of how the invention may be used to control bacterially induced corrosion or to reduce environmental pollution.

Acid Mine Drainage: In acid mine drainage, bacterial growth can increase acidity in the environment. A reaction scheme exists for the creation of acid and, therefore, potential environmental damage. The problem of acid mine drainage is recognised throughout the world as a severe environmental problem. The origin of acid mine drainage is the weathering and oxidation of pyritic and other sulphide containing minerals. Mine drainage is formed when pyrite, an iron sulfide, is exposed and reacts with air and water to form sulphuric acid and dissolved iron. Some or all of this iron can precipitate to form the red, orange, or yellow sediments in the bottom of streams containing mine drainage. The acid run-off further dissolves heavy metals such as copper, lead, mercury into ground or surface water. The rate and degree by which acid-mine drainage proceeds can be increased by the action of certain bacteria.

In an example, the system is therefore a mine or comprised by a mine. The fluid is mine drainage fluid and the method reduces sulphuric acid caused by mine drainage. In an example, the surface is in contact with mine drainage fluid.

In an example, the first host cells are *Acidithiobacillus ferrooxidans, Acidithiobacillus thiooxidans, Acidithiobacillus denitrificans, Leptospirillum ferrooxidans* or *Sulfobacillus thermosulfidooxidans* cells or a mixture of two or more of these.

Hydraulic Fracturing: Hydraulic fracturing is a method to fracture rock formations to facilitate the extraction of gas and other hydrocarbons. Essentially, once a gas bearing formation is identified, wells are bored into the earth in both vertical and horizontal directions to access the gas. The wells are then used to fracture the shale using high pressure water, sand and a plethora of chemicals to maintain the fractures and fissures from being closed by the intense pressure of the overburden once the hydrofracturing is completed. Millions of gallons of water are used to frac a well. Between 30% and 70% of the frac fluid returns to the surface as "flowback". Flowback contains any matter that is dissolved in the frac water, including salt. What is dissolved depends on the location. The flowback is held in plastic lined pits at the well site until it is trucked and treated prior to disposal. At some point in time the high flow and relatively low salinity water converts to a lower flow, but much higher salinity "produced water" to distinguish it from "flowback" water.

In either case the problem of microbially induced corrosion (MIC) exists. Of particular interest are the SRB. In an example, therefore, the system is hydraulic fracturing system and the fluid is a hydraulic fracturing liquid (eg, flowback water or produced water) or the surface to be treated is in contact with such a liquid. The method, for example, reduces SRB viability (eg, kills SRB and/or reduces SRB proliferation in the liquid) and the first host cells are SRB.

For example, the first host cells are *Acidithiobacillus* bacteria, *Acidithiobacillus thiooxidans, Ferrobacillus ferrooxidans, Thiobacillus thiooxidans, Thiobacillus thioparus, Thiobacillus concretivorus, Desulphovibrio* (eg, *salixigens,* vulgaris, *desulphuricans* or *africanus*) or *Desulphotomaculum* (eg, *orientis* or *nigrificans*) cells, or a mixture of two or more of these species.

Cooling Equipment (eg, Cooling Towers): The presence of bacteria in cooling equipment, such as cooling towers, can adversely affect the functioning of the cooling in several ways. For example, SRB support the creation of acid conditions on the walls of cooling towers, heat exchangers, etc., which leads to corrosion and potential shutdown of the cooling system while repairs are made. Additionally, biofilms on the walls of, for example, the heat exchangers, reduce the heat transfer coefficient of the heat exchangers, resulting in decreased operational efficiency of the cooling system.

Additionally, the corrosion of iron-containing components can be especially detrimental. Oxidation of iron to iron(II) and reduction of sulphate to sulphide ion with resulting precipitation of iron sulphide and generation of corrosive hydrogen ions in situ may take place via the SRB. The corrosion of iron by sulphate reducing bacteria is rapid and, unlike ordinary rusting, it is not self-limiting. Tubercles produced by *Desulphovibrio* consist of an outer shell of red ferric oxide mixed' with black magnetic iron oxide, containing a soft, black center of ferrous sulphide.

In an example, therefore, the system is a cooling system and the fluid is a fluid (eg, water or an aqueous liquid) comprised by the system or the surface to be treated is a surface of cooling equipment in contact with such a fluid. In an example, the first host cells are SRB (eg, any SRB disclosed herein). In an example, the surface is an iron-containing surface.

In an example, the first host cells are *Legionella* cells. Such species are detrimental to human health and propagated in water cooling, heating, processing or storage equipment. In an example, therefore, the system is such an equipment.

Pipeline Corrosion: Hydrocarbon and petrochemical pipelines often include sufficient moisture to permit bacterial growth, resulting in MIC eg, caused by SRB. The MIC is often caused by biofilms of aerobic bacteria which protect SRB which is anaerobic and in direct contact with the pipeline's inner surface. This creates acid conditions and other metal-corroding conditions, which will result in localised corrosion and eventual failure of the pipe.

In an example, the system comprises an equipment surface (eg, pipeline or drilling equipment) comprising a surface in contact with the first host cells (eg, SRB). For example, the system is a crude oil, hydrocarbon, petrochemical (eg, diesel or petroleum), gas or water recovery, processing, storage or transportation system. For example, the pipeline is a petrochemicals pipeline. For example, the pipeline is comprised by an oil or gas rig. For example, the pipeline surface is in contact with sea water. For example, the pipeline surface is in contact with a petrochemical fluid, crude oil or natural gas.

Wastewater Treatment: Wastewater treatment involves adding activated sludge downstream of a wastewater treatment plant in order to remove organic pollutants. Thus, after water is treated in a waste treatment facility, many organic pollutants are present which can be "digested" by bacteria. Thus, the activated sludge is added to the treated water in a tank/container to treat the effluent from the wastewater treatment facility.

However, sometimes bacteria in the tank/container (whether originating from the activated sludge, the wastewater itself, or the surrounding environment), will dominate and grow very rapidly. Such rapid growth can result in a filamentous-shaped bacterial growth. Filaments can form up to 20-30% of the bacterial population in the tank or container, and they float. This filamentous growth results in what is known as bulking sludge. The present invention can be utilised for bulking sludge control, which is an important Aspect in wastewater treatment.

Thus, in one example, the system is a water treatment system and the surface is a surface of a container of the system, wherein the surface is in contact with water and the first host cells; or the fluid to be treated comprises said water and cells. In an example, the method controls bacterial growth in sludge of a wastewater system.

Shipping & Transportation: Ships and boats can experience MIC on their outer surfaces (eg, hulls) in contact with sea water or waterways (eg, rivers, lakes, ponds or fresh water). Inner hull surfaces can also be subject to MIC since they are typically in contact with moisture or liquids that can harbour MIC-mediating microbes such as bacteria, for example in contact with ballast water. For example, sea water is often carried in the hulls of ships (such as oil tankers) to provide stability at sea; such sea water harbours bacteria that can mediate SRB. Other transportation vehicles, such as motor-driven vehicles (cars, trucks, vans or lorries), trains, spacecraft and aircraft can also be susceptible.

Thus, in one example, the system is a transportation vehicle (eg, for transporting goods and/or people or livestock, eg, a cars, truck, van or lorry, train, spacecraft or aircraft). For example, the vehicle is a ship or boat, eg, an oil, gas or petrochemicals sea vessel (eg, an oil tanker). In an example, the surface to be treated is in contact with sea water. In an example, the surface is an outer surface of a ship or boat hull. In an example, the surface is an inner surface of a ship or boat hull.

Bacterial Persistence or Growth (Biofouling) in Ballast Water: A specific application of the invention is the treatment of marine vehicle (eg, ship or boat) ballast water to reduce undesirable bacteria, such as *Vibrio cholerae, E coli* and/or Enterococci sp.

Shipping moves over 90% of the world's commodities and is responsible for the global transfer of approximately 2-3 billion tons of ballast water, which is routinely carried by ships to maintain their stability. A similar volume of ballast water may also be transferred domestically within countries and regions each year (GloBallast Partnerships, www.globallast.imo.org). Ballast water has been recognized as the main source of invasive marine organisms that threaten naturally evolved biodiversity, the consequences of which are increasingly being realized (Anil et al. 2002). The unintentional introduction of disease-causing pathogenic bacteria, which are transported from the place of origin or formed during transportation, can have direct impact on society and human health. Ship ballast tanks hold different non-indigenous vertebrates, invertebrates, plants, microscopic algae, bacteria, etc. (Williams et al. 1988; Carlton and Geller 1993; Smith et al. 1996; Ruiz et al. 2000; Drake et al. 2002, 2005, 2007; Mimura et al. 2005). Microorganisms, such as bacteria are introduced into alien environments in larger numbers than other organism owing to their high natural abundance, capability to form resting stages, and capability to withstand a wide range of environmental conditions. Although all the organisms taken onboard into ballast tanks may not survive, bacteria and micro-algae are well capable of surviving prolonged periods of unfavorable conditions by forming cysts, spores, or other physiological resting stages (Roszak et al. 1983; Hallegraeff and Bolch 1992; Anil et al. 2002; Carney et al. 2011). Once released these microorganisms are well suited to be invasive owing to their small size which facilitates their passive dispersal and simpler requirements for survival than metazoans (Deming 1997). The concentration of cells of *Vibrio* species in ballast samples examined from ships in Singapore Harbour were in the range of $1.1$-$3.9 \times 10^4$ $ml^{-1}$ (Joachimsthal et al. 2004). The unintentional introduction of disease-causing pathogenic bacteria can have direct societal impacts, including effects on human health. In an earlier study it was found that most of the pathogens introduced to Chesapeake Bay originated from bacteria associated with plankton rather than the water column itself (Ruiz et al. 2000). Thus, ballast water microorganisms such as bacteria and archaea are of major concern in ballast water treatment/management programs.

The International Maritime Organization (IMO) has developed a convention aimed at preventing these harmful effects, adopting the International Convention for the Control and Management of Ships' Ballast Water and Sediments (the Ballast Water Management Convention) in 2004. In the US, the United States Coast Guard's Final Rule on Ballast Water Management entered into force in June 2012, applying to ballast water discharge in US waters.

Ballast-water exchange at sea is not considered an ideal method of ballast-water management, and considerable efforts are being made to develop treatment methods. These methods must be in accordance with Standard D-2 of the IMO's Ballast Water Management Convention. Standard D2 specifies that treated and discharged ballast water must have:

fewer than ten viable organisms greater than or equal to 50 micrometers in minimum dimension per cubic metre
fewer than ten viable organisms less than 50 micrometres in minimum dimension and greater than or equal to 10 micrometers in minimum dimension per millilitre.

In addition, Standard D2 specifies that the discharge of the indicator microbes shall not exceed specified concentrations as follows:

toxicogenic *Vibrio cholerae* (O1 and O139) with less than one colony-forming unit (cfu) per 100 millilitres or less than 1 cfu per 1 gram (wet weight) zooplankton samples

*Escherichia coli* less than 250 cfu per 100 millilitres intestinal Enterococci less than 100 cfu per 100 millilitres.

These are the indicator microbes, as a human health standard, but they are not limited to these types. Indeed, it has been suggested that in fact, in some cases the ballast water treatment used may make things worse. By removing small organisms that eat bacteria, some treatment systems have turned ballast tanks into bacteria incubators, so that the treated discharges consistently contained higher concentrations of bacteria, in some trials, thousands of times higher, than discharges that were left untreated. The increased bacteria may include human pathogens.

In an example of the invention (eg, according to Aspect 70 or an Aspect dependent from Aspect 70), therefore, the system is a ship or boat or marine vehicle (eg, a ship or boat, eg, an oil tanker in a harbour, dock or at sea). In an example, the fluid comprising the first host cells is ballast water of ship or boat a marine vehicle (eg, ship or boat ballast water, eg, oil tanker ballast water). In an example, the system is a sea container or a platform or rig (eg, oil or gas rig), eg at sea. In an example, the fluid is ballast water of such a container, platform or rig.

In an embodiment, the detrimental bacteria (first host cells according to the invention, eg, according to Aspect 70 or an Aspect dependent from Aspect 70) are of a species selected from the group consisting of *Vibrio cholerae*; *Vibrio rumoiensis*; *Vibrio* sp.; *E coli*; *Enterococcus* sp.; *Pseudomonas synxantha*; *Pseudomonas stutzeri*; *Vibrio lentus*; *Pseudoalteromonas marina Pseudoalteromonas tetraodonis*; *Pseudoalteromonas* sp.; *Pseudomonas putida*; *Pseudomonas oleovorans*; *Vibrio splendidus*; *Vibrio cyclitrophicus*; *Enterococcus* hirae; *Enterococcus faecium Vibrio rotiferianus*; *Pseudoalteromonas undina*; *Serratia plymuthica*; *Pseudomonas fulva*; *Pseudomonas tolaasii*; *Pseudomonas stutzeri*; *Pseudomonas stutzeri*; *Vibrio tubiashii*; *Halomonas venusta*; *Idiomarina loihiensis*; *Vibrio cyclitrophicus*; *Vibrio tubiashii*; *Serratia plymuthica*; *Pseudoalteromonas* sp.; *Pseudoalteromonas atlantica*; *Pseudomonas synxantha*; *Pseudomonas stutzeri*; *Pseudoalteromonas carrageenovora*; *Tenacibaculum* sp.; *Bacillus mycoides*; *Vibrio natriegens*; *Bacillus baekryungensis*; *Enterococcus* hirae; *Lactobacillus pentosus*; *Pseudoalteromonas carrageenovora*; and *Pseudomonas aeruginosa*.

In an example, the first host cells are aerobic heterotrophic bacteria. In an example, the first host cells are *Vibrio cholerae* cells (eg, strain O1 and/or O139). In an example, the first host cells are *E coli* cells. In an example, the first host cells are *Enterococcus* sp. cells. [000257]"Characterization of Bacteria in Ballast Water Using MALDI-TOF Mass Spectrometry", Kaveh E et al, PLoS One. 2012; 7(6): e38515; Published online 2012 Jun. 7. doi: 10.1371/journal.pone.0038515 (incorporated herein by reference) discloses a suitable rapid and cost-effective method for monitoring bacteria in ballast water.

A specific example of the invention is as follows:—

A method of controlling bacterial biofouling in ballast water of a ship or boat, wherein the water comprises a population of first host cells of a first microbial species (such as Cholera, *E coli* or Enterococci sp) that mediates said biofouling, the method comprising (i) contacting the population with a plurality of vectors that are capable of transforming or transducing the cells, each vector comprising a CRISPR array whereby CRISPR arrays are introduced into the host cells, wherein (a) each CRISPR array comprises one or more sequences for expression of a crRNA and a promoter for transcription of the sequence(s) in a host cell; and (b) each crRNA is capable of hybridising to a target sequence of a host cell to guide Cas (eg, a Cas nuclease) in the host cell to modify the target sequence (eg, to cut the target sequence); the target sequence being a gene sequence for mediating host cell viability; and (ii) allowing expression of said cRNAs in the presence of Cas in host cells, thereby modifying target sequences in host cells, resulting in reduction of host cell viability and control of said biofouling.

In an example, step (i) comprises mixing the ballast water with the vectors, eg, in the hull of a ship or boat.

In an example, the ship or boat is a marine vehicle and the water is sea water. Instead of a ship or boat, in an alternative the ballast water is comprised by a container or a drilling platform at sea, eg, an oil platform or oil rig.

The invention also comprises a method of discharging ballast water from a ship or boat, wherein the discharged ballast water comprises water treated by the method of the specific example above. In an example, the water is discharged into a body of water, eg, a sea, ocean or waterway (eg, a river, canal, lake or reservoir).

The invention also comprises ship or boat ballast water comprising CRISPR arrays, wherein the ballast water is obtained or obtainable by the specific example above. The invention also comprises a sea container ballast water comprising CRISPR arrays, wherein the ballast water is obtained or obtainable by the specific example above. The invention also comprises ballast water of a platform or rig (eg, oil or gas rig) at sea, the water comprising CRISPR arrays, wherein the ballast water is obtained or obtainable by the specific example above. The arrays are as recited in (a) and (b) of the specific example.

REFERENCES

1. Anil A C, Venkat K, Sawanr S S, Dileepkumar M, Dhargalkar V K, Ramaiah N, Harkantra S N and Ansari Z A (2002) *Marine bioinvasion: Concern for Ecology and Shipping.* Current Science 83(3): 214-218;
2. Azam F and Malfatti F (2007) *Microbial structuring of marine ecosystems.* Nature Reviews Microbiology 5: 782-791;
3. Belkin S and Colwell R R (2005) *Ocean and health: pathogens in the marine environment.* New York, NY: Springer;
4. Carlton J T and Geller J R (1993) *Ecological roulette: the global transfer of non-indigenous marine organisms.* Science 261: 78-82;
5. Carman K R and Dobbs F C (1997) *Epibiotic microorganisms in copepods and other marine crustaceans.* Microscopy Research and Technique 37: 116-135,
6. Carney K J, Delany J E, Sawant S S, Mesbahi E (2011) *The effects of prolonged darkness on temperate and*

*tropical marine phytoplankton, and their implications for ballast water risk management. Marine Pollution Bulletin* 62(6):1233-1244;
7. Colwell R R (1996) *Global climate and infectious disease: the cholera paradigm. Science* 274: 2025-2031;
8. Conway D V P, White R G, Hugues-Dit-Ciles J, Gallienne C P, Robins D B (2003) *Guide to the coastal and surface zooplankton of the southwestern Indian Ocean.* In: *Marine Biological Association of the United Kingdom Occasional Publication.* UKDEFRA Darwin Initiative Project 162/09/004 Zooplankton of the Mascarene Plateau, vol 15, pp 1-354;
9. Daley R J and Hobbie J E (1975) *Direct counts of aquatic bacteria by a modified epifluorescence technique. Limnology and Oceanography* 20: 875-882;
10. Deming J W (1997) *Unusual or extreme high-pressure marine environments.* In: *ASM Manual of Environmental Microbiology,* Hurst C J, Knudsen G R, McInerney M J, Stetzenbach L D, Walter M V (editors), Washington, DC: ASM Press, pp 366-376;
11. Drake L A, Ruiz G M, Galii B S, Mullady T L, Friedmann D O and Dobbs F C (2002) *Microbial ecology of ballast water during a transoceanic voyage and the effects of open-ocean exchange. Marine Ecology Progress Series* 233: 13-20;
12. Drake L A, Meyer A E, Forsberg R L, Baier R E, Doblin M A, Heinemann S, Johnson W P, Koch M, Rublee P A and Dobbs F C (2005) *Potential invasion of microorganisms and pathogens via 'interior hull fouling': biofilms inside ballast water tanks. Biological Invasions* 7: 969-982;
13. Drake L A, Doblin M A and Dobbs F C (2007) *Potential microbial bioinvasions via ship's ballast water, sediment and biofilm. Marine Pollution Bulletin* 55: 333-341;
14. Dawson M P, Humphrey B A and Marshall K C (1981) *Adhesion: A tactic in the survival strategy of a marine Vibrio during starvation. Current Microbiology* 6: 195-199;
15. Foladori P, Bruni L, Andreottola G and Ziglio G (2007) *Effects of sonication on bacteria viability in wastewater treatment plants evaluated by flow cytometry-fecal indictors, wastewater and activated sludge. Water Research* 41: 235-243;
16. Hallegraeff G M and Bolch C J (1992) *Transport of diatoms and dinoflagellate resting spores in ships ballast water: implications for plankton biogeography and aquaculture. Journal of Plankton Research* 14(8): 1067-1084;
17. Harris J M (1993) *The presence, nature and role of gut microflora in aquatic invertebrates: a synthesis. Microbial Ecology* 25: 195-231;
18. Heidelberg J F, Heidelberg K B and Colwell R R (2002) *Bacteria of the gamma-subclass Proteobacteria associated with zooplankton in Chesapeake Bay. Applied and Environmental Microbiology* 68: 5498-5507;
19. Hood M A, Ness G E, Rodrick G E, Blake N J (1984) *The ecology of Vibrio cholerae in two Florida estuaries.* In: *Vibrios in the Environment,* Colwell R (editor), New York, NY: Wiley, pp 399-409;
20. Huq A, West P A, Small E B and Colwell R R (1984) *Influence of water temperature, salinity and pH on survival and growth of toxigenic Vibrio cholerae serovar O1 associated with live copepods in laboratory microcosms. Applied and Environmental Microbiology* 48: 420-424;
21. International Maritime Organization (IMO) (2004) *International convention for the control and management of ships' ballast water and sediments.* London: International Maritime Organization;
22. Joachimsthal E L, Ivanov V, Tay S T-L and Tay J-H (2004) *Bacteriological examination of ballast water in Singapore Harbour by flow cytometry with FISH. Marine Pollution Bulletin* 49: 334-343;
23. Jyoti K K and Pandit A B (2001) *Water disinfection by acoustic and hydrodynamic cavitation. Biochemical Engineering Journal* 7: 201-212;
24. Kasturirangan L R (1963) *A key for the identification of the more common planktonic copepoda of Indian coastal waters.* In: *Indian National Committee on Oceanic Research,* Panikkar N K (editor), New Delhi: Council of Scientific and Industrial Research, p 87;
25. Khandeparker L & Anil A C; *Ecohealth.* 2013 September; 10(3):268-76. doi: 10.1007/s10393-013-0857-z. Epub 2013 Jul. 12, *"Association of bacteria with marine invertebrates: implications for ballast water management";*
26. Krieg N R (1984) *Bergey's manual of systematic bacteriology,* Vol 1. Williams & Wilkins, Baltimore;
27. Lee B G and Fisher N S (1992) *Decomposition and release of elements from zooplankton debris. Marine Ecology Progress Series* 88: 117-128;
28. Lloyd's Register (2010) *Ballast water treatment technology guide;*
29. McFall-Ngai M J and Ruby E G (1991) *Symbiont recognition and subsequent morphogenesis as early events in an animal-bacterial mutualism. Science* 254: 1491-1494;
30. Mimura H, Katakura R and Ishida H (2005) *Changes of microbial populations in a ship's ballast water and sediments on a voyage from Japan to Qatar. Marine Pollution Bulletin* 50: 751-757;
31. Munro P M and Colwell R R (1996) *Fate of Vibrio cholerae O1 in sea water microcosms. Water Research* 30(1): 47-50;
32. Pfeffer C and Oliver D J (2003) *A comparison of thiosulphate-citrate-bile salts-sucrose (TCBS) agar and thiosulphate-chloride-iodide (TCI) agar for the isolation of Vibrio species from estuarine environments. Letters in Applied Microbiology* 36: 150-151;
33. Peter H and Sommaruga R (2008) *An evaluation of methods to study the gut bacterial community composition of fresh water zooplankton. Journal of Plankton Research* 30: 997-1006;
34. Polz M F, Distel D L, Zarda B, Amann R, Felbeck H, Ott J A and Cavanaugh C M (1994) *Phylogenetic analysis of a highly specific association between ectosymbiotic, sulfuroxidizing bacteria and a marine nematode. Applied and Environmental Microbiology.* 60: 4461-4467;
35. Pruzzo C, Vezzulli L and Colwell R R (2008) *Global impact of Vibrio cholerae interactions with chitin. Environmental Microbiology* 10(6):1400-1410;
36. Rehnstam-Holm A-S, Godhe A, Härnström K, Raghunath P, Saravanan V, Collin B, Karunasagar I and Karunasagar I (2010) *Association between phytoplankton and Vibrio spp. along the southwest coast of India: a mesocosm experiment. Aquatic Microbial Ecology* 58: 127-139;
37. Richard C (1993) *Chromobacterium violaceum, opportunistic pathogenic bacteria in tropical and subtropical regions. Bulletin de la Société de Pathologie exotique* 86: 169-173;
38. Roszak D B, Grimes D J and Colwell R R (1983) *Viable but nonrecoverable stage of Salmonella enteritidis aquatic systems. Canadian Journal of Microbiology* 30: 334-338;

39. Ruiz G M, Rawlings T K, Dobbs F C, Drake L A, Mullady T, Huq A and Colwell R R (2000) *Global spread of microorganisms by ships—Ballast water discharged from vessels harbours a cocktail of potential pathogens.* Nature 408: 49-50;
40. Sawant S S, Anil A C, Krishnamurthy V, Gaonkar C, Kolwalkar J, Khandeparker L, Desai D V, Mahulkar A V, Ranade V V and Pandit A B (2008) *Effect of hydrodynamic cavitation on zooplankton: A tool for disinfection.* Biochemical Engineering Journal 42: 320-328;
41. Seth N, Chakravarty P, Khandeparker L, Anil A C and Pandit A B (2010) *Quantification of the energy required for the destruction of Balanus amphitrite larva by ultrasonic treatment.* Journal of the Marine Biological Association of the United Kingdom 90 (7):1475-1482;
42. Smith L D, Wonham M J, McCann L D, Reid D M, Carlton J T, Ruiz G M (1996) *Biological Invasions by Nonindigenous Species in United States Waters: Quantifying the Role of Ballast Water and Sediments.* Parts I and II. Report Number CG-D-02-97, Groton, CT: US Coast Guard Research and Development Center;
43. Tang K W (2005) *Copepods as microbial hotspots in the ocean: effects of host feeding activities on attached bacteria.* Aquatic Microbial Ecology 38: 31-40;
44. Tang K W, Freund C S and Schweitzer C L (2006) *Occurrence of copepod carcasses in the lower Chesapeake Bay and their decomposition by ambient microbes.* Estuarine, Coastal and Shelf Science 68: 499-508;
45. Tang K W, Dziallas C, Huialle-Schmelzer K and Grossart H P (2009) *Effects of food on bacterial community composition associated with the copepod Acartia tonsa Dana.* Biological Letters 5: 549-553;
46. Thompson C C, Thompson F L, Vandemeulebroecke K, Hoste B, Dawyndt P and Swings J (2004) *Use of recA as an alternative phylogenetic marker in the family Vibrionaceae.* International Journal of Systematic and Evolutionary Microbiology 54:919-929;
47. Todd C D, Laverack M S, Boxshall G A (1966) *Coastal marine zooplankton: A practical manual for students*, London, UK: The Natural History Museums, p 106;
48. Vinas M D, Diovisalvi N R and Cepeda G D (2010) *Individual biovolume of some dominant copepod species in coastal waters off Buenos Aires Province, Argentine sea.* Brazilian Journal of Oceanography 58(2): 177-181;
49. Williams R J, Griffiths F B, Van der Wal E J and Kelly J (1988) *Cargo vessel ballast water as a vector for the transport of nonindigenous marine species.* Estuarine, Coastal and Shelf Science 26: 409-420.

The invention also provides vectors and CRISPR arrays as follows.

85. A vector comprising a CRISPR array for introduction into a bacterial host cell, wherein the bacterium is capable of water-borne transmission, wherein
 (a) the CRISPR array comprises a sequence for expression of a crRNA and a promoter for transcription of the sequence in a said host cell;
(b) the crRNA is capable of hybridising to a host cell target sequence to guide a Cas (eg, a Cas nuclease) in the host cell to modify the target sequence (eg, to cut the target sequence); the target sequence being a nucleotide sequence (eg, a gene or regulatory sequence) for mediating host cell viability;
(c) wherein the sequence of (a) comprises a sequence R1-S1-R1 for expression and production of the crRNA, wherein R1 is a first CRISPR repeat, R1' is a second CRISPR repeat, and R1 or R1' is optional; and S1 is a first CRISPR spacer that comprises or consists of a nucleotide sequence that is 80% or more identical (eg, 85, 90, 91, 92, 93, 94, 95, 96, 97, 98, 99 or 100% identical) to the host cell target sequence.

By "water-borne transmission" is meant that cells of said bacterium are capable of being spread in water or an aqueous liquid between different organisms, within an organism, between different environments, or between an organism and an environment. Examples are *Vibrio cholera, Enterococcus* spp and *E coli. Vibrio cholerae* is a gram negative comma-shaped bacterium with a polar flagellum. It belongs to the class of the Gamma Proteobacteria. There are two major biotypes of *V. cholerae*, classical and El Tor, and numerous serogroups. *V. cholerae* is the etiological agent of cholera, a severe bacterial infection of the small intestine, and a major cause of death in developing countries. The pathogenicity genes of *V. cholerae* are interesting targets to detect and to study *V. cholerae* infections. Most of these genes are located in two pathogenicity islands, named TCP (Toxin-Coregulated Pilus) and CTX (Cholera ToXins), organized as prophages 1, 2. TCP contains a cluster of genes involved in host adhesion via pili, while CTX genes are involved in the synthesis of the cholera toxin3.

In an embodiment, the vector is an isolated vector (ie, a vector not in a said host cell). In an example, the vector is an engineered or synthetic vector (ie, a non-naturally occurring vector).

In an example, the array is an ICP1 array, ie, an array of an ICP1 *V cholerae* phage, eg, wherein the phage is ICP1_2003_A, ICP1_2004_A, ICP1_2005_A, ICP1_2006_E or ICP1_20011_A. In an example the array is a CR1 or CR2 ICP1 phage array, eg, an engineered or non-naturally occurring derivative of such an array.

In an example, the CRISPR array and Cas are type 1-E or type 1-F, eg, subtype system 17.

In an example, the CRISPR array comprises a plurality of sequences, each for expression of a respective crRNA and a associated with a promoter for transcription of the sequence in a said host cell.

In an example, the vector or each vector comprises a plurality (eg, 2, 3, 4, 5, 6, 7, 8, 9, 10 or more) of said CRISPR arrays.

In an example, the vector comprises a nucleotide sequence encoding said Cas.

In another example, the vector is devoid of such a sequence. For example, in this case, the array(s) are operable with one or more Cas produced by the host cell.

86. The vector of Aspect 85, wherein the cell is a *Vibrio cholerae, Enterococcus* or *E coli* cell.

87. The vector of Aspect 85 or 86, wherein the vector is devoid of a nucleotide sequence that is capable of expressing said Cas.

In an example, therefore the vector does not encode a Cas nuclease. In an alternative the vector encodes a said Cas.

88. The vector of Aspect 85, 86 or 87, wherein the target sequence is a protospacer sequence of 17-45 contiguous nucleotides, eg, 18, 19, 20 or 21 contiguous nucleotides.

In an example, each spacer (S1) is a nucleotide sequence of 17-45 contiguous nucleotides, eg, 18, 19, 20, 21, 30, 31, 32 or 33 contiguous nucleotides. The protospacer sequence for *V cholerae* PLE is, for example, 32 contiguous nucleotides and a vector targeting this can, for example, have a spacer sequence of 32 contiguous nucleotides that is 100% or at least 80, 90 or 95% identical to the 32 nucleotide PLE sequence. Where the vector comprises a plurality of spacers, the spacers can be a mixture of different spacers, or can be identical spacers. For example, the array comprises a plurality of spacers, wherein a sub-set of spacers are identical. The identical spacers can be homologous to protospacer sequence of a gene encoding a pathogenicity factor of the host cell, for example. Using multiple spacers may be advantageous if the host cuts one or more of the spacers once the vector is inside the cell—uncut spacers are still able to form crRNAs and home to target sequences. Using a mixture of different spacers in the vector or in an array is advantageous to minimise the risk of adaptation of the host to the invading vector, thereby minimising resistance.

89. The vector of any one of Aspects 85 to 88, wherein the target sequence is a virulence, resistance or essential gene sequence. In an example, the target sequence is a sequence of a PICI-like element (PLE), eg, a *V. cholerae* PLE. Eg, PLE1.

90. The vector of any one of Aspects 85 to 89, wherein the target sequence is a pathogenicity island sequence, optionally wherein the host cell is a *Vibrio cholera* cell and the target sequence is a TCP, CTX or VPI sequence. In an example (eg, wherein the host is *Vibrio*) pathogenicity island is TCP (Toxin-Coregulated Pilus) or CTX (Cholera ToXins). The *Vibrio* pathogenicity island (VPI) contains genes primarily involved in the production of toxin coregulated pilus (TCP). It is a large genetic element (about 40 kb) flanked by two repetitive regions (att-like sites), resembling a phage genome in structure. The VPI contains two gene clusters, the TCP cluster, and the ACF cluster, along with several other genes. The acf cluster is composed of four genes: acfABCD. The tcp cluster is composed of 15 genes: tcpABCDEFHIJPQRST and regulatory gene toxT.

91. The vector of any one of Aspects 85 to 90, wherein the host cell is *Vibrio cholera* and the target sequence is a CTXφ gene sequence. The genes for cholera toxin are carried by CTXphi (CTXφ), a temperate bacteriophage inserted into the *V. cholerae* genome. CTX9 can transmit cholera toxin genes from one *V. cholerae* strain to another, one form of horizontal gene transfer. The genes for toxin coregulated pilus are coded by the VPI pathogenicity island (VPI).

92. The vector of any one of Aspects 85 to 90, wherein the host cell is *Vibrio cholera* and the target sequence is a ctxB, tcpA, ctxA, tcpB, wbet, hlyA, hapR, rstR, mshA or tcpP sequence.

93. The vector of any one of Aspects 85 to 92, wherein the target sequence is 17-45 contiguous nucleotides (eg, 18, 19, 20 or 21 contiguous nucleotides) and at least 80% (eg, 85, 90, 91, 92, 93, 94, 95, 96, 97, 98, 99 or 100% identical) identical to a sequence of a phage inducible chromosomal island (PICI) of a Gram-positive bacterium, eg, a *Staphylococcus aureus* pathogenicity island (SaPI). Examples of ICP1 phage (aka ICP1-related phage) spacer sequences are provided below. These spacer sequences are homologous to target sequences (protospacer sequences) in *V cholera*.

94. The vector of any one of Aspects 85 to 93, wherein the host cell is *Vibrio cholera* and the crRNA is capable of hybridising to a target sequence within 5, 4 or 3 nucleotides of a protospacer adjacent motif (PAM) in a *Vibrio cholerae* cell, wherein the PAM is GA.

95. The vector of any one of Aspects 85 to 94, wherein the host cell is *Vibrio cholera* and the cell is an El Tor, O1 or O139 *Vibrio cholerae* cell. In an example, the *V. cholerae* is serotype O1 El Tor N16961; El Tor biotype18; or El Tor strain MJ-1236. In an example, the host cell is a *E. coli* O157:H7 cell.

96. The vector of any one of Aspects 85 to 95, wherein vector is a bacteriophage that is capable of infecting a said host cell. In an example, the host cell is *E coli*, and the phage is a lambda or T4 phage. In an example, the host cell is an *Enterococcus* cell and the phage is a *Enterococcus* phage IME-EF1, phiEF24C, #Ef1 or EFDG1 (see Appl Environ Microbiol. 2015 April; 81(8):2696-705. doi: 10.1128/AEM.00096-15. Epub 2015 Feb. 6, "Targeting *Enterococcus faecalis* biofilms with phage therapy", Khalifa L et al).

97. The vector of Aspect 96, wherein the host cell is *Vibrio cholera* and the vector is a bacteriophage capable of infecting a *Vibrio cholerae* cell.

98. The vector of Aspect 97, wherein the bacteriophage is selected from CTXφ, an ICPI phage and a myovirus, eg, wherein the phage is ICP1_2003_A, ICP1_2004_A, ICP1_2005_A, ICP1_2006_E or ICP1_20011_A, optionally an engineered and non-naturally occurring phage.

99. The vector of any one of Aspects 85 to 98, wherein the vector is or comprises an ICE, eg, a transposon. The ICE can comprise any of the features of an ICE described herein.

100. The vector of Aspect 99, wherein the transposon is a conjugative transposon capable of transfer from a first to a second said host cell.

101. The vector of Aspect 99 or 100, wherein the transposon leaves a copy of the CRISPR array in the first cell.

102. The vector of any one of Aspects 85 to 101, wherein the or each array is comprised by a respective mobile genetic element (MGE), wherein the MGE comprises an origin of transfer (oriT) operable in the host cell. The MGE can be according to any MGE described herein.

103. The vector of any one of Aspects 85 to 102, wherein the vector is an engineered vector.

104. A water or food treatment composition comprising a plurality of vectors according to any one of Aspects 85 to 103.

In an example, the water is ballast water, sea water, brackish water, fresh water, drinking water, waterway water (eg, estuary water) or industrial water. In an example, the water is water in human GI tract fluid.

In an example, the host cell is comprised by shellfish, fish, rice or grains. In an example, the composition is for treating food and the host cell is a *E. coli* O157:H7 cell. In an example, the target sequence is a sequence encoding a Shiga toxin in an *E coli* (eg, O157:H7) host cell. In an alternative to the water-borne species described so far, the host cell is a *Salmonella* or *Listeria* cell.

105. A medicament for treatment or prevention of *Vibrio cholerae* infection in a human, the medicament comprising a plurality of vectors according to any one of Aspects 85 to 103. In an alternative, the invention provides a medicament for treatment or prevention of *E coli* infection in a human, the medicament comprising a plurality of vectors of the invention. In an alternative, the invention provides a medicament for treatment or prevention of *Enterococcus* infection in a human, the medicament comprising a plurality of vectors of the invention.

106. The composition or medicament of Aspect 104 or 105, further comprising an anti-host cell antibiotic or an anti-host cell biocide.

Example 5 below is an example relating to cholera.

Any of the general features (see below) also may apply to the present configuration (sixth configuration). Any configuration below is combinable with the present configuration, eg, to provide combinations of features for inclusion in one or more claims herein.

Regulating Cas Activity

These aspects of the invention are useful for regulating Cas activity, eg, in a cell or in vitro. The invention involves targeting a Cas-encoding gene to restrict Cas activity, which is advantageous for temporal regulation of Cas. The invention may also be useful in settings where increased stringency of Cas activity is desirable, eg, to reduce the chances for off-target Cas cutting in when modifying the genome of a cell. Applications are, for example, in modifying human, animal or plant cells where off-target effects should be minimised or avoided, eg, for gene therapy or gene targeting of the cell or a tissue or an organism comprising the cell. For example, very high stringency is required when using Cas modification to make desired changes in a human cell (eg, iPS cell) that is to be administered to a patient for gene therapy or for treating or preventing a disease or condition in the human. The disclosure provides these applications as part of the methods and products of the invention.

The Invention Thus Provides the Following Clauses:—

1. A method of modifying an expressible gene encoding a first Cas, the method comprising
    (a) combining a guide RNA (gRNA1) with the Cas gene in the presence of first Cas that is expressed from said gene; and
    (b) allowing gRNA1 to hybridise to a sequence of said Cas gene (eg, a promoter or a first Cas-encoding DNA sequence thereof) and to guide first Cas to the gene, whereby the Cas modifies the Cas gene.

In an example, the method is a cell-free method (eg, recombineering method) in vitro. In another example, the method is carried out in a cell, eg, wherein the gene is cut by Cas that it encodes itself (ie, endogenous Cas is used to cut the gene).

2. The method of clause 1, wherein the Cas is a nuclease and the Cas gene is cut.
3. The method of clause 1 or 2, wherein the Cas gene is mutated, down-regulated or inactivated.
4. The method of any one of clauses 1 to 3, wherein the first Cas is a Cas9.
5. The method of any one of clauses 1 to 4, wherein gRNA1 is a single guide RNA.
6. The method of any one of clauses 1 to 5, wherein the method is carried out in a host cell.
7. The method of clause 6, wherein the cell is a prokaryotic cell, eg, a bacterial or archaeal cell (eg, an *E coli* cell).
8. The method of clause 6, wherein the method is a recombineering method.
9. The method of clause 6, 7 or 8, wherein the cell is of a human or non-human animal pathogen species or strain (eg, *S aureus*).
10. The method of any one of clauses 6 to 9, wherein the cell is a cell of a human microbiome species, eg, a human gut microbiome species.
11. The method of any one of clauses 6 to 10, wherein the Cas gene is comprised by a host CRISPR/Cas system.

Optionally an exogenous first Cas-encoding sequence is not used in the method, for example when the host cell comprises a wild-type endogenous Cas nuclease that is cognage to gRNA1.

12. The method of clause 6, wherein the cell is a eukaryotic cell (eg, a human, non-human animal, yeast or plant cell).
13. The method of clause 12, wherein the method is carried out in a non-human embryo; non-human zygote; non-human germ cell; or a human or animal (eg, wherein the method is a cosmetic method); optionally wherein the method is not a method for treatment of the human or animal body by surgery or therapy or diagnosis.
14. The method of any one of clauses 6 to 3, wherein the Cas gene is comprised by a nucleic acid that is introduced into the cell in step (a).
15. The method of any one of clauses 6 to 4 for reducing the development of host cell resistance to transformation by a nucleic acid vector or maintenance of a nucleic acid vector in the host cell.
16. The method any one of clauses 1 to 15, or a nucleic acid or cell product thereof for human or animal medical therapy, prophylaxis or diagnosis (eg, for gene therapy of a human or animal, human or animal cell when the method is carried out in a human or animal cell; or for treating or preventing a bacterial infection in a human or animal when the method is carried out in a bacterial cell).
17. The method any one of clauses 1 to 6, wherein the method is carried out in vitro.
18. The method any one of clauses 1 to 16, wherein the method is carried out in vivo, optionally not in a human embryo and optionally wherein the method is not a method for treatment of the human or animal body by surgery or therapy or diagnosis.
19. The method any one of clauses 1 to 18, wherein gRNA1 is produced by transcription from a first nucleic acid that is combined with the Cas gene in step (a).
20. The method of clause 19, wherein the method is carried out in a cell and the first nucleic acid encoding gRNA1 is introduced into the cell in step (a); or a first nucleic acid encoding a crRNA is introduced into the cell in step (a) wherein the crRNA forms gRNA1 with a tracrRNA in the cell.
21. The method of clause 19 or 20, wherein the Cas gene is combined with a target nucleic acid comprising a target site (CS-t) to be modified by first Cas, and wherein
    I. the Cas gene comprises a first protospacer (PS1) adjacent a PAM (P1) that is cognate to the first Cas, wherein PS1 is modified (eg, cut) at a first site (CS1) by first Cas;
    II. gRNA1 comprises a sequence that is complementary to PS1 for guiding first Cas wherein PS1 is modified at CS1 in step (b);
    III. the target nucleic acid comprises a protospacer sequence (PS-t) adjacent a PAM (P-t), wherein P-t is cognate to the first Cas;
    IV. before or during step (b) the method comprises combining a guide RNA (gRNA-t) with the target nucleic acid and first Cas expressed from said gene, wherein gRNA-t hybridises to PS-t and guides first Cas to modify CS-t; and
    V. the method optionally comprises isolating or sequencing the modified target nucleic acid.
22. The method of any clause 21, wherein gRNA-t is produced by transcription from a nucleic acid (eg, said first nucleic acid) that is combined with the Cas in step IV.
23. The method of clause 22, wherein the method is carried out in a cell and the nucleic acid encodes a crRNA, wherein the crRNA forms gRNA-t with a tracrRNA in the cell.
24. The method of any one of clauses 21 to 23, wherein the production of gRNA1 is commenced after the production of gRNA-t, whereby PS-t is modified (eg, cut) in copies of the target nucleic acid before PS1 is modified (eg, cut) to down-regulate or inactivate first Cas expression.
25. The method of any one of clauses 1 to 24, further comprising combining the cut target nucleic acid with a further nucleic acid, whereby homologous recombination between the nucleic acids takes place and
    (i) a nucleotide sequence of the target nucleic acid is deleted;
    (ii) a nucleotide sequence of the further nucleic acid is deleted;

(iii) a nucleotide sequence of the target nucleic acid is inserted into the further nucleic acid; and/or
(iv) a nucleotide sequence of the further nucleic acid is inserted into the target nucleic acid.

26. The method of clause 25, wherein (i) takes place, thereby inactivating a nucleotide sequence or regulatory element of the target nucleic acid.

27. The method of clause 25, wherein (i) takes place, thereby activating a nucleotide sequence or regulatory element of the target nucleic acid.

28. The method of clause 25, 26 or 27, wherein (ii) takes place, thereby inactivating a nucleotide sequence or regulatory element of the further nucleic acid.

29. The method of clause 25, 26 or 27, wherein (ii) takes place, thereby activating a nucleotide sequence or regulatory element of the further nucleic acid.

30. The method of any one of clauses 25 to 29, wherein (iii) takes place, optionally placing the inserted sequence in functional relationship with a regulatory element of the further nucleic acid and/or creating a new marker sequence.

31. The method of any one of clauses 25 to 30, wherein (iv) takes place, optionally placing the inserted sequence in functional relationship with a regulatory element of the target nucleic acid and/or creating a new marker sequence.

32. The method of clause 30 or 31, further comprising detecting the new marker sequence or an expression product thereof to determine that homologous recombination has taken place.

33. The method of any one of clauses 21 to 32, further comprising isolating or sequencing the target nucleic acid product, the further nucleic acid product and/or the first vector product.

34. The method of any one of clauses 1 to 33, wherein the first vector is as defined in any one of clauses 35 to 55.

35. A first (eg, isolated) nucleic acid vector or combination of vectors, eg, for use in the method of clause 1, wherein
(a) the first vector or a vector of said combination comprises an expressible nucleotide sequence that encodes a guide RNA (gRNA1, eg, a single gRNA) that is complementary to a predetermined protospacer sequence (PS1) for guiding a first Cas to modify PS1 at a first site (CS1), wherein PS1 is adjacent a PAM (P1) that is cognate to the first Cas; or the expressible sequence encodes a crRNA that forms gRNA1 with a tracrRNA; and
(b) PS1 and P1 are sequences of an expressible first Cas-encoding gene and PS1 is capable of being modified at CS1 by the first Cas.

Each vector herein in any configuration can be a linear or circular (eg, closed circular, optionally supercoiled) DNA carrying the specified sequence(s).

36. The vector or combination of clause 35, wherein the first Cas is a nuclease, wherein CS1 is capable of being cut by the nuclease.

37. The vector or combination of clause 35 or 36, wherein the first Cas is a Cas9.

38. The vector or combination of any one of clauses 35 to 37, wherein gRNA1 is a single guide RNA.

39. The vector or combination of any one of clauses 35 to 38, wherein the nucleotide sequence is expressible in a prokaryotic cell (eg, a bacterial or archaeal cell) for producing gRNA1.

40. A recombineering kit comprising the vector or combination of clause 39 (eg, wherein the cell is a recombineering-permissive *E coli* cell).

41. The vector or combination of any one of clauses 35 to 38, wherein the nucleotide sequence is expressible in a eukaryotic cell (eg, a human, animal, plant or yeast cell) for producing gRNA1.

42. The vector or combination of any one of clauses 35 to 41, wherein the first vector or a vector of said combination (eg, the second vector) comprises an expressible nucleotide sequence that encodes a guide RNA (gRNA-t, eg, a single gRNA) that is complementary to a predetermined protospacer sequence (PS-t) of a target nucleic acid for guiding first Cas to modify (eg, cut) PS-t; or the expressible sequence encodes a crRNA that forms gRNA-t with a tracrRNA; the target nucleic acid comprises PS-t adjacent a PAM (P-t), wherein P-t is cognate to the first Cas for modifying PS-t.

43. The vector or combination of clause 42, further in combination with said target nucleic acid.

44. The vector or combination of clause 43, wherein said target nucleic acid is a chromosomal or episomal nucleic acid of a cell.

45. The vector or combination of clause 44, wherein the cell is the cell is of a human or non-human animal pathogen species or strain (eg, *S aureus*).

46. The vector or combination of clause 44 or 45, wherein the cell is a cell of a human microbiome species, eg, a human gut microbiome species.

47. The vector or combination of any one of clauses 44 to 46, wherein PS-t is comprised by an essential gene, virulence gene or antibiotic resistance gene sequence of the cell (eg, a prokaryotic cell).

48. The vector or combination of clause 47, wherein the gene is down-regulated or inactivated when first Cas modifies (eg, cuts) PS-t.

49. The vector or combination of clause 47, wherein the gene is up-regulated or activated when first Cas modifies PS-t.

50. The vector or combination of any one of clauses 35 to 49 in combination with said gene encoding the first Cas (eg, comprised by the first vector).

51. The vector or combination of any one of clauses 35 to 50 when inside a cell, wherein the cell comprises a CRISPR/Cas system comprising said gene encoding the first Cas.

52. The vector or combination of any one of clauses 35 to 51 for treating, preventing or diagnosing a disease or condition in a human or non-human animal, eg, for gene therapy of a human or animal, human or animal cell when the method is carried out in a human or animal cell; or for treating or preventing a bacterial infection in a human or animal when the method is carried out in a bacterial cell.

53. A foodstuff, food ingredient or precursor ingredient, beverage, water (eg, intended for human consumption), an industrial or environmental substance (eg, oil, petroleum product, soil or a waterway or reservoir; or equipment for recovering or processing oil, petroleum product, soil, water, a foodstuff, foodstuff ingredient or precursor, or a beverage or beverage ingredient of precursor) comprising a first vector or combination according to any one of clauses 35 to 52.

54. An antibiotic (eg, anti-bacterial or anti-archaeal) composition a first vector or combination according to any one of clauses 35 to 52.

55. A medicament for treating or preventing a disease or condition (eg, a bacterial infection or obesity) in a human or animal, the medicament comprising a first vector or combination according to any one of clauses 35 to 52.

In an example, the vector, combination, medicament or antibiotic is comprised by a medical device or medical container (eg, a syringe, inhaler or IV bag).

Any of the general features (see below) also may apply to the present configuration. Any configuration below is combinable with the present configuration, eg, to provide combinations of features for inclusion in one or more claims herein.

Generally Applicable Features

The following features apply to any configuration (eg, in any of its aspects, embodiments, concepts, paragraphs or examples) of the invention:—

In an example, the target sequence is a chromosomal sequence, an endogenous host cell sequence, a wild-type host cell sequence, a non-viral chromosomal host cell sequence, not an exogenous sequence and/or a non-phage sequence (ie, one more or all of these), eg, the sequence is a wild-type host chromosomal cell sequence such as antibiotic resistance gene or essential gene sequence comprised by a host cell chromosome. In an example, the sequence is a host cell plasmid sequence, eg, an antibiotic resistance gene sequence.

In an example, at least two target sequences are modified by Cas, for example an antibiotic resistance gene and an essential gene. Multiple targeting in this way may be useful to reduce evolution of escape mutant host cells.

In an example, the Cas is a wild-type endogenous host cell Cas nuclease and/or each host cell is a wild-type host cell. Thus, in an embodiment the invention uses host cells without the need to de-repress endogenous Cas first to provide relevant Cas activity. In an example, each host cell has constitutive Cas nuclease activity, eg, constitutive wild-type Cas nuclease activity. In an example, the host cell is a bacterial cell; in an other example the host cell is an archael cell. Use of an endogenous Cas is advantageous as this enables space to be freed in vectors encoding HM- or PM-cRNA or gRNA. For example, Type II Cas9 nucleotide sequence is large and the use of endogenous Cas of the host cell instead is advantageous in that instance when a Type II CRISPR/Cas system is used for host cell modification in the present invention. The most commonly employed Cas9, measuring in at 4.2 kilobases (kb), comes from *S pyogenes*. While it is an efficient nuclease, the molecule's length pushes the limit of how much genetic material a vector can accommodate, creating a barrier to using CRISPR in the tissues of living animals and other settings described herein (see F. A. Ran et al., "In vivo genome editing using *Staphylococcus aureus* Cas9," Nature, doi:10.1038/nature14299, 2015). Thus, in an embodiment, the vector of the invention is a AAV vector or has an exogenous DNA insertion capacity no more than an AAV vector, and the Cas is an endogenous Cas of the host cell, wherein the cell is a bacterial or archaeal cell.

S thermophilus Cas9 (UniProtKB—G3ECR1 (CAS9_STRTR)) nucleotide sequence has a size of 1.4 kb.

In an embodiment, therefore, the invention provides

A nucleic acid vector comprising more than 1.4 kb or more than 4.2 kb of exogenous DNA sequence encoding components of a CRISPR/Cas system, wherein the sequence comprises an engineered array or engineered sequence (optionally as described herein) for expressing one or more HM- or PM-crRNAs or gRNAs in host cells (any cell herein, eg, human, animal or bacterial or archael host cells), wherein the array or engineered sequence does not comprise a nucleotide sequence encoding a Cas nuclease that is cognate to the cRNA(s) or gRNA(s); optionally wherein at least 2, 3 or 4 cRNAs or gRNAs are encoded by the exogenous DNA.

In an embodiment, the host cell is a bacterial or archael cell that expresses a Cas nuclease that is cognate to the crRNAs or gRNAs. In another example, such as for use with human or animal (eg, rodent, rat or mouse) cells the Cas nuclease is encoded by a different nucleic acid vector. In an example, wherein the cell is a human or animal cell, the vector is an AAV or lentiviral vector. In an example, the invention comprises a host cell comprising such a vector, wherein the host cell expresses said Cas. In an example, the host cell is a human or animal cell ex vivo.

The invention also provides

A nucleic acid vector comprising more than 1.4 kb or more than 4.2 kb of exogenous DNA sequence, wherein the exogenous DNA encodes one or more components of a CRISPR/Cas system and comprises an engineered array or sequence (eg, any such one described herein) for expressing one or more HM-crRNAs or gRNAs in host cells, wherein the exogenous sequence is devoid of a nucleotide sequence encoding a Cas nuclease that is cognate to the cRNA(s) or gRNA(s); optionally wherein at least 2 different cRNAs or gRNAs are encoded by the exogenous DNA. In an example, the invention comprises a host cell comprising such a vector, wherein the host cell expresses said Cas. In an example, the cRNAs or gRNAs are capable of hybridising in host cells to respective target protospacer sequences, wherein each protospacer sequence is comprised by an antibiotic resistance or essential host gene. This is exemplified by the worked examples herein where we show selective host cell growth inhibition by at least 10-fold in a mixed and non-mixed cell population. The mixture simulates a combination of species and strains found in human microbiota.

By "exogenous DNA sequence encoding components of a CRISPR/Cas system" is meant DNA that is inserted into a vector backbone, or such DNA in a progeny of a vector into which said insertion has previously taken place (eg, using recombinant DNA technology, such as recombineering). In an example, the exogenous DNA is 95, 90, 80, 85, 70 or 60% of the insertion capacity of the vector.

In an example, the vector is a viral vector. Viral vectors have a particularly limited capacity for exogenous DNA insertion, thus virus packaging capacity needs to be considered. Room needs to be left for sequences encoding vital viral functions, such as for expressing coat proteins and polymerase. In an example, the vector is a phage vector or an AAV or lentiviral vector. Phage vectors are useful where the host is a bacterial cell.

The invention provides a combination product kit (eg, for treating or preventing a disease or condition in a human or animal subject as described herein), wherein the kit comprises an array, vector, system, cell, engineered cRNA or gRNA-encoding sequence or the cRNA or gRNA, which is in combination with an antibiotic (first antibiotic), wherein the cRNA or gRNA is capable of hybridising to a protospacer sequence comprised by a bacterial host cell antibiotic resistance gene wherein the antibiotic is said first antibiotic. The antibiotic can be any antibiotic disclosed herein. In an embodiment, the antibiotic is combined in a formulation with the array, vector, system, cell, engineered cRNA or gRNA-encoding sequence or the cRNA or gRNA. In an example, the kit comprises the antibiotic in a container separate from a container comprising the array, vector, system, cell, engineered cRNA or gRNA-encoding sequence or the cRNA or gRNA.

In an embodiment, unless otherwise specified the or each cell is a bacterial cell, archaeal cell, algal cell, fungal cell, protozoan cell, invertebrate cell, vertebrate cell, fish cell, bird cell, mammal cell, companion animal cell, dog cell, cat cell, horse cell, mouse cell, rat cell, rabbit cell, eukaryotic cell, prokaryotic cell, human cell, animal cell, rodent cell, insect cell or plant cell. Additionally, in this case preferably the cells are of the same phylum, order, family or genus.

By use of the term "engineered" it will be readily apparent to the skilled addressee that the array, sequence, vector, MGE or any other configuration, concept, aspect, embodiment, paragraph or example etc of the invention is non-naturally occurring. For example, the MGE, vector or array comprises one or more sequences or components not naturally found together with other sequences or components of the MGE, vector or array. For example, the array is recombinant, artificial, synthetic or exogenous (ie, non-endogenous or not wild-type) to the or each host cell.

In an example, the array or vector of the invention is isolated, for example isolated from a host cell. In an example, the array or vector is not in combination with a Cas endonuclease-encoding sequence that is naturally found in a cell together with repeat sequences of the array.

In an example, the vector, MGE or array is not in combination with a Cas endonuclease-encoding sequence when not in a host cell. In an example, the vector or MGE does not comprise a Cas endonuclease-encoding sequence.

In an example, the target modification or cutting is carried out by a dsDNA Cas nuclease (eg, a Cas9, eg, a spCas9 or saCas9), whereby repair of the cut is by non-homologous end joining (NHEJ). This typically introduces mutation (indels) at the repair site, which is useful for inactivation of the target site (eg, phage gene or regulatory element, such as an essential gene or regulatory element thereof). In another example, the cutting is carried out by a ssDNA Cas nuclease (eg, a Cas9 nuclease) that cuts in a single strand (but does not do double stranded DNA cuts). This is useful for favouring HDR repair of the cut, which reduces the chances of indels. This may be useful where the target site (or gene or regulatory element comprising it) is desired, eg, where a HM- or PM-DNA is inserted at the target site for desired modification of the site. For example, in this case the modified gene produces a fusion protein comprising HM-DNA-encoded amino acid fused to host DNA-encoded sequence, or PM-DNA-encoded amino acid sequence fused to phage DNA-encoded sequence. The invention also provides a sequence encoding a fusion protein obtained or obtainable by such a method. In another example, the HM- or PM-DNA comprises a regulatory element (eg a promoter, enhancer, repressor or inducible switch for regulating gene expression), such that the fusion product comprises said DNA fused to host or phage gene or regulatory element DNA, thereby producing a fusion gene. The invention also provides a fusion gene obtained or obtainable by such a method. In an embodiment, the invention provides a vector (eg, a virus, virion, phage, phagemid, prophage or plasmid) comprising such a fusion gene, optionally wherein the vector is contained in a bacterial cell (eg, a prokaryotic, eukaryotic, bacterial, archaeal or yeast cell). In an example, the cell is in vitro.

In an example, the HM- or PM-DNA is vector DNA inside the cell. For example, the HM- or PM-DNA in the vector can be flanked by site-specific recombination sites (eg, frt or lox sites) which are cut by the action of a site-specific recombinase which is encoded by either a host cell or vector sequence. In another example, the vector comprises DNA that is transcribed into RNA copies of the HM- or PM-DNA and a reverse transcriptase (eg, encoded by the vector nucleic acid sequence) for producing HM- or PM-DNA from the RNA. This is useful for producing many copies of the desired HM- or PM-DNA to increase the chances of efficient and effective introduction at one or more of the target sites. In another embodiment, the HM- or PM-DNA is, or is encoded by, nucleic acid of a second vector (eg, a second phage or plasmid) that has transduced or transformed the host cell. For example, this could be a helper phage (which may also encode one or more coat proteins required for packaging of the first page vector). In another example, the DNA is provided in vector DNA and flanked by arms, wherein the 5' arm comprises a PAM that is recognised by a Cas nuclease when the vector is contained in the host cell and the 3 arm is flanked immediately downstream (3) by such a PAM, whereby in the host cell Cas cleavage liberates the HM- or PM-DNA with its flanked arms that can be designed to be homologous to host sequences flanking the cut in the host target sequence, whereby the HM-DNA is integrated into the host genome, or the PM-DNA is integrated into the phage genome. In one aspect, the invention provides a nucleic acid comprising such a HM- or PM-DNA and arms or a vector (eg, a phage or packaged phage) comprising such a nucleic acid, optionally wherein the vector is contained by a host cell. Optionally, the HM-DNA is in combination with a HM-array as herein defined. Optionally, the PM-DNA is in combination with a PM-array as herein defined.

A particular application of the invention is the alteration of the proportion of Bacteroidetes (eg, *Bacteroides*) bacteria in a mixed bacterial population ex- or in vivo. As discussed above, this may be useful for environmental treatment such as treatment of waterways or drinking water infected with undesired Bacteroidetes, or for favouring useful commensal or symbiotic Bacteroidetes in humans or animals, eg, for producing bacterial cultures for administration to humans or animals for such purpose. In an example of the latter, the invention is useful for increasing the relative ratio of Bacteroidetes versus Firmicutes, which has been associated with lower of body mass and thus finds utility in treating or preventing obesity for medical or cosmetic purposes.

Studies suggest that *Bacteroides* have a role in preventing infection with *Clostridium difficile*. The development of the immune response that limits entry and proliferation of potential pathogens is profoundly dependent upon *B fragilis*. Also, Paneth cell proteins may produce antibacterial peptides in response to stimulation by *B thetaiotomicron*, and these molecules may prevent pathogens from colonizing the gut. In addition, *B thetaiotomicron* can induce Paneth cells to produce a bactericidal lectin, RegIII, which exerts its antimicrobial effect by binding to the peptidoglycan of gram-positive organisms. Thus, the use of the invention in any of its configurations for increasing the proportion of *Bacteroides* (eg, *thetaiotomicron* and/or *fragalis*) in a mixed population of gut bacteria is useful for limiting pathogenic bacterial colonisation of the population or a gut of a human or non-human animal.

Hooper et al demonstrated that *B thetaiotomicron* can modify intestinal fucosylation in a complex interaction mediated by a fucose repressor gene and a signaling system. Using transcriptional analysis it was demonstrated that *B thetaiotaomicron* can modulate expression of a variety of host genes, including those involved in nutrient absorption, mucosal barrier fortification, and production of angiogenic factors.

In an embodiment, the mixed population consists of the first and second bacteria (ie, and no further bacterial population).

In an example, the or each array is recombinant array in a vector and/or an isolated array in a vector. In an example, the array is contained in a host cell (eg, a microbial, bacterial or archaeal cell). In an example, said Cas is an endogenous Cas nuclease (eg Cas9) of the host cell. By harnessing the Cas of the host, this enables efficient use of host-type repeats in the array and possibility of using endogenous crRNA too—freeing up capacity which is otherwise limited in vectors, such as viruses or phage (noting that the Cas gene sequence such as Type II Cas9 is large).

In an example, the host CRISPR/Cas system is a Type I system. In an example, the host CRISPR/Cas system is a Type II system. In an example, the host CRISPR/Cas system is a Type III system.

The cas guided by the HM-crRNA or gRNA of the invention is a host endogenous Cas or a vector-encoded Cas compatible with the PAM in the target sequence.

Optionally, the host (or first and/or second bacteria) is a gram negative bacterium (eg, a *spirilla* or *vibrio*). Optionally, the host (or first and/or second bacteria) is a gram positive bacterium. Optionally, the host (or first and/or second bacteria) is a *Mycoplasma*, chlamydiae, spirochete or *Mycobacterium*. Optionally, the host (or first and/or second bacteria) is a *Streptococcus* (eg, *pyogenes* or *thermophilus*) host. Optionally, the host (or first and/or second bacteria) is a *Staphylococcus* (eg, *aureus*, eg, MRSA) host. Optionally, the host (or first and/or second bacteria) is an *E. coli* (eg, O157: H7) host, eg, wherein the Cas is encoded by the vecor or an endogenous host Cas nuclease activity is de-repressed. Optionally, the host (or first and/or second bacteria) is a *Pseudomonas* (eg, *aeruginosa*) host. Optionally, the host (or first and/or second bacteria) is a *Vibrio* (eg, *cholerae* (eg, O139) or *vulnificus*) host. Optionally, the host (or first and/or second bacteria) is a *Neisseria* (eg, gonnorrhoeae or *meningitidis*) host. Optionally, the host (or first and/or second bacteria) is a *Bordetella* (eg, *pertussis*) host. Optionally, the host (or first and/or second bacteria) is a *Haemophilus* (eg, *influenzae*) host. Optionally, the host (or first and/or second bacteria) is a *Shigella* (eg, *dysenteriae*) host. Optionally, the host (or first and/or second bacteria) is a *Brucella* (eg, *abortus*) host. Optionally, the host (or first and/or second bacteria) is a *Francisella* host. Optionally, the host (or first and/or second bacteria) is a *Xanthomonas* host. Optionally, the host (or first and/or second bacteria) is a *Agrobacterium* host. Optionally, the host (or first and/or second bacteria) is a *Erwinia* host. Optionally, the host (or first and/or second bacteria) is a *Legionella* (eg, *pneumophila*) host. Optionally, the host (or first and/or second bacteria) is a *Listeria* (eg, *monocytogenes*) host. Optionally, the host (or first and/or second bacteria) is a *Campylobacter* (eg, *jejuni*) host. Optionally, the host (or first and/or second bacteria) is a *Yersinia* (eg, *pestis*) host. Optionally, the host (or first and/or second bacteria) is a *Borrelia* (eg, *burgdorferi*) host. Optionally, the host (or first and/or second bacteria) is a *Helicobacter* (eg, *pylori*) host. Optionally, the host (or first and/or second bacteria) is a *Clostridium* (eg, *dificile* or *botulinum*) host. Optionally, the host (or first and/or second bacteria) is a *Ehrlichia* (eg, *chaffeensis*) host. Optionally, the host (or first and/or second bacteria) is a *Salmonella* (eg, *typhi* or *enterica*, eg, serotype *typhimurium*, eg, DT 104) host. Optionally, the host (or first and/or second bacteria) is a *Chlamydia* (eg, *pneumoniae*) host. Optionally, the host (or first and/or second bacteria) is a *Parachlamydia* host. Optionally, the host (or first and/or second bacteria) is a *Corynebacterium* (eg, *amycolatum*) host. Optionally, the host (or first and/or second bacteria) is a *Klebsiella* (eg, *pneumoniae*) host. Optionally, the host (or first and/or second bacteria) is a *Enterococcus* (eg, *faecalis* or faecim, eg, linezolid-resistant) host. Optionally, the host (or first and/or second bacteria) is a *Acinetobacter* (eg, *baumannii*, eg, multiple drug resistant) host.

In an example, the cell is a prokaryotic cell. In an example, the cell is a bacterial cell. In an example, the cell is a archaeal cell. In an example, the cell is a microbe cell. In an example, the cell is a protozoan cell. In an example, the cell is a fish cell. In an example, the cell is a bird cell. In an example, the cell is a reptilian cell. In an example, the cell is an arachnid cell. In an example, the cell is a yeast cell (eg, a *Saccharomyces* cell). In an example, the host cell is a plant cell. In an example, the host cell is an animal cell (eg, not a human cell, eg, not a rodent cell). In an example, the host cell is a human cell (eg, not a cell in an embryo or in a human), for example a host cell in vitro. In an example, the cell is a livestock or companion pet animal cell (eg, a cow, pig, goat, sheep, horse, dog, cat or rabbit cell). In an example, the host cell is an insect cell (an insect at any stage of its lifecycle, eg, egg, larva or pupa). In an example, the host cell is a protozoan cell. In an example, the cell is a cephalopod cell.

Optionally the array, system, engineered nucleotide sequence or vector nucleic acid further comprises a (eg, one, tow or more) nuclear localisation signal (NLS), eg, for targeting to the nucleus when the host cell is a eukaryotic cell, eg, a plant or animal. In an example, a NLS flanks each end of a Cas-encoding nucleic acid sequence of the invention and/or an array of the invention—particularly for use in targeting in a eukaryotic host cell.

A tracrRNA sequence may be omitted from a array or vector of the invention, for example for Cas systems of a Type that does not use tracrRNA.

In an example, the Cas guided to the target is an exonuclease. Optionally a nickase as mentioned herein is a double nickase.

An example of a nickase is a Cas9 nickase, ie, a Cas9 that has one of the two nuclease domains inactivated—either the RuvC and/or HNH domain.

Optionally the host system is a Type I system (and optionally the array, HM-crRNA or gRNA is of a different CRISPR system, eg, Type II or III). Optionally the array or engineered sequence is in combination in a virus or plasmid with a nucleotide sequence encoding a Cas of the same system as the array, HM-crRNA or gRNA, eg, where the Cas does not operate or operate efficiently with the host system. Optionally the host system is a Type II system (and optionally the array, HM-crRNA or gRNA is of a different CRISPR system, eg. Type I or III). Optionally the array or engineered sequence is in combination in a virus or plasmid with a nucleotide sequence encoding a Cas of the same system as the array, HM-crRNA or gRNA, eg, w here the Cas does not operate or operate efficiently with the host system. Optionally the host system is a Type III system (and optionally the array, HM-crRNA or gRNA is of a different CRISPR system, eg, Type I or II). Optionally the array of engineered sequence is in combination in a virus or plasmid with a nucleotide sequence encoding a Cas of the same system as the array, eg, where the Cas does not operate or operate efficiently with the host system.

Mention herein of using vector DNA can also in an alternative embodiment apply mutatis mutandis to vector RNA where the context allows. For example, where the vector is an RNA vector. All features of the invention are therefore in the alternative disclosed and to be read as "RNA" instead of "DNA" when referring to vector DNA herein when the context allows. In an example, the or each vector also encodes a reverse transcriptase.

In an example, the or each array or engineered nucleotide sequence is provided by a nanoparticle vector or in liposomes.

In an example, the Cas is a Cas nuclease for cutting, dead Cas (dCas) for interrupting or a dCas conjugated to a transcription activator for activating the target.

In an example, the host CRISPR/Cas system comprises a host CRISPR array and a cognate host Cas for nucleotide sequence targeting in the host. In an example, the host target sequence comprises at least 5, 6, 7, 8, 9, 10, 20, 30 or 40 contiguous nucleotides. In an example, the target sequence is cut by Cas, eg, a Cas9. In an embodiment, the sequence is not in a spacer.

In an example, the or each array or engineered sequence comprises an exogenous promoter functional for transcription of the crRNA or gRNA in the host.

In an example, the or each array repeats are identical to repeats in the host array, wherein the CRISPR array does not comprise a PAM recognised by a Cas (eg, a Cas nuclease, eg, Cas9) of the host CRISPR/Cas system. This applies mutatis mutandis to repeat sequence of the HM-crRNA and gRNA. This embodiment is advantageous since it simply enables the CRISPR array to use the endogenous host Cas to target the host target sequence. This then is efficient as the array is tailored for use by the host machinery, and thus aids functioning in the host cell. Additionally, or alternatively (eg where the array is provided in combination with an exogenous (non-host endogenous) Cas-encoding sequence) this embodiment enables the CRISPR array to use the endogenously-encoded tracrRNA, since the CRISPR array repeats will hybridise to the endogenous tracrRNA for the production of pre-crRNA and processing into mature crRNA that hybridises with the host target sequence. The latter complex can then guide the endogenous Cas nuclease (eg, Cas9) or guide Cas produced from the sequence comprised by the CRISPR array. This embodiment therefore provides the flexibility of simply constructing a vector (eg, packaged virus or phage) containing the CRISPR array but not comprising a tracrRNA- and/or Cas nuclease-encoding sequence. This is more straightforward for vector construction and also it frees up valuable space in the vector (eg, virus or phage) which is useful bearing in mind the capacity limitation for vectors, particularly viral vectors (eg, phage). The additional space can be useful, for example, to enable inclusion of many more spacers in the array, eg, to target the host genome for modification, such as to inactivate host genes or bring in desired non-host sequences for expression in the host. Additionally or alternatively, the space can be used to include a plurality of CRISPR arrays in the vector. These could, for example, be an arrangement where a first array is of a first CRISPR/Cas type (eg, Type II or Type II-A) and the second array could be of a second type (eg, Type I or III or Type II-B). Additionally or alternatively, the arrays could use different Cas nucleases in the host (eg, one array is operable with the host Cas nuclease and the second array is operable with an exogenous Cas nuclease (ie, a vector-encoded nuclease)). These aspects provide machinery for targeting in the host once the vector has been introduced, which is beneficial for reducing host resistance to the vector, as the host would then need to target a greater range of elements. For example, if the host were able to acquire a new spacer based on the first CRISPR array sequence, the second CRISPR array could still function in the host to target a respective target sequence in the host cell. Thus, this embodiment is useful to reduce host adaptation to the vector.

Another benefit is that it is possible (for example, with this arrangement) to include in the CRISPR array (or distributed over a plurality of such arrays in the vector) multiple copies of the same spacer (eg, a spacer used to target a target site in the host cell). This is beneficial since it has been proposed that adaptation of hosts, such as bacteria and archaea, may involve loss of spacers from their arrays where the spacers target beneficial host DNA (PLoS Genet. 2013; 9(9):e1003844. doi: 10.1371/journal.pgen.1003844. Epub 2013 Sep. 26, "Dealing with the evolutionary downside of CRISPR immunity: bacteria and beneficial plasmids", Jiang W et al). It is thought that the removal of spacer-repeat units occurs through recombination of repeat sequences. Thus, according to the present aspect of the invention, there is provided one, two, three, four, five, six or more CRISPR arrays or engineered sequences of the invention comprising a plurality (eg, 2, 3, 4 5, 10, 15, 20, 25, 30, 35, 40, 45, 50, 55, 60, 70, 80, 90, 100 or more) copies of a spacer for hybridising to a host target sequence. This reduces the chances of all of these spacers being lost by recombination in the host cell. In a further application of this aspect, the CRISPR arrays comprise a first array comprising one or more (eg, 2, 3, 4 5, 10, 15, 20, 25, 30, 35, 40, 45, 50, 55, 60, 70, 80, 90 or more) of the spacer copies and a second array comprising one or more (eg, 2, 3, 4 5, 10, 15, 20, 25, 30, 35, 40, 45, 50, 55, 60, 70, 80, 90 or more) of the identical spacer copies, wherein spacer copies in the first array are each flanked by first repeats and the identical spacer copies in the second array are each flanked by second repeats, wherein the first repeats are different from the second repeats. This has the benefit that at least one of the first and second repeats can be selected not to be recognised by a host Cas nuclease (or the same host Cas nuclease), to reduce the chances of host adaptation involving more than one of the arrays. In an example, the first array is in combination with a Cas nuclease sequence that is not encoded by the host cell and which is a cognate Cas for the first repeats. Optionally, also the second array is in combination with a Cas nuclease sequence (eg, the same or different from that for the first array) that is not encoded by the host cell and which is a cognate Cas for the second repeats.

An embodiment provides a first array contained in a first vector and a second array contained in a second vector which does not contain the first array (eg, wherein the vectors are plasmids or virions (eg, of the same virus type) or packaged phage (eg, of the same phage type). This is useful since the vectors can be simultaneously or sequentially introduced into the same host cell. Thus, when the host gains resistance to the first array, the second is introduced to provide a second array with which the resistant host (eg, bacterium or archaeon) has not previously co-evolved, thereby providing a second modification (eg, knock-down) wave against the host cell. This also provides flexibility since a third such vector, comprising a spacer or array that is different from the first and second arrays and spacers, can be introduced into the host cell simultaneously or sequentially with the second vector to provide a further route to host cell modification that has not previously been present during evolution of the hosts that are resistant to a spacer in the first array. Instead of arrays, engineered nucleotide sequences of the invention can be used.

Thus, in one embodiment, the invention provides a composition for modifying a host cell, wherein the composition provides any array or engineered sequence as described herein. Thus, in one embodiment, the invention provides a composition for modifying a host cell, wherein the composition provides a first array as described herein in a first vector (eg, virion or packaged phage) and a second first such array as described herein in a second vector (eg, virion or packaged phage respectively), wherein the second array comprises one or more spacers that target one or more host target sequences and which is/are not comprised by the first array. Instead of arrays, engineered nucleotide sequences of the invention can be used.

In an embodiment the array or engineered sequence is contained in a virophage vector and the host is alternatively a virus which can infect a cell. For example, the host is a large virus that may have infected an amoeba cell. For example, the host is a Sputnik virus, Pithovirus, mimivirus, mamavirus, Megavirus or Pandoravirus, eg, wherein the host virus is in water. In an example of this embodiment, the invention is for water or sewage treatment (eg, purification, eg, waterway, river, lake, pond or sea treatment).

In an embodiment the or each vector or engineered sequence is or is comprised by a ΦNM1 phage, eg, wherein the host cell(s) is a *S. aureus* (eg, MRSA) cell.

The general features also provide the following clauses:—

1. An antimicrobial composition (eg, an antibiotic, eg, a medicine, disinfectant or mouthwash), comprising an array, engineered sequence, virus, virion, phage, phagemid, prophage, population or collection according to any aspect of the invention.

2. The composition of clause 1 for medical or dental or ophthalmic use (eg, for treating or preventing an infection in an organism or limiting spread of the infection in an organism.

In an example, the organism is a plant or animal, eg, vertebrate (eg, any mammal or human disclosed herein) or crop or food plant.

3. A composition comprising an array, engineered sequence, system, collection, virus, virion, phage, phagemid, prophage, composition, population, collection, use or method according to the invention for cosmetic use (eg, use in a cosmetic product, eg, make-up), or for hygiene use (eg, use in a hygiene product, eg, soap).

4. Use of a composition comprising an array, engineered sequence, collection, virus, virion, phage, phagemid, prophage, population or collection according to any one of clauses 1 to 35, in medicine or for dental therapeutic or prophylactic use.

5. Use of a composition comprising an array, engineered sequence, collection, system, virus, virion, phage, phagemid, prophage, composition, population, collection, use or method according to the invention, in cosmetic use (eg, use in a cosmetic product, eg, make-up), or for hygiene use (eg, use in a hygiene product, eg, a soap).

6. Use of an array, engineered sequence, system, collection, virus, virion, phage, phagemid, prophage, composition, population or collection according to the invention in a host modifying (HM) CRISPR/Cas9 system (eg, Type I, II or III) that is capable of modifying a target nucleotide sequence of a host cell, wherein the array, engineered sequence, system, virus, virion, phage, phagemid, prophage, population or collection is according to the present invention.

7. The use of clause 4, 5 or 6, wherein the array, engineered sequence, system, collection, virus, virion, phage, phagemid, prophage, population or collection is not in a host cell.

8. The use of clause 5 or 6, wherein the array, engineered sequence, collection, system, virus, virion, phage, phagemid, prophage, population or collection is in a host cell (eg, a microbe, bacterium or archaeon cell).

9. The use of any one of clauses 4 to 6 for modifying a microbial cell (eg, for killing or reducing growth of the cell or a culture of microbe cells).

10. A method of modifying a target nucleotide sequence in a host cell (eg a microbe bacterium or archaeon), the method comprising transforming the host cell with the array, engineered sequence, system, collection, virus, virion, phage, phagemid, population or collection according to the present invention, whereby the target nucleotide sequence is Cas modified, wherein the host target sequence is a nucleotide sequence of a host CRISPR/Cas system of the cell.

11. A method of reducing the development of host cell resistance to transformation by a nucleic acid vector or maintenance of a nucleic acid vector in the host cell, wherein the host cell comprises a target nucleotide sequence, the method comprising transforming the host cell with the array, engineered sequence, collection, system, virus, virion, phage, phagemid, population or collection according to the invention, whereby the target nucleotide sequence is Cas modified (eg, cut, mutated or knocked-down).

12. The method of clause 11, wherein the vector is a virus that is capable of infecting the host cell and the transforming step comprises infecting the host cell with the vector.

13. The method of clause 11 or 12, wherein the host cell is a bacterial or archaeal cell and the vector is a phage or phagemid.

14. The method of any one of clauses 11 to 13, wherein the host target sequence is essential to host CRISPR/Cas-mediated acquisition of vector sequence spacers.

15. The array, engineered sequence, system, vector, cell, collection, composition, use or method of any preceding clause, wherein at least component (ii) is contained in a virus (eg, a phage) that is capable of expressing an endolysin for host cell lysis, optionally wherein the endolysin is a phage phi11, phage Twort, phage P68. phage phiWMY or phage K endolysin (eg, MV-L endolysin or P-27/HP endolysin).

16. The array, engineered sequence, system, vector, collection, cell, composition, use or method of clause 15 in combination with an endolysin for host cell lysis, eg, in combination with MV-L endolysin or P-27/HP endolysin or a functional homologue thereof.

17. The array, engineered sequence, system, vector, collection, cell, composition, use or method of any preceding clause in combination with an antimicrobial, eg, antibiotic agent, eg, a beta-lactam antibiotic.

18. The array, engineered sequence, system, vector, collection, cell, composition, use or method of any preceding clause, wherein the host cell is a *Staphylococcus, Streptococcus, Pseudomonas, Salmonella, Listeria, E coli, Desulfovibrio* or *Clostridium* host cell.

19. The array, engineered sequence, system, vector, collection, cell, composition, use or method of any preceding clause, wherein the host cell is a *Staphylococcus* (eg, *S aureus*) host cell and at least component (ii) is contained in a Class I, II or III *Staphylococcus* phage (eg, a packaged phage), optionally a Caudovirales or Myoviridae phage.

20. The array, engineered sequence, system, vector, cell, collection, composition, use or method of any preceding clause, wherein the host cell is a beta-lactam antibiotic-resistant *Streptococcus aureus*, methicillin-resistant *Streptococcus aureus* (MRSA), vancomycin-resistant *Streptococcus aureus* or teicoplanin-resistant *Streptococcus aureus* and optionally the target sequence is a sequence of a host beta-lactam antibiotic-resistance gene, methicillin-resistance gene, vancomycin-resistance gene or teicoplanin-resistance gene respectively.

Suitable methods for producing and testing phage vectors of the invention are, for example, general methods disclosed in WO2014/124226.

Mobile Genetic Elements, Transposons & Carriers
(for any Configuration of the Invention)

Plasmids are very common in *Bacteroides* species and are found in 20 to 50% of strains. Many plasmids possess oriT and a transacting mobilisation gene, which allow them to be transferred by conjugation. Thus, in an example, the vector is a plasmid comprising oriT and/or a mobilisation gene, eg, wherein the first or second bacteria are *Bacteroides*. In an example, the engineered sequence is comprised by such a vector.

In an example, the host cells, or the first or second bacteria naturally comprise transposons. Transposons, both mobilisable and conjugative, do not replicate independently; rather, they excise from and integrate into chromosomal DNA and are copied along with the chromosomal DNA. Conjugative transposons have a mechanism of excision and integration that resemble some features of both plasmids and bacteriophage. Conjugative transposons are practically ubiquitous among the *Bacteroides*: over 80% of *Bacteroides* strains contain at least one conjugative transposon. The conjugative transposons of *Bacteroides* belong to at least two families; CTnDot is the best described. Often, the name of the strain in which they are found is added to the designation (e.g., CTnDot, found in the DOT strain of *B thetaiotaomicron*). In addition to being able to insert into the chromosome, *Bacteroides* conjugative transposons can insert into coresident plasmids and mobilise them in cis (i.e., they can act on entities that are physically adjacent) by integrating themselves into the plasmid and facilitating transfer of the plasmid-conjugative transposon hybrid into another cell. They can also mobilise coresident plasmids "in trans" by supplying factors needed to facilitate transfer of the plasmid, while remaining physically separate from the plasmid.

Conjugative transposons do not exclude each other as do plasmids, so a strain can accumulate more than one conjugative transposon. Furthermore, there is some evidence that the presence of more than one copy of the conjugative transposon in the strain results in a stimulation of transposition (transactivation). Theoretically, this suggests that as more conjugative transposons accumulate in the environment, the transfer of the transposon genes to other bacteria will also increase, and there will be a significant upward spiraling of distribution of the genes. Many of the *Bacteroides* transposons carry the tetQ gene and thus confer tetracycline resistance. Further, self-transfer and other activities are significantly stimulated by low levels of tetracycline, regulated by the tetQ-rteA-rteB operon. Tetracycline increases transcription of rteA and -B, which code for the sensor and activator components of a two-component regulatory system. In turn, RteB activates expression of rteC, which is necessary for self-transfer.

In an example, the vector (eg, the vector comprising the engineered sequence) comprises a transposon, wherein the transposon comprises the engineered sequence, HM- or PM-array of the invention, wherein the transposon is operable in the host cell(s) or in the first or second bacteria host cell species. In an embodiment, the transposon is a *Bacteroides* transposon (eg, a CTnDot transposon, eg, a *B thetaiotaomicron* or *B fragalis* CTnDot transposon) and the host cells, or the first or second bacteria are or comprise *Bacteroides* (eg, of the same species as said CTnDot transposon). In an example, the transposon is a conjugative transposon. In an example, the transposon is a mobilisable transposon. In an example, the transposon is transferrable between *Bacteroides* cells. In an example, the transposon comprises an intDOT sequence. In an example, the transposon comprises an oriT. In an example, the transposon encodes one or more mating pore proteins for conjugative transfer of the transposon between host cells.

In an example, the invention provides a transposon that comprises a *Bacteroides* tetQ gene. In an example, the transposon further comprises a *Bacteroides* tetQ-rteA-rteB operon. In an example, the first or second bacteria are *Bacteroides*. In an example, the transposon is a *Bacteroides* CTnDot transposon that encodes one or more mating pore proteins for conjugative transfer of the transposon between host cells and comprises one or more arrays or engineered sequences of the invention, an oriT, an intDOT sequence and a tetQ-rteA-rteB operon, and is optionally for administration or is administered to said human or non-human animal as mentioned herein in combination with tetracycline. Transfer of most *Bacteroides* CTns is stimulated by tetracycline. The transposon is operable with an integrase in a host cell or is operable with an exogenous integrase carried on the same or a different vector to the transposon. In an embodiment, the vector is a phage (eg, a packaged phage) comprising the transposon and a nucleotide sequence encoding a cognate integrase. The phage is capable of infecting a host bacterial cell for replication and excision of the transposon, eg, for conjugative transfer to neighbouring host cells in a mixed bacterial population (eg, a gut microbiota population).

In an embodiment, the transposon is comprised by a vector that carries one or more gene sequences necessary for transposon transfer between host cells, wherein said gene sequences are outside of the transposon on the vector nucleic acid. For example, the vector is a packaged phage that is capable of infecting a host cell (eg, a *Bacteroides* host cell), wherein the phage nucleic acid comprises a said transposon comprising a array of the invention and upstream or downstream of the transposon one or more genes operable for conjugative transfer of the transposon (eg, one or more genes encoding relaxases, coupling proteins and/or mating bridge proteins for transposon conjugative transfer; and/or one or both of mob and tra operons), wherein one, more or all these genes is not comprised by the transposon. In an example, these genes are genes for excision of the transposon from chromosomal DNA inside a first host cell. Thus, the transposon is able to mobilise inside that cell and carries with it genes necessary for the subsequent conjugative transfer into a second host cell. By providing some of the transposon genes in this way on the vector outside the transposon, this frees up room in the transposon for inclusion of engineered sequence or array DNA of the invention so that this can be accommodated and carried by mobilised transposons. The invention provides such a vector comprising one or more such transposons for use in the method, use or system of the invention or generally for introduction into bacterial cells (in this case instead of targeting a phage sequence, the array included in the transposon can target a bacterial target sequence to modify the sequence, eg, cut it using Cas in a cell harbouring the transposon).

Molecular mechanisms of CTnDot excision and integration more closely resemble that of bacteriophage rather than transposition. The CTnDOT integrase and excision proteins themselves are quite similar to those from bacteriophage. Thus, in one embodiment the function of one or more integrase and/or excision proteins of the transposon of the invention are provided by the phage integrase and/or excision proteins respectively, and the transposon does not comprise corresponding gene(s) encoding such integrase or excision proteins whose functions are provided by phage proteins.

In an example, the transposon comprises rteC and the operon xis2c-xis2d-orf3-exc. Optionally, additionally the vector comprises mob and tra operons outside of the transposon (eg, upstream or downstream of the transposon in the vector nucleic acid). Thus, this frees up space in the transposon for providing CRISPR array sequence or engineered sequence of the invention.

Many conjugative transposons are able to mobilise other elements. For example, many coresident plasmids are mobilized by a conjugative transposon in trans. This occurs when a plasmid containing an oriT utilizes the CTn-provided mating pore proteins for transfer to a recipient cell. The *Bacteroides* CTns have also been shown to mobilize elements when in cis, a feature that is not typical for CTns. For example, if CTnDOT excises from the chromosome and integrates on a plasmid, it can provide the mating pore, an oriT, and the mobilization (relaxase/coupling) proteins, allowing it to transfer the entire plasmid by acting "in cis." This ability to use both trans and cis mechanisms of mobilization is unusual and suggests that the *Bacteroides* CTns have a greater capacity to mobilize other elements.

In an example, the vector of the invention is a plasmid comprising one or more engineered sequences or arrays of the invention and an oriT that is cognate to a host cell species CTnDot transposon that encodes mating pore proteins, whereby the plasmid is mobilisable in a host cell comprising a said CTnDot transposon. Thus, the plasmid is capable of horizontal transfer between host cells, thereby spreading arrays of the invention in a population of such host cells (eg, *Bacteroides* cells). In an example, the invention provides a composition comprising a population of carrier bacteria, wherein the carrier bacteria are compatible with such a plasmid vector of the invention, whereby the vector is capable of horizontal transfer to recipient host bacteria cells (eg, *Bacteroides* or Firmicutes, eg, *Streptococcus* cells) comprising cognate CTnDot transposons when the carrier and recipient bacteria are mixed. In an example, the carrier bacteria are comprised by a beverage (eg, probiotic drink, such as one described herein) or foodstuff for human or non-human animal consumption, whereby the carrier bacteria can mix with recipient bacteria harboured by the human or animal (eg, in the oral cavity or in the gut). Other transposons within the CTnDOT-like family include CTnERL and CTn341, although these elements differ from CTnDOT, and thus instead of a CTnDot transposon, the transposon of the general aspect of the invention can be a CTnERL or CTn341 transposon carrying one or more desired CRISPR arrays or engineered sequences for targeting one or more bacterial or phage nucleotide target sites when the transposon is comprised by a bacterial or archaeal host cell.

In order for transfer of the conjugative transposon to occur, there are three main steps that take place. The first step is excision from the chromosome to form a covalently closed circular intermediate. Second, a single-stranded copy is then transferred through the mating pore to a recipient cell, after which the copy becomes double stranded. Third, the intact double-stranded CTn integrates into the chromosome of the recipient. Conjugative transposition is replicative, as a copy of the CTn is retained in the donor cell. Because the element resides within the chromosome, it is also transferred vertically to progeny cells. This is important because when desired CRISPR arrays or engineered sequences (and optionally Cas sequence) are present on CTns, they are not only transferred readily within the population, but they are also very stably maintained from generation to generation. This is as seen, for example, with retained antibiotic resistance determinants. Further, it is believed that *Bacteroides* may serve as a reservoir of antibiotic resistance determinants which disseminates these genes to other organisms outside the *Bacteroides* genus, possibly even transferring these elements to organisms that are transiently passing through the gut. Similarly, a reservoir of arrays or engineered sequences of the invention can be created using vectors of the invention that are administered to a human or non-human animal, eg, for treating or preventing obesity, diabetes or IBD or any other disease or condition disclosed herein.

In an example, one can exploit the reservoir of desired CRISPR arrays or engineered sequences by using one or more arrays or sequences comprised by a transposon (eg, a CTnDot) that is capable of being harboured by *Bacteroides* cells (eg, in the gut or oral cavity of a human or non-human animal), wherein the array(s)/sequence(s) do not target a sequence of the host *Bacteroides* cell, but do target a nucleotide sequence comprised by a gut microbiota cell (eg, bacterial cell) of a different species (eg, a Firmicutes cell or pathogenic bacterial cell, eg, *Streptococcus, C dificile, H pylori, Salmonella, Listeria, Yersinia, Shigella* or *Campylobacter* cell). Thus, in this way transfer of the arrays or sequences of the invention to neighbouring recipient pathogenic or undesired bacteria can take place, and once inside the recipient cell the array(s) of the invention are operable to guide Cas to the respective target site in the host cell to modify (eg, cut) the site. In this case, the array/sequence can comprise repeat sequences that are found in the recipient cell of interest so that the array/sequence can operate with an endogenous CRISPR/Cas system inside the recipient cell. This avoids the need to include Cas and/or tracrRNA-encoding sequences in the vector, engineered sequence or transposon of the invention, thereby freeing up space and simplifying construction. Increased space is useful for enabling inclusion of more spacers to target more target sites in the recipient cell. In an alternative, the transposon array(s) or sequence(s) comprises a Type II Cas9-encoding sequence and cognate repeat sequences. For example, the Cas9 (any Cas9 mentioned herein) is a *S pyogenes, S thermophilus* or *S aureus* Cas9 and may optionally be a nickase or dCas9 ("dead Cas9"). As *Bacteroides* are obligate anaerobes (or have a strong preference for anaerobic environments) and typically are pathogenic outside the gut environment, it may not be desirable to use *Bacteroides* cells as carriers for the vectors or transposons of the invention, eg, when administering to the gut or oral cavity of a human or animal. To address this, the invention provides a carrier population of bacteria harbouring vectors, engineered sequence(s) or transposons of the invention, wherein the carrier bacteria are compatible with such a vector, sequence or transposon, whereby the vector, sequence or transposon is capable of horizontal transfer to recipient host bacteria cells (eg, *Bacteroides*) in gut microbiota when the carrier and recipient bacteria are mixed. In an example, the carrier bacteria are comprised by a beverage (eg, probiotic drink, such as one described herein) or foodstuff for human or non-human animal consumption, whereby the carrier bacteria can mix with recipient bacteria harboured by the human or animal (eg, in the oral cavity or in the gut). In an embodiment, the vectors, sequences or transposons comprise CRISPR arrays of the invention, wherein the arrays target nucleotide sequences comprised by the recipient cells to modify the target sequences, eg, by cutting the sequences to inactivate genes comprising the target sequences. In an alternative, the vectors, sequences or transposons are capable of horizontal transfer (eg, conjugative transposon transfer) to a second recipient population of bacteria, which are of a different species to the first recipient bacteria, wherein the nucleotide sequence target sites are comprised by the second recipient bacteria but not comprised by the first recipient bacteria, whereby the target sites are modified by Cas in the second recipient bacteria (host cells).

In an example, the first recipient bacteria are *Bacteroides* bacteria and the second recipient bacteria are Firmicutes or pathogenic bacteria, eg, gut bacteria. In an example, the carrier bacteria comprise vectors of the invention (eg, phage or plasmids) comprising one or more conjugative transposons (eg, CTnDot transposons) that are capable of being harboured by the carrier bacteria, first bacteria and second bacteria, eg, wherein the transposons comprise oriT and the carrier bacteria, first bacteria and second bacteria are compatible with oriT.

In an alternative, the carrier bacteria are capable of transferring the vector, engineered sequence or transposon of the invention directly to Firmicutes or pathogenic bacteria, eg, in an animal or non-human animal, eg, in the gut, oral cavity or systemically (eg, in the blood). In an example, the pathogenic bacteria are *C dificile, H pylori*, pathogenic *E coli, Salmonella, Listeria, Yersinia, Shigella, S aureus, Streptococcus* or *Campylobacter* bacteria.

In an example, the carrier bacteria are bacteria of one or more species selected from the group consisting of a *Lactobacillus* species (eg, *acidophilus* (eg, La-5, La-14 or NCFM), *brevis, bulgaricus, plantarum, rhammosus, fermentum, caucasicus, helveticus, lactis, reuteri* or *casei* eg, *casei* Shirota), a *Bifidobacterium* species (eg, *bifidum, breve, longum* or *infantis*), *Streptococcus thermophilus* and *Enterococcus faecium*. For example, the bacteria are *L acidophilus* bacteria.

Mobilisable transposons, like mobilisable plasmids, cannot self-transfer but can transfer between cells in the presence of the TcR helper element. The most commonly discussed *Bacteroides* transposons of this class include Tn4399, Tn4555, and the nonreplicating *Bacteroides* units. The mobilisable transposon Tn4555, for example, was first detected during studies of transmissible cefoxitin resistance in a clinical isolate of *Bacteroides vulgatus*. In an embodiment, therefore, the transposon of the invention is a mobilisable transposon (eg, a *Bacteroides* mobilisable transposon), eg, a Tn4399 or Tn4555 comprising one or more arrays or sequences of the invention. The transposon is in combination with a TcR helper element.

In an example, the transposon of the invention is *Enterococcus* Tn916 or Gram-positive Tn1546 transposon. A transposon (eg, as a CTnDot, Tn4399 or Tn4555 transposon) can be characterised for example according to its terminal repeats and/or transposase- or resolvase-encoding sequence(s). In an alternative example, the vector or transposon comprises an origin of replication selected from pMB1, pBR322, ColE1, R6K (in combination with a pir gene), p15A, pSC101, F1 and pUC. In an example, the transposon is in combination with a factor (eg, an antibiotic, eg, tetracycline) that is required for transposon mobilisation or transfer. In an example, the transposon comprises an antibiotic resistance gene (eg, tetracycline resistance gene) and the transposon is in combination with said antibiotic (eg, administered simultaneously or sequentially to the human with said antibiotic). In an example, the transposon is a piggyBac, Mariner or Sleeping Beauty transposon in combination with a cognate transposase. In an example, the transposon is a Class I transposon. In an example, the transposon is a Class II transposon. In an example, the transposon is a Tn family transposon.

Targeting Antibiotic Resistance in Bacterial Hosts

Antibiotic resistance is a worldwide problem. New forms of antibiotic resistance can cross international boundaries and spread between continents with ease. Many forms of resistance spread with remarkable speed. World health leaders have described antibioticresistant microorganisms as "nightmare bacteria" that "pose a catastrophic threat" to people in every country in the world. Each year in the United States, at least 2 million people acquire serious infections with bacteria that are resistant to one or more of the antibiotics designed to treat those infections. At least 23,000 people die each year as a direct result of these antibiotic-resistant infections. Many more die from other conditions that were complicated by an antibioticresistant infection. In addition, almost 250,000 people each year require hospital care for *Clostridium difficile* (*C. difficile*) infections. In most of these infections, the use of antibiotics was a major contributing factor leading to the illness. At least 14,000 people die each year in the United States from *C. difficile* infections. Many of these infections could have been prevented. Antibiotic-resistant infections add considerable and avoidable costs to the already overburdened U.S. and other healthcare systems. In most cases, antibiotic-resistant infections require prolonged and/or costlier treatments, extend hospital stays, necessitate additional doctor visits and healthcare use, and result in greater disability and death compared with infections that are easily treatable with antibiotics. The total economic cost of antibiotic resistance to the U.S. economy has been difficult to calculate. Estimates vary but have ranged as high as $20 billion in excess direct healthcare costs, with additional costs to society for lost productivity as high as $35 billion a year (2008 dollars). The use of antibiotics is the single most important factor leading to antibiotic resistance around the world. Antibiotics are among the most commonly prescribed drugs used in human medicine. However, up to 50% of all the antibiotics prescribed for people are not needed or are not optimally effective as prescribed. Antibiotics are also commonly used in food animals to prevent, control, and treat disease, and to promote the growth of food-producing animals. The use of antibiotics for promoting growth is not necessary, and the practice should be phased out. Recent guidance from the U.S. Food and Drug Administration (FDA) describes a pathway toward this goal. It is difficult to directly compare the amount of drugs used in food animals with the amount used in humans, but there is evidence that more antibiotics are used in food production.

The other major factor in the growth of antibiotic resistance is spread of the resistant strains of bacteria from person to person, or from the non-human sources in the environment, including food. There are four core actions that will help fight these deadly infections: 1. preventing infections and preventing the spread of resistance; 2. tracking resistant bacteria; 3. improving the use of today's antibiotics; and 4. promoting the development of new antibiotics and developing new diagnostic tests for resistant bacteria. Bacteria will inevitably find ways of resisting the antibiotics we develop, which is why aggressive action is needed now to keep new resistance from developing and to prevent the resistance that already exists from spreading.

The invention provides improved means for targeting antibiotic-resistant hosts and for reducing the likelihood of hosts developing further resistance to the compositions of the invention.

Further examples of host cells and targeting of antibiotic resistance in such cells using the present invention are as follows:—

1. Optionally the host cell(s) are *Staphylococcus aureus* cells, eg, resistant to an antibiotic selected from methicillin, vancomycin, linezolid, daptomycin, quinupristin, dalfopristin and teicoplanin and the host target site (or one or more of the target sites) is comprised by a gene conferring host resistance to said antibiotic.

2. Optionally the host cell(s) are *Pseudomonas aeruginosa* cells, eg, resistant to an antibiotic selected from cephalosporins (eg, ceftazidime), carbapenems (eg, imipenem or meropenem), fluoroquinolones, aminoglycosides (eg, gentamicin or tobramycin) and colistin and the host target site (or one or more of the target sites) is comprised by a gene conferring host resistance to said antibiotic.

3. Optionally the host cell(s) are *Klebsiella* (eg, *pneumoniae*) cells, eg, resistant to carbapenem and the host target site (or one or more of the target sites) is comprised by a gene conferring host resistance to said antibiotic.

4. Optionally the host cell(s) are *Streptococcus* (eg, *thermophilus, pneumoniae* or *pyogenes*) cells, eg, resistant to an antibiotic selected from erythromycin, clindamycin, beta-lactam, macrolide, amoxicillin, azithromycin and penicillin and the host target site (or one or more of the target sites) is comprised by a gene conferring host resistance to said antibiotic.

5. Optionally the host cell(s) are *Salmonella* (eg, serotype *Typhi*) cells, eg, resistant to an antibiotic selected from ceftriaxone, azithromycin and ciprofloxacin and the host target site (or one or more of the target sites) is comprised by a gene conferring host resistance to said antibiotic.

6. Optionally the host cell(s) are *Shigella* cells, eg, resistant to an antibiotic selected from ciprofloxacin and azithromycin and the host target site (or one or more of the target sites) is comprised by a gene conferring host resistance to said antibiotic.

7. Optionally the host cell(s) are *Mycobacterium tuberculosis* cells, eg, resistant to an antibiotic selected from Resistance to isoniazid (INH), rifampicin (RMP), fluoroquinolone, amikacin, kanamycin and capreomycin and azithromycin and the host target site (or one or more of the target sites) is comprised by a gene conferring host resistance to said antibiotic.

8. Optionally the host cell(s) are *Enterococcus* cells, eg, resistant to vancomycin and the host target site (or one or more of the target sites) is comprised by a gene conferring host resistance to said antibiotic.

9. Optionally the host cell(s) are Enterobacteriaceae cells, eg, resistant to an antibiotic selected from a cephalosporin and carbapenem and the host target site (or one or more of the target sites) is comprised by a gene conferring host resistance to said antibiotic.

10. Optionally the host cell(s) are *E. coli* cells, eg, resistant to an antibiotic selected from trimethoprim, itrofurantoin, cefalexin and amoxicillin and the host target site (or one or more of the target sites) is comprised by a gene conferring host resistance to said antibiotic.

11. Optionally the host cell(s) are *Clostridium* (eg, *dificile*) cells, eg, resistant to an antibiotic selected from fluoroquinolone antibiotic and carbapenem and the host target site (or one or more of the target sites) is comprised by a gene conferring host resistance to said antibiotic.

12. Optionally the host cell(s) are *Neisseria gonnorrhoea* cells, eg, resistant to an antibiotic selected from cefixime (eg, an oral cephalosporin), ceftriaxone (an injectable cephalosporin), azithromycin and tetracycline and the host target site (or one or more of the target sites) is comprised by a gene conferring host resistance to said antibiotic.

13. Optionally the host cell(s) are *Acinetobacter baumannii* cells, eg, resistant to an antibiotic selected from beta-lactam, meropenem and a carbapenem and the host target site (or one or more of the target sites) is comprised by a gene conferring host resistance to said antibiotic.

14. Optionally the host cell(s) are *Campylobacter* cells, eg, resistant to an antibiotic selected from ciprofloxacin and azithromycin and the host target site (or one or more of the target sites) is comprised by a gene conferring host resistance to said antibiotic.

15. Optionally, the host cell(s) produce Beta (β)-lactamase.

16. Optionally, the host cell(s) are bacterial host cells that are resistant to an antibiotic recited in any one of examples 1 to 14.

In an embodiment, the host cell is a USA300 *S aureus* strain cell.

In an example, the or each host target sequence is comprised by a plasmid of the host cell, eg, a *S aureus* plasmid (eg, of a USA300 strain), eg, a target comprised by the pUSA01, pUSA02 or pUSA03 plasmid of a *S aureus* cell. In an example, the first and/or second target is comprised by a host mecA, mecA2 or sek gene sequence (eg, of a *S aureus* strain cell). In an example, the first and/or second target is comprised by a host pathogenicity island nucleotide (eg, DNA) sequence. In example, a spacer of the invention comprises or consists of a spacer disclosed in Table 1 on page 26 of WO2014/124226, which spacer sequences are incorporated herein by reference. In an example, the engineered sequence, HM-crRNA or gRNA comprises such a spacer.

The composition, use, method system, vector, collection, array, engineered sequence, virus, phage, phagemid, prophage or virion of the invention which is effective to reduce or kill or inhibit growth of an antibiotic-resistant bacterial host in a mouse skin colonisation assay (eg, as disclosed in WO2014/124226, Kugelberg E, et al. Establishment of a superficial skin infection model in mice by using *Staphylococcus aureus* and *Streptococcus pyogenes*. Antimicrob Agents Chemother. 2005; 49:3435-3441 or Pastagia M, et al. A novel chimeric lysin shows superiority to mupirocin for skin decolonization of methicillin-resistant and -sensitive *Staphylococcus aureus* strains. Antimicrob Agents Chemother. 2011; 55:738-744) wherein the first and/or second target is comprised by a host gene that confers resistance to said antibiotic, eg, wherein the host is a *S aureus* (eg, USA300 strain) host.

Reference *S pyogenes* sequence is available under Genbank accession number NC_002737. with the cas9 gene at position 854757-858863. The *S pyogenes* Cas9 amino acid sequence is available under number NP_269215. These sequences are incorporated herein by reference for use in the present invention. Further sequences as disclosed in 20150079680, whether explicitly or incorporated by reference therein, are also incorporated herein by reference for use in the present invention. Reference is also made to the disclosure of sequences and methods in WO2013/176772, which is incorporated herein by reference. Example tracrRNA sequences are those disclosed on page 15 of WO2014/124226, which are incorporated herein by reference for use in the present invention.

In an example, the or each repeat comprises or consists of from 20 to 50 (eg, from 24 to 47, eg, 30, 29, 28, 27, 26, 25 or 24) contiguous nucleotides in length.

In an example, the or each spacer comprises or consists of from 18 to 50 (eg, from 24 to 47, or 20 to 40, eg, 30, 29, 28, 27, 26, 25, 24, 23, 22, 21, 20, 19, 18), eg, 19 or 20 contiguous nucleotides in length.

In an example, the first repeat (most 5' in the HM-array of the invention) is immediately 5' of a spacer sequence that is complementary to a sequence comprising the first host target. This is useful, in view of the observation that newly acquired spacers (eg of invading phage sequence) are commonly incorporated at this position in bacteria, and thus positioning of the first spacer of the invention in this way is useful to promote its use.

In an example, the virus (eg, phage) nucleic acid comprises an origin of replication (ori) and a packaging site. In an example, the nucleic acid of the virus also comprises one, more or all genes encoding essential capsid proteins. eg, rinA, terS and terL genes. In an example, one, more or all of these is instead comprised by a companio helper virus (eg, helper phage) that is for con-infection with the virus of the invention—this frees up space in the latter for including more HM-array nucleic acid and/or more Cas-encoding nucleic acid operable in the host. In an example, the virus nucleic acid comprises a fragment of a wild-type phage genome, wherein the fragment consists of consecutive nucleotides of the genome comprising at least the rinA, terS and terL genes or equivalent genes encoding phage proteins.

In an example, the host cell is of a strain or species found in human microbiota.

In an example, the or each target site is comprised by a gene that mediates host pathogenic adhesion, colonisation, invasion, immune response inhibition, virulence, essential protein or function expression or toxin generation. In an example, the gene is a gene encoding a cytotoxin, alpha-haemolysin, beta-haemolysin, gamma-haemolysin, leukocidin, Panton-Valentine lekocidin (PVL), exotoxin, TSST-1, enterotoxin, SEA, SEB, SECn, SED, SEE, SEG, SEH, SEI, exfoliative toxin, ETA or ETB, optionally wherein the host is *S aureus*, eg, MRSA.

In an example, the or each CRISPR array is an array according to any of the configurations, embodiments, examples, concepts, aspects, paragraphs or clauses disclosed herein. In an example, the or each engineered nucleotide sequence is an engineered nucleotide sequence according to any of the configurations, embodiments, examples, concepts, aspects, paragraphs or clauses disclosed herein.

In an example, the or each vector is a vector according to any of the configurations, embodiments, examples, concepts, aspects, paragraphs or clauses disclosed herein.

In an example according to any of the configurations, embodiments, examples, Aspects, paragraphs or clauses disclosed herein, the vector or MGE is or comprises a casposon. MGEs are described further below. In an example, the casposon is a family 1, 2 or 3 casposon. In an example, an MGE of the invention comprises casposon terminal inverted repeats and optionally a casposon Cas1-encoding sequence. In an example, an MGE of the invention is or comprises a casposon minus Cas1 and operable for mobilisation with Cas1 of a host cell. See BMC Biol. 2014 May 19; 12:36. doi: 10.1186/1741-7007-12-36, "Casposons: a new superfamily of self-synthesizing DNA transposons at the origin of prokaryotic CRISPR-Cas immunity", Krupovic M et al for details of casposons.

FURTHER EXAMPLE APPLICATIONS OF THE PRESENT INVENTION

In an example, the composition (eg, HM-composition or engineered sequence in combination with antibiotic) is as any of the following: In an example, the composition is a medical, ophthalmic, dental or pharmaceutical composition (eg, comprised by a an anti-host vaccine). In an example, the composition is a an antimicrobial composition, eg, an antibiotic or antiviral, eg, a medicine, disinfectant or mouthwash. In an example, the composition is a cosmetic composition (eg, face or body make-up composition). In an example, the composition is a herbicide. In an example, the composition is a pesticide (eg, when the host is a *Bacillus* (eg, *thuringiensis*) host). In an example, the composition is a beverage (eg, beer, wine or alcoholic beverage) additive. In an example, the composition is a food additive (eg, where the host is an *E coli, Salmonella, Listeria* or *Clostridium* (eg, *botulinum*) host). In an example, the composition is a water additive. In an example, the composition is a additive for aquatic animal environments (eg, in a fish tank). In an example, the composition is an oil or petrochemical industry composition or comprised in such a composition (eg, when the host is a sulphate-reducing bacterium, eg, a *Desulfovibrio* host). In an example, the composition is a oil or petrochemical additive. In an example, the composition is a chemical additive. In an example, the composition is a disinfectant (eg, for sterilizing equipment for human or animal use, eg, for surgical or medical use, or for baby feeding). In an example, the composition is a personal hygiene composition for human or animal use. In an example, the composition is a composition for environmental use, eg, for soil treatment or environmental decontamination (eg, from sewage, or from oil, a petrochemical or a chemical, eg, when the host is a sulphate-reducing bacterium, eg, a *Desulfovibrio* host). In an example, the composition is a plant growth stimulator. In an example, the composition is a composition for use in oil, petrochemical, metal or mineral extraction. In an example, the composition is a fabric treatment or additive. In an example, the composition is an animal hide, leather or suede treatment or additive. In an example, the composition is a dye additive. In an example, the composition is a beverage (eg, beer or wine) brewing or fermentation additive (eg, when the host is a *Lactobacillus* host). In an example, the composition is a paper additive. In an example, the composition is an ink additive. In an example, the composition is a glue additive. In an example, the composition is an anti-human or animal or plant parasitic composition. In an example, the composition is an air additive (eg, for air in or produced by air conditioning equipment, eg, where the host is a *Legionella* host). In an example, the composition is an anti-freeze additive (eg, where the host is a *Legionella* host). In an example, the composition is an eyewash or ophthalmic composition (eg, a contact lens fluid). In an example, the composition is comprised by a dairy food (eg, the composition is in or is a milk or milk product; eg, wherein the host is a *Lactobacillus, Streptococcus, Lactococcus* or *Listeria* host). In an example, the composition is or is comprised by a domestic or industrial cleaning product (eg, where the host is an *E coli, Salmonella, Listeria* or *Clostridium* (eg, *botulinum*) host). In an example, the composition is comprised by a fuel. In an example, the composition is comprised by a solvent (eg, other than water). In an example, the composition is a baking additive (eg, a food baking additive). In an example, the composition is a laboratory reagent (eg, for use in biotechnology or recombinant DNA or RNA technology). In an example, the composition is comprised by a fibre retting agent. In an example, the composition is for use in a vitamin synthesis process. In an example, the composition is an anti-crop or plant spoiling composition (eg, when the host is a saprotrophic bacterium). In an example, the composition is an anti-corrosion compound, eg, for preventing or reducing metal corrosion (eg, when the host is a sulphate-reducing bacterium, eg, a *Desulfovibrio* host, eg for use in reducing or preventing corrosion of oil extraction, treatment or containment equipment; metal extraction, treatment or containment equipment; or mineral extraction, treatment or containment equipment). In an example, the composition is an agricultural or farming composition or comprised in such a composition. In an example, the composition is a silage additive. The invention provides a HM-CRISPR array, HM-CRISPR/Cas system, HM-crRNA, HM-spacer, HM-DNA, HM-Cas, HM-composition or gRNA as described herein for use in any of the compositions described in this paragraph or for use in any application described in this paragraph, eg, wherein the host cell is a microbial cell or a bacterial or archaeal cell. The invention provides a method for any application described in this paragraph, wherein the method comprises combining a HM-CRISPR array, HM-CRISPR/Cas system, HM-crRNA, HM-spacer, HM-DNA, HM-Cas, gRNA or HM-composition of the invention with a host cell (eg, microbial, bacterial or archaeal cell). In an embodiment, the host cell is not present in or on a human (or human embryo) or animal.

Any aspect of the present invention is for an industrial or domestic use, or is used in a method for such use. For example, it is for or used in agriculture, oil or petroleum industry, food or drink industry, clothing industry, packaging industry, electronics industry, computer industry, environmental industry, chemical industry, aerospace industry, automotive industry, biotechnology industry, medical industry, healthcare industry, dentistry industry, energy industry, consumer products industry, pharmaceutical industry, mining industry, cleaning industry, forestry industry, fishing industry, leisure industry, recycling industry, cosmetics industry, plastics industry, pulp or paper industry, textile industry, clothing industry, leather or suede or animal hide industry, tobacco industry or steel industry.

Herein, where there is mention of a *Desulfovibrio* host, the host can be instead a *Desulfobulbus*, *Desulfobacter*, *Desulfobacterium*, *Desulfococcus*, *Desulfomonile*, *Desulfonema*, *Desulfobotulus* or *Desulfoarculus* host or any other sulphur-reducing bacterium disclosed herein. In an embodiment for oil, water, sewage or environmental application, the host is a *Desulfovibrio capillatus* host.

Extensive microbiological analysis and 16S rRNA sequencing have indicated that the genus *Desulfovibrio* is but one of about eight different groups of sulfate-reducing eubacteria that can be isolated from the environment. Seven of these groups are gram-negative, while one represents the gram-positive bacteria (*Desulfotomaculum*). The genus *Desulfovibrio* has a rather small genome. Initial estimates were 1.7 Mbp and 1.6 Mbp for the genomes of *D. vulgaris* and *D. gigas* (which may be hosts according to the invention), respectively. This aids identification of desired target sequences (eg, a sequence in an essential or resistance gene) for use in the invention. Characterization of an indigenous plasmid of *D. desulfuricans* (which may be a host according to the invention) G200 has allowed the construction of a shuttle vector (Wall 1993, which vector may be used as a vector for the present invention), and the isolation and characterization of two bacteriophages from *D. vulgaris* Hildenborough (which may be a host according to the invention) (Seyedirashti, 1992) may provide other ways to efficiently genetically manipulate *Desulfovibrio* spp. In an example, the vector is a mu or mu-like bacteriophage.

An example host is *Desulfovibrio vulgaris* subsp. vulgaris Postgate and Campbell (ATCC® 29579™) strain designation: NCIB 8303 [DSM 644, Hildenborough].

Treatment of the bacteria with mitomycin C or UV has previously been used to induce phage from the bacteria (Driggers & Schmidt), and this is a suitable method for obtaining suitable host-matched phage for generating a vector for use in any example or aspect of the present invention.

An application of the invention is in the dairy industry (eg, cheese or butter or milk products manufacture) or fermenting (eg, wine or vinegar or soy) or beer brewing or bread making industries. For example, for dairy industry application, a method of the invention is a method for producing a dairy food, comprising fermenting a culture of lactic acid-producing bacteria (eg, *Lactobacillus* host cells) for a period of time to produce lactic acid from the culture, and thereafter inhibiting growth of the bacteria by causing expression of crRNA from one or more arrays, systems, vectors, populations or collections of the invention mixed with the bacteria, whereby lactic acid production by the bacteria is reduced or inhibited. This is useful for reducing food/drink spoiling or undesirable food/drink taste and/or odour. On an example there is included an inducible HM-array in the bacteria, wherein the method comprises adding an inducer agent after the first period.

REFERENCES

Wall, J. D., B. J. Rapp-Giles, and M. Rousset. 1993. "Characterization of a small plasmid from *Desulfovibrio desulfuricans* and its use for shuttle vector construction". J. Bacteriol. 175:4121-4128;

Seyedirashti S et al; J Gen Microbiol. 1992 July; 138(7): 1393-7, "Molecular characterization of two bacteriophages isolated from *Desulfovibrio vulgaris* NCIMB 8303 (Hildenborough)";

Driggers & Schmidt, J. gen. Virol. (1970), 6, 421-427, "Induction of Defective and Temperate Bacteriophages in *Caulobacter*".

Concepts

Altering the Relative Ratio of Sub-Populations of First and Second Bacteria in a Mixed Population of Bacteria, Eg, in Microbiota 1. Use of a host modifying (HM) CRISPR/Cas system for altering the relative ratio of sub-populations of first and second bacteria in a mixed population of bacteria, the second bacteria comprising host cells,
   for each host cell the system comprising components according to (i) to (iv):—
   (i) at least one nucleic acid sequence encoding a Cas nuclease;
   (ii) a host cell target sequence and an engineered host modifying (HM) CRISPR array comprising a spacer sequence (HM-spacer) and repeats encoding a HM-crRNA, the HM-crRNA comprising a sequence that hybridises to the host cell target sequence to guide said Cas to the target in the host cell to modify the target sequence;
   (iii) an optional tracrRNA sequence or a DNA sequence expressing a tracrRNA sequence;
   (iv) wherein said components of the system are split between the host cell and at least one nucleic acid vector that transforms the host cell, whereby the HM-crRNA guides Cas to the target to modify the host CRISPR/Cas system in the host cell; and
wherein the target sequence is modified by the Cas whereby the host cell is killed or host cell growth is reduced.
2. A host modifying (HM) CRISPR/Cas system for the use of concept 1 for modifying a target nucleotide sequence of a bacterial host cell, the system comprising components according to (i) to (iv):—
  (i) at least one nucleic acid sequence encoding a Cas nuclease;
  (ii) a host cell target sequence and an engineered host modifying (HM) CRISPR array comprising a spacer sequence (HM-spacer) and repeats encoding a HM-crRNA, the HM-crRNA comprising a sequence that is capable of hybridising to the host target sequence to guide said Cas to the target in the host cell to modify the target sequence;
  (iii) an optional tracrRNA sequence or a DNA sequence for expressing a tracrRNA sequence;
  (iv) wherein said components of the system are split between the host cell and at least one nucleic acid vector that can transform the host cell, whereby the HM-crRNA guides Cas to the target to modify the host CRISPR/Cas system in the host cell.
3. The system of concept 2, wherein the vector or vectors lack a Cas (eg, a Cas9) nuclease-encoding sequence.
4. The use or system of any preceding concept, wherein each host cell is of a strain or species found in human microbiota.
5. The use of concept 1 or 4 for (a) the alteration of the proportion of Bacteroidetes bacteria in a mixed bacterial population; (b) reducing the proportion of a Firmicutes sub-population (host cells) in a mixed bacterial population; (c) reducing the proportion of a first Firmicutes species (host cells) in a mixed population, wherein the mixed population comprises a second Firmicutes species whose growth is not inhibited by said cRNA; (d) reducing the proportion of a first gram positive bacterial species (host cells) in a mixed bacterial population, wherein the mixed population comprises a second gram positive bacterial species whose growth is not inhibited by said cRNA; (e) reducing the proportion of a bacterial species (host cells) in a mixed bacterial population, wherein the mixed population comprises a different bacterial species whose growth is not inhibited by said cRNA, wherein the first species has 16s ribosomal RNA-encoding DNA sequence that is at least 80, 82, 83, 84, 85, 90 or 95% identical to an 16s ribosomal RNA-encoding DNA sequence of the other species; (f) reducing the proportion of a first bacterial human gut microbiota species (host cells, eg, a Firmicutes) in a mixed bacterial population, wherein the mixed population comprises a different bacterial species, wherein the different species is a human gut probiotic species whose growth is not inhibited by said cRNA; or (g) reducing the proportion of a bacterial human gut microbiota species ((host cells, eg, a Firmicutes) in a mixed bacterial population, wherein the mixed population comprises a different bacterial species, wherein the different species is a human gut commensal species whose growth is not inhibited by said cRNA.
6. The system of concept 2 or 3 for (a) the alteration of the proportion of Bacteroidetes bacteria in a mixed bacterial population; (b) reducing the proportion of a Firmicutes sub-population (host cells) in a mixed bacterial population; (c) reducing the proportion of a first Firmicutes species (host cells) in a mixed population, wherein the mixed population comprises a second Firmicutes species whose growth is not inhibited by said cRNA; (d) reducing the proportion of a first gram positive bacterial species (host cells) in a mixed bacterial population, wherein the mixed population comprises a second gram positive bacterial species whose growth is not inhibited by said cRNA; (e) reducing the proportion of a bacterial species (host cells) in a mixed bacterial population, wherein the mixed population comprises a different bacterial species whose growth is not inhibited by said cRNA, wherein the first species has 16s ribosomal RNA-encoding DNA sequence that is at least 80, 82, 83, 84, 85, 90 or 95% identical to an 16s ribosomal RNA-encoding DNA sequence of the other species; (f) reducing the proportion of a first bacterial human gut microbiota species (host cells, eg, a Firmicutes) in a mixed bacterial population, wherein the mixed population comprises a different bacterial species, wherein the different species is a human gut probiotic species whose growth is not inhibited by said cRNA; or (g) reducing the proportion of a bacterial human gut microbiota species (host cells, eg, a Firmicutes) in a mixed bacterial population, wherein the mixed population comprises a different bacterial species, wherein the different species is a human gut commensal species whose growth is not inhibited by said cRNA; wherein (a) to (g) are for treating or preventing in a human or animal subject (i) a microbiota infection by said bacterial species whose proportion is reduced; or (ii) a disease or condition mediated by said bacterial species whose proportion is reduced.
7. The use or system of concept 5 or 6 for increasing the relative ratio of Bacteroidetes versus Firmicutes.
8. The use or system of any preceding concept, wherein said Cas nuclease is provided by an endogenous Type II CRISPR/Cas system of the cell.
9. The use or system of any preceding concept, wherein component (i) is endogenous to the host cell.
10. The use or system of any preceding concept, wherein the target sequence is comprised by an antibiotic resistance gene, virulence gene or essential gene of the host cell.
11. The use or system of any preceding concept, wherein the target sequence is a host chromosomal sequence.
12. The use or system of any preceding concept, wherein alternatively HM-crRNA and tracrRNA are comprised by a single guide RNA (gRNA), eg provided by the vector.
13. The use or system of any preceding concept, wherein the host cell comprises a deoxyribonucleic acid strand with a free end (HM-DNA) encoding a HM-sequence of interest and/or wherein the system comprises a sequence encoding the HM-DNA, wherein the HM-DNA comprises a sequence or sequences that are homologous respectively to a sequence or sequences in or flanking the target sequence for inserting the HM-DNA into the host genome (eg, into a chromosomal or episomal site).
14. An engineered nucleic acid vector for the use of concept 1 for modifying a bacterial host cell comprising an endogenous CRISPR/Cas system, the vector
  (g) comprising nucleic acid sequences for expressing a plurality of different crRNAs (eg, comprised by gRNAs) for use in a CRISPR/Cas system or use according to any preceding concept; and (h) optionally lacking a nucleic acid sequence encoding a Cas nuclease, wherein a first of said crRNAs is capable of hybridising to a first nucleic acid sequence in said host cell; and a second of said crRNAs is capable of hybridising to a second nucleic acid sequence in said host cell, wherein said second sequence is different from said first sequence; and (i) the first sequence is comprised by an antibiotic resistance gene (or RNA thereof) and the second sequence is comprised by an antibiotic resistance gene (or RNA thereof); optionally wherein the genes are different;

(j) the first sequence is comprised by an antibiotic resistance gene (or RNA thereof) and the second sequence is comprised by an essential or virulence gene (or RNA thereof);

(k) the first sequence is comprised by an essential gene (or RNA thereof) and the second sequence is comprised by an essential or virulence gene (or RNA thereof); or (l) the first sequence is comprised by a virulence gene (or RNA thereof) and the second sequence is comprised by an essential or virulence gene (or RNA thereof).

15. The vector of concept 14 inside a host cell comprising one or more Cas that are operable with cRNA (eg, single guide RNA) encoded by the vector.

16. The use, system or vector of any preceding concept, wherein the HM-CRISPR array comprises multiple copies of the same spacer.

17. The use, system or vector of any preceding concept, wherein the vector(s) comprises a plurality of HM-CRISPR arrays.

18. The use, system or vector of any preceding concept, wherein each vector is a virus or phage.

19. The use, system or vector of any preceding concept, wherein the system or vector comprises two, three or more of copies of nucleic acid sequences encoding crRNAs (eg, gRNAs), wherein the copies comprise the same spacer sequence for targeting a host cell sequence (eg, a virulence, resistance or essential gene sequence).

20. The use, system or vector of concept 20, wherein the copies are split between two or more vector CRISPR arrays.

21. A bacterial host cell comprising a system or vector recited in any preceding concept.

22. The use, system, vector or cell of any preceding concept, wherein the array is in combination with an antibiotic agent; or the use comprising exposing the host cells to a first antibiotic, wherein the target sequence is comprised by an antibiotic resistance gene for resistance to said first antibiotic.

23. The use, system, vector or cell of any preceding concept, wherein the host cell is a *Staphylococcus, Streptococcus, Pseudomonas, Salmonella, Listeria, E coli, Desulfovibrio*, or *Clostridium* host cell.

24. The use, system or cell of any one of concepts 1 to 13 or 16 to 23, wherein each vector is according to concept 14 or 15.

25. The use, system, vector or cell of any preceding concept wherein host cell population growth is reduced by of at least 5-fold compared to the growth of a population of said host cells not transformed with said HM-array or a nucleotide sequence encoding said gRNA.

26. The use, system, vector or cell of any preceding concept wherein host cell population growth on a surface is inhibited. In an example, the population is in contact with a human tissue surface (eg, a gut tissue surface, eg, in vivo or ex vivo).

27. The use, system, vector or cell of any preceding concept wherein the first bacteria are probiotic, commensal or symbiotic with humans (eg, in the human gut).

28. The use, system, vector or cell of any preceding concept wherein the first and second bacteria are both Firmicutes and are bacteria of different species or strains; or wherein the first bacteria are Enterobacteriaceae and the second bacteria are Firmicutes.

29. The use, system, vector or cell of any preceding concept wherein the host cells are archaeal cells instead of bacterial cells or each population is an archaeal population instead of a bacterial population.

30. The use of any one of concepts 1, 4, 5, 7-13, 16-20 and 22-29 for treating an industrial or an ex vivo medical fluid, surface, apparatus or container; or for treating a waterway, water, a beverage, a foodstuff or a cosmetic, wherein the host cell(s) are comprised by or on the fluid, surface, apparatus, container, waterway, water, beverage, foodstuff or cosmetic.

31. The use, system, vector or cell of any preceding concept, wherein the HM-cRNA or gRNA comprises a sequence that is capable of hybridising to a host cell target protospacer sequence that is a adjacent a NNAGAAW or NGGNG protospacer adjacent motif (PAM).

32. A nucleic acid vector according to, or for use in, the use, system or cell of any preceding concept, the vector comprising more than 1.4 kb of exogenous DNA sequence, wherein the exogenous DNA encodes one or more components of a CRISPR/Cas system and comprises an engineered array for expressing HM-crRNAs or gRNAs in host cells, wherein the exogenous sequence is devoid of a nucleotide sequence encoding a Cas nuclease that is cognate to the cRNA(s) or gRNA(s); wherein at least 2 different cRNAs or gRNAs are encoded by the exogenous DNA (eg, by at least 2 HM-CRISPR arrays).

33. The vector of concept 32, wherein the vector is a viral vector capable of transforming host cells.

34. The vector of concept 32 or 33, wherein the cRNAs or gRNAs are capable of hybridising in host cells to respective target protospacer sequences, wherein each protospacer sequence is comprised by an antibiotic resistance or essential host gene.

35. The vector of any one of concepts 34 to 36, wherein the host cells are cells of a human microbiota species.

EMBODIMENTS

Harnessing Wild-Type Endogenous Cas for Population Growth Inhibition & Treatment of Bacteria on Surfaces 1. Use of wild-type endogenous Cas nuclease activity of a bacterial host cell population to inhibit growth of the population, wherein the population comprises a plurality of host cells and each host cell has an endogenous CRISPR/Cas system having wild-type Cas nuclease activity, the use comprising transforming host cells of the population, wherein each transformed host cell is transformed with an engineered nucleotide sequence for providing host modifying (HM) cRNA or guide RNA (gRNA) in the host cell, the HM-cRNA or gRNA comprising a sequence that is capable of hybridising to a host cell target protospacer sequence for guiding endogenous Cas to the target, wherein the cRNA or gRNA is cognate to an endogenous Cas nuclease of the host cell that has said wild-type nuclease activity and following said transformation of the host cells growth of the population is inhibited.

The host cells may be of the same species or strain.

2. The use of embodiment 1, wherein the inhibition of host cell population growth is a reduction in growth of at least 5-fold compared to the growth of a population of said host cells not transformed with said engineered nucleotide sequence.

3. The use of embodiment 1, wherein population growth on a surface is inhibited.

4. The use of embodiment 2, wherein population growth on a surface is inhibited.

5. The use of embodiment 1, said inhibiting comprising using a HM-CRISPR/Cas system for killing or reducing the growth of said host cells, for each host cell the system comprising components according to (i) to (iv):—
   (i) at least one nucleic acid sequence encoding said Cas nuclease;
   (ii) an engineered host modifying HM-CRISPR array comprising a spacer sequence (HM-spacer) and repeats encoding said HM-crRNA:
   (iii) an optional tracrRNA sequence or a DNA sequence expressing a tracrRNA sequence;
   (iv) wherein said components of the system are split between the host cell and at least one nucleic acid vector that transforms the host cell, whereby the HM-crRNA guides said Cas to the target to modify the target sequence;
   wherein the target sequence is modified in host cells by the Cas whereby the host cells are killed or host cell growth is reduced.

6. The use of any preceding embodiment, for altering the relative ratio of sub-populations of first and second bacteria in a mixed population of bacteria, the second bacteria comprising said host cells.

7. The use of embodiment 6, wherein the host cells are of a strain or species found in human microbiota.

8. The use of embodiment 6 or 7, wherein the host cells are mixed with cells of a different strain or species, wherein the different cells are Enterobacteriaceae or bacteria that are probiotic, commensal or symbiotic with humans (eg, in the human gut).

9. The use of any preceding embodiment for the alteration of the proportion of Bacteroidetes bacteria in a mixed bacterial population comprising Bacteroidetes bacteria and other bacteria, optionally for increasing the relative ratio of Bacteroidetes versus one, more or all Firmicutes species (eg, versus *Streptococcus*) in the population.

10. The use of any preceding embodiment for altering the relative ratio of first bacteria versus second bacteria in a mixed population, wherein the first and second bacteria are both Firmicutes and are bacteria of different species or strains, the second bacteria comprising host cells. In an example, the use increases the proportion of first to versus second bacteria.

11. The use of embodiment 1, wherein the engineered nucleotide sequence is not in combination with an exogenous Cas nuclease-encoding sequence.

12. The use of embodiment 5, wherein the vector or vectors lack a Cas nuclease-encoding sequence.

13. The use of embodiment 1, wherein each host cell is of a strain or species found in human microbiota.

14. The use of embodiment 6, wherein each host cell is of a strain or species found in human microbiota.

15. The use of embodiment 13, wherein each host cell is mixed with cells of a different strain or species, wherein the different cells are Enterobacteriaceae or bacteria that are probiotic, commensal or symbiotic with humans (eg, in the human gut).

16. The use of embodiment 1, wherein the use alters the proportion of Bacteroidetes bacteria in a mixed bacterial population comprising Bacteroidetes bacteria and other bacteria, optionally wherein the use alters the relative ratio of Bacteroidetes versus one, more or all Firmicutes (eg, *Streptococcus*) species in the population.

17. The use of embodiment 1, wherein the first and second bacteria are both Firmicutes and the use alters the relative ratio of the first versus the second bacteria in the mixed population. In an example, the use increases the proportion of first to versus second bacteria.

18. The use of embodiment 1, wherein said Cas nuclease is provided by a host cell endogenous Type II CRISPR/Cas system and/or the HM-cRNA or gRNA comprises a sequence that is capable of hybridising to a host cell target protospacer sequence that is a adjacent a 5'-NNAGAAW-3' protospacer adjacent motif (PAM).

19. The use of embodiment 5, wherein said Cas nuclease is provided by a host cell endogenous Type II CRISPR/Cas system.

20. The use of embodiment 5, wherein component (iii) is endogenous to the host cell.

21. The use of embodiment 5, wherein each transformed host cell comprises an endogenous RNase III that is operable with component (ii) in the production of said HM-crRNA in the cell.

22. The use of embodiment 1, wherein the target sequence is comprised by an antibiotic resistance gene, virulence gene or essential gene of the host cell.

23. The use of embodiment 1, wherein the engineered nucleotide sequence is in combination with an antibiotic agent.

24. The use of embodiment 5, wherein the HM-crRNA and tracrRNA are comprised by a single guide RNA (gRNA).

25. The use of embodiment 1, wherein transformed host cells each comprise a deoxyribonucleic acid strand with a free end (HM-DNA) encoding a HM-sequence of interest, wherein the HM-DNA comprises a sequence or sequences that are homologous respectively to a sequence or sequences in or flanking the target sequence for inserting the HM-DNA into the host genome, wherein HM-DNA sequences are inserted into host cell genomes.

26. The use of embodiment 1, comprising expressing in host cells a plurality of different crRNAs (or gRNAs) for hybridising to host cell protospacer target sequences; wherein a first of said crRNAs (or gRNAs) is capable of hybridising to a first protospacer nucleic acid sequence; and a second of said crRNAs (or gRNAs) is capable of hybridising to a second protospacer nucleic acid sequence, wherein said second sequence is different from said first sequence; and
   (a) the first sequence is comprised by an antibiotic resistance gene (or RNA thereof) and the second sequence is comprised by an antibiotic resistance gene (or RNA thereof); optionally wherein the genes are different;
   (b) the first sequence is comprised by an antibiotic resistance gene (or RNA thereof) and the second sequence is comprised by an essential or virulence gene (or RNA thereof);
   (c) the first sequence is comprised by an essential gene (or RNA thereof) and the second sequence is comprised by an essential or virulence gene (or RNA thereof); or (d) the first sequence is comprised by a virulence gene (or RNA thereof) and the second sequence is comprised by an essential or virulence gene (or RNA thereof).

27. The use of embodiment 6, wherein the host cells are comprised by a mixed bacterial population comprised by a human or animal subject and the use (i) treats in the subject an infection by said host cells comprised by the mixed population; (ii) treats or reduces the risk in the subject of a condition or disease mediated by said host cells; (iii) reduces body odour of the human that is caused or mediated by said host cells; or (iv) is a personal hygiene treatment of the human.

28. The use of embodiment 1, wherein the use treats or reduces the risk of an infection by said host cells in a human or animal subject, wherein host cells each comprise an antibiotic resistance gene (for resistance to a first antibiotic) which comprises said target protospacer sequence, wherein the use comprises administering the engineered nucleotide sequence and the first antibiotic to the subject, wherein the infection is reduced or prevented in the subject.

29. The use of embodiment 1, wherein each engineered nucleotide sequence further comprises an antibiotic resistance gene, wherein the HM-crRNA or gRNA does not target the antibiotic resistance gene and the use comprises exposing the population to said antibiotic and a plurality of said engineered sequences, thereby promoting maintenance of HM-crRNA or gRNA-encoding sequences in host cells.

30. The use of embodiment 1, wherein the host cells are gram positive cells or *Streptococcus, Staphylococcus, Pseudomonas, Salmonella, Listeria, E coli, Desulfovibrio, V cholerae* or *Clostridium* cells.

31. The use of embodiment 1 for treating an industrial or medical fluid, surface, apparatus or container; or for treating a waterway, water, a beverage, a foodstuff or a cosmetic, wherein the host cells are comprised by or on the fluid, surface, apparatus, container, waterway, water, beverage, foodstuff or cosmetic, and wherein growth of the host cell population is inhibited thereby carrying out said treatment.

In an alternative, any embodiment is dependent from any preceding embodiment.

Aspects

Horizontal Transfer Between Carrier & Host Cells in Mixed Populations

1. A method for producing a mixed bacterial population comprising carrier bacteria, wherein the population comprises first and second sub-populations of first and second bacteria respectively, wherein the sub-populations are bacteria of first and second species that are different from each other and the second bacteria comprise a plurality of host cells, wherein the carrier bacteria are first bacteria cells each comprising an engineered nucleotide sequence for providing host cell modifying (HM) cRNA or guide RNA (gRNA) in the host cells, the HM-cRNA or gRNA comprising a sequence that is capable of hybridising to a host cell target protospacer sequence for guiding a first Cas nuclease to the target to modify the target, wherein the carrier bacteria do not comprise the target sequence, the method comprising
   a. Providing a plurality of nucleic acids, each comprising a said engineered nucleotide sequence;
   b. Combining said plurality of nucleic acids with a first mixed population comprising first and second sub-populations of the first and second bacterial species respectively, the second sub-population comprising host cells;
   c. Allowing the nucleic acids to transform cells of said first sub-population in the presence of the host cells, thereby producing a second mixed population comprising said carrier cells and said host cells, wherein said engineered nucleotide sequence comprised by carrier cells is capable of horizontal transfer to host cells to transform host cells for production of said HM-cRNA or gRNA in transformed host cells.

2. The method of aspect 1, further comprising obtaining the second mixed population.

3. The method of aspect 1, further comprising isolating a plurality of carrier cells from the second mixed population.

4. The method of aspect 1, further comprising producing said HM-cRNA or gRNA in the transformed host cells, wherein said HM-crRNA or gRNA sequence hybridises to target protospacer sequence in said transformed host cells and guides the first Cas nuclease to the target, thereby modifying the target with the first Cas nuclease.

5. The method of aspect 4, further comprising obtaining host cells comprising said target modification (eg, wherein the host cells are comprised by a mixed population comprising said first bacterial species).

6. The method of aspect 1, wherein the cRNA or gRNA is cognate to an endogenous Cas nuclease of the host cells, wherein the nuclease is said first Cas nuclease.

7. The method of aspect 1, wherein the cRNA or gRNA is cognate to an endogenous Cas nuclease of the carrier cells, wherein the nuclease is said first Cas nuclease.

8. The method of aspect 7, wherein the nuclease has wild-type nuclease activity.

9. The method of aspect 1, 6, 7 or 8, wherein the first Cas nuclease is a Cas9.

10. The method of aspect 9, wherein the Cas9 is a *Streptococcus* Cas9.

11. The method of aspect 1, wherein each engineered nucleotide sequence is comprised by a respective nucleic acid vector, wherein the vectors are capable of horizontal transfer between the carrier and host cells.

12. The method of aspect 1 or 11, wherein each engineered sequence is comprised by a respective mobile genetic element, eg, a transposon or plasmid.

13. The method of aspect 1, wherein following said transformation of host cells, growth of the host cell sub-population is inhibited.

14. The method of aspect 13, wherein the inhibition of host cell population growth is at least 5-fold compared to the growth of a population of said host cells not transformed with said engineered nucleotide sequence.

15. The method of aspect 13 or 14, wherein host cell population growth on a surface is inhibited.

In an alternative, any aspect is dependent from any preceding aspect.

In an example, the method is a method of treating or preventing a disease or condition in a human, animal or plant subject, eg, as described herein, wherein the method effects said treatment or prevention. The invention provides a mixed bacterial population obtained or obtainable by the method for such a method of treating or preventing.

In an example, the method is carried out on a mixed bacterial population of an environment, equipment, apparatus, container, waterway, water, fluid, foodstuff, beverage, microbiota, microbiome or cosmetic, eg, as described herein, wherein the method reduces the proportion of host cells compared to first cells.

In an example, the product of the method is for administration to the gut of a human or non-human animal for treating or preventing obesity, diabetes or IBD of the human or animal.

In an example, the first and second species are species of human or non-human animal gut commensal or symbiotic bacteria.

The product of the method is useful as it can be administered (eg, intranasally) to a human or animal so that the bacteria populate one or more microbiomes (eg, gut microbiome) of the human or animal. The first cells act as carriers, especially when those cells are non-pathogenic to the human or animal (eg, non-pathogenic in the gut microbiome). The microbiome can be any other microbiome or microbiota population disclosed herein.

In an example, the first second bacterial species is capable of populating the gut microbiota of a human or non-human animal, and the first bacteria are commensal or symbiotic with humans or animals. Usefully, the first bacteria can be safely administered to the human or animal and can act as a carrier for transfer of engineered sequences thereafter to host cells of the microbiota.

In an example, the engineered sequence is comprised by any array or vector disclosed herein. In an example, the method uses any CRISPR/Cas system disclosed herein.

In an example the first cell is a Bacteroidetes (eg, Bacteroidales or *Bacteroides*) cell; *Lactobacillus* (eg, *acidophilus* (eg, La-5, La-14 or NCFM), *brevis, bulgaricus, plantarum, rhammosus, fermentum, caucasicus, helveticus, lactis, reuteri* or *casei* eg, *casei* Shirota); *Bifidobacterium* (eg, *bifidum, breve, longum* or *infantis*); *Streptococcus thermophiles; Enterococcus faecium; Alistipes; Alkaliflexus; Parabacteroides; Tannerella; E coli;* or *Xylanibacter* cell.

In an example, the host cells are of a human microbiota species and the carrier cells are cells of a species that is non-pathogenic in said human microbiota, wherein the target sequence is not comprised by the genome of the carrier cells, the engineered sequence being comprised by a MGE comprising an oriT that is operable in the carrier and host cells, wherein the MGE is capable of horizontal transfer from the carrier cell to the host cell. In an example, the engineered sequence, MGE or vector is comprised by a bacteriophage, the bacteriophage being capable of infecting the first cells (carriers) to introduce the MGE into the first (carrier) cells. Thereafter the MGE is capable of horizontal transfer to host cells.

In an example, the first cells are Bacteroidetes or *Prevotella* cells; optionally wherein the MGE is capable of horizontal transfer from the first cell species to Firmicutes species (host cells) of said human microbiota. The latter is useful, for example, for treating or preventing obesity in a human when the target sequence is comprised by the Firmicutes, but not the first (carrier) cells.

The following numbered paragraphs describe some of the aspects of the invention. The invention provides, at least:

1. A method of modifying a mixed population of microbiota bacteria, the mixed population comprising a first and a second bacterial sub-population of a first and a second microbiota species respectively, wherein the species are different, the second bacterial sub-population comprising a host cell population, the method comprising combining the mixed population of microbiota bacteria with multiple copies of engineered nucleic acid sequences encoding host modifying (HM) crRNAs, and expressing HM-crRNAs in host cells, wherein each engineered nucleic acid sequence is operable with a Cas nuclease in a respective host cell to form a HM-CRISPR/Cas system and the engineered sequence comprises spacer and repeat sequences encoding a HM-crRNA; the HM-crRNA comprising a sequence that is capable of hybridizing to a host cell target sequence to guide Cas nuclease to the target sequence in the host cell; and optionally the HM-system comprises a tracrRNA sequence or a DNA sequence expressing a tracrRNA sequence; whereby HM-crRNAs guide Cas modification of host target sequences in host cells, whereby host cells are killed or the host cell population growth is reduced, thereby reducing the proportion of said host cell population and altering the relative ratio of said sub-populations of bacteria in the mixed bacterial population.

2. The method of paragraph 1, comprising using endogenous Cas nuclease of host cells for modification of target nucleotide sequences.

3. The method of paragraphs 1 or 2, comprising reducing host cell population growth by at least 5-fold compared to the growth of a control population of host cells that have not received said Cas modification.

4. The method of paragraphs 1, 2 or 3, comprising inhibiting host cell population growth on a surface.

5. The method of paragraphs 1, 2, 3, or 4, wherein the first species has a 16s ribosomal RNA-encoding DNA sequence that is at least 80% identical to an 16s ribosomal RNA-encoding DNA sequence of the host cell species, wherein the growth of the first bacteria in the mixed population is not inhibited by said HM-system.

6. The method of any of the paragraphs 1-5, wherein the first species is a human gut commensal species and/or a human gut probiotic species.

7. The method of any of the paragraphs 1-6, wherein the first species is a Bacteroidetes (eg, *Bacteroides*) and optionally the host cells are gram positive bacterial cells.

8. The method of any of the paragraphs 1-7, wherein the host cells are Firmicutes cells.

9. The method of any of the paragraphs 1-8, wherein the host cells are Firmicutes cells.

10. The method of any of the paragraphs 1-9, wherein the host cells are Firmicutes cells.

11. The method of any of the paragraph 1-10, wherein for each host cell the system comprises components according to (i) to (iv): (i) at least one nucleic acid sequence encoding a Cas nuclease; (ii) an engineered HM-CRISPR array comprising a spacer sequence and repeats encoding a HM-crRNA, the HM-crRNA comprising a sequence that hybridises to a host cell target sequence to guide said Cas to the target in the host cell to modify the target sequence; (iii) an optional tracrRNA sequence or a DNA sequence expressing a tracrRNA sequence; (iv) wherein said components of the system are split between the host cell and at least one nucleic acid vector that transforms the host cell, whereby the HM-crRNA guides Cas to the target to modify the host target sequence in the host cell; and wherein the target sequence is modified by the Cas whereby the host cell is killed or host cell growth is reduced; the method comprising introducing the vectors of (iv) into host cells and expressing said HM-crRNA in the host cells, allowing HM-cRNA to hybridise to host cell target sequences to guide Cas to the targets in the host cells to modify target sequences, whereby host cells are killed or host cell growth is reduced, thereby altering the relative ratio of said sub-populations in the mixed population of bacteria.

12. The method of paragraph 11, wherein component (i) is endogenous to each host cell.

13. The method of paragraph 12, wherein each vector is a virus or phage.

14. The method of paragraph 11, wherein each target sequence is adjacent a NNAGAAW or NGGNG protospacer adjacent motif (PAM).

15. The method of any of the paragraphs 1-14, wherein alternatively HM-crRNA and tracrRNA are comprised by a single guide RNA (gRNA), the method comprising introducing said gRNA into host cells or expressing the gRNA in host cells.

16. The method of any of the paragraphs 1-15 wherein each of the first and second species is a respective Firmicutes species and the growth of the first bacteria is not inhibited by the HM-system.

17. The method of any of the paragraphs 1-16 wherein each of the first and second species is a respective gram-positive species and the growth of the first bacteria is not inhibited by the HM-system.

18. The method of any one of the paragraphs 1-17 for treating a host cell infection of a human or animal subject, the method comprising exposing the host cells to a first antibiotic, wherein target sequences are each comprised by an antibiotic resistance gene for resistance to said first antibiotic, wherein the host cell infection is treated in the subject.

19. The method of any one of the paragraphs 1-18 for treating or reducing the risk of a disease or condition in a human or animal subject, wherein the disease or condition is mediated by said second bacterial species, wherein the first bacteria are probiotic, commensal or symbiotic with humans (eg, in human gut) and wherein the first bacteria cells do not comprise said target sequence, wherein target sequence modification by said Cas is carried out and growth of the host cells is inhibited in said subject but growth of first cells is not inhibited, wherein the disease or condition is treated or risk of the disease or condition in said subject is reduced.

20. The method of any one of the paragraphs 1-19, for treating an industrial or medical fluid, surface, apparatus or container; or for treating a waterway, water, a beverage, a foodstuff or a cosmetic, wherein said host cells are comprised by or on the fluid, surface, apparatus, container, waterway, water, beverage, foodstuff or cosmetic, wherein host cells growth is inhibited, thereby carrying out said treatment.

21. The method of any one of the paragraphs 1-20, wherein each host cell is a *Staphylococcus, Streptococcus, Pseudomonas, Salmonella, Listeria, E coli, Desulfovibrio, Vibrio* or *Clostridium* cell.

22. The method of any one of the paragraphs 1-21, wherein each target sequence is comprised by an antibiotic resistance gene, virulence gene or essential gene of the host cell.

23. The method of paragraph 7 for increasing the proportion of *Bacteroides* in the mixed population, wherein said increase is carried out.

24. The method of paragraph 23, wherein the proportion of *B thetaiotomicron* and/or *fragalis* is increased.

25. The method of paragraph 7, wherein the relative ratio of Bacteroidetes versus Firmicutes or gram-positive host cells comprised by the mixed population is increased.

26. The method of paragraph 25, wherein the proportion of *B thetaiotomicron* and/or *fragalis* is increased.

27. The method of any of the paragraph 1-24 for favouring commensal or symbiotic Bacteroidetes in a human or animal.

28. The method of paragraph 27 comprising producing a bacterial culture comprising the product of claim 1, and administering the culture to a human or animal thereby favouring commensal or symbiotic Bacteroidetes in said human or animal.

29. The method of claim 1 for Paneth cell stimulation by gut *Bacteroides* (e.g., B *thetaiotamicron*)) in a human or animal, wherein the mixed population comprises gut bacteria comprising *Bacteroides* first bacteria and the product of claim 1 is produced in said human or animal or administered to the human or animal, whereby Paneth cells are stimulated.

30. The method of claim 1 for developing an immune response to gut *Bacteroides* (e.g., *B fragalis*) in a human or animal, wherein the mixed population comprises gut bacteria comprising *Bacteroides* first bacteria and the product of claim 1 is produced in said human or animal or administered to the human or animal, whereby said immune response is developed.

FURTHER EXAMPLES

Example 1: Environmental Treatment or Decontamination

Oil, Metal & Mineral Industry

In an embodiment, the host cell is in an a mineral mine or field; in a metal mine or field; in an oil field or in oil or a petrochemical (eg, for any of these when the host is an anaerobic sulphate-reducing bacterium, eg, a *Desulfovibrio* bacterium). In an example, this composition comprises an oxidising agent (eg, sodium hypochlorite), a quaternary ammonium compound or isothiazolone or is administered simultaneously or sequentially with sodium hypochlorite, a quaternary ammonium compound or isothiazolone. An example of a suitable vector for use in the present invention for modifying a *Desulfovibrio* bacterial host is a bacteriophage. The references below describe suitable methods for isolating phage that infect *Desulfovibrio*. For use as a vector in the present invention, the bacteriophage described by any of the references may be used. Alternatively, the vector is provided by nanoparticles.

Heidelberg et al describe the two copies of the nearly identical mu-like bacteriophage DVUO189-221, DVU2847-79, DVU2688-733 and remnants of bacteriophage are present in the genome of *Desulfovibrio vulgaris* Hildenborough. Such a phage can be a basis on which to design a phage vector for use in the present invention.

REFERENCES

Seyedirashti S et al, J Gen Microbiol. 1991 July; 137(7): 1545-9, "Induction and partial purification of bacteriophages from *Desulfovibrio vulgaris* (Hildenborough) and *Desulfovibrio desulfuricans* ATCC 13541;

Seyedirashti S et al, J Gen Microbiol. 1992 July; 138(7): 1393-7, "Molecular characterization of two bacteriophages isolated from *Desulfovibrio vulgaris* NCIMB 8303 (Hildenborough)";

*Walker C B et al; Environ Microbiol. 2006 November; 8(11):1950-9, "Recovery of temperate *Desulfovibrio vulgaris* bacteriophage using a novel host strain";

*[The sequences described in this article have been deposited in GenBank under Accession No. DQ826728-DQ826732, incorporated herein by reference]

Miranda et al, Corrosion Science 48 (2006) 2417-2431, "Biocorrosion of carbon steel alloys by an hydrogenotrophic sulfate-reducing bacterium *Desulfovibrio capillatus* isolated from a Mexican oil field separator";

Eydal et al, The ISME Journal (2009) 3, 1139-1147; doi: 10.1038/ismej.2009.66; published online 11 Jun. 2009, "Bacteriophage lytic to *Desulfovibrio aespoeensis* isolated from deep groundwater";

Walker C B et al; Environ Microbiol. 2009 September; 11(9):2244-52. doi: 10.1111/j.1462-2920.2009.01946.x, "Contribution of mobile genetic elements to *Desulfovibrio vulgaris* genome plasticity".

Example 2: Water or Sewage Treatment or Environmental (Eg, Soil) Metal Decontamination An alternative application of the invention provides a HM-CRISPR array, HM-CRISPR/Cas system, HM-crRNA. HM-spacer, HM-DNA, HM-Cas or HM-composition as described herein for water or sewage treatment, eg wherein the host is a sulphate-reducing bacterium, eg, a *Desulfovibrio* bacterium.

In an example, the target nucleotide sequence in the host is a sequence of a heavy metal resistance gene. Optionally also the host is a *Desulfovibrio* bacterium, eg, *D vulgaris*.

Example 3: Medical Use

An alternative application of the invention provides a HM-CRISPR array, HM-CRISPR/Cas system, HM-crRNA. HM-spacer, HM-DNA, HM-Cas or HM-composition as described herein for treating, preventing or reducing (eg, reducing spread of or expansion of) a bacterial infection in a human or animal.

In a first example, the infection is caused by MRSA host cells in a human. The host cell is a *Staphylococcus aureus* host cell and a HM-array of the invention is contained in a population of Class I, II or III *Staphylococcus* packaged phage (Caudovirales or Myoviridae phage). The phage population is administered to a MRSA-infected patient with or without methicillin or vancomycin. In one trial, the phage HM-arrays target (i) the region of 20 nucleotides at the 3' of the leader promoter of endogenous *S aureus* CRISPR arrays and (ii) the methicillin resistance genes in the host cells. When vancomycin is administered, a lower dose than usual is administered to the patient. It is expected that host cell infection will be knocked-down and resistance to the phage medicine will not be established or established at a lower rate or severity than usual. In other trials, the design is identical except that the phage in those trials also target the essential *S aureus* gene ftsZ (Liang et al, Int J Infect Dis. 2015 January; 30:1-6. doi: 10.1016/j.ijid.2014.09.015. Epub 2014 Nov. 5, "Inhibiting the growth of methicillin-resistant *Staphylococcus aureus* in vitro with antisense peptide nucleic acid conjugates targeting the ftsZ gene").

A further trial repeated the trials above, but phage K endolysin was administered in addition or instead of methicillin.

REFERENCES

1. Jiang W et al, Nucleic Acids Res. 2013 November; 41(20):e188. doi: 10.1093/nar/gkt780. Epub 2013 Sep. 2, "Demonstration of CRISPR/Cas9/sgRNA-mediated targeted gene modification in *Arabidopsis*, tobacco, sorghum and rice";
2. Seed K D et al, Nature. 2013 Feb. 28; 494(7438):489-91. doi: 10.1038/nature11927, "A bacteriophage encodes its own CRISPR/Cas adaptive response to evade host innate immunity";
3. Semenova E et al, Proc Natl Acad Sci USA. 2011 Jun. 21; 108(25):10098-103. doi: 10.1073/pnas.1104144108. Epub 2011 Jun. 6, "Interference by clustered regularly interspaced short palindromic repeat (CRISPR) RNA is governed by a seed sequence";
4. Heler R et al, Mol Microbiol. 2014 July; 93(1):1-9. doi: 10.1111/mmi.12640. Epub 2014 Jun. 4, "Adapting to new threats: the generation of memory by CRISPR-Cas immune systems";
5. Gomaa A et al, MBio. 2014 Jan. 28; 5(1):e00928-13. doi: 10.1128/mBio.00928-13, "Programmable removal of bacterial strains by use of genome-targeting CRISPR-Cas systems";
6. Fineran P C et al, Proc Natl Acad Sci USA. 2014 Apr. 22; 111(16):E1629-38. doi: 10.1073/pnas.1400071111. Epub 2014 Apr. 7, "Degenerate target sites mediate rapid primed CRISPR adaptation";
7. Wiedenheft et al, Nature. 2011 Sep. 21; 477(7365):486-9. doi: 10.1038/nature10402, "Structures of the RNA-guided surveillance complex from a bacterial immune system;
8. Bondy-Denomy et al, Nature 493, 429-432 (17 Jan. 2013) doi:10.1038/nature11723, "Bacteriophage genes that inactivate the CRISPR/Cas bacterial immune system";
9. Nunez J K et al, Nature. 2015 Mar. 12; 519(7542):193-8. doi: 10.1038/nature14237. Epub 2015 Feb. 18, "Integrase-mediated spacer acquisition during CRISPR-Cas adaptive immunity".

Example 4: Altering the Ratio of Bacteria in a Mixed Gut Microbiota Population

Alteration of the ratio of bacteria will be performed according to the present example, which is described by reference to knocking-down *Clostridium dificile* bacteria in a mixed gut microbiota sample. The sample will contain *Bacteroides* and metronidazole (MTZ)-resistant *C dificile* strain 630 sub-populations. Ex vivo the mixed population is combined with a population of carrier bacteria (*Lactobacillus acidophilus* La-14 and/or La-5) that have been engineered according to the invention to contain CRISPR arrays.

Each CRISPR array is comprised on a plasmid that is compatible with the carrier bacterium and *C dificile* cells. The array is comprised by a *Bacteroides thetaiotamicron* CTnDot transposon that also comprises oriT, an intDOT sequence, a tetQ-rteA-rteB operon, rteC and the operon xis2c-xis2d-orf3-exc. In one experiment, mob and tra operons are excluded (instead relying on these supplied by *Bacteroides* cells to which the transposons are transferred in the mixture combined with the carrier bacteria). In another experiment, the mob and tra operons are included in the transposons.

Protein translocation across the cytoplasmic membrane is an essential process in all bacteria. The Sec system, comprising at its core an ATPase, SecA, and a membrane channel, SecYEG, is responsible for the majority of this protein transport. A second parallel Sec system has been described in a number of Gram-positive species. This accessory Sec system is characterized by the presence of a second copy of the energizing ATPase, SecA2; where it has been studied, SecA2 is responsible for the translocation of a subset of Sec substrates. In common with many pathogenic Gram-positive species, *Clostridium difficile* possesses two copies of SecA. Export of the S-layer proteins (SLPs) and an additional cell wall protein (CwpV) is dependent on SecA2. Accumulation of the cytoplasmic precursor of the SLPs SipA and other cell wall proteins is observed in cells expressing dominant-negative secA1 or secA2 alleles, concomitant with a decrease in the levels of mature SLPs in the cell wall. Furthermore, expression of either dominant-negative allele or antisense RNA knockdown of SecA1 or SecA2 dramatically impairs growth, indicating that both Sec systems are essential in *C. difficile*.

*C. difficile* Strain 630 (epidemic type X) has a single circular chromosome with 4,290,252 bp (G+C content=29.06%) and a circular plasmid with 7,881 bp (G+C content=27.9%). The whole genome has been sequenced and found that 11% of the genome consists of mobile genetic elements such as conjugative transposons. These elements provide *C. difficile* with the genes responsible for its antimicrobial resistance, virulence, host interaction and the production of surface structures. For example, the cdeA gene of *C. difficile* produces a multidrug efflux pump which was shown to be homologous to known efflux transporters in the multidrug and toxic compound extrusion (MATE) family. The protein facilitates energy-dependent and sodium-coupled efflux of drugs from cells. In addition, the cme gene in *C. difficile* has been shown to provide multidrug resistance in other bacteria.

The array comprises a R1-S1-R1' CRISPR unit for targeting a sequence in an essential gene (SecA2) of *C dificile* cells. In another experiment, targeting is to the cdeA gene in the presence of MTZ and optionally one or more other anti-*C dificile* antibiotics. Each spacer (S) comprises a 20mer nucleotide sequence of the SecA or cdeA gene, wherein the sequence comprises a PAM of a *C dificile* strain 630 CRISPR/Cas system that is cognate to the repeat sequences. Each repeat is identical to a *C dificile* strain 630 repeat and has the sequence (SEQ ID NO: 118)
5'-ATTTACATACCACTTAGTTAATATAAAAC-3'

In an alternative set of experiments, the following sequence is used for the repeats:

(SEQ ID NO: 119)
5'-GTTTTATATTAACTAAGTGGTATGTAAAT-3'

The repeats function with Cas that is endogenous to the *C dificile* cells in the mixed population. The mixed population of bacteria is retrieved as an ex vivo sample from a stool sample of a human patient suffering from *C dificile* infection. The mixed population is mixed with the carrier bacteria in vitro and incubated at 37 degrees centigrade under anaerobic conditions to simulate gut conditions in the presence of tetracycline. It is expected that transposons containing the CRISPR arrays will be transferred to *Bacteroides* and *C dificile* cells in the mixture. Furthermore, it is expected that the target sites in the latter cells will be cut by Cas nuclease action, thus reducing the proportion of *C dificile* in the mixed population (and increasing the ratio of *Bacteroides* versus *C dificile*).

In a follow-on experiment, a drink is produced comprising the carrier bacteria and this is consumed by the human patient once or twice for several consecutive days. The patient is also administered with tetracycline during the treatment period. It is expected that stool analysis will reveal that the proportion of *C dificile* in the stool samples will reduce (and the ratio of *Bacteroides* versus *C dificile* will increase).

Example 5: Cholera Treatment or Prevention

Reference is made to the World Health Organisation (WHO) Cholera Fact sheet No 107 (Updated July 2015). Cholera is an acute diarrhoeal infection caused by ingestion of food or water contaminated with the bacterium *Vibrio cholerae*. Researchers have estimated that every year, there are roughly 1.4 to 4.3 million cases, and 28 000 to 142 000 deaths per year worldwide due to cholera. The short incubation period of 2 hours to 5 days, is a factor that triggers the potentially explosive pattern of outbreaks. Cholera is an extremely virulent disease. It affects both children and adults and can kill within hours. About 80% of people infected with *V. cholerae* do not develop any symptoms, although the bacteria are present in their faeces for 1-10 days after infection and are shed back into the environment, potentially infecting other people. Among people who develop symptoms, 80% have mild or moderate symptoms, while around 20% develop acute watery diarrhoea with severe dehydration. This can lead to death if left untreated.

Two serogroups of *V. cholerae*—O1 and O139—cause outbreaks. *V. cholerae O*1 causes the majority of outbreaks, while O139—first identified in Bangladesh in 1992—is confined to South-East Asia. Non-O1 and non-O139 *V. cholerae* can cause mild diarrhoea but do not generate epidemics. Recently, new variant strains have been detected in several parts of Asia and Africa. Observations suggest that these strains cause more severe cholera with higher case fatality rates. The main reservoirs of *V. cholerae* are people and water-borne sources such as brackish water and estuaries, often associated with algal blooms.

Reference is made to Nature. 2013 Feb. 28; 494(7438): 489-91. doi: 10.1038/nature11927, "A bacteriophage encodes its own CRISPR/Cas adaptive response to evade host innate immunity", Seed K D et al (incorporated herein by reference), which describes that *Vibrio cholerae* serogroup O1 is the primary causative agent of the severe diarrhoeal disease cholera, and lytic *V. cholerae* phages have been implicated in impacting disease burden particularly in the endemic region surrounding the Bay of Bengal. The authors described the isolation of the ICP1 (for the International Centre for Diarrhoeal Disease Research, Bangladesh cholera phage 1)-related, *V. cholerae O*1-specific virulent myoviruses that are omnipresent amongst cholera patient rice-water stool samples collected from 2001 to 201114 and in the study described in their publication.

The authors explain that ICP1 CRISPR/Cas system consists of two CRISPR loci (designated CR1 and CR2) and six cas genes whose organization and protein products are most homologous to Cas proteins of the type 1-F (*Yersinia pestis*) subtype system 17. *V. cholerae* is divided into two biotypes, classical and El Tor, the former of which is associated with earlier pandemics and has since been replaced by the El Tor biotype18. The classical strain, *V. cholerae* 0395, has a CRISPR/Cas system belonging to the type I-E (*Escherichia coli*) subtype17, and to date there has not been any description of El Tor strains possessing a CRISPR/Cas system. Thus, the origin of the CRISPR/Cas system in ICP1 phage is unknown.

The RNA sequence of the CR1 and CR2 consensus direct repeat with the partially palindromic sequence forming the predicted stem in the crRNA underlined is as follows:—

[SEQ ID NO: 75]
GUUAGCAGCCGCAUAGGCUGCUUAAAUA

In an example of the invention, the or each repeat of the array comprises or consists of a sequence that is at least 80, 90, 95, 96, 97, 98 or 99% identical to SEQ ID NO: 75 (or is identical to SEQ ID NO: 75).

The majority of spacers in the ICP1 CRISPR show 100% identity to sequences within an 18 kb island found in a subset of *V cholerae* strains that include the classical strain O395 isolated in India in 1964, El Tor strain MJ-1236 isolated in Bangladesh in 1994, and several El Tor strains collected at the ICDDR, B between 2001-2011. The 18 kb island resembles the phage inducible chromosomal islands (PICIs) of Gram-positive bacteria, including the prototype *Staphylococcus aureus* pathogenicity islands (SaPIs). SaPIs are induced to excise, circularize and replicate following infection by certain phages. They use varied mechanisms to interfere with the phage reproduction cycle to enable their own promiscuous spread and this can protect the surrounding bacterial population from further phage predation. The organization of the *V. cholerae* 18 kb island targeted by the ICP1 CRISPR/Cas system is similar in length, base composition, and organization to that observed in the SaPIs subset of PICIs, with an integrase homologue at one end and a GC content lower than that of the host species (37% compared to 47.5%). The 18 kb element is therefore referred to as the *V. cholerae* PICI-like element (PLE).

```
V. cholerae PLE(wt)
AAT TTA AAT AGG GAA GAT AAG CAA AGG GTT GAC
 N   L   N   R   E   D   K   Q   R   V   D
```

[the nucleotide sequence=SEQ ID NO: 76 (The 32 bp protospacer sequence (SEQ ID NO: 77) is shaded in grey, the present disclosure includes a sequence that starts at the first T shaded grey and ends at the last C shaded grey; and the amino acid sequence=SEQ ID NO: 78]

Seed et al determined that the CR1 and CR2 arrays operate by recognition of a GA PAM sequence. Seed et al also found that the majority of spacers in the studied ICP1-related phage CRISPR arrays showed identity to *V. cholera* PLEs. The spacers are shown in the following Table 3; S1 in an array of the invention is, for example, selected from any one of these sequences. In an embodiment, S1 is selected from any one of the underlined sequences.

In an example, the array of the invention (or each array) is an engineered array comprising one, more or all of the underlined spacer sequences. The array spacers can comprise a non-naturally occurring arrangement as follows:—

For example, the array comprises a spacer of type 8a and/or 9a, and 0, 1, 2, 3, 4, 5 or 6 (but not 7) of types 1a-7a. For example, the array comprises a spacer of type 4b, and 0, 1 or 2, 3 (but not 3 or more) of 1b-3b. For example, the array comprises a spacer of type 8a and one, more or all of 9a, 4b, 1c, 3d, 1e and 3e. For example, the array comprises a spacer of type 9a and one, more or all of 8a, 4b, 1c, 3d, 1e and 3e. For example, the array comprises a spacer of type 4b and one, more or all of 8a, 9a, 1c, 3d, 1e and 3e. For example, the array comprises a spacer of type 1c and one, more or all of 8a, 9a, 4b, 3d, 1e and 3e. For example, the array comprises a spacer of type 3d and one, more or all of 8a, 9a, 4b, 1c, 1e and 3e. For example, the array comprises a spacer of type 1e and one, more or all of 8a, 9a, 4b, 1c, 3d and 3e. For example, the array comprises a spacer of type 3e and one, more or all of 8a, 9a, 4b, 1c, 3d and 1e.

In another non-naturally occurring arrangement, the vector comprises first and second arrays of the invention, wherein the arrays comprise at least two spacers selected from 1a to 1g (eg, at least two spacers selected from 8a, 9a, 4b, 1c, 3d, 1e and 3e) wherein the spacers are not spacers of the same ICP1 phage genome, eg, not all spacers of ICP1_2011_A, or ICP1_2006_E, or ICP1_2005_A or ICP1_2004_A (by reference to the spacers in the table above). Thus, in an embodiment:—

The first array comprises an ICP1_2011_A spacer sequence (eg, 8a and/or 9a), and the second array comprises a spacer sequence of ICP1_2006_E, ICP1_2005_A or ICP1_2004_A (eg, one or more spacers selected from 4b, 1c, 3d, 1e and 3e).

In an example, the vector comprises 1, 2, 3, 4, 5, 6 or all 7 spacer types selected from 8a, 9a, 4b, 1c, 3d, 1e and 3e. In an example, the vector comprises multiple copies of one or more of said selected types. In an example, the, some or each array in the vector comprises a first spacer (nearest the promoter of the array), wherein the first spacer is selected from 8a, 9a, 4b, 1c, 3d, 1e and 3e. Positioning in this way is advantageous as natural arrays use the first spacer most frequently.

Reference is made to Nucleic Acids Res. 2013 October; 41(19):9033-48. doi: 10.1093/nar/gkt654. Epub 2013 Jul. 30, "High-resolution definition of the *Vibrio cholerae* essential gene set with hidden Markov model-based analyses of transposon-insertion sequencing data", Chao M C et al (incorporated by reference), which discloses the coupling of high-density transposon mutagenesis to high-throughput DNA sequencing (transposon-insertion sequencing) enables simultaneous and genome-wide assessment of the contributions of individual loci to bacterial growth and survival. HMM results indicate that 128 genes are required for optimal growth of *V. cholerae* in LB. The target sequence of the invention can be a sequence of any one of these genes (which gene names and sequences are explicitly incorporated herein by reference for use in providing target sequences of the vectors of the present invention and for possible inclusion in the claims herein).

For example, insertion mutants in vc0309 and vc0753, which had average reads of 5.6 and 4.7, respectively, were severely attenuated in growth. Likewise, vc0237 and vc1773 mutants were less fit than wild-type cells in an in vitro competition experiment. The list also includes a number of antitoxin genes from putative toxin/antitoxin addiction loci, including vca0360, vca0477, vca0486 and vca0488. Such genes are presumed to be essential when associated with active toxins.

The authors found the essential *V cholerae* genes in Table 4. The authors identified more than 200 intergenic regions that appear to be essential.

Thus, in an example of the invention when the host cell is a *Vibrio cholerae* cell, the target sequence is a vc0631, vc2024, vc2626, vc2763-vc2767 or vc2768-vc2770 sequence. In an example of the invention when the host cell is a *Vibrio cholerae* cell, the target sequence is a vc0309 and vc0753, vc0237 and vc1773, vca0360, vca0477, vca0486 or vca0488 sequence.

Reference is made to Infect Immun. 2015 September; 83(9):3381-95. doi: 10.1128/IAI.00411-15. Epub 2015 Jun. 8, "A Genome-Wide Screen Reveals that the *Vibrio cholerae* Phosphoenolpyruvate Phosphotransferase System Modulates Virulence Gene Expression", Wang Q et al (incorporated by reference). The authors used a transposon insertion site (TIS) sequencing-based strategy to identify new factors required for expression of tcpA, which encodes the major subunit of TCP, the organism's chief intestinal colonization factor. Besides identifying most of the genes known to modulate tcpA expression, the screen yielded ptsI and ptsH, which encode the enzyme I (EI) and Hpr components of the *V. cholerae* phosphoenolpyruvate phosphotransferase system (PTS). In addition to reduced expression of TcpA, strains lacking EI, Hpr, or the associated EIIA(Glc) protein produced less cholera toxin (CT) and had a diminished capacity to colonize the infant mouse intestine. The PTS modulates virulence gene expression by regulating expression of tcpPH and aphAB, which themselves control expression of toxT, the central activator of virulence gene expression.

Thus, in an example of the invention when the host cell is a *Vibrio cholerae* cell, the target sequence is a tcpA sequence or a tcpA modulator sequence (ie, a nucleotide sequence that modulates tcpA itself or via its expression product). For example, the sequence is a ptsI or ptsH sequence. In an example, the target sequence is sequence of the phosphoenolpyruvate phosphotransferase system (PTS), or a tcpPH, aphAB or toxT sequence. In an example the target sequence is a gene sequence encoding EIIA(Glc) protein.

Suitable target sequences for the present invention are also as shown in Table 5—sequence of any one of the following (Pathogenicity genes are underlined).

In an embodiment, the cell is a *Vibrio* (eg, cholera) cell and the target sequence is a sequence if any of these genes.

Pathogenicity genes are shown in Table 6.

In an embodiment, the cell is a *Vibrio* (eg, cholera) cell and the target sequence is a sequence if any of these genes.

Genes from TCP and CTX Pathogenicity Islands

In an embodiment, the cell is a *Vibrio* (eg, cholera) cell and the target sequence is an ace, cep, ctxA, ctxB, orfU, zot, rstA, rstB, rstR, acfA, acfB, acfC, tagE, aldA, int, tagA, tagD, tcpA, tcpB, tcpC, tcpD, tcpE, tcpF, tcpH, tcpI, tcpJ, tcpP, tcpQ, tcpR, tcpS, tcpT or toxT sequence.

Example 6: Specific Microbiota Bacterial Population Growth Inhibition by Harnessing Wild-Type Endogenous Cas

1. Material and Methods 1. 1. Strains

The following strains were used in the course of this Example and Examples 7 and 8: *E. coli* MG1655, *E. coli* TOP10, *Streptococcus thermophilus* LMD-9 (ATCC BAA-491, Manassas, Virginia), *Streptococcus thermophilus* DSM 20617(T) (DSMZ, Braunschweig, Germany), *Lactococcus lactis* MG1363 and *Streptococcus mutans* Clarke 1924 DSM 20523 (DSMZ, Braunschweig, Germany).

During the course of media selection and testing of the genetic constructs different Streptococci strains were used. *Streptococcus thermophilus* LMD-9 (ATCC BAA-491) and *Escherichia coli* TOP10 were considered because of their compatible growth requirements. All strains were cultivated in Todd-Hewitt broth (TH) (T1438 Sigma-Aldrich), in aerobic conditions and at 37° C., unless elsewhere indicated. The strains were stored in 25% glycerol at −80° C.

1. 2. Differential Growth Media

All strains were grown on TH media at 37° C. for 20 hours. Selective media for *S. thermophilus* was TH media supplemented with 3 g $l^{-1}$ of 2-phenylethanol (PEA). PEA was added to the media and autoclaved at 121° C. for 15 minutes at 15 psi. Agar plates were prepared by adding 1.5% (wt/vol) agar to the corresponding media. When necessary for selection or plasmid maintenance 30 μg $ml^{-1}$ kanamycin was used for both *S. thermophilus* strains and *E. coli*, and 500 μg $ml^{-1}$ for *S. mutans*.

In some cases, depending on the strain and plasmid, a longer incubation, up to 48 hours, may be needed to see growth on media supplemented with PEA. In order to control for the viability of the organisms used, a control TH agar must be done in parallel.

1. 3. Cloning

*E. coli* (One Shot® ThermoFischer TOP10 Chemically Competent cells) was used in all subcloning procedures. PCR was carried out using Phusion polymerase. All PCR products were purified with Nucleospin Gel and PCR Clean-up by Macherey-Nagel following the manufacturer's protocol. The purified fragments were digested with restriction enzyme DpnI in IX FD buffer with 1 μl enzyme in a total volume of 34 μl. The digested reaction was again purified with Nucleospin Gel and PCR Clean-up by Macherey-Nagel following the manufacturer's protocol. Gibson assembly was performed in 10 μl reactions following the manufacturer's protocol (NewEngland Biolab).

Plasmid DNA was prepared using Qiagen kits according to the manufacturer's instructions. Modifications for Gram-positive strains included growing bacteria in a medium supplemented with 0.5% glycine and lysozyme to facilitate cell lysis.

1. 4. Transformation 1. 4.1 Electro-Competent *E. coli* Cells and Transformation Commercially electrocompetent cells were used for cloning and the experiments (One Shot® ThermoFischer TOP10 Chemically Competent *E. coli*). Electroporation was done using standard settings: 1800 V, 25 μF and 200Ω using an Electro Cell Manipulator (BTX Harvard Apparatus ECM630). Following the pulse, 1 ml LB-SOC media was added and the cells were incubated at 37° C. for 1 hour. The transformed cells were plated in LB-agar containing 50 μg $ml^{-1}$ of kanamycin.

1. 4.2 Preparation of Electro-Competent *S. thermophilus* Cells

The electroporation protocol was modified from Somkuti and Steinberg, 1988. An overnight culture of *Streptococcus thermophilus* in TH Broth supplemented with 40 mM DL-threonine (T8375 Sigma-Aldrich) was diluted 100-fold in 5 ml of the same media and grown to an $OD_{600}$ between 0.3-0.5 (approximately 2.5 hours after inoculation). The cells were collected by centrifugation at 10,000×g for 10 min at 4° C. and washed three times with 5 ml of ice cold wash buffer (0.5 M sucrose+10% glycerol). After the cells were washed, they were suspended to an $OD_{600}$ of 15-30 in electroporation buffer (0.5 M sucrose, 10% glycerol and 1 mM $MgCl_2$). The cells in the electroporation buffer may be kept at 4° C. until use (within one hour) or aliquot 50 μl in eppendorf tubes, freezing them in liquid nitrogen and stored at −80° C. for later use.

1. 4.3 Electroporation *S. thermophilus* Cells

1 μl of purified plasmid DNA was added to 50 μl of the cell suspension and electroporation was carried out in 2 mm-gap electroporation cuvettes pre-cooled. The electroporation setting were 2500 V, 25 μF and 200Ω using an Electro Cell Manipulator (BTX Harvard Apparatus ECM630). Immediately after the electric pulse, 1 ml of TH broth was added to the cells and the suspension was kept on ice for 10 minutes, subsequently the cells were incubated for 3 h at 37° C. After allowing time for expression of the resistance gene the cells were plated onto TH-agar plates containing 30 μg $ml^{-1}$ of kanamycin. Depending on the construct, colonies were visible between 12 and 48 h of incubation at 37° C.

1. 5. Construction of XylS Plasmid

All the plasmids used in this work were based on pBAV1K-T5, which is a broad-host range expression vector derived from the a cryptic plasmid pWV01 from *Streptococcus cremoris* (Bryksin & Matsumura, 2010), the backbone was amplified using that contain overhangs for assembly with the other fragments using Gibson's method.

The xylose inducible system was constructed by cloning the promoter gyrA in front of the XylR repressor (FIG. 1). The XylR repressor was amplified from *Bacillus Subtilis* strain SCK6 (Zhang et al. 2011) with the a reverse primer that includes an overhang for Gibson assembly and a forward primer, that is an ultramer used to introduce the gyrA promoter (Xie et al. 2013) and the corresponding overhang for assembly into pBAV1KT5 backbone. The resulting fragment was flanked by an mCherry amplified from pCL002 (unpublished work) with an ultramer that include Pldha+ PxylA hybrid promoter (Xie et al. 2013). The three resulting PCR products were assembled in a Gibson Master Mix® (NewEngland Biolab) according to manufacturer's instructions. The product was finally transformed in *E. coli* TOP10 electrocompetent cells. See FIG. 1.

1. 6. Design and Construction of CRISPR Array Plasmid

Figure 2:
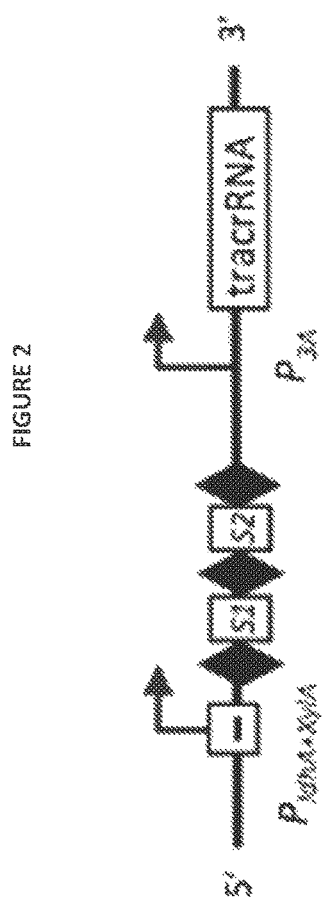
FIG. 2 shows a ST1-CRISPR array.

*Streptococcus thermophilus* has 4 distinct CRISPR systems (Sapranauskas, et al. 2011), for this work the type II CRISPR1 (ST1-CRISPR) system was chosen. The design of the target sequence was based on the available genome sequence of LMD-9 (GenBank: CP000419.1). The ST1-CRISPR array was designed to contain only the CRISPR array repeats and spacers under a xylose inducible promoter (Xie et al. 2013), followed by the corresponding tracrRNA under a strong constitutive promoter for Streptococci species (Sorg et al. 2014) (FIG. 2, SEQ ID Nos:).

The tracrRNA plays a role in the maturation of crRNA and it is processed by *S. thermophilus* endogenous RNase III, forming a complex with crRNA. This complex acts as a guide for the endonuclease ST1-Cas9 (Horvath & Barrangou, 2010). After transcription of the synthetic array from the xylose inducible promoter, the endogenous Cas9 and RNAses will process it into a functional gRNA. The gRNA/Cas9 complex will cause a double stranded break at the target location.

The design of the array used 2 specific target sequences high on GC content and a reduced portion of the tracrRNA (ie, a less than complete tracrRNA sequence), which has been suggested not to be necessary for proper maturation of crRNA (Horvath & Barrangou, 2010).

The 2 targets were an essential gene (DNA polymerase III subunit alpha) and an antibiotic resistance gene (tetA-like gene) (SEQ ID NOs:).

Primers were used to amplify pBAV1KT5-XylR-PldhA backbone. The CRISPR array gBlock and the backbone with overhangs were assembled in a Gibson Master Mix® according to manufacturer's instructions (NewEngland Biolabs). The product was finally transformed in *E. coli* TOP10 electrocompetent cells.

1. 7. Characterization of Xylose Inducible System in *Streptococcus thermophilus* LMD-9

Overnight stationary-phase cultures were diluted 1:100 into TH broth with corresponding antibiotic. Mid-log cells were induced with different concentration of D-(+)-xylose (0, 0.001, 0.01, 0.1, 0.5 and 1% wt/vol) and the cell cultures were measured either directly in medium to assess the extent of autofluorescence of the media, on the cell suspension or the suspension buffer (PBS buffer). 20 µl samples of the cell cultures were diluted 1/10 on PBS buffer, on 96-well plates with flat bottoms. Fluorescence of cell suspensions or media was read on a plate reader. mCherry fluorescence was measured using an excitation wavelength of 558 nm and emission at 612 nm. Absorbance of the resuspended cells was measured at OD 600 nm. A minimum of three independent biological replicates was done for each experiment.

1.8. Activation of CRISPR Array in *S. thermophilus*

*S. thermophilus* LMD-9 and *E. coli* TOP10 both with the plasmid containing the CRISPR array targeting the DNA polymerase III and tetA of *S. thermophilus* were grown overnight in 3 ml cultures supplemented with 30 µg ml$^{-1}$ of kanamycin for plasmid maintenance. The next day 96 well deep well plates were inoculated with 500 µl of 1/100 of overnight culture in fresh TH media, supplemented with 30 µg ml$^{-1}$ kanamycin. Mid-log cell cultures were induced with 1% xylose. The killing effect was tested on *S. thermophilus* and *E. coli* alone. For each strain and condition tested a negative control was kept without xylose. The cells were grown till ~OD 0.5 and next 10-fold serially diluted in TH media and using a 96-well replicator (Mettler Toledo Liquidator™ 96) 5 µL volume drops were spotted on TH agar and TH agar supplemented with g l$^{-1}$ PEA plates. The plates were incubated for 24H at 37° C. and the colony forming units (CFU) were calculated from triplicate measurements.

2. Results 2.1 Growth Condition and Selective Media

We first set out to establish the bacterial strains and cultivation protocol that would support growth for all strains we planned to use for the co-cultivation experiments. We used *S. thermophilus* strain LMD-9 which was able to support a similar growth as *E. coli* in TH broth at 37° C. (FIG. 3).

Distinguishing the different bacteria from a mixed culture is important in order to determine cell number of the different species. With MacConkey agar is possible to selectively grow *E. coli*, however there is no specific media for selective growth of *S. thermophilus*. PEA agar is a selective medium that is used for the isolation of gram-positive (*S. thermophilus*) from gram-negative (*E. coli*). Additionally, we found that different concentrations of PEA partially inhibit the growth of other gram positives, which allow for selection between the other gram-positive bacteria used in this work (FIG. 4). 3 g l$^{-1}$ of PEA proved to selectively grow *S. thermophilus* LMD-9 while limiting growth of *E. coli*.

2.2 Design and Validation of Inducible System

An induction system for *Streptococcus* species was previously developed based on the *Bacillus megaterium* xylose operon (FIG. 5) by creating a heterologous xylose induction cassette (Xyl-S). The xylR and xylA promoters were replaced with *S. mutans*' constitutively expressed gyrA and ldh promoters respectively. This expression cassette for *Streptococcus* species showed differences in sensitivity and expression levels between different species, however the system was not tested in *S. thermophilus* (Xie et al. 2013). Therefore we first set out to validate the xylose induction cassette in *S. thermophilus*.

An alternative version of the induction cassette was constructed by only replacing the xylR promoter with the *S. mutans*' gyrA promoter but left the endogenous *B. megaterium* xylA promoter intact. During the design of the xylose inducible system we considered both versions of the inducible promoter, the natural $P_{xylA}$ promoter found in *Bacillus megaterium* and a hybrid promoter of the highly conserved promoter $P_{ldha}$ fused with the repressor binding sites of $P_{xylA}$ promoter (FIG. 5). Only a few *Streptococcus* species have been reported to metabolize xylose, and thus the presence of a regulatory machinery to recognize the xylA promoter in the other *Streptococcus* species is not likely. Therefore we constructed both xylose induction systems but only tested the inducibility of mCherry with the $P_{ldha+xylA}$ system.

Figure 6:
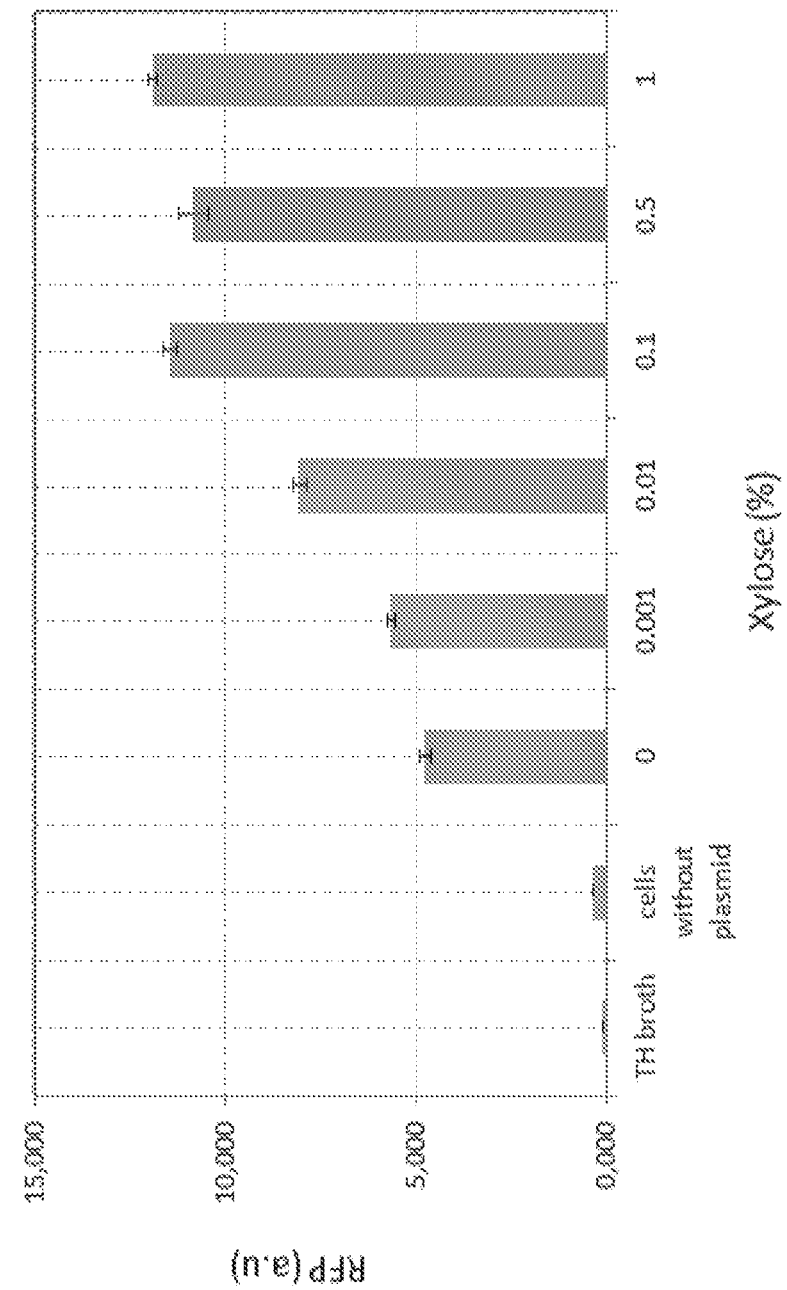
FIG. 6 demonstrated characterization of the xylose inducible cassette in Streptococcus thermophilus LMD-9 with the plasmid pBAV1KT5-XylR-mCherry-Pldha. A clear response in fluorescence can be observed with increasing amount of xylose.

In order to determine mCherry inducible expression by xylose, mid-log cultures of cells with the plasmid (pBAV1KT5-XylR-mCherry-P$_{ldha+XylA}$) were induced with different concentrations of xylose. Six hours after the induction we measured mCherry fluorescence in the cultures, where we observed substantially higher overall expression levels in cells carrying the plasmid (FIG. 6). It is worth noticing that the system showed a substantial level of basal expression even in the cultures where xylose was not added. This means that the system is 'leaky' and in context of the kill-array this can lead to cell death even before the system is induced with xylose. However, in the subsequent course of this study we used both versions of the plasmid (pBAV1KT5-XylR-mCherry-P$_{ldha+XylA}$ and pBAV1KT5-XylR-mCherry-P$_y$lA).

2. 3 Design of CRISPR/CAS9 Array

Figure 7:
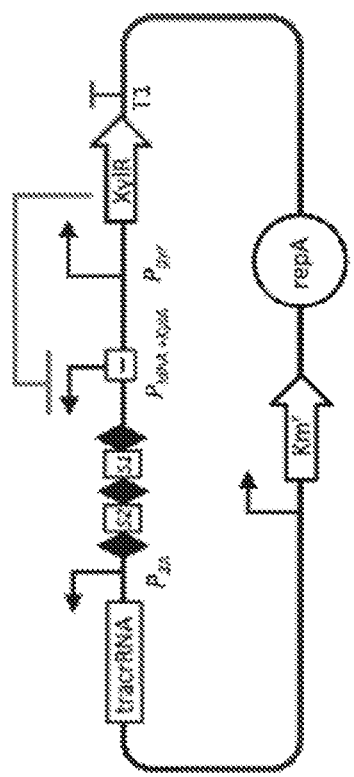
FIG. 7 illustrates the design of CRISPR array in pBAV1KT5-XylR-mCherry-P$_{ldha+xylA}$. The array contains 2 spacer sequences that target S. thermophilus genes under an inducible xylose promoter and a tracrRNA under a strong constitutive promoter P$_{3,4}$.

In order to determine if the genomic targeting spacers in a CRISPR array can cause death in *S. thermophilus* LMD-9, we inserted the CRISPR array we designed into the two xylose inducible systems previously constructed (pBAV1KT5-XylR-mCherry-P$_{ldha+XylA}$ and pBAV1KT5-XylR-mCherry-P$_{XylA}$). In these plasmids we replaced mCherry with the gBlock containing the CRISPR array (FIG. 7). The variant with the P$_{ldha+XylA}$ promoter was expected to be stronger and have a higher basal activity than the P$_{xylA}$ (Xie et al. 2013).

2. 4 Inhibition of Bacterial Population Growth Using Endogenous Cas9

Figure 8:
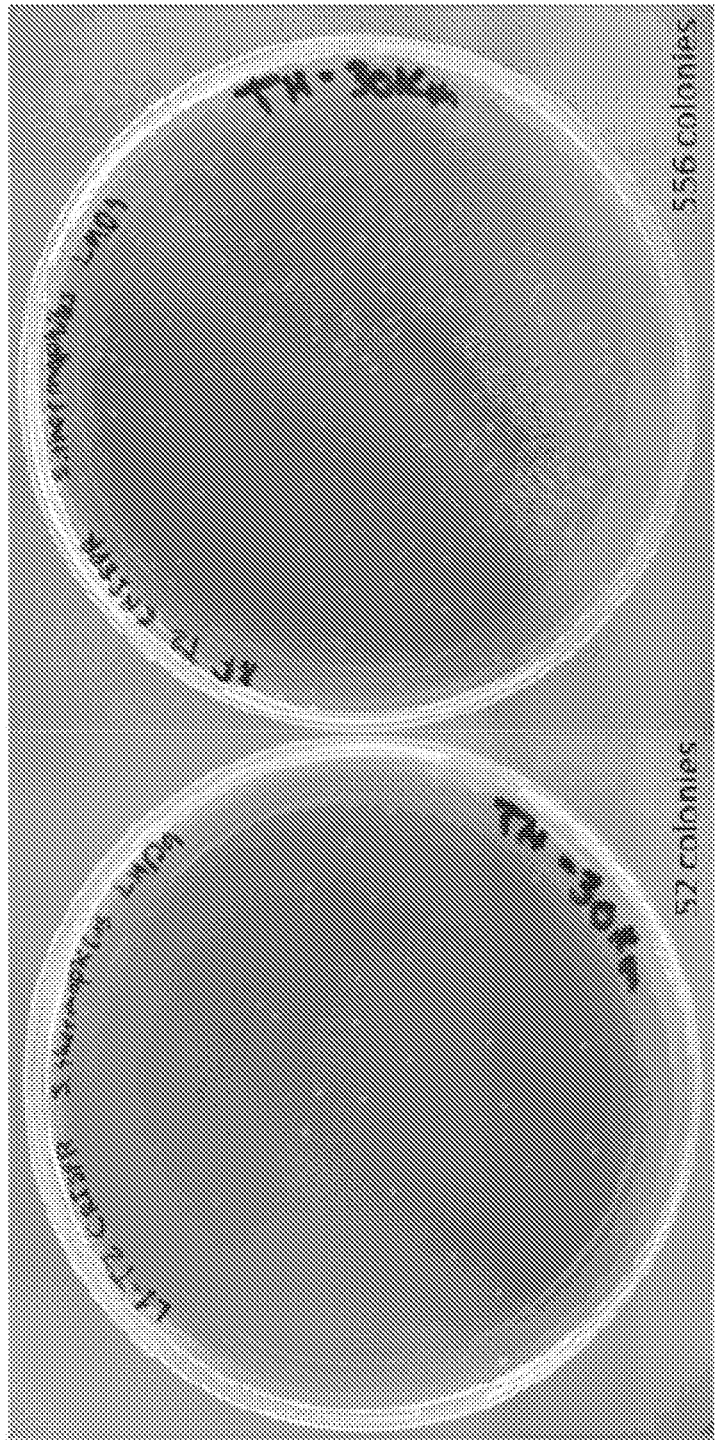
FIGS. 8A-8B show transformation efficiency of Streptococcus thermophilus LMD-9 with the plasmid pBAV1KT5-XylR-CRISPR-P$_{ldh+XylA}$ (FIG. 8A) and with pBAV1KT5-XylR-CRISPR-P$_{XylA}$ (FIG. 8B).

After we constructed the plasmids in *E. coli*, we transformed the plasmids into *S. thermophilus*. This would allow us to determine if we could cause cell death of a specific bacterial species. Interestingly, bacterial host population size (indicated by growing bacteria and counting colony numbers on agar plates) in *S. thermophilus* exposed to the plasmid containing the strong P$_{ldh+XylA}$ hybrid promoter was 10-fold less when compared to *S. thermophilus* exposed to the plasmid containing the weak, normal P$_{xylA}$ promoter (FIG. 8; 52 colonies with the strong array expression versus 556 colonies with weak array expression, 10.7-fold difference), the 2 strains having been transformed in parallel using the same batch of electrocompetent *S. thermophilus* cells. This suggests to us that the plasmid carrying the CRISPR array targeting *S. thermophilus* genes is able to kill the cells using the endogenous Cas nuclease and RNase III, thereby inhibiting population growth by 10-fold.

We expect that weak array expression in host cells transformed by the plasmid comprising the P$_{xylA}$ promoter led to a degree of cell killing, albeit much less than with the strong promoter plasmid. We expect that population growth inhibition that is greater than the observed 10-fold inhibition would be determined if a comparison of the activity of strong array expression was made with *S thermophilus* that is not exposed to any array-encoding plasmid (such as bacteria directly isolated from gut microbiota). Thus, we believe that array (or single guide RNA) expression in host cells for harnessing endogenous Cas nuclease will be useful for providing effective growth inhibition of target host cells in environmental, medical and other settings mentioned herein. Co-administration of antibiotic may also be useful to enhance the growth inhibition, particularly when one or more antibiotic resistance genes are targeted.

3. Discussion and Outlook

In this study we set out to design a CRISPR-array to specifically kill *S. thermophilus* using the endogenous Cas9 system. In order to gain control over the killing signal we sought to apply an inducible system that can be applied in *S. thermophilus*. The xylose inducible XylR system from *B. megaterium* was previously applied in *S. mutans* (Xie, 2013) but not in *S. thermophilus*. In this study we demonstrated the functionality of the xylR induction system using the designed XylR-mCherry-Pldha circuit in *S. thermophilus*. We found 0.1% wt/vol is sufficient to fully induce the XylR system in *S. thermophilus* (FIG. 6).

In order to observe abundance when co-culturing *S. thermophilus* and *E. coli* we established that supplementation of the culture media with 3 g l$^{-1}$ of PEA, allows for the selective growth of *S. thermophilus* while limiting the growth of *E. coli* (FIG. 4).

Figure 9:
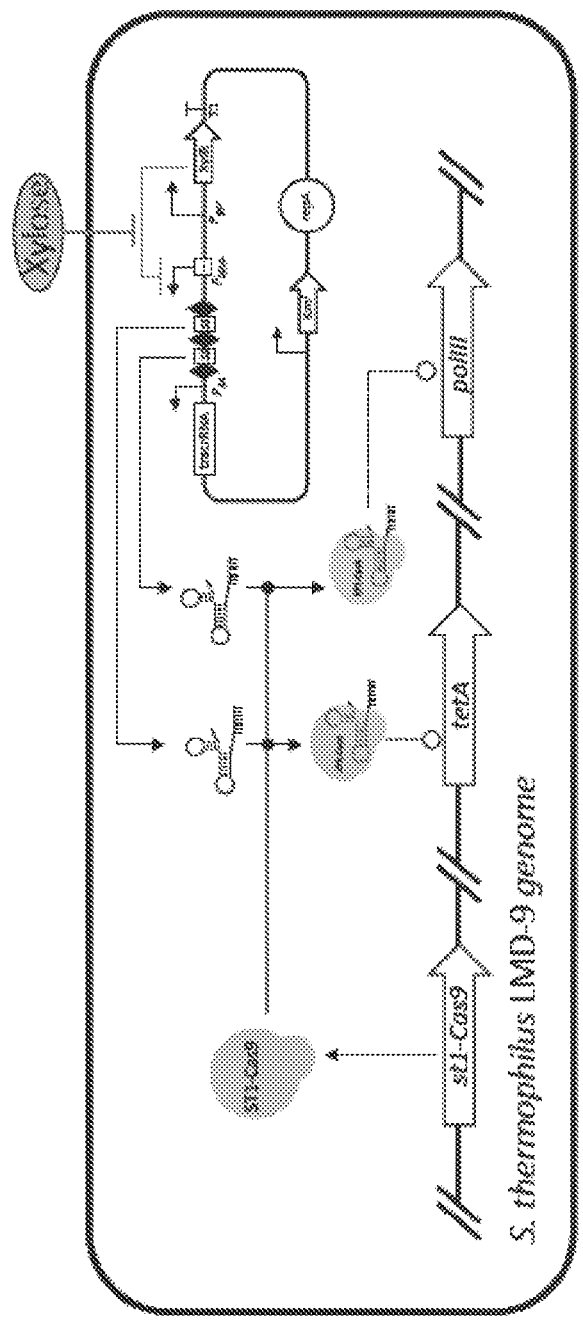
FIG. 9 shows a schematic of the xylose-inducible CRISPR device. Upon induction of xylose the CRISPR array targeting both polIII and tetA on the S. thermophiles LMD-9 genome are expressed. Together with the constitutively expressed tracrRNA a complex is formed with Cas9. This complex will introduce a double stranded break in the tetA and polIII genes in the S. thermophilus LMD-9 genome resulting in limited cell viability.

A ST1-CRISPR array, targeting the DNA polymerase III subunit alpha and a tetA like gene in the *S. thermophilus* LMD-9 genome, was placed under the xylose inducible promoter (Xie et al. 2013). Targeting these regions should lead to a double strand break and thus limit *S. thermophilus* viability (FIG. 9). Since the engineered array was designed to target *S. thermophilus* genome using the endogenous CRISPR/Cas machinery to process the encoded CRISPR array, the array is expected to have no influence on growth of unrelated strains such as *E. coli*, even similar targets could be found on its genome. This was successfully tested in a mixed bacterial population (simulating aspects of a human microbiota) as discussed in Example 8.

The demonstration of the invention's ability to inhibit host cell growth on a surface is important and desirable in embodiments where the invention is for treating or preventing diseases or conditions mediated or caused by microbiota as disclosed herein in a human or animal subject. Such microbiota are typically in contact with tissue of the subject (eg, gut, oral cavity, lung, armpit, ocular, vaginal, anal, ear, nose or throat tissue) and thus we believe that the demonstration of activity to inhibit growth of a microbiota bacterial species (exemplified by *Streptococcus*) on a surface supports this utility.

Example 7: Specific Microbiota Bacterial Population Growth Inhibition in Different Strains Example 6 demonstrated specific growth inhibition of *Streptococcus thermophilus* LMD-9. Here we demonstrate growth inhibition can also be obtained in a second strain: *Streptococcus thermophilus* DSM 20617. Methods described in Example 6 were, therefore, applied to the latter strain (except that selective media for *S. thermophilus* DSM 20617 was TH media supplemented with 2.5 g l$^{-1}$ of 2-phenylethanol (PEA)).

*Streptococcus thermophilus* DSM 20617 transformed with the CRISPR array plasmids were incubated for recovery in liquid media for a period of 3 hours at 37° C. that would allow for expression of kanamycin resistance. After a recovery period, cells were plated in different selection media in presence of 1% xylose in order to induce cell death, and without xylose as a control (FIG. 10). It is evident that; (1) by xylose induction the growth of *S. thermophilus* can be inhibited (around 10-fold for the 'strong' promoter plasmid versus control), (2) the 'strong' system (pBAV1KT5-XylR-CRISPR-P$_{ldha}$) results in more growth reduction than the 'weak' system (pBAV1KT5-XylR-CRISPR-P$_{xylA}$).

Example 8: Selective Bacterial Population Growth Inhibition in a Mixed Consortium of Different Microbiota Species We next demonstrated selective growth inhibition of a specific bacterial species in a mixed population of three species. We selected species found in gut microbiota of humans and animals (*S thermophilus* DSM 20617(T), *Lactobacillus lactis* and *E coli*). We included two gram-positive species (the *S thermophilus* and *L lactis*) to see if this would affect the ability for selective killing of the former species; furthermore to increase difficulty (and to more closely simulate situations in microbiota) *L lactis* was chosen as this is a phylogenetically-related species to *S thermophilus* (as indicated by high 16s ribosomal RNA sequence identity between the two species). The *S thermophilus* and *L lactis* are both Firmicutes. Furthermore, to simulate microbiota, a human commensal gut species (*E coli*) was included.

1. Materials & Methods

Methods as set out in Example 6 were used strain (except that selective media was TH media supplemented with 2.5 g $l^{-1}$ of 2-phenylethanol (PEA)).

1.1 Preparation of Electro-Competent *L. lactis* Cells

Overnight cultures of *L. lactis* in TH media supplemented with 0.5 M sucrose and 1% glycine were diluted 100-fold in 5 ml of the same media and grown at 30° C. to an $OD_{600}$ between 0.2-0.7 (approximately 2 hours after inoculation). The cells were collected at 7000×g for 5 min at 4° C. and washed three times with 5 ml of ice cold wash buffer (0.5 M sucrose+10% glycerol). After the cells were washed, they were suspended to an $OD_{600}$ of 15-30 in electroporation buffer (0.5 M sucrose, 10% glycerol and 1 mM $MgCl_2$). The cells in the electroporation buffer were kept at 4° C. until use (within one hour) or aliquot 50 µl in eppendorf tubes, freezing them in liquid nitrogen and stored at −80° C. for later use.

Electroporation conditions for all species were as described in Example 6.

1.2 Activation of CRISPR Array: Consortium Experiments.

*S. thermophilus* DSM 20617, *L. lactis* MG1363 and *E. coli* TOP10 were genetically transformed with the plasmid containing the CRISPR array targeting the DNA polymerase III and tetA of *S. thermophilus*. After transformation all cells were grown alone and in co-culture for 3 hours at 37° C. allowing for recovery to develop the antibiotic resistance encoded in the plasmid. We decided to use transformation efficiency as a read out of CRISPR-encoded growth inhibition. Therefore, after allowing the cells for recovery the cultures were plated in TH media, TH supplemented with PEA and MacConkey agar all supplemented with Kanamycin, and induced by 1% xylose.

2. Results 2.0 Phylogenetic Distance Between *L. lactis, E. Coli* and *S. thermophilus*

Figure 11:
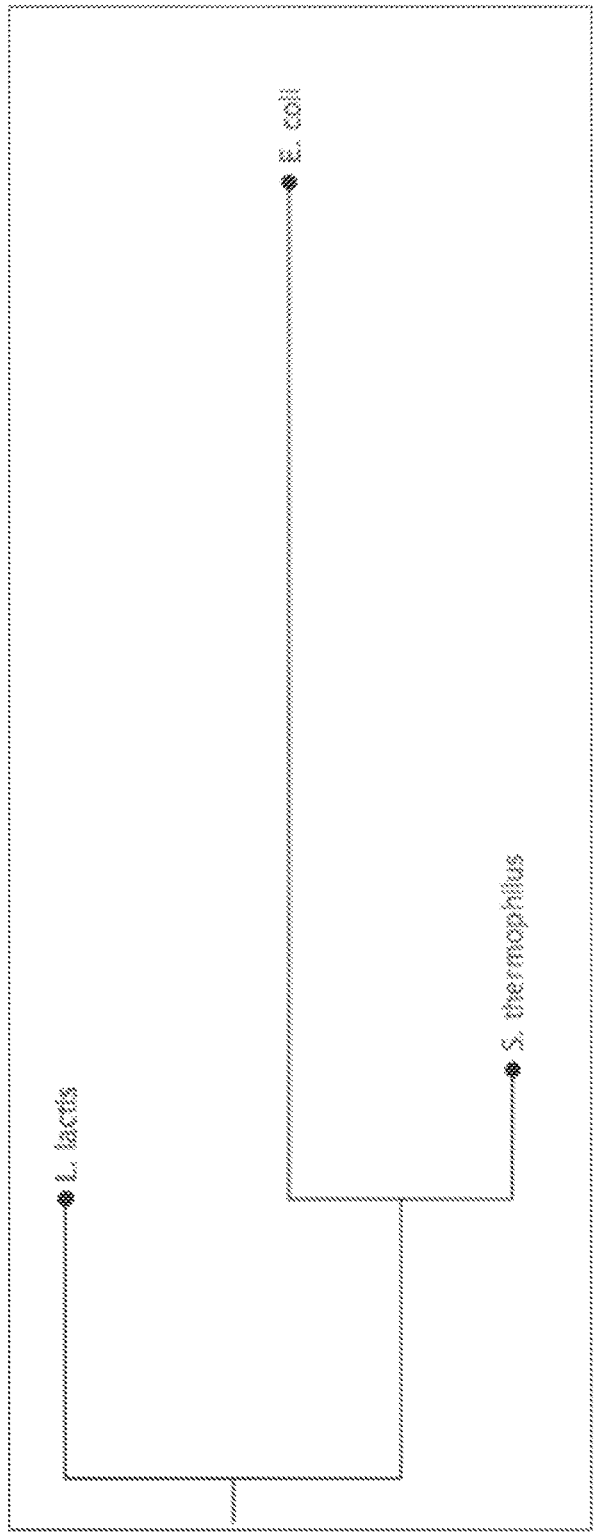
FIG. 11 shows a maximum-likelihood phylogenetic tree of 16S sequences from S. thermophilus, L. lactis and E. coli.

The calculated sequence similarity in the 16S rRNA-encoding DNA sequence of the *S. thermophilus* and *L. lactis* was determined as 83.3%. The following 16S sequences were used: *E. coli*: AB030918.1, *S. thermophilus*: AY188354.1, *L. lactis*: AB030918. The sequences were aligned with needle (ebi.ac.uk/Tools/psa/emboss_needle/nucleotide.html) with the following parameters: -gapopen 10.0 -gapextend 0.5 -endopen 10.0 -endextend 0.5 -aformat3 pair -snucleotide1-snucleotide2. FIG. 11 shows the maximum-likelihood phylogenetic tree of 16S sequences from *S. thermophilus, L. lactis* and *E. coli*.

2.1 Growth Condition and Selective Media

*S. thermophilus* and *L. lactis* are commonly used in combination in many fermented foods and yoghurt. We chose these strains since they are commonly known to be gut microbes that form an intimate association with the host and previous characterizations of the 16S ribosomal RNA region of *S. thermophilus* and *L. lactis* have shown that these organisms are phylogenetically closely related (Ludwig et al., 1995). In parallel we also evaluated the growth of *E. coli* for our mixed population co-culture experiments, since this organism is also commonly found in gut microbe communities. We first set out to establish the bacterial strains and cultivation protocol that would support growth for all strains we planned to use for the co-cultivation experiments. We found that all strains were able to support growth in TH broth at 37° C. (FIG. 3).

Distinguishing the different bacteria from a mixed culture is important in order to determine cell number of the different species. With MacConkey agar is possible to selectively grow *E. coli*, however there is no specific media for selective growth of *S. thermophilus*. PEA agar is a selective medium that is used for the isolation of gram-positive (*S. thermophilus*) from gram-negative (*E. coli*). Additionally, different concentrations of PEA partially inhibit the growth of the different grams positive species and strains, which allow for selection between the other gram-positive bacteria used in this work. Using 2.5 g $l^{-1}$ of PEA proved to selectively grow *S. thermophilus* while limiting growth of *L. lactis* and *E. coli*.

All strains were transformed with a plasmid that used the vector backbone of pBAV1KT5 that has a kanamycin selection marker; we found that using media supplemented with 30 ug $ml^{-1}$ of kanamycin was enough to grow the cells while keeping the plasmid.

2. 3 Transformation & Selective Growth Inhibition in a Mixed Population

We transformed *S. thermophilus, L. lactis* and *E. coli* with plasmid containing the CRISPR array and cultured them in a consortium of all the bacterial species combined in equal parts, which would allow us to determine if we could cause cell death specifically in *S. thermophilus*. We transformed all the species with either the pBAV1KT5-XylR-CRISPR-P$_{XylA}$ or pBAV1KT5-XylR-CRISPR-P$_{ldhA+XylA}$ plasmid.

FIG. 12 shows the selective *S thermophilus* growth inhibition in a co-culture of *E. coli, L. lactis* and *S. thermophiles* harboring either the pBAV1KT5-XylR-CRISPR-P$_{XylA}$ or the pBAV1KT5-XylR-CRISPR-P$_{ldhA+XylA}$ plasmid. No growth difference is observed between *E. coli* harboring the pBAV1KT5-XylR-CRISPR-P$_{XylA}$ or the pBAV1KT5-XylR-CRISPR-P$_{ldhA+XylA}$ plasmid (middle column). However, *S. thermophiles* (selectively grown on TH agar supplemented with 2.5 g$l^{-1}$ PEA, last column) shows a decrease in transformation efficiency between the pBAV1KT5-XylR-CRISPR-P$_{XylA}$ (strong) or the pBAV1KT5-XylR-CRISPR-P$_{ldhA+XylA}$ (weak) plasmid as we expected. We thus demonstrated a selective growth inhibition of the target *S thermophilus* sub-population in the mixed population of cells.

REFERENCES

Barrangou, R., Fremaux, C., Deveau, H., Richards, M., Patrick Boyaval, Moineau, S., . . . Horvath, P. (2007). CRISPR Provides Acquired Resistance Against Viruses in Prokaryotes. *Science*, 315 (March), 1709-1712.

Bryksin, A. V, & Matsumura, I. (2010). Rational design of a plasmid origin that replicates efficiently in both gram-positive and gram-negative bacteria. *PloS One*, 5(10), e13244.

Chan C T Y, Lee J W, Cameron D E, Bashor C J, Collins J J: "Deadman" and "Passcode" microbial kill switches for bacterial containment. *Nat Chem Biol* 2015, 12 (December):1-7.

Horvath, P., Romero, D. A., Couté-Monvoisin, A.-C., Richards, M., Deveau, H., Moineau, S., . . . Barrangou, R. (2008). Diversity, activity, and evolution of CRISPR loci in *Streptococcus thermophilus*. *Journal of Bacteriology*, 190(4), 1401-12.

Ludwig, E. S., Klipper, R., Magrum L., Wose C., & Stackebrandt, E. (1985). The phylogenetic position of *Streptococcus* and *Enterococcus*. *Journal of Gencwl Microhiologj.*, 131, 543-55 1.

Mercenier, A. (1990). Molecular genetics of *Streptococcus thermophilus*. *FEMS Microbiology Letters*, 87(1-2), 61-77.

Samaržija, D., Antunac, N., & Havranek, J. (2001). Taxonomy, physiology and growth of *Lactococcus lactis*: a review. *Mljekarstvo*, 51(1), 35-48. Retrieved from Sapranauskas, R., Gasiunas, G., Fremaux, C., Barrangou, R., Horvath, P., & Siksnys, V. (2011). The *Streptococcus thermophilus* CRISPR/Cas system provides immunity in *Escherichia coli*. *Nucleic Acids Research*, 39(21), 9275-9282.

Somkuti, G. A., & Steinberg, D. H. (1988). Genetic transformation of *Streptococcus thermophilus* by electroporation. *Biochimie*, 70(4), 579-585

Sorg, R. A., Kuipers, O. P., & Veening, J.-W. (2014). Gene expression platform for synthetic biology in the human pathogen *Streptococcus pneumoniae*. ACS Synthetic Biology, 4(3), 228-239.

Suvorov, a. (1988). Transformation of group A streptococci by electroporation. *FEMS Microbiology Letters*, 56(1), 95-99.

Xie, Z., Qi, F., & Merritt, J. (2013). Development of a tunable wide-range gene induction system useful for the study of streptococcal toxin-antitoxin systems. *Applied and Environmental Microbiology*, 79(20), 6375-84.

Zhang, X. Z., & Zhang, Y. H. P. (2011). Simple, fast and high-efficiency transformation system for directed evolution of cellulase in *Bacillus subtilis*. *Microbial Biotechnology*, 4(1), 98-105.

Tables

TABLE 1

Repeat Sequences of SRBs For Use in the Invention
Each of R1 and R1' can be selected from these repeat consensus sequences, eg, when the system is an crude oil, natural gas or water recovery, processing or storage equipment.

| BACTERIUM | CRISPR_ID | START POSITION | END POSITION | NUMBER OF SPACERS | DR (REPEAT) CONSENSUS | SEQ ID NO: | NOTES |
|---|---|---|---|---|---|---|---|
| Desulphovibrio desulphuricans ND132 | NC_016803_1 | 2325998 | 2326074 | 1 | CCTGGCCTGCCCCAAGTGCAAGG | 50 | |
| Desulphovibrio desulphuricans ND132 | NC_016803_4 | 3491653 | 3498191 | 98 | GTCGCCCCCACGCGGGGCGTGGATTGAAAC | 51 | 1 |
| Desulphovibrio vulgaris subsp. vulgaris str. Hildenborough | NC_005863_3 | 175898 | 177711 | 28 | GTCGCCCCCACGCGGGGCGTGGATTGAAAC | 125 | 1 |
| Desulphobulbus propionicus DSM 2032 | NC_014972_1 | 1701541 | 1707620 | 92 | GTCGCCCCCACGCGGGGCGTGGATTGAAAC | 126 | 1 |
| Desulphovibrio vulgaris RCH1 | NC_017311_1 | 170455 | 172268 | 28 | GTCGCCCCCACGCGGGGCGTGGATTGAAAC | 125 | 1 |
| Desulphovibrio desulphuricans subsp. desulphuricans str. (ATCC 27774) | NC_011883_1 | 676246 | 676547 | 3 | TGGAGCGGGAAACGGGATTTGAACCCGC | 52 | |
| Desulphovibrio desulphuricans subsp. desulphuricans str. (ATCC 27774) | NC_011883_2 | 1083779 | 1085579 | 29 | GTGTTCCCCACGGGCGTGGGGATGAACCG | 53 | |
| Desulphovibrio gigas DSM 1382 (ATCC 19364) | NC_022444_2 | 430661 | 430743 | | AACCTTTCTGCAAAAAGGTTTCCCC | 54 | 2 |
| Desulphovibrio gigas DSM 1382 (ATCC 19364) | NC_022444_3 | 915564 | 915638 | | CCGCTGGATCCGGCTGCAGCGCC | 55 | |
| Desulphovibrio gigas DSM 1382 (ATCC 19364) | NC_022444_4 | 1994976 | 1995063 | | GTTCACTGCCGCATAGGCAGCTCAGAAA | 56 | |

TABLE 1-continued

Repeat Sequences of SRBs For Use in the Invention
Each of R1 and R1' can be selected from these repeat consensus sequences, eg, when the
system is an crude oil, natural gas or water recovery, processing or storage equipment.

| BACTERIUM | CRISPR_ID | START POSITION | END POSITION | NUMBER OF SPACERS | DR (REPEAT) CONSENSUS | SEQ ID NO: | NOTES |
|---|---|---|---|---|---|---|---|
| Desulphovibrio gigas DSM 1382 (ATCC 19364) | NC_022444_5 | 2555284 | 2555600 | 4 | CACCCGACTATTGAAGTCGGGCCTCATTGAAG | 57 | |
| Desulphurispirillum indicum S5 | | | | | AACCTTTCTGCAAAAAGGTTTCCCC | 127 | 2 |
| Desulphovibrio hydrothermalis | NC_022579_1 | 10819 | 11067 | 3 | GTCAAAACCCATACCGATATGGATACCTCTTTTGAG | 58 | |
| Desulphovibrio hydrothermalis | NC_022579_2 | 24430 | 24678 | 3 | GTCAAAACCCATACCGATATGGATACCTCTTTTGAG | 59 | |
| Desulphovibrio hydrothermalis | NC_022579_3 | 36027 | 36275 | 3 | GTCAAAACCCATACCGATATGGATACCTCTTTTGAG | 60 | |
| Desulphovibrio hydrothermalis | NC_022579_4 | 118127 | 118736 | 8 | GTCAAAACCCATACCGATATGGATACCTCTTTTGAG | 61 | |
| Desulphovibrio hydrothermalis | NC_022579_5 | 2366564 | 2366737 | 2 | CTCAAAAGAGGTATCCATATCGGTATGGGTTTTGAC | 62 | |
| Desulphovibrio hydrothermalis | NC_022579_6 | 2574826 | 2575933 | 18 | GTTCACTGCCGGATAGGCAGCTTAGAAA | 63 | |
| Desulphovibrio magneticus RS-1 | NC_012796_1 | 1589785 | 1591828 | 30 | GTCGCCCCTGCGCGGGGGCGTGGATTGAAAC | 64 | |
| Desulphovibrio magneticus RS-1 | NC_012796_3 | 4725356 | 4726585 | 20 | TTTTCTGAGCTGCCTATGCGGCAGTGAAC | 65 | |
| Desulphovibrio vulgaris str. 'Miyazaki F' | NC_011769_1 | 241933 | 242082 | 1 | CATCGACGACGAACCCGGGCACCGCCTGATGGTCCACGCCGTCATG | 66 | |
| Desulphovibrio vulgaris str. 'Miyazaki F' | NC_011769_3 | 2444693 | 2448088 | 51 | GTCGCCCCTCACGCGGGGGCGTGGATAGAAAC | 67 | |
| Desulphovibrio vulgaris subsp. vulgaris DP4 | NC_008741_1 | 29677 | 32622 | 44 | GTTTCAATCCACGCCCCCGCACGGGGGGCGAC | 68 | |
| Desulphurispirillum indicum S5 | NC_014836_1 | 994780 | 997087 | 38 | TTTCTGAGCTGCCTATGCGGCAGTGAAC | 69 | 3 |
| Desulphurispirillum indicum S5 | NC_014836_2 | 1123444 | 1127359 | 54 | GACCGAAGACCTGTCGGAAACGACGGGGATTGAGAC | 70 | |
| Desulphovibrio gigas DSM 1382 (ATCC 19364) | | | | | TTTCTGAGCTGCCTATGCGGCAGTGAAC | 128 | 3 |
| Desulphovibrio gigas DSM 1382 (ATCC 19364) | NC_022444_4 | 1994976 | 1995063 | 2 | GTTCACTGCCGCATAGGCAGCTCAGAAA | 49 | |
| Desulphurivibrio alkaliphilus AHT2 | NC_014216_2 | 1780099 | 1782570 | 40 | CGGTTCATCCCCGCGAGTGCGGGGAACAT | 71 | |
| Desulphurivibrio alkaliphilus AHT2 | NC_014216_3 | 1785014 | 1791956 | 115 | TTTCTGAGCTGCCTGTGCGGCAGTGAAC | 72 | |

TABLE 1-continued

Repeat Sequences of SRBs For Use in the Invention
Each of R1 and R1' can be selected from these repeat consensus sequences, eg, when the
system is an crude oil, natural gas or water recovery, processing or storage equipment.

| BACTERIUM | CRISPR_ID | START POSITION | END POSITION | NUMBER OF SPACERS | DR (REPEAT) CONSENSUS | SEQ ID NO: | NOTES |
|---|---|---|---|---|---|---|---|
| Desulphurobacterium thermolithotrophum DSM 11699 | NC_015185_1 | 267992 | 268349 | 5 | GTTTTATCTGAACGTAGTGGGATATAAAG | 73 | |
| Desulphovibrio desulphuricans G20 | NC_007519_1 | 885036 | 886223 | 19 | CGGTTCATCCCCGCGGGTGCGGGGAACAC | 74 | |
| Desulphovibrio desulphuricans ND132 | NC_016803_4 | 3491653 | 3498191 | 98 | GTCGCCCCCCACGCGGGGGCGTGGATTGAAAC | 51 | 1 |

A CRISPR array is found in *Desulphovibrio desulphuricans* ND132 starting at position 3491653 and ending at position 3498191, wherein the array has 98 spacer sequences, each flanked by repeats, where the repeats each have the sequence of SEQ ID NOS 51 and 125-126. Such a repeat is also found in an array of the other bacteria under note number 1 (last column in the table).

TABLE 2

| SBQ ID NO: | SPECIES/STRAIN | REPEAT SEQUENCE |
|---|---|---|
| | BACTEROIDES REPEATS | |
| 107 | 1. *Bacteroides fragilis* NCTC 9343 | GTTGTGATTTGCTTTCAAATTAGTATCTTTGAACCA TTGGAAACAGC |
| | 2. *Bacteroides fragilis* 638R | |
| 108 | 3. *Bacteroides fragilis* NCTC 9343 | ATTTCAATTCCATAAGGTACAATTAATAC |
| | 4. *Bacteroides fragilis* YCH46 | |
| 109 | 5. *Bacteroides helcogenes* P36-108 | GTTTCAATCCACACACCCGTATAGGGTGTGAC |
| 110 | 6. *Bacteroides* sp. CF30 | ACTGTTTCTGATATGTCAAAGATAAAATTTTGAAAG CAAATCACAAC |
| 111 | 7. *Bacteroides themariotaomicron* VPF. 5482 | GAAAAAATACAGTTTCGCTCTCA |
| | PREVOTELLA REPEATS | |
| 112 | 8. *Prevotella dentalis* DSM 3688 | GTCGCGTCTCACGTAGGCGCGTGGATTGAAAC |
| 113 | 9. *Prevotella denticola* F0289 | ATTGTGCTTGCTACTGCAAAGATACACATTTTGAAG CAATTCACAAC |
| 114 | 10. *Prevotella denticola* F0289 | CTCAATGAGTATCTTCCATTAAAACAAGGATTAAGA C |
| 115 | 11. *Provorella intermedia* 17 | GTTGTTTTTACCTTGCAAACAGCAGGCAGATACAAC |
| 116 | 12. *Prevotella intermedia* 17 | GTTGTATTTGCCAATGCAAAGATACTAATTTTAAAG CTAATCACAAC |
| 117 | 13. *Prevotella ruminicola* 23 | GTTGTATATCATTCCTTTCCTACATCAAACCACAAC |

TABLE 3

Underlined = CRISPR spacers that have 100% identity
to sequences within the *V. cholerae* PLE

| PHAGE SOURCE | ARRAY | SPACER | SPACER SEQUENCE | SEQ ID NO: |
|---|---|---|---|---|
| ICP1_2011_A | CR1 | 1a | CATTGCAACTATGCAAAATGATGAAGCTAAAA | 79 |
| | | 2a | TGTTAGAGTCGGTAGTATCTGGATGATCGATA | 80 |
| | | 3a | TTATGTATTGACCCCGACACGCCCCCCGACTG | 81 |
| | | 4a | TTACAGACGACCTAACTCTTCAGTACCATGAT | 82 |
| | | 5a | TACATAAGCTGCAACACGGTGTTCGTTTAAGT | 83 |
| | | 6a | AAAATACGCCTTTTTCCCTTCATCGTTTAAAG | 84 |
| | | 7a | ACCAACAAATCCCATAAACTGATAACCACGTT | 85 |
| | | 8a | <u>GTCAACCCTTTGCTTATCTTCCCTATTTAAAT</u> | 86 |
| | | 9a | <u>TGTTAACCACCGCTTGAAATAATCATGATGCA</u> | 87 |
| ICP1_2006_B | CR1 | 1b | TGTGTCTATACTCAACCAATTTAAGCGCCGCA | 88 |
| | | 2b | CTACTCTCCCCAATATTAGCCATTCCTAATTC | 89 |
| | | 3b | GTCACCTTACCGTAAGACAGGCAGTAAAATTA | 90 |
| | | 4b | <u>AAACTAGTGGACGTAATGCAGTATTCACGGTT</u> | 91 |
| | CR2 | 1c | <u>ATCCACACTACAAATAGAACACTCAACCGTGA</u> | 92 |
| ICP1_2005_A | CR1 | 1d | TGTGTCTATACTCAACCAATTTAAGCGCCGCA | 93 |
| | | 2d | CTACTCTCCCCAATATTAGCCATTCCTAATTC | 94 |
| | | 3d | <u>AAACTAGTGGACGTAATGCAGTATTCACGGTT</u> | 95 |
| | | 4d | ATAATCGTTTTGAGTCTCACCAGCTTTTAGGC | 96 |
| | CR2 | 1e | <u>ATCCACACTACAAATAGAACACTCAACCGTGA</u> | 97 |
| | | 2e | TATTGATTGGTCTCTAACCTTGGGATGATTAA | 98 |
| | | 3e | <u>TTCACGGGTAGCAACAGGGTAATAAACCAATA</u> | 99 |
| ICP1_2004_A | CR1 | 1f | CATTGCAACTATGCAAAATGATGAAGCTAAAA | 100 |
| | | 2f | TGTTAGAGTCGGTAGTATCTGGATGATCGATA | 101 |
| | | 3f | TAGAAGAGTAATAGGAGCTACTGCAAACTTGT | 102 |
| | | 4f | TAACTATGTGTGGTTTATATTTTGTGTGCAAG | 103 |
| | | 5f | TTTTGAAACTATTGACAGAAGGTTGGGAACCT | 104 |
| | | 6f | TTGAGGTTGAACCTCTTCCGGTTCCTCTTCTG | 105 |
| | CR2 | 1g | GTGTATTGCTTGCAGTGGGTTACACACAAGAA | 106 |

TABLE 4

| Essential homolog in *V. cholerae* | Neutral homolog in *V. cholerae* | Homolog in *E. coli* | Essential In *E. coli*? | Annotated function |
|---|---|---|---|---|
| vc0631 | vc0465 | tyrS | Yes | Tyrosyl tRNA synthetase |
| vc2024 | vc0093 | plsB | Yes | Glycerol 3 phosphate acyltransferase |
| vc2626 | | dam | No | Adenine Methyltransferase |

TABLE 4-continued

| Essential homolog in *V. cholerae* | Neutral homolog in *V. cholerae* | Homolog in *E. coli* | Essential In *E. coli*? | Annotated function |
|---|---|---|---|---|
| vc2763-vc2767 | | atpCDGAH | No | F1 ATP synthase (ε, β, γ, α, δ) subunits |
| vc2768-vc2770 | | atpFEB | No | F0 ATP synthase (B, C, A) subunits |

TABLE 5

| Gene | Feature |
|---|---|
| dnaE | DNA polymerase III holoenzyme alpha subunit |
| recA | recombinase A |
| ctxB | cholera toxin B |
| mdh | malate dehydrogenase |
| gyrB | DNA gyrase subunit B |
| tcpA | toxin co-regulated pilin A |
| ctxA | cholera toxin A subunit |
| rpoA | RNA polymerase alpha subunit |
| tcpB | toxin co-regulated pilus biosynthesis protein B |
| asd | aspartate-semialdehyde dehydrogenase |

TABLE 6

| Gene | Feature |
|---|---|
| ctxB | cholera toxin B |
| tcpA | toxin co-regulated pilin A |
| ctxA | cholera toxin A subunit |

TABLE 6-continued

| Gene | Feature |
|---|---|
| tcpB | toxin co-regulated pilus biosynthesis protein B |
| wbet | ogawa specific antigen |
| hlyA | hemolysin A |
| hapR | hemagglutinin/protease regulatory protein |
| rstR | cryptic phage ctxphi transcriptional repressor |
| mshA | mannose-sensitive hemagglutinin A |
| tcpP | toxin co-regulated pilus biosynthesis protein P |

SEQUENCES

In an example, one or more spacers of the invention target a respective sequence in this sequence listing. SEQ ID NOs: 1-44 are Type II CRISPR/Cas system sequences, eg, *Streptococcus* sequences.

| SEQ ID NO: | SEQUENCES (ALL 5' TO 3') |
|---|---|
| | PROMOTER |
| 1 | TTGAC |
| 2 | TATAAT |
| | TRANSCRIBED LEADER SEQ |
| 3 | TATGAAAA |
| 4 | ATTTGAG |
| 5 | ATTTGAGG |
| 6 | GAG |
| 7 | GAGG |
| 8 | TGAG |
| 9 | TGAGG |
| 10 | TTGAG |
| 11 | TGAGG |
| 12 | TTTGAG |
| 13 | TTTGAGG |
| 14 | ATTTGAG |
| 15 | AATTTGAG |
| 16 | CATTTGAG |
| 17 | GATTTGAG |

-continued

| SEQ ID NO: | SEQUENCES (ALL 5' TO 3') |
|---|---|
| 18 | TATTTGAG |
| 19 | CGATTTGAG |
| 20 | ACGATTTGAG |
| 21 | TCATTTGAG |
| 22 | TTCATTTGAG |
| 23 | ATCATTTGAG |
| 24 | TTTCATTTGAG |
| 25 | AATCATTTGAG |
| 26 | AATTCATTTGAG |
| 27 | AAATCATTTGAG |
| 28 | AAATTCATTTGAG |
| 29 | AAAATCATTTGAG |
| 30 | AAAATTCATTTGAG |
| | REPEAT |
| 31 | GTT |
| 32 | GTTT |
| 33 | GTTTT |
| 34 | GTTTTT |
| 35 | GTTTTTG |
| 36 | GTTTTTGT |
| 37 | GTTTTTGTA |
| 38 | GTTTTTGTAC |
| 39 | GTTTTTGTACT |
| 40 | GTTTTTGTACTC |
| 41 | GTTTTTGTACTCT |
| 42 | GTTTTTGTACTCTC |
| 43 | GTTTTTGTACTCTCA |
| 44 | GTTTTTGTACTCTCAA |
| 45 The CRISPR leader in the CRISPR1 locus of *Streptococcus thermophilus* strain CNRZI 066 | CAAGGACAGTTATTGATTTTATAATCACTATGTGGGTATAAAAACGTCAA AATTTCATTTGAG |
| 46 The CRISPR leader in the CRISPR1 locus of *E. coli* W3110 CRISPR system | AAACAAAGAATTAGCTGATCTTTAATAATAAGGAAATGTTACATTAAGGT TGGTGGGTTGTTTTTATGGGAAAAAATGCTTTAAGAACAAATGTATACTT AGA |
| 47 >tr\|J7RUA5\| J7RUA5_STAAU CRISPR-associated endonuclease Cas9 OS = *Staphylococcus* | MKRNYILGLDIGITSVGYGIIDYETRDVIDAGVRLFKEANVENNEGRRSK RGARRLKRRRHRIQRVKKLLFDYNLLTDHSELSGINPYEARVKGLSQKL SEEEFSAALLHLAKRRGVHNVNEVEEDTGNELSTKEQISRNSKALEEKYV AELQLERLKKDGEVRGSINRFKTSDYVKEAKQLLKVQKAYHQLDQSFIDT YIDLLETRRTYYEGPGEGSPFGWKDIKEWYEMLMGHCTYFPEELRSVKYA YNADLYNALNDLNNLVITRDENEKLEYYEKFQUIENVFKQKKKPTLKQIA |

| SEQ ID NO: | SEQUENCES (ALL 5' TO 3') |
| --- | --- |
| aureus subsp. aureus GN = cas9 PE = 3 SV = 1 | KEILVNEEDIKGYRVTSTGKPEFTNLKVYHDIKDITARKEIIENAELLDQ IAKILTIYQSSEDIQEELTNLNSELTQEEIEQISNLKGYTGTHNLSLKAI NLILDELWHTNDNOIAIFNRLKLVPKKVDLSQQKEIPTTLVDDFILSPVV KRSFIQSIKVINAIIKKYGLPNDIIIELAREKNSKDAQKMINEMQKRNRQ TNERIEEIIRTTGKENAKYLIEKIKLHDMQEGKCLYSLEAIPLEDLLNNP FNYEVDHIIPRSVSFDNSFNNKVLVKQEENSKKGNRTPFQYLSSSDSKIS YETFKKHILNLAKGKGRISKTKKEYLLEERDINRFSVQKDFINRNLVDTR YATRGLMNLLRSYFRVNNLDVKVKSINGGFTSFLRRKWKFKKERNKGYKH HAEDALIIANADFIFKEWKKLDKAKKVMENQMFEEKQAESMPEIETEQEY KEIFITPHQIKHIKDFKDYKYSHRVDKKPNRELINDTLYSTRKDDKGNTL IVNNLNGLYDKDNDKLKKLINKSPEKLLMYHHDPQTYQKLKLIMEQYGDE KNPLYKYYEETGNYLTKYSKKDNGPVIKKIKYYGNKLNAHLDITDDYPNS RNKVVKLSLKPYRFDVYLDNGVYKFVTVKNLDVIKKENYYEVNSKCYEEA KKLKKISNQAEFIASFYNNDLIKINGELYRVIGVNNDLLNRIEVNMIDIT YREYLENMNDKRPPRIIKTIASKTQSIKKYSTDILGNLYEVKSKKHPQII KKG |
| 48 >sp\|Q99ZW2\| CAS9_STRP1 CRISPR-associated endonuclease Cas9/Csn1 OS = Streptococcus pyogenes serotype MI GN = cas9 PE = 1 SV = 1 | MDKKYSIGLDIGTNSVGWAVITDEYKVPSKKFKVLGNTDRHSIKKNLIGA LLFDSGETAEATRLKRTARRRYTRRKNRICYLQEIFSNEMAKVDDSFFHR LEESFLVEEDKKHERHPIFGNIVDEVAYHEKYPTIYHLRKKLVDSTDKAD LRLIYLALAHMIKERGHFLIEGDLNPDNSDVDKLFIQLVQTYNQLFEENP INASGVDAKAILSARLSKSRRLENLIAQLPGEKKNGLFGNLIALSLGLTP NFKSNFDLAEDAKLQLSKDTYDDDLDNLLAQIGDQYADLFLAAKNLSDAI LLSDILRVNTEITKAPLSASMIKRYDEHHQDLTLLKALVRQQLPEKYKEI FFDQSKNGYAGYIDGGASQEEFYKFIKPILEKMDGTEELLVKLNREDLLR KQRTFDNGSIPHQIHLGELHAILRRQEDFYPFLKDNREKIEKILTFRIPY YVGPLARGNSRFAWMTRKSEETITPWNFEEVVDKGASAQSFIERMTNFDK NLPNEKVLPKHSLLYEYFTVYNELTKVKYVTEGMRKPAFLSGEQKKAIVD LLFKTNRKVTVKQLKEDYFKKIECFDSVEISGVEDRFNASLGTYHDLLKI IKDKDFLDNEENEDILEDIVLTLTLFEDREMIEERLKTYAHLFDDKVMKQ LKRRRYTGWGRLSRKLINGIRDKQSGKTILDFLKSDGFANRNFMQLIHDD SLTFPKEDIQKAQVSGQGDSLHEHIANLAGSPAIKKGILQTVKVVDELVKV MGRHKPENIVIEMARENQTTQKGQKNSRERMKRIEEGIKELGSQILKEHP VENTQLQNEKLYLYYLQNGRDMYVDQELDINRLSDYDVDHIVPQSFLKDD SIDNKVLTRSDKNRGKSDNVPSEEVVKKMKNYWRQLLNAKLITORKFDNL TKAERGGLSELDKAGFIKRQLVETROITKHVAQILDSRMNTKYDENDKLI REVKVITLKSKLVSDFRKDFQFYKVREINNYHHAHDAYLNAVVGTALIKK YPKLESEFVYGDYKVYDVRKMIAKSEQEIGKATAKYFFYSNIMNFFKTEI TLANGEIRKRPLIETNGETGEIVWDKGRDFATVRKVLSMPQVNIVKKTEV QTGGFSKESILPKRNSDKLIARKKDWDPKKYGGFDSPTVAYSVLVVAKVE KGKSKKLKSVKELLGITIMERSSFEKNPIDFLEAKGYKEVKKDLIIKLPK YSLFELENGRKRMLASAGELQKGNELALPSKYVNFLYLASHYEKLKGSPE DNEQKQLFVEQHKHYLDEIIEQISEFSKRVILADANLDKVLSAYNKHRDK PIREQAENIIHLFTLTNLGAPAAFKYFDTTIDRKRYTSTKEVLDATLIHQ SITGLYETRIDLSQLGGD |
| 49 >ENA\|HE980450\| HE980450.1 Staphylococcus aureus subsp. aureus ORFX gene and pseudo SCCmec-SCC-SCCCRISPR element, strain M06/0171 | [SEQUENCE IS INCORPORATED HEREIN BY REFERENCE FOR USE IN THE PRESENT INVENTION] |
| 123 pBAVIKTXyIR-short1 CRISPR array | GCGGATAACAATTACTAGAGAAAGAGGAGAAATACTATTCTTCTCCTCTT TAAATAACGAAAACACCCTGCCATAAAATGACAGGGTGTTGATTTCGGCA TGAAGCCTTATCTTTGTAGCTTCTGCAAGATTTAAGTAACTGTGTAAGGC GTCCCTTACACTTGCATGTATAGTTATTATACCAGGGGGACAGTGCAATG TCAAGAATAAACTGTAGAATGACTAGTGACTTAAATCTTGAGAGTACAAA AACCCGTTGGAATCGTGATTAATAGTAACTGTTGTTGTACAGTTACTTAA ATCTTGAGAGTACAAAAACGGCCGAGAAAAGGAGCTGATTCATAGGACAG TTGTACAGTTACTTAAATCTTGAGAGTACAAAAACTCAAACTTGCCCGTA GTTTATCTTATAGCCGTTGTACAGTTACTTAAATCTTGAGAGTACAAAAA CATTTACCTCCTTTGATTTAAGTGAACAAGTTTATCC |
| 124 Repeat-spacers sequence | TTAAATCTTGAGAGTACAAAAACCCGTTGGAATCGTGATTAATAGTAACT GTTGTTGTACAGTTACTTAAATCTTGAGAGTACAAAAACGGCCGAGAAAA GGAGCTGATTCATAGGACAGTTGTACAGTTACTTAAATCTTGAGAGTACA AAAACTCAAACTTGCCCGTAGTTTATCTTATAGCCGTTGTACAGTTACTT AAATCTTGAGAGTACAAAAAC |

-continued

| SEQ ID NO: | SEQUENCES (ALL 5' TO 3') |
|---|---|
| 120<br>tracrRNA-encoding sequence | TTAAATAACGAAAACACCCTGCCATAAAATGACAGGGTGTTGATTTCGGC<br>ATGAAGCCTTATCTTTGTAGCTTCTGCAAGATTTAAGTAACTGTGTAAGG<br>CGTCCCTTACAC |
| 121<br>S1. spacer 1 (DNA Pol III)<br>[PAM = AAAGAAA, in the target is immediately 3' of the 3' terminal GCC] | TGTCCTATGAATCAGCTCCTTTTCTCGGCC |
| 122<br>S2. spacer 2 (tetA)<br>[PAM = TAAGAAA, in the target is immediately 3' of the 3' terminal TGA] | GGCTATAAGATAAACTACGGGCAAGTTTGA |
| S thermophilus Consensus PAM | NNAGAAW |

What is claimed is:

1. A method of modifying a mixed population of bacteria, wherein the mixed population comprises a first bacterial sub-population and a second bacterial sub-population, wherein the first bacterial sub-population comprises target host cells of a first bacterial species and the second bacterial sub-population comprises second cells of a second bacterial species, wherein the first bacterial species is different from the second bacterial species, wherein the second cells comprise a conjugative plasmid comprising an origin of transfer (oriT) and a nucleic acid sequence for producing a CRISPR RNA (crRNA), and wherein the method comprises:
   a. transferring the conjugative plasmid from second cells of the second bacterial sub-population to the target host cells, and
   b. producing the crRNA in the target host cells,
      wherein the host cells comprise an exogenous nucleotide sequence for producing a desired protein in the host cell,
      wherein the nucleic acid sequence for producing the crRNA is under control of an inducible promoter in the host cell, and
      wherein the crRNA comprises a nucleic acid sequence that is capable of hybridizing to a target nucleotide sequence in the target host cells to guide a Cas to modify the target nucleotide sequence in the target host cells, wherein the modification of the target sequence inhibits expression of the desired protein in the host cell.

2. The method of claim 1, wherein the target nucleotide sequence is a host cell plasmid sequence.

3. The method of claim 1, wherein the desired protein is an antibiotic.

4. The method of claim 1, wherein the crRNA and Cas are comprised by a Type I, II or III CRISPR/Cas system.

5. The method of claim 1, wherein the crRNA and Cas are comprised by a Type I CRISPR/Cas system.

6. The method of claim 1, wherein the crRNA and Cas are comprised by a Type II CRISPR/Cas system.

7. The method of claim 1, wherein the crRNA and Cas are comprised by a Type III CRISPR/Cas system.

8. The method of claim 1, wherein the Cas is a Cas9.

9. The method of claim 1, wherein the Cas is a Cas nuclease.

10. The method of claim 9, wherein the crRNA guides the Cas to modify the target nucleotide sequence by cutting the target nucleotide sequence to inactivate a gene comprising the target sequence.

11. The method of claim 1, wherein the Cas is a dead Cas.

12. The method of claim 1, wherein the exogenous nucleotide sequence for producing the desired protein comprises the target nucleotide sequence.

13. The method of claim 1, wherein the Cas is an endogenous Cas of the host cell.

14. The method of claim 1, wherein the Cas is an exogenous Cas.

15. A modified bacterial population produced by a method of modifying a mixed population of bacteria, wherein the mixed population comprises a first bacterial sub-population and a second bacterial sub-population, wherein the first bacterial sub-population comprises target host cells of a first bacterial species and the second bacterial sub-population comprises second cells of a second bacterial species, wherein the second cells comprise a conjugative plasmid comprising an origin of transfer (oriT) and a nucleic acid sequence for producing a crRNA, and wherein the method comprises:

a. transferring the conjugative plasmid from second cells of the second bacterial sub-population to the target host cells, and b. producing the crRNA in the target host cells,
   wherein the host cells comprise an exogenous nucleotide sequence for producing a desired protein in the host cell,
   wherein the nucleic acid sequence for producing the crRNA is under the control of an inducible promoter in the host cells, and
   wherein the crRNA comprises a nucleic acid sequence that is capable of hybridizing to a target nucleotide sequence in the target host cells to guide a Cas to modify the target nucleotide sequence in the target host cells, wherein the modification of the target sequence inhibits expression of the desired protein in the host cells.

16. The modified bacterial population of claim 15, wherein the target nucleotide sequence is a host cell plasmid sequence.

* * * * *